(12) United States Patent
Dorok et al.

(10) Patent No.: US 12,127,473 B2
(45) Date of Patent: Oct. 22, 2024

(54) DI-, TRI- AND TETRAPHENYLINDANE DERIVATES AND THEIR USE IN ORGANIC ELECTRONICS

(71) Applicant: Dottikon ES Holding AG, Dottikon (CH)

(72) Inventors: Sascha Dorok, Dresden (DE); Marcus Papmeyer, Nossen (DE); Carsten Fleck, Waldshut-Tiengen (DE); Thorsten Beck, Murg (DE); Stephan Kirschbaum, Wettingen (CH); Yves Aeschi, Biberstein (CH)

(73) Assignee: Dottikon ES Holding AG, Dottikon (CH)

( * ) Notice: Subject to any disclaimer, the term of this patent is extended or adjusted under 35 U.S.C. 154(b) by 645 days.

(21) Appl. No.: 17/292,221

(22) PCT Filed: Nov. 8, 2019

(86) PCT No.: PCT/EP2019/080695
§ 371 (c)(1),
(2) Date: May 7, 2021

(87) PCT Pub. No.: WO2020/094847
PCT Pub. Date: May 14, 2020

(65) Prior Publication Data
US 2022/0006020 A1    Jan. 6, 2022

(30) Foreign Application Priority Data
Nov. 9, 2018   (EP) ..................................... 18205503

(51) Int. Cl.
*C07C 209/36* (2006.01)
*C07C 209/60* (2006.01)
(Continued)

(52) U.S. Cl.
CPC ......... *H10K 85/631* (2023.02); *C07C 209/36* (2013.01); *C07C 209/60* (2013.01); *C07C 209/62* (2013.01); *C07C 211/54* (2013.01); *C07C 211/60* (2013.01); *C07C 211/61* (2013.01); *C07C 213/02* (2013.01); *C07C 217/92* (2013.01); *C09K 11/06* (2013.01); *H10K 85/633* (2023.02); *C07B 2200/07* (2013.01);
(Continued)

(58) Field of Classification Search
CPC .. H10K 85/631; H10K 85/633; H10K 10/484; H10K 30/30; H10K 50/11; H10K 85/615; H10K 85/626; H10K 2101/10; H10K 30/50; H10K 50/18; H10K 50/15; C07C 209/36; C07C 209/60; C07C 209/62; C07C 211/54; C07C 211/60; C07C 211/61; C07C 213/02; C07C 217/92; C07C 2602/08; C07C 2603/18; C07C 2602/24; C07C 211/50; C07C 211/45; C07C 209/68; C07C 209/90; C07C 211/49; C07C 211/57; C09K 11/06; C09K 2211/1007; C09K 2211/1011; C09K 2211/1014; C09K 2211/1416; C09K 2211/1425; C07B 2200/07; Y02E 10/549
See application file for complete search history.

(56) References Cited

U.S. PATENT DOCUMENTS

2020/0075862 A1    3/2020   Dorok et al.

FOREIGN PATENT DOCUMENTS

| CN | 108218721 A | 6/2018 |
|---|---|---|
| CN | 108218763 A | 6/2018 |

(Continued)

*Primary Examiner* — Mark Kopec
*Assistant Examiner* — Jaison P Thomas
(74) *Attorney, Agent, or Firm* — Weston R. Gould; Dinsmore & Shohl LLP

(57) ABSTRACT

The present invention relates to indane derivatives of the formula (I) and mixtures thereof, wherein X is selected from groups of the formulae -A-NH2 or -A-(NAr₂), wherein A is a chemical bond or phenylene which is unsubstituted or substituted by 1, 2, 3 or 4 substituents selected from $C_1$-$C_6$ alkyl and $C_1$-$C_6$-alkoxy; Ar is unsubstituted or substituted aryl, wherein two groups Ar bound to the same nitrogen atom may together with the nitrogen atom also form a fused ring system having 3 or more than 3 unsubstituted or substituted rings; and the variables $R^A$, $R^B$, Y, k, l, m, p, q and r are as defined in the claims and the description. The invention further relates to methods for preparing such compounds and their use in organic electronics, in particular as hole transport material or electron blocking material.

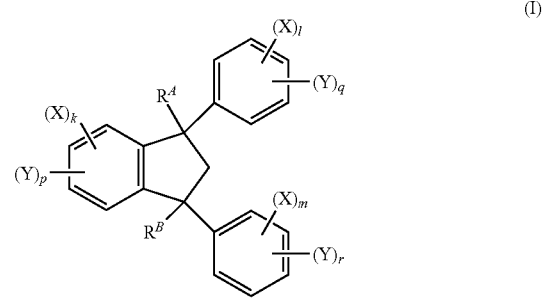

(I)

12 Claims, No Drawings

(51) Int. Cl.
   *C07C 209/62*   (2006.01)
   *C07C 211/54*   (2006.01)
   *C07C 211/60*   (2006.01)
   *C07C 211/61*   (2006.01)
   *C07C 213/02*   (2006.01)
   *C07C 217/92*   (2006.01)
   *C09K 11/06*    (2006.01)
   H10K 85/60  (2023.01)
   *H10K 10/46*    (2023.01)
   *H10K 30/30*    (2023.01)
   *H10K 50/11*    (2023.01)
   *H10K 101/10*   (2023.01)

(52) U.S. Cl.
   CPC ...... *C07C 2602/08* (2017.05); *C07C 2603/18* (2017.05); *C09K 2211/1007* (2013.01); *C09K 2211/1011* (2013.01); *C09K 2211/1014* (2013.01); *H10K 10/484* (2023.02); *H10K 30/30* (2023.02); *H10K 50/11* (2023.02); *H10K 85/615* (2023.02); *H10K 85/626* (2023.02); *H10K 2101/10* (2023.02)

(56) References Cited

FOREIGN PATENT DOCUMENTS

| | | | |
|---|---|---|---|
| CN | 108456142 A | 8/2018 | |
| CN | 108456159 A | 8/2018 | |
| EP | 0138766 A2 * | 4/1985 | ........... C07C 13/455 |
| EP | 3085693 A1 | 10/2016 | |
| JP | 2012-025731 A | 2/2012 | |
| JP | 2012140517 A * | 7/2012 | |
| WO | 2017/036573 A1 | 3/2017 | |

* cited by examiner

DI-, TRI- AND TETRAPHENYLINDANE DERIVATES AND THEIR USE IN ORGANIC ELECTRONICS

SUBJECT MATTER OF THE INVENTION

The present invention relates to di-, tri- and tetraphenylindane derivatives bearing at least one primary amino group and the corresponding diarylamino indanes and to methods for their preparation. The invention further relates to the use of the di-, tri- and tetraphenylindane derivatives bearing at least one primary amino group as intermediates for the synthesis of the corresponding diarylamino indanes and valuable component for the chemical synthesis. The invention further relates to the use of the diarylamino indane derivatives in organic electronics, in particular as hole transport material (HTM) or electron blocking material (EBM).

BACKGROUND OF THE INVENTION

"Organic electronics" is concerned principally with the development, characterization and application of new materials and manufacturing processes for the production of electronic components based on organic small molecules or polymers with desirable electronic properties. These include in particular organic field-effect transistors (OFETs), like organic thin-film transistors (OTFTs), organic electroluminescent devices, like organic light-emitting diodes (OLEDs), organic solar cells (OSCs), e.g. excitonic solar cells, dye sensitized solar cells (DSSCs) or Perovskite solar cells, electrophotography, in particular photoconductive materials in an organic photoconductor (OPC), organic optical detectors, organic photoreceptors, organic field-quench devices (OFQDs), light-emitting electrochemical cells (LECs) and organic laser diodes. In many cases, organic semiconductors have advantages over classical inorganic semiconductors, for example a better substrate compatibility and a better processability of the semiconductor components based on them. They allow inter alia processing on flexible substrates and enable their interface orbital energies to be adjusted to the particular application sector. Great potential for development is ascribed to organic field-effect transistors, for example in memory elements and integrated optoelectronic devices. Organic light-emitting diodes (OLEDs) exploit the property of materials of emitting light when they are excited by electrical current. Even today, OLEDs are particularly of interest as alternatives to liquid-crystal displays for producing flat visual display units. Owing to the very compact design and the intrinsically lower power consumption, devices which comprise OLEDs are suitable especially for mobile applications, for example for applications in cellphones, laptops, etc.

"Organic photovoltaics" denotes the direct conversion of radiative energy, principally solar energy, to electrical energy using organic components. In contrast to inorganic solar cells, the light does not directly generate free charge carriers in organic solar cells, but rather excitons are formed first, i.e. electrically neutral excited states in the form of electron-hole pairs. These excitons can be separated at suitable photoactive interfaces (organic donor-acceptor interfaces or interfaces to an inorganic semiconductor). For this purpose, it is necessary that excitons which have been generated in the volume of the organic material can diffuse to this photoactive interface. The diffusion of excitons to the active interface thus plays a critical role in organic solar cells. There is a great demand for the development of materials which have maximum transport widths and high mobilities for light-induced excited states (high exciton diffusion lengths) and which are thus advantageously suitable for use as an active material in so-called excitonic solar cells.

In recent years, also dye-sensitized solar cells (DSSCs) have attracted much attention. DSSCs have several advantages compared to silicon-based solar cells such as lower production and material costs because an inexpensive metal oxide semiconductor such as titanium dioxide can be used without the necessity of a high degree of purity. Other advantages include their flexibility, transparency and light weight. The construction of a DSSC is generally based on a transparent substrate (e.g. glass), which is coated with a transparent conductive layer, the working electrode. An n-conductive metal oxide is generally applied to this electrode or in the vicinity thereof, for example a nanoporous $TiO_2$ layer. On the surface thereof, in turn, a monolayer of a light-sensitive dye, for example a ruthenium complex or an organic dye, is typically adsorbed, which can be converted to an excited state by light absorption. The function of the DSSC is based on the fact that light is absorbed by the dye, and electrons are transferred from the excited dye to the n-semiconductive metal oxide semiconductor and migrate thereon to the anode. Although dye-sensitized solar cells are one of the most efficient alternative solar cell technologies at present, there is an ongoing need for further improvement. In liquid DSSCs the area between the two electrodes is filled with a redox electrolyte, for example a solution of iodine ($I_2$) and lithium iodide (LiI), which ensures that a photocurrent can be collected at the front and back contacts of the solar cell. Nevertheless, in many cases liquid DSSCs suffer from durability problems, such as electrode corrosion and electrolyte leakage. Therefore, suitable replacements that can be used for hole conduction in lieu of a liquid electrolyte have been searched for.

Another approach in solar cell technology is the use of organometallic Perovskites as light harvesting compounds. These solar cells are called Perovskite-sensitized solar cells (PSCs). Actual PSCs based on lead iodide allow an energy conversion efficiency exceeding 9%. A variant of the PSCs are hybrid solar cells based on methylammonium lead iodide chloride as crystalline Perovskite absorber material. In those cells mesoporous alumina is used instead of titanium dioxide. The $Al_2O_3$ does not act as n-type oxide but as a meso-scale "scaffold" upon which the device is structured.

Photoconductivity is an optical and electrical phenomenon in which a material becomes electrically conductive due to the absorption of electromagnetic radiation such as visible light, ultraviolet light, infrared light, or gamma radiation. An organic photoconductor (OPC) is one of the components in an electrophotographic (EP) printer. A latent image, which is a surface charge pattern, is created on the OPC prior to contact with a development system containing charged marking particles. This is accomplished by uniformly charging the OPC surface, followed by selective illumination that locally generates opposite charges which then move to the surface and locally neutralize deposited charges. The OPC frequently has two layers: an inner layer for generating charges (charge generation layer—CGL) and an outer layer containing molecular moieties for facilitating charge movement (charge transport layer—CTL).

There is an ongoing demand for new compounds with advantageous properties in the afore-mentioned applications. They should be available by effective and economic routes of synthesis.

It is generally known that certain triarylamines are suitable for the use in organic electronic applications.

EP3511316 describes arylamine compounds and organic electroluminescent elements comprising them.

WO 2017/036573 describes triphenyl-substituted aminofluorene derivatives and their use as hole transport material in organic electroluminescent devices (OLEDs).

EP 3085693 describes phenyl substituted aminofluorene derivates and their use in organic electronic devices.

WO 2012/034627 describes compounds of the formula (A)

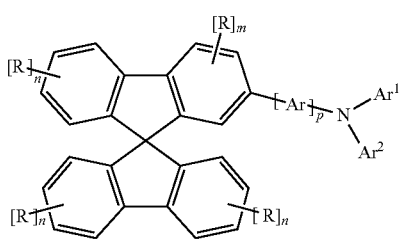

(A)

wherein
Ar is an aromatic ring system;
$Ar^1$, $Ar^2$ are an aromatic or heteroaromatic ring system having 6 to 60 C atoms;
R are selected from the group consisting of H, D, F, Cl, Br, I, CN, $Si(R^2)_3$, a straight-chain alkyl, alkoxy or thioalkyl group having 1 to 40 C atoms or a branched or cyclic alkyl, alkoxy or thioalkyl group having 3 to 40 C atoms, an aromatic or heteroaromatic ring system having 6 to 60 C atoms or an aralkyl group having 5 to 60 aromatic ring atoms,
m is 0, 1, 2 or 3;
n is on each occurrence, identically or differently, 0, 1, 2, 3 or 4;
p is 0, 1 or 2.

The compounds are used in an electronic device, preferably selected from organic electroluminescent devices, organic integrated circuits, organic field-effect transistors, organic thin-film transistors, organic light-emitting transistors, organic solar cells, organic dye-sensitised solar cells, organic optical detectors, organic photoreceptors, organic field-quench devices, light-emitting electrochemical cells, organic laser diodes and organic plasmon emitting devices, in particular in an organic electroluminescent device.

Unpublished PCT/EP2018/062212 (now WO 2018/206769) describes 1,1,3-trimethyl-3-phenylindane derivatives substituted with at least two diarylamino moieties and their use for organic electronics.

There is an ongoing demand for new organic compounds with good electronic application properties. They should be prepared from readily available educts by effective and economic preparation methods.

It has now been found that, surprisingly, the indane derivatives of the invention are advantageously suitable as hole conductors (p-semiconductors, electron donors) in organic photovoltaics. They are especially suitable as hole transport material (HTM) or electron blocking material (EBM).

SUMMARY OF INVENTION

Therefore, in a first aspect the present invention relates to a compound of the general formula (I)

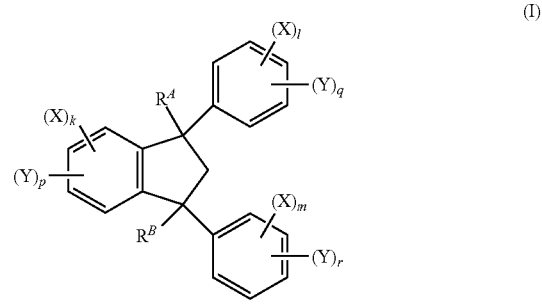

(I)

and mixtures thereof,
wherein
$R^A$ is $C_1$-$C_6$-alkyl, $C_3$-$C_8$-cycloalkyl or a group of the formula (RA-I)

(RA-I)

$R^B$ is $C_1$-$C_6$-alkyl, $C_3$-$C_8$-cycloalkyl or a group of the formula (RB-I)

(RB-I)

# denotes the bonding site to the remainder of the molecule;
X is independently on each occurrence selected from groups of the formulae -A-$NH_2$ and -A-($NAr_2$), wherein
A is independently on each occurrence a chemical bond or phenylene which is unsubstituted or substituted by 1, 2, 3 or 4 substituents independently selected from the group consisting of $C_1$-$C_6$ alkyl and $C_1$-$C_6$-alkoxy;
Ar is independently on each occurrence selected from in each case unsubstituted or substituted aryl, wherein two groups Ar bound to the same nitrogen atom may together with the nitrogen atom also form a fused ring system having 3 or more than 3 unsubstituted or substituted rings;
Y is independently on each occurrence selected from hydrogen, $C_1$-$C_6$-alkyl, $C_1$-$C_6$-alkoxy, $C_3$-$C_8$-cycloalkyl, $C_1$-$C_6$-cycloalkoxy, phenyl and phenoxy, wherein each of the cyclic rings in the four last-mentioned groups are unsubstituted or substituted by 1, 2 or 3 $C_1$-$C_6$-alkyl groups;
k is 0, 1 or 2; l is 0, 1 or 2; m is 0, 1 or 2; n is 0, 1 or 2; o is 0, 1 or 2;

with the proviso that the sum of k, l, m, n and o is 1, 2, 3 or 4;

p is 2, 3 or 4, wherein 0, 1, 2, 3 or 4 of the p Y groups are different from hydrogen;

q is 3, 4 or 5, wherein 0, 1, 2, 3, 4 or 5 of the q Y groups are different from hydrogen;

r is 3, 4 or 5, wherein 0, 1, 2, 3, 4 or 5 of the r Y groups are different from hydrogen;

s is 3, 4 or 5, wherein 0, 1, 2, 3, 4 or 5 of the s Y groups are different from hydrogen;

t is 3, 4 or 5, wherein 0, 1, 2, 3, 4 or 5 of the t Y groups are different from hydrogen;

the sum of k and p is 4; the sum of q and l is 5; the sum of m and r is 5; the sum of s and n is 5; and the sum of o and t is 5.

One special embodiment are primary amine compounds represented by the formula (I) above, wherein each X stands for a group of the formula -A-$NH_2$.

A further special embodiment are diarylamine compounds represented by the formula (I) above, wherein each X is independently selected from groups of the formulae -A-($NAr_2$).

A further aspect relates to the use of a compound of the general formula (I) as defined above in the Summary and below in the Detailed Description or of a composition comprising at least two different compounds of the general formula (I) as defined above in the Summary and below in the Detailed Description

- as a hole transport material (HTM) in organic electronics;
- as an electron blocking material (EBM) in organic electronics;
- as a semiconductor material in organic field-effect transistors (OFETs), in particular in thin-film transistors (TFTs);
- in organic solar cells (OSCs), solid-state dye sensitized solar cells (DSSCs) or Perovskite solar cells, in particular as a hole transport material in organic solar cells, as replacement of the liquid electrolyte in dye sensitized solar cells, as a hole transport material in Perovskite solar cells;
- in organic light-emitting diodes (OLEDs), in particular for displays on electronic devices and lighting;
- for electrophotography, in particular as photoconductive material in an organic photoconductor (OPC);
- for organic optical detectors, organic photoreceptors, organic field-quench devices (O-FQDs), light-emitting electrochemical cells (LECs) and organic laser diodes.

Yet another aspect of the invention relates to an organic field-effect transistor comprising a substrate having at least one gate structure, a source electrode and a drain electrode and at least one compound of the formula (I) as defined above in the Summary and below in the Detailed Description or of a composition comprising at least two different compounds of the general formula (I) as defined above in the Summary and below in the Detailed Description as a semiconductor material.

Yet another aspect of the invention relates to a substrate comprising a plurality of organic field-effect transistors, at least some of the field-effect transistors comprising at least one compound of the formula (I) as defined above in the Summary and below in the Detailed Description or of a composition comprising at least two different compounds of the general formula (I) as defined above.

Yet another aspect of the invention relates to a semiconductor unit comprising at least one substrate as defined above.

Yet another aspect of the invention relates to an electroluminescent arrangement comprising an upper electrode, a lower electrode, wherein at least one of said electrodes is transparent, an electroluminescent layer and optionally an auxiliary layer, wherein the electroluminescent arrangement comprises at least one compound of the formula (I) as defined above in the Summary and below in the Detailed Description or of a composition comprising at least two different compounds of the general formula (I) as defined above in the Summary and below in the Detailed Description, preferably in a hole-transporting layer or electron blocking layer.

Yet another aspect of the invention relates to an organic solar cell, comprising: a cathode, an anode, one or more photoactive region comprising at least one donor material and at least one acceptor material in separate layers or in form of a bulk heterojunction layer, optionally at least one further layer selected from exciton blocking layers, electron conducting layers, hole transport layers, wherein the organic solar cell comprises at least one compound of the formula (I) as defined above in the Summary and below in the Detailed Description or of a composition comprising at least two different compounds of the general formula (I) as defined above in the Summary and below in the Detailed Description.

Yet another aspect of the present invention relates to processes for preparing compounds of the formula (I).

DETAILED DESCRIPTION OF THE INVENTION

The compounds of the general formula (I) and the methods for their preparation have at least one of the following advantages:

- The compounds of the formula (I) are characterized by a good thermal stability and environmental stability. Most compounds (I) have a high glass transition temperature. They are usually sublimable, can be purified by fractional sublimation and allow the fabrication of devices by physical vapor deposition.
- The compounds of the formula (I) are in particular suitable as organic semiconductors. They function generally as p-semiconductors. Preferred applications of the compounds (I) are as hole transport material (HTM) or electron blocking material (EBM).
- OFETs, in particular OTFTs produced from the compounds of the formula (I) are characterized by at least one of the following properties: a high charge transport mobility, a high on/off ratio, low threshold voltages and air stability. The compounds of the invention allow the formation of well-ordered thin films. OTFTs usually show well-defined linear- and saturation-regime output characteristics.
- The compounds of the formula (I) further have good properties in OPV (organic photovoltaic) applications. They allow that the excited states (excitons) generated by the absorbed photons can be passed on over very large distances, i.e. they have good exciton diffusion lengths. The invention further allows providing compounds of the formula (I), where the size of the semiconductor band gap is adjusted to very effectively utilize the solar light.
- The processes of the invention allow a very effective and economic synthesis of a great variety of compounds of the formula (I). Thus, it is possible to easily provide a compound (I) with optimized properties for the intended use.

The present invention relates to compounds of the formula (I),

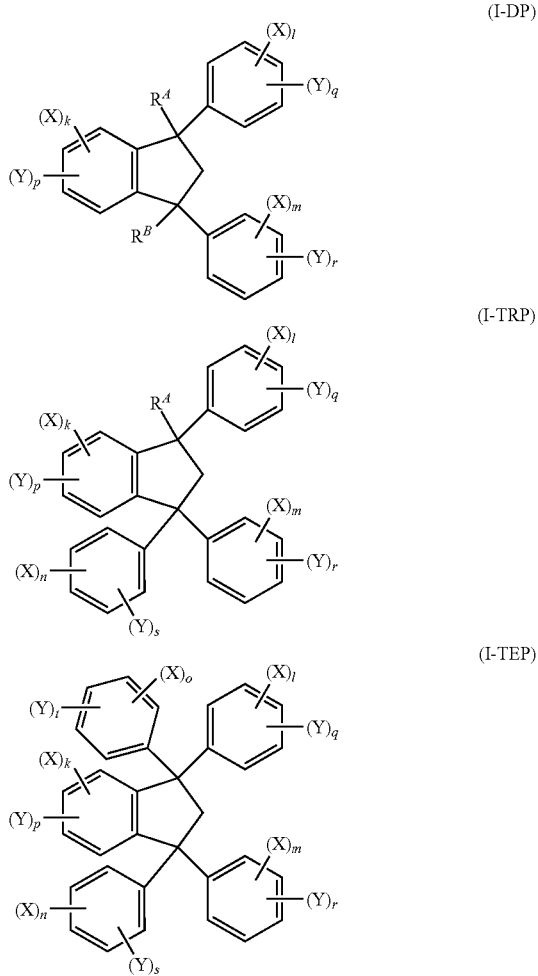

wherein $R^A$ is $C_1$-$C_6$-alkyl or $C_3$-$C_8$-cycloalkyl and $R^B$ is $C_1$-$C_6$-alkyl or $C_3$-$C_8$-cycloalkyl. These compounds are also referred to as compounds (I-DP). The present invention also relates to compounds of the formula (I), wherein $R^A$ is $C_1$-$C_6$-alkyl or $C_3$-$C_8$-cycloalkyl and $R^B$ is a group (RB-I). These compounds are also referred to as compounds (I-TRP). The present invention also relates to compounds of the formula (I), wherein $R^A$ is a group (RA-I) and $R^B$ is a group (RB-I). These compounds are also referred to as compounds (I-TEP). In the compounds of the formulae (I-DP), (I-TRP) and (I-TEP) the radicals $(X)_k$, $(X)_l$, $(X)_m$, $(Y)_p$, $(Y)_q$, $(Y)_r$, if present $(X)_n$, $(X)_o$, $(Y)_s$ and $(Y)_t$ are as described in the Summary and below in the Detailed Description of the Invention.

Depending on the kind of substituents, the compounds of formula (I) may have one or more centers of chirality, in which case they may be present as mixtures of enantiomers or diastereomers but also in the form of the pure enantiomers or pure diastereomers. The invention provides achiral compounds of the formula (I) as well as chiral compounds of formula (I) including the pure enantiomers or pure diastereomers of the compounds of formula (I), and their mixtures and the use according to the invention of the achiral compounds of formula (I) as well as the chiral compounds of formula (I) including pure enantiomers or pure diastereomers of the compound of formula (I) or its mixtures. The compound of formula (I) can be obtained in enantiomerically enriched form and diastereomerically enriched form, respectively, or in pure form by standard methods known in the art, which includes e.g. chiral separation or by preparing the compounds of formula (I) by using an appropriate chiral indane compound as starting material. Suitable compounds of the formula (I) also include all possible regioisomers and mixtures thereof.

The compounds of formula (I) are indane derivatives which are indicated herein also as 2,3-dihydro-1H-indene derivatives.

It is noted that in the formulae depicted herein, a methyl group may be indicated as a solid line. Thus, for example, the solid lines at position 9 of 9,9-dimethylfluorene depicted below signify the two methyl groups.

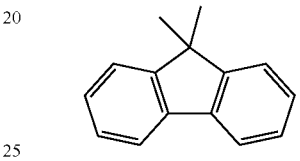

It is also noted that in general hydrogen atoms are not depicted in a formula, unless the formula clearly dictates otherwise. In other words, in some specific formulae of this application the hydrogen atoms are explicitly shown but in most cases not, as is the usual practice.

As used in this specification and the claims, the singular form "a", "an", and "the" include plural forms unless the context clearly indicates otherwise.

The definitions of the variables specified in the above formulae use collective terms which are generally representative of the respective substituents. The definition $C_n$-$C_m$ gives the number of carbon atoms possible in each case in the respective substituent or substituent moiety.

The expression "halogen" denotes in each case fluorine, bromine, chlorine or iodine, particularly chlorine, bromide or iodine. Similarly, the term "halo" denotes in each case fluoro, chloro, bromo or iodo.

The term "unbranched" as used herein is also referred to as linear or straight-chain.

The term "$C_n$-$C_m$-alkyl" as used herein refers to a branched or unbranched saturated hydrocarbon group having n to m carbon atoms, e.g., 1 to 2 ("$C_1$-$C_2$-alkyl"), 1 to 4 ("$C_1$-$C_4$-alkyl") or 1 to 6 ("$C_1$-$C_6$-alkyl"). $C_1$-$C_2$-Alkyl is methyl or ethyl. Examples for $C_1$-$C_4$-alkyl are, in addition to those mentioned for $C_1$-$C_2$-alkyl, propyl, isopropyl, butyl, 1-methylpropyl (sec-butyl), 2-methylpropyl (isobutyl) or 1,1-dimethylethyl (tert-butyl). Examples for $C_1$-$C_5$-alkyl are, in addition to those mentioned for $C_1$-$C_4$-alkyl, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methyl propyl.

The term "$CH_2$-($C_6$-$C_{10}$-aryl)" as used herein denotes benzyl, 1-naphthylmethyl or 2-naphthylmethyl.

Similarly, the term "$C_n$-$C_m$-alkoxy" refers to straight-chain or branched alkyl groups having n to m carbon atoms, e.g. 1 to 2 carbon atoms or 1 to 4 carbon atoms or 1 to 6 carbon atoms (as mentioned above) attached via an oxygen atom at any bond in the alkyl group to the remainder of the molecule. $C_1$-$C_2$-Alkoxy is methoxy or ethoxy. Examples for $C_1$-$C_4$-alkoxy are, in addition to those mentioned for $C_1$-$C_2$-alkoxy, n-propoxy, 1-methylethoxy (isopropoxy), butoxy, 1-methylpropoxy (sec-butoxy), 2-methylpropoxy (isobutoxy) or 1,1-dimethylethoxy (tert-butoxy). Examples for $C_1$-$C_6$-alkoxy are, in addition to those mentioned for $C_1$-$C_4$-alkoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

The term "$C_n$-$C_m$-cycloalkyl" as used herein refers to a monocyclic n- to m-membered saturated cycloaliphatic radical having, e.g. 3 to 8 carbon atoms. Examples for $C_3$-$C_8$-cycloalkyl are cyclopropyl, cyclobutyl, cyclopentyl, cyclohexyl, cycloheptyl and cyclooctyl.

Similarly, the term "$C_n$-$C_m$-cycloalkoxy" refers to a monocyclic n- to m-membered saturated cycloaliphatic radical, e.g. $C_3$-$C_8$-cycloalkyl (as mentioned above) bonded through O linkage to the skeleton.

The term "aryl" as used herein refers to monocyclic, bicyclic, tricyclic and tetracyclic aromatic hydrocarbon radicals with 6 to 18 ring carbon atoms, in which the rings are all condensed (fused) or two of the aromatic rings may also be joined to one another by a chemical bond and a divalent radical selected from —CH$_2$—, —O—, —S— or —N(H)—. Examples include phenyl, naphthyl, anthracenyl, phenanthrenyl, fluorenyl, dibenzofuranyl (dibenzofuryl), dibenzothienyl, carbazolyl, 11H-benzo[b]fluorenyl, naphtho[2,3-b]benzofuryl, naphtho[2,3-b]benzothienyl and 5H-benzo[b]carbazolyl. Aryl may be substituted at one, two, three, four, more than four or all substitutable positions. Suitable substituents are in general $C_1$-$C_6$-alkyl, $C_1$-$C_6$-alkoxy, carbazol-9-yl (N-bound carbazolyl), which is unsubstituted or substituted by $C_1$-$C_4$-alkyl, $C_1$-$C_4$-alkoxy and phenyl, wherein phenyl on its part may be substituted by 1, 2, 3 or 4 different or identical substituents selected from $C_1$-$C_4$-alkyl and $C_1$-$C_4$-alkoxy. In addition, suitable substituents attached at aryl are in general also diphenylamino, $C_5$-$C_8$-cycloalkyl, phenyl, biphenylyl, terphenylyl, naphthyl, anthracenyl and phenanthryl, wherein each of the cyclic rings in the 8 last-mentioned groups are unsubstituted or substituted by 1, 2, 3, 4 or 5 different or identical substituents selected from $C_1$-$C_4$-alkyl, $C_1$-$C_4$-alkoxy and carbazol-9-yl which is unsubstituted or substituted by $C_1$-$C_4$-alkyl, $C_1$-$C_4$-alkoxy and phenyl, wherein phenyl on its part may be substituted by 1, 2, 3 or 4 different or identical substituents selected from $C_1$-$C_4$-alkyl and $C_1$-$C_4$-alkoxy. In addition, two substituents bonded to the same carbon atom of fluorenyl or 11H-benzo[b]fluorenyl, together may form an alkylene group (CH$_2$), with r being 4, 5, 6 or 7 thus forming a 5- to 8-membered saturated carbocycle, in which 1 or 2 hydrogen atoms in this group may be replaced by a group $C_1$-$C_4$-alkyl or $C_1$-$C_4$-alkoxy or two substituents bonded to the same carbon atom of fluorenyl or 11H-benzo[b]fluorenyl together may form an alkylene group (CH$_2$), with r being 4, 5, 6 or 7 thus forming a 5- to 8-membered saturated carbocycle, which may be benz-annelated with one or two benzene groups, where the benzene ring(s) is (are) optionally substituted by 1, 2, 3 or 4 identical or different $C_1$-$C_4$-alkyl or $C_1$-$C_4$-alkoxy.

If a moiety is described as being "optionally substituted", the moiety may be either unsubstituted or substituted.

If a moiety is described as "substituted", a non-hydrogen radical is in the place of hydrogen radical of any substitutable atom of the moiety. If there are more than one substitution on a moiety, each non-hydrogen radical may be identical or different (unless otherwise stated).

The remarks made above and in the following with respect to preferred aspects of the invention, e.g. to preferred meanings of the radicals RA, RB, X and Y and the indices k, l, m, p, q and r of compounds of the formula (I), to preferred compounds of formula (I) and to the use according to the invention, apply in each case on their own or in particular to combinations thereof:

Preferred compounds according to the invention are compounds of the formula (I), wherein $R^A$ is $C_1$-$C_4$-alkyl, $C_5$-$C_8$-cycloalkyl or a group of the formula (RA-I). More preferably, $R^A$ is methyl or a group of the formula (RA-I).

Likewise preferred are compounds of the formula (I), wherein $R^B$ is $C_1$-$C_4$-alkyl, $C_5$-$C_8$-cycloalkyl or a group of the formula (RB-I). More preferably, $R^B$ is methyl or a group of the formula (RB-I).

Amongst the compounds of the formula (I), more preference is given to compounds, wherein $R^A$ is methyl and $R^B$ is methyl. Likewise, more preference is given to compounds of formula (I), wherein $R^A$ is methyl and $R^B$ is a group of the formula (RB-I).

Compounds of the formula (I), wherein $R^A$ and $R^B$ are both methyl are hereinafter termed compounds of the formula (I.DP). Compounds of the formula (I), wherein $R^A$ is methyl and $R^B$ is a group (RB-I) are hereinafter termed compounds of the formula (I.TRP). Compounds of the formula (I), wherein $R^A$ is a group (RA-I) and $R^B$ is a group (RB-I) are hereinafter termed compounds of formula (I.TEP).

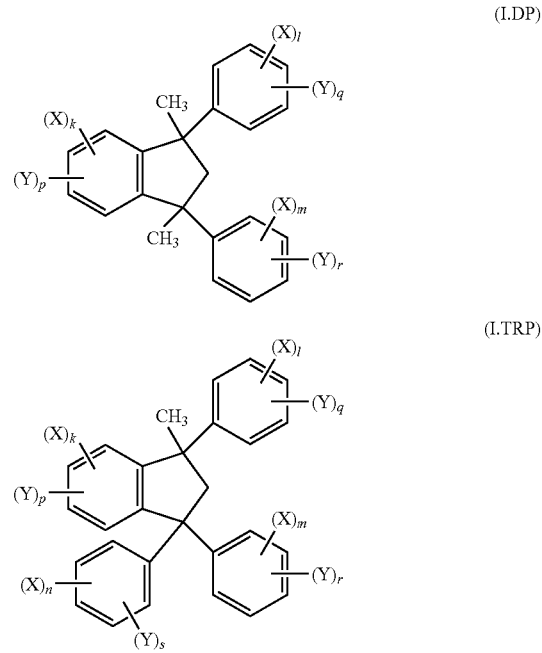

-continued

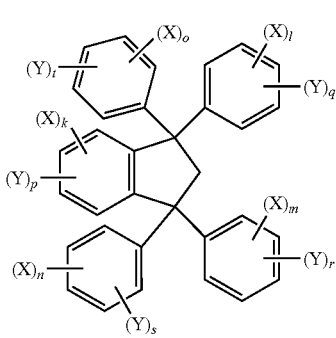
(I.TEP)

In the compounds of the formulae (I.DP), (I.TRP) and (I.TEP), X, Y, k, l, m, n, o, p, q, r, s and t are as defined above in the Summary and below in the Detailed Description.

In one embodiment, in formula (I) each X is -A-NH$_2$ or -A-NAr$_2$. In an alternative embodiment, in formula (I) each X is individually selected from groups -A-NAr$_2$.

The group A is a divalent phenylene group. Irrespectively of its occurrence, A is selected from the group consisting of the groups of the formulae (A1), (A2) and (A3),

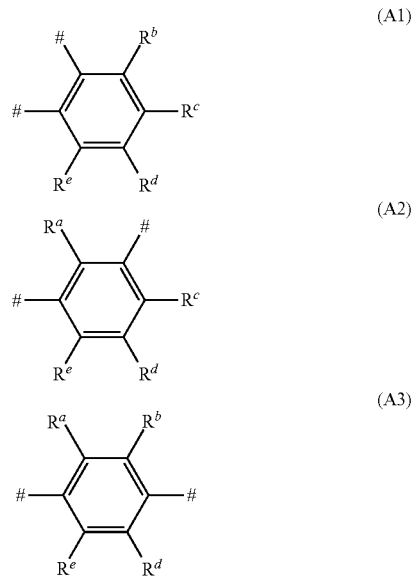

wherein
# are the bonding sites to the benzene ring and the nitrogen atom, respectively; and
$R^a$, $R^b$, $R^c$, $R^d$ and $R^e$ if present, are each independently selected from hydrogen, straight-chain and branched $C_1$-$C_4$-alkyl or straight-chain and branched $C_1$-$C_4$-alkoxy.

In a specific embodiment each group A is a divalent phenylene group as defined above. In a more specific embodiment, each group A is a divalent phenylene group and all groups A have the same meaning. Preferably, $R^a$, $R^b$, $R^c$, $R^d$ and $R^e$, if present, are each hydrogen. Likewise preferably, at least one of the radicals $R^a$, $R^b$, $R^c$, $R^d$ and $R^e$, if present, is different from hydrogen and the remaining radicals $R^a$, $R^b$, $R^c$, $R^d$ and $R^e$, if present, are each hydrogen. More preferably, one of $R^a$, $R^b$, $R^c$, $R^d$ and $R^e$, if present, are methoxy or methyl and the remaining $R^a$, $R^b$, $R^c$, $R^d$ and $R^e$, if present, are each hydrogen.

In another embodiment, the group A is a chemical bond. Among the compounds of the formula (I), more preference is given to those compounds of formula (I), (I.DP), (I.TRP) and (I.TEP), wherein each group A is a chemical bond.

Preference is given to compounds of the formula (I), where the radical X is -A-NH$_2$, wherein A is as defined above. Compounds of the formula (I) wherein X is -A-NH$_2$ are especially useful intermediate compounds, for example for preparing compounds of the formula (I) wherein X is -A-NAr$_2$ or for preparing triarylamine compounds different from those of the present invention. Synthetic routes for preparing compounds of the formula (I), wherein X is NH$_2$ are described below in detail as part of the synthetic routes for preparing compounds of the formula (I), wherein X is NAr$_2$.

Preferred compounds of formulae (I), (I.DP), (I.TRP) and (I.TEP), wherein X is -A-NH$_2$, include the compounds of formulae (I.DP-MAH-1), (I.DP-MAH-2), (I.DP-DAH-1), (I.DP-DAH-2), (I.DP-DAH-3), (I.DP-TRAH-1), (I.TRP-MAH-1), (I.TRP-MAH-2), (I.TRP-MAH-3), (I.TRP-DAH-1), (I.TRP-DAH-2), (I.TRP-DAH-3), (I.TRP-TEAH-1), (I.TRP-TEAH-2), (I.TRP-TEAH-3), (I.TEP-MAH-1), (I.TEP-MAH-2), (I.TEP-DAH-1), (I.TEP-DAH-2), (I.TEP-DAH-3), (I.TEP-DAH-4):

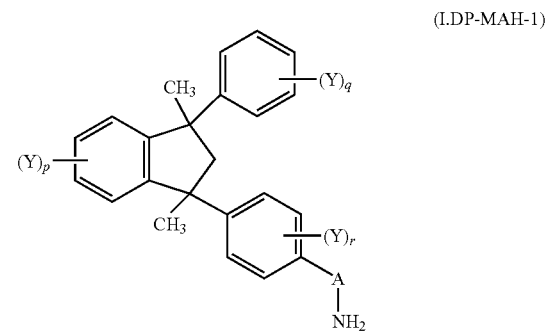
(I.DP-MAH-1)

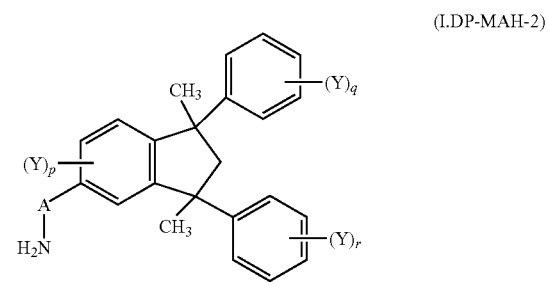
(I.DP-MAH-2)

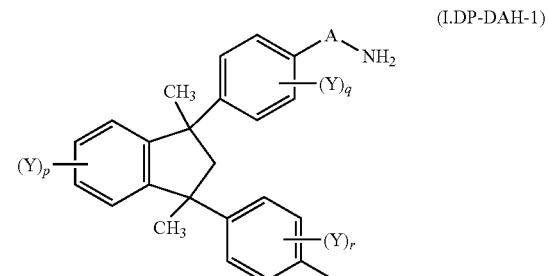
(I.DP-DAH-1)

-continued
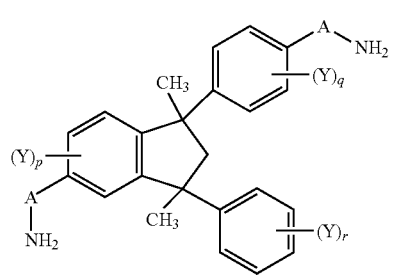
(I.DP-DAH-2)
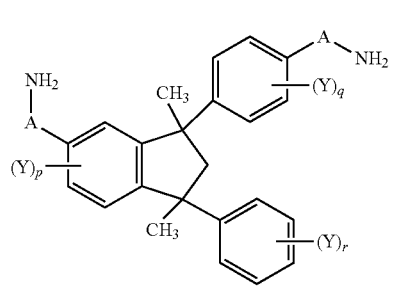
(I.DP-DAH-3)
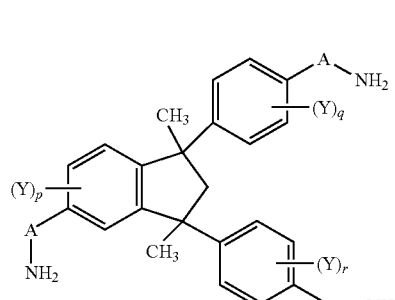
(I.DP-TRAH-1)
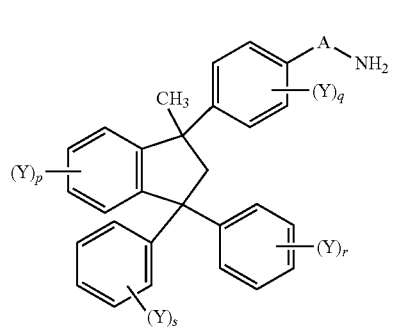
(I.TRP-MAH-1)
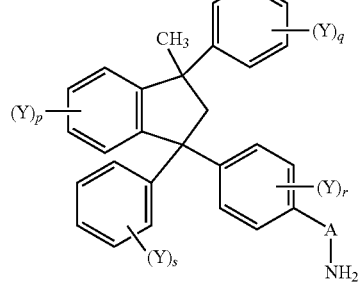
(I.TRP-MAH-2)
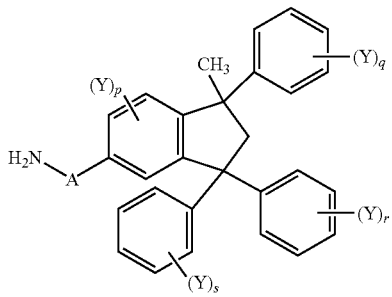
(I.TRP-MAH-3)
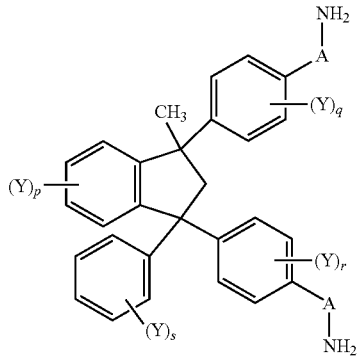
(I.TRP-DAH-1)
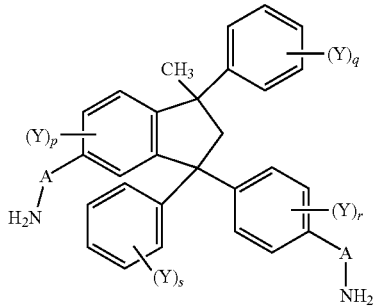
(I.TRP-DAH-2)
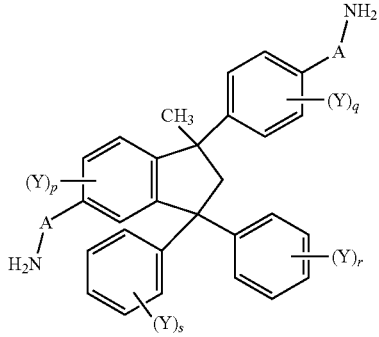
(I.TRP-DAH-3)

(I.TRP-TEAH-1)
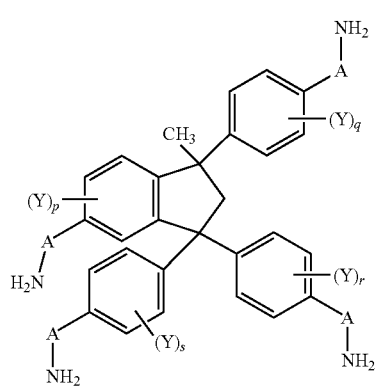
(I.TRP-TEAH-2)
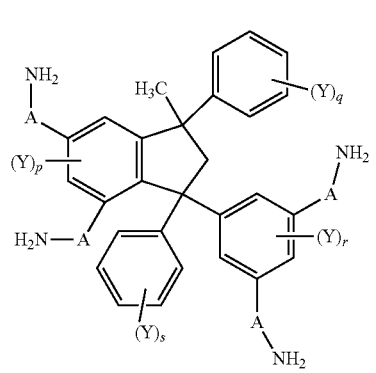
(I.TRP-TEAH-3)
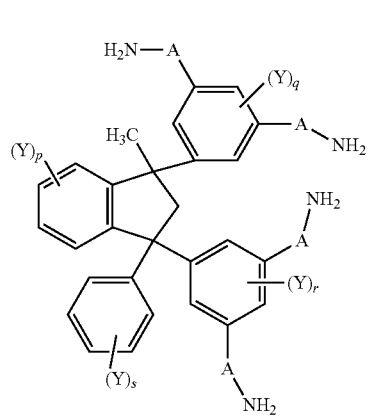
(I.TEP-MAH-1)
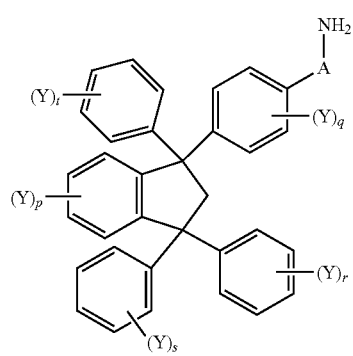
(I-TEP-MAH-2)
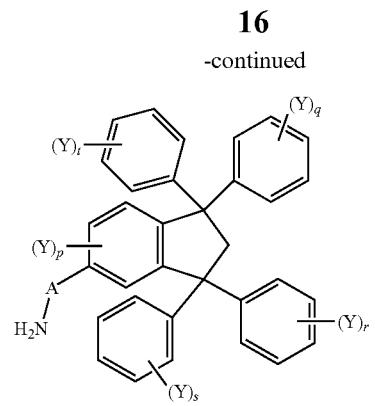
(I.TEP-DAH-1)
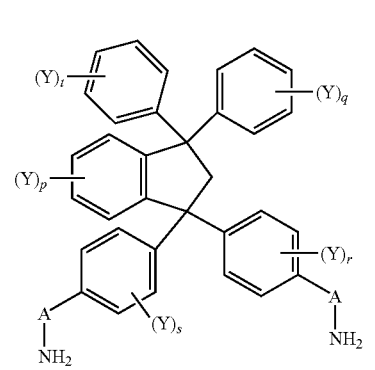
(I.TEP-DAH-2)
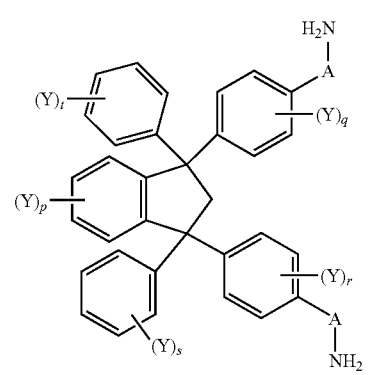
(I.TEP.DAH-3)
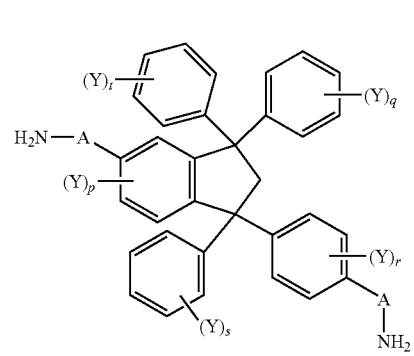

-continued (I.TEP-DAH-4)

wherein the radicals Y and A are as defined herein;
where in formula (I.DP-MAH-1):
p is 4, wherein 0, 1, 2, 3 or 4 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
where in formula (I.DP-MAH-2):
p is 3, wherein 0, 1, 2 or 3 of the p Y groups are different from hydrogen;
q is 5, wherein 0, 1, 2, 3, 4 or 5 of the q Y groups are different from hydrogen;
r is 5, wherein 0, 1, 2, 3, 4 or 5 of the r Y groups are different from hydrogen;
where in formula (I.DP-DAH-1):
p is 4, wherein 0, 1, 2, 3 or 4 of the p Y groups are different from hydrogen;
q is 4, wherein 0, 1, 2, 3, or 4 of the q Y groups are different from hydrogen;
r is 4, wherein 0, 1, 2, 3 or 4 of the r Y groups are different from hydrogen;
where in formula (I.DP-DAH-2):
p is 3, wherein 0, 1, 2 or 3 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
where in formula (I.DP-DAH-3):
p is 3, wherein 0, 1, 2 or 3 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
where in formula (I.DP-TRAH-1):
p is 3, wherein 0, 1, 2 or 3 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
where in formula (I.TRP-MAH-1):
p is 4, wherein 0, 1, 2, 3 or 4 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
where in formula (I.TRP-MAH-2):
p is 4, wherein 0, 1, 2, 3 or 4 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
where in formula (I.TRP-MAH-3):
p is 3, wherein 0, 1, 2 or 3 of the p Y groups are different from hydrogen;
q is 5, wherein 0, 1, 2, 3, 4 or 5 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
where in formula (I.TRP-DAH-1):
p is 4, wherein 0, 1, 2, 3 or 4 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
where in formula (I.TRP-DAH-2):
p is 3, wherein 0, 1, 2 or 3 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
where in formula (I.TRP-DAH-3):
p is 3, wherein 0, 1, 2 or 3 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
where in formula (I.TRP-TEAH-1):
p is 3, wherein 0, 1, 2 or 3 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
s is 4, wherein 0, 1, 2, 3 or 4 of the s Y groups are different from hydrogen;
where in formula (I.TRP-TEAH-2):
p is 2, wherein 0, 1 or 2 of the p Y groups are different from hydrogen;
q is 5, wherein 0, 1, 2, 3, 4 or 5 of the q Y groups are different from hydrogen;
r is 3, wherein 0, 1, 2 or 3 of the r Y groups are different from hydrogen;
s is 5, wherein 0, 1, 2, 3, 4 or 5 of the s Y groups are different from hydrogen;

where in formula (I.TRP-TEAH-3):
p is 4, wherein 0, 1, 2, 3 or 4 of the p Y groups are different from hydrogen;
q is 3, wherein 0, 1, 2 or 3 of the q Y groups are different from hydrogen;
r is 3, wherein 0, 1, 2 or 3 of the r Y groups are different from hydrogen;
s is 5, wherein 0, 1, 2, 3, 4 or 5 of the s Y groups are different from hydrogen;
where in formula (I.TEP-MAH-1):
p is 4, wherein 0, 1, 2, 3 or 4 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
t is 5, wherein 0, 1, 2, 3, 4 or 5 of the t Y groups are different from hydrogen;
where in formula (I.TEP-MAH-2):
p is 3, wherein 0, 1, 2 or 3 of the p Y groups are different from hydrogen;
q is 5, wherein 0, 1, 2, 3, 4 or 5 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
t is 5, wherein 0, 1, 2, 3, 4 or 5 of the t Y groups are different from hydrogen;
where in formula (I.TEP-DAH-1):
p is 4, wherein 0, 1, 2, 3 or 4 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
s is 4, wherein 0, 1, 2, 3 or 4 of the s Y groups are different from hydrogen;
t is 5, wherein 0, 1, 2, 3, 4 or 5 of the t Y groups are different from hydrogen;
where in formula (I.TEP-DAH-2):
p is 4, wherein 0, 1, 2, 3 or 4 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
t is 5, wherein 0, 1, 2, 3, 4 or 5 of the t Y groups are different from hydrogen;
where in formula (I.TEP-DAH-3):
p is 3, wherein 0, 1, 2 or 3 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
t is 5, wherein 0, 1, 2, 3, 4 or 5 of the t Y groups are different from hydrogen;
where in formula (I.TEP-DAH-4):
p is 3, wherein 0, 1, 2 or 3 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
t is 5, wherein 0, 1, 2, 3, 4 or 5 of the t Y groups are different from hydrogen.

Likewise preferred are the compounds of formulae (I.DP-TEAH-1), (I.TRP-DAH-4), (I.TRP-DAH-5) and (I.TRP-TRA-1)

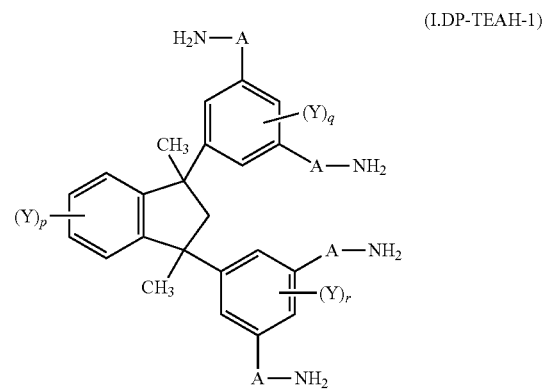

(I.DP-TEAH-1)

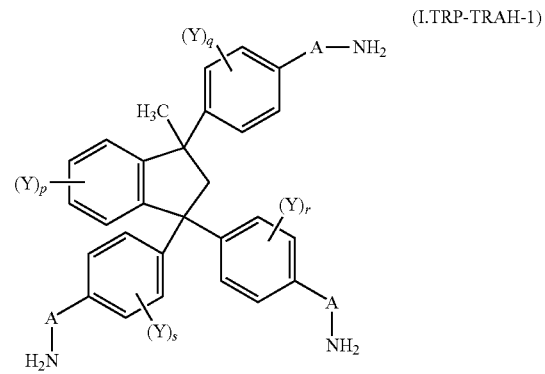

(I.TRP-TRAH-1)

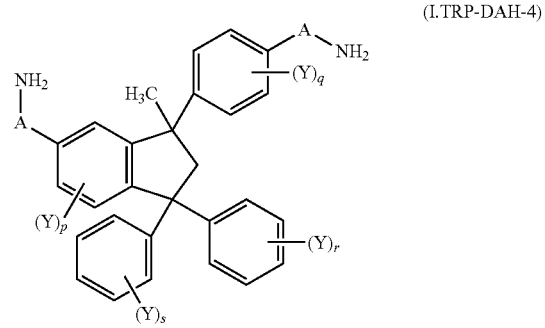

(I.TRP-DAH-4)

(I.TRP-DAH-5)

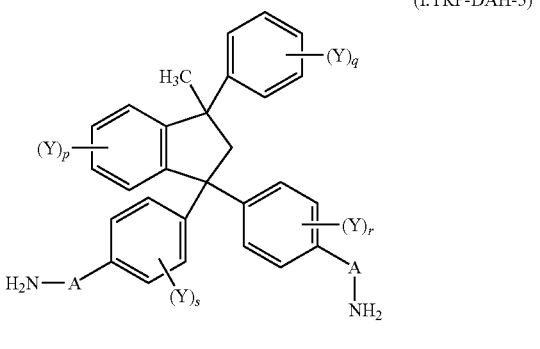

where in formula (I.DP-TEA-1)
p is 4, wherein 0, 1, 2, 3 or 4 of the p Y groups are different from hydrogen;
q is 3, wherein 0, 1, 2 or 3 of the q Y groups are different from hydrogen;
r is 3, wherein 0, 1, 2 or 3 of the r Y groups are different from hydrogen;
where in formula (I.TRP-TRAH-1):
p is 4, wherein 0, 1, 2, 3 or 4 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
s is 4, wherein 0, 1, 2, 3 or 4 of the s Y groups are different from hydrogen;
where in formula (I.TRP-DAH-4):
p is 3, wherein 0, 1, 2 or 3 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
where in formula (I.TRP-DAH-5):
p is 4, wherein 0, 1, 2, 3 or 4 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
s is 4, wherein 0, 1, 2, 3 or 4 of the s Y groups are different from hydrogen.

In formulae (I.DP-MAH-1), (I.DP-MAH-2), (I.DP-DAH-1), (I.DP-DAH-2), (I.DP-DAH-3), (I.DP-TRAH-1), (I.TRP-MAH-1), (I.TRP-MAH-2), (I.TRP-MAH-3), (I.TRP-DAH-1), (I.TRP-DAH-2), (I.TRP-DAH-3), (I.TRP-TEAH-1), (I.TRP-TEAH-2), (I.TRP-TEAH-3), (I.TEP-MAH-1), (I.TEP-MAH-2), (I.TEP-DAH-1), (I.TEP-DAH-2), (I.TEP-DAH-3), (I.TEP-DAH-4), each of the groups A is preferably a chemical bond. In formulae (I.DP-TEAH-1), (I.TRP-DAH-4), (I.TRP-DAH-5) and (I.TRP-TRAH-1), each of the groups A is preferably a chemical bond.

Preference is also given to compounds of the invention, where the radical X is -A-NAr$_2$, wherein A is as defined above. Preferred compounds of formulae (I), (I.DP), (I.TRP) and (I.TEP) include the compounds of formulae (I.DP-MA-1), (I.DP-MA-2), (I.DP-DA-1), (I.DP-DA-2), (I.DP-DA-3), (I.DP-TRA-1), (I.TRP-MA-1), (I.TRP-MA-2), (I.TRP-MA-3), (I.TRP-DA-1), (I.TRP-DA-2), (I.TRP-DA-3), (I.TRP-TEA-1), (I.TRP-TEA-2), (I.TRP-TEA-3), (I.TEP-MA-1), (I.TEP-MA-2), (I.TEP-DA-1), (I.TEP-DA-2), (I.TEP-DA-3) and (I.TEP-DA-4)

(I.DP-MA-1)

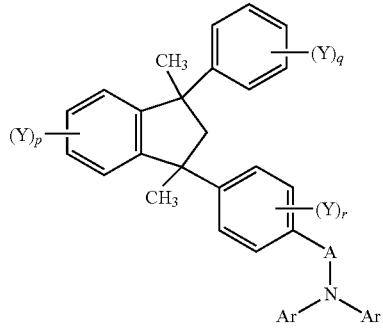

(I.DP-MA-2)

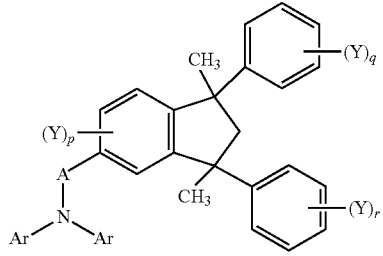

(I.DP-DA-1)

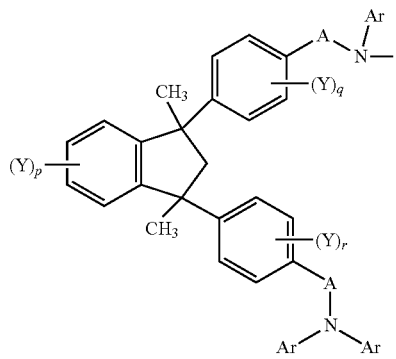

(I.DP-DA-2)

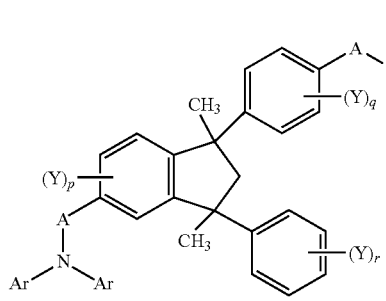

(I.DP-DA-3)

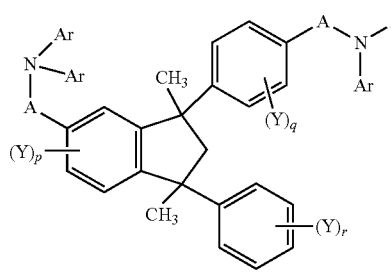

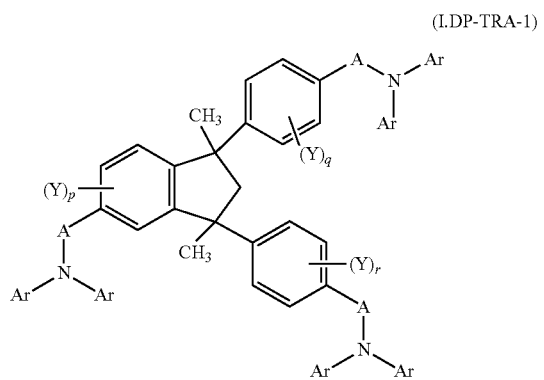
(I.DP-TRA-1)
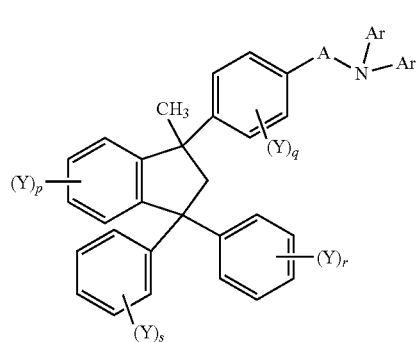
(I.TRP-MA-1)
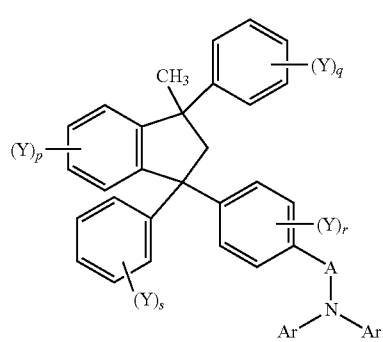
(I.TRP-MA-2)
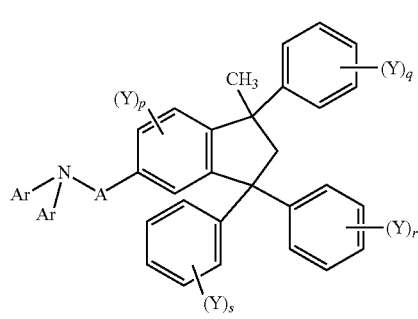
(I.TRP-MA-3)
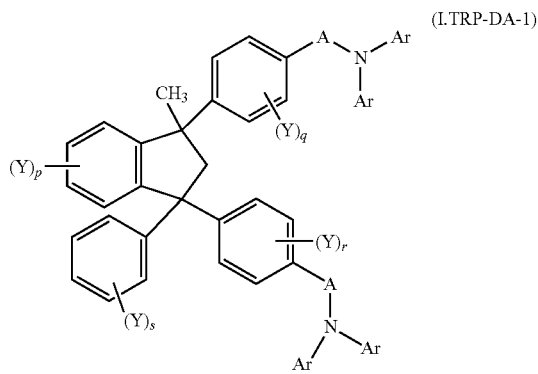
(I.TRP-DA-1)
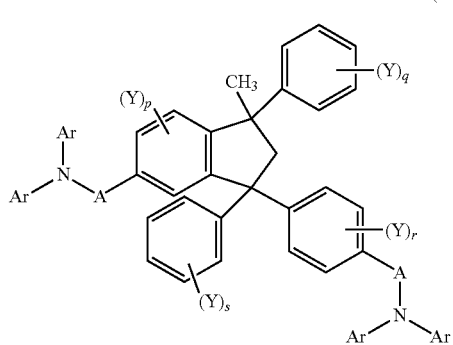
(I.TRP-DA-2)
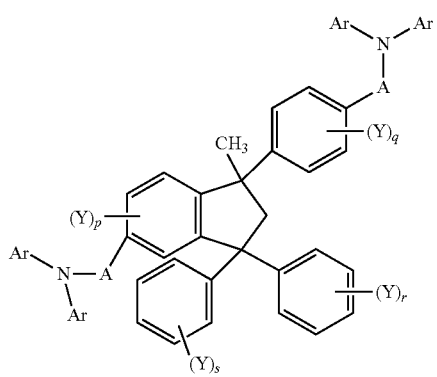
(I.TRP-DA-3)
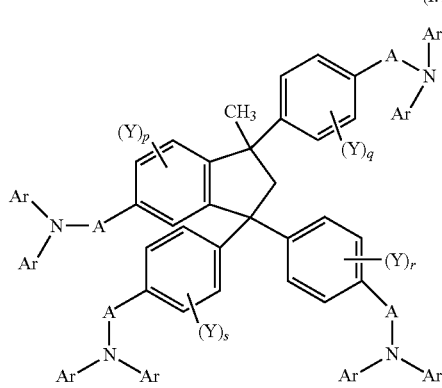
(I.TRP-TEA-1)

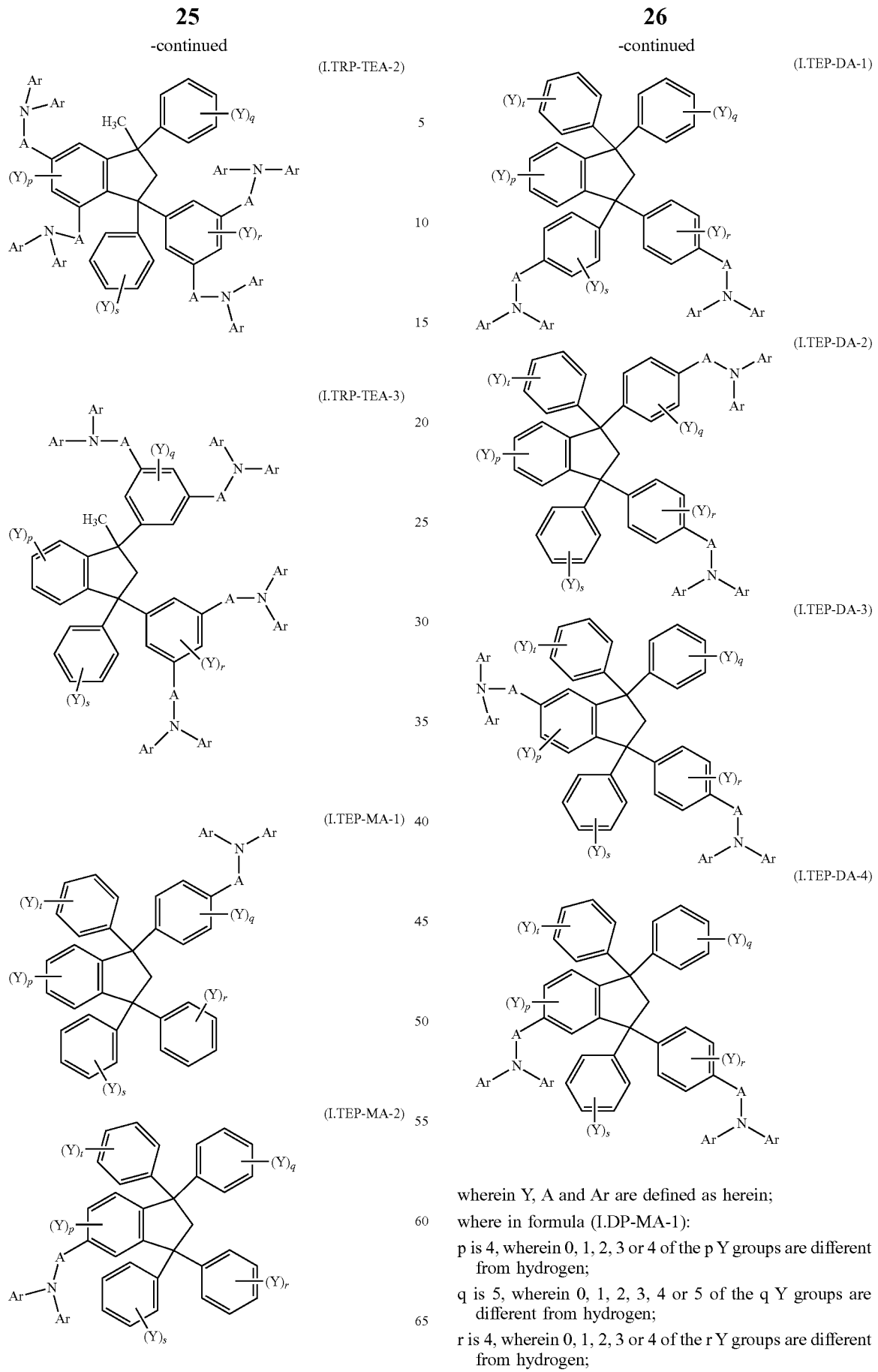
wherein Y, A and Ar are defined as herein;
where in formula (I.DP-MA-1):
p is 4, wherein 0, 1, 2, 3 or 4 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;

where in formula (I.DP-MA-2):
p is 3, wherein 0, 1, 2 or 3 of the p Y groups are different from hydrogen;
q is 5, wherein 0, 1, 2, 3, 4 or 5 of the q Y groups are different from hydrogen;
r is 5, wherein 0, 1, 2, 3, 4 or 5 of the r Y groups are different from hydrogen;
where in formula (I.DP-DA-1):
p is 4, wherein 0, 1, 2, 3 or 4 of the p Y groups are different from hydrogen;
q is 4, wherein 0, 1, 2, 3, or 4 of the q Y groups are different from hydrogen;
r is 4, wherein 0, 1, 2, 3 or 4 of the r Y groups are different from hydrogen;
where in formula (I.DP-DA-2):
p is 3, wherein 0, 1, 2 or 3 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
where in formula (I.DP-DA-3):
p is 3, wherein 0, 1, 2 or 3 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
where in formula (I.DP-TRA-1):
p is 3, wherein 0, 1, 2 or 3 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
where in formula (I.TRP-MA-1):
p is 4, wherein 0, 1, 2, 3 or 4 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
where in formula (I.TRP-MA-2):
p is 4, wherein 0, 1, 2, 3 or 4 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
where in formula (I.TRP-MA-3):
p is 3, wherein 0, 1, 2 or 3 of the p Y groups are different from hydrogen;
q is 5, wherein 0, 1, 2, 3, 4 or 5 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
where in formula (I.TRP-DA-1):
p is 4, wherein 0, 1, 2, 3 or 4 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
where in formula (I.TRP-DA-2):
p is 3, wherein 0, 1, 2 or 3 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
where in formula (I.TRP-DA-3):
p is 3, wherein 0, 1, 2 or 3 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
where in formula (I.TRP-TEA-1):
p is 3, wherein 0, 1, 2, or 3 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
s is 4, wherein 0, 1, 2, 3 or 4 of the s Y groups are different from hydrogen;
where in formula (I.TRP-TEA-2):
p is 2, wherein 0, 1 or 2 of the p Y groups are different from hydrogen;
q is 5, wherein 0, 1, 2, 3, 4 or 5 of the q Y groups are different from hydrogen;
r is 3, wherein 0, 1, 2 or 3 of the r Y groups are different from hydrogen;
s is 5, wherein 0, 1, 2, 3, 4 or 5 of the s Y groups are different from hydrogen;
where in formula (I.TRP-TEA-3):
p is 4, wherein 0, 1, 2, 3 or 4 of the p Y groups are different from hydrogen;
q is 3, wherein 0, 1, 2 or 3 of the q Y groups are different from hydrogen;
r is 3, wherein 0, 1, 2 or 3 of the r Y groups are different from hydrogen;
s is 5, wherein 0, 1, 2, 3, 4 or 5 of the s Y groups are different from hydrogen;
where in formula (I.TEP-MA-1):
p is 4, wherein 0, 1, 2, 3 or 4 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
t is 5, wherein 0, 1, 2, 3, 4 or 5 of the t Y groups are different from hydrogen;
where in formula (I.TEP-MA-2):
p is 3, wherein 0, 1, 2 or 3 of the p Y groups are different from hydrogen;
q is 5, wherein 0, 1, 2, 3, 4 or 5 of the q Y groups are different from hydrogen;
r is 5, wherein 0, 1, 2, 3, 4 or 5 of the r Y groups are different from hydrogen;

s is 5, wherein 0, 1, 2, 3, 4 or 5 of the s Y groups are different from hydrogen;

t is 5, wherein 0, 1, 2, 3, 4 or 5 of the t Y groups are different from hydrogen;

where in formula (I.TEP-DA-1):

p is 4, wherein 0, 1, 2, 3 or 4 of the p Y groups are different from hydrogen;

q is 5, wherein 0, 1, 2, 3, 4 or 5 of the q Y groups are different from hydrogen;

r is 4, wherein 0, 1, 2, 3 or 4 of the r Y groups are different from hydrogen;

s is 4, wherein 0, 1, 2, 3 or 4 of the s Y groups are different from hydrogen;

t is 5, wherein 0, 1, 2, 3, 4 or 5 of the t Y groups are different from hydrogen;

where in formula (I.TEP-DA-2):

p is 4, wherein 0, 1, 2, 3 or 4 of the p Y groups are different from hydrogen;

q is 4, wherein 0, 1, 2, 3 or 4 of the q Y groups are different from hydrogen;

r is 4, wherein 0, 1, 2, 3 or 4 of the r Y groups are different from hydrogen;

s is 5, wherein 0, 1, 2, 3, 4 or 5 of the s Y groups are different from hydrogen;

t is 5, wherein 0, 1, 2, 3, 4 or 5 of the t Y groups are different from hydrogen;

where in formula (I.TEP-DA-3):

p is 3, wherein 0, 1, 2 or 3 of the p Y groups are different from hydrogen;

q is 5, wherein 0, 1, 2, 3, 4 or 5 of the q Y groups are different from hydrogen;

r is 4, wherein 0, 1, 2, 3 or 4 of the r Y groups are different from hydrogen;

s is 5, wherein 0, 1, 2, 3, 4 or 5 of the s Y groups are different from hydrogen;

t is 5, wherein 0, 1, 2, 3, 4 or 5 of the t Y groups are different from hydrogen;

where in formula (I.TEP-DA-4):

p is 3, wherein 0, 1, 2 or 3 of the p Y groups are different from hydrogen;

q is 5, wherein 0, 1, 2, 3, 4 or 5 of the q Y groups are different from hydrogen;

r is 4, wherein 0, 1, 2, 3 or 4 of the r Y groups are different from hydrogen;

s is 5, wherein 0, 1, 2, 3, 4 or 5 of the s Y groups are different from hydrogen;

t is 5, wherein 0, 1, 2, 3, 4 or 5 of the t Y groups are different from hydrogen.

Likewise preferred compounds of formula (I), wherein X is -A-NAr$_2$ include the compounds of formulae (I.DP-TEA-1), (I.TRP-DA-4), (I.TRP-DA-5) and I.TRP-TRA-1,

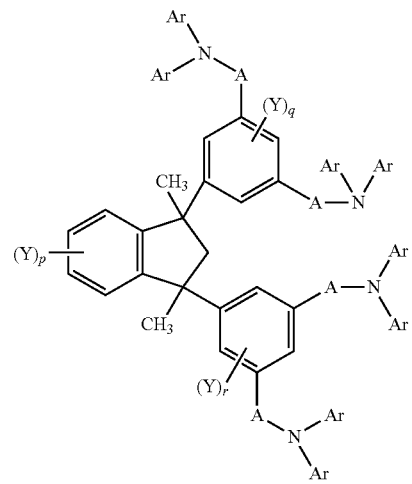
(I.DP-TEA-1)

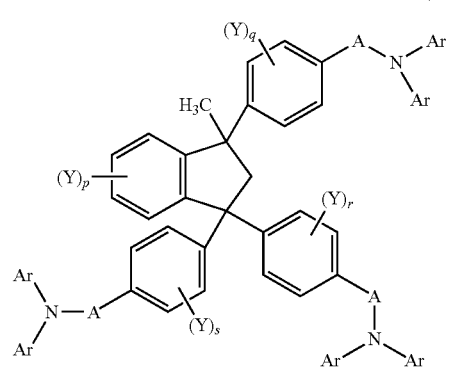
(I.TRP-TRA-1)

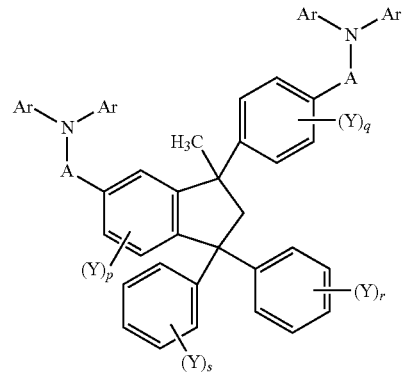
(I.TRP-DA-4)

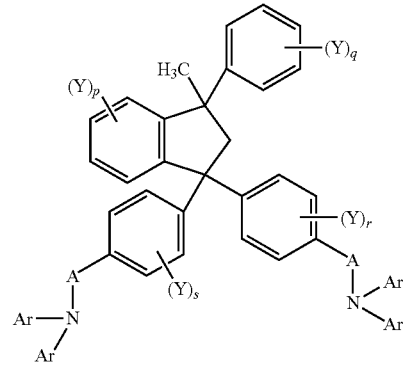
(I.TRP-DA-5)

where in formula (I.DP-TEA-1):
p is 4, wherein 0, 1, 2, 3 or 4 of the p Y groups are different from hydrogen;
q is 3, wherein 0, 1, 2 or 3 of the q Y groups are different from hydrogen;
r is 3, wherein 0, 1, 2 or 3 of the r Y groups are different from hydrogen;
where in formula (I.TRP-DA-4):
p is 3, wherein 0, 1, 2 or 3 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
where in formula (I.TRP-DA-5):
p is 4, wherein 0, 1, 2, 3 or 4 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
s is 4, wherein 0, 1, 2, 3 or 4 of the s Y groups are different from hydrogen;
where in formula (I.TRP-TRA-1):
p is 4, wherein 0, 1, 2, 3 or 4 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
s is 4, wherein 0, 1, 2, 3 or 4 of the s Y groups are different from hydrogen.

In formulae (I), (I.DP), (I.TRP), (I.TEP), (I.DP-MA-1), (I.DP-MA-2), (I.DP-DA-1), (I.DP-DA-2), (I.DP-DA-3), (I.DP-TRA-1), (I.TRP-MA-1), (I.TRP-MA-2), (I.TRP-MA-3), (I.TRP-DA-1), (I.TRP-DA-2), (I.TRP-DA-3), (I.TRP-TEA-1), (I.TRP-TEA-2), (I.TRP-TEA-3), (I.TEP-MA-1), (I.TEP-MA-2), (I.TEP-DA-1), (I.TEP-DA-2), (I.TEP-DA-3), (I.TEP-DA-4), each of the groups A is preferably a chemical bond. In formulae (I.DP-TEA-1), (I.TRP-DA-4), (I.TRP-DA-5) and (I.TRP.TRA-1) each of the groups A is preferably a chemical bond.

Preference is also given to compounds of the formulae (I), (I.DP), (I.TRP), (I.TEP), (I.DP-MAH-1), (I.DP-MAH-2), (I.DP-DAH-1), (I.DP-DAH-2), (I.DP-DAH-3), (I.DP-TRAH-1), (I.DP-TEAH-1), (I.TRP-MAH-1), (I.TRP-MAH-2), (I.TRP-MAH-3), (I.TRP-DAH-1), (I.TRP-DAH-2), (I.TRP-DAH-3), (I.TRP-TEAH-1), (I.TRP-TEAH-2), (I.TRP-TEAH-3), (I.TEP-MAH-1), (I.TEP-MAH-2), (I.TEP-DAH-1), (I.TEP-DAH-2), (I.TEP-DAH-3), (I.TEP-DAH-4), (I.DP-MA-1), (I.DP-MA-2), (I.DP-DA-1), (I.DP-DA-2), (I.DP-DA-3), (I.DP-TRA-1), (I.TRP-MA-1), (I.TRP-MA-2), (I.TRP-MA-3), (I.TRP-DA-1), (I.TRP-DA-2), (I.TRP-DA-3), (I.TRP-DA-4), (I.TRP-DA-5), (I.TRP.TRA-1), (I.TRP-TEA-1), (I.TRP-TEA-2), (I.TRP-TEA-3), (I.TEP-MA-1), (I.TEP-MA-2), (I.TEP-DA-1), (I.TEP-DA-2), (I.TEP-DA-3), (I.TEP-DA-4), (I.TRP-TRA-1), (I.TRP-TEA-1), (I.TRP-TEA-2), (I.TRP-TEA-3), (I.TEP-MA-1), (I.TEP-MA-2), (I.TEP-DA-1), (I.TEP-DA-2), (I.TEP-DA-3), (I.TEP-DA-4), in which each $(Y)_p$, $(Y)_q$, $(Y)_r$, if present, $(Y)_s$ and $(Y)_t$ irrespectively of its occurrence, is independently selected from hydrogen, $C_1$-$C_4$-alkyl, $C_1$-$C_4$-alkoxy, phenyl, tolyl, xylyl, mesityl, phenoxy, O-tolyl, -xylyl or O-mesityl, specifically hydrogen, methyl, methoxy or phenyl. Especially, 0 or 1 of the p Y groups is different from hydrogen. Especially, 0 or 1 of the q Y groups is different from hydrogen. Especially, 0 or 1 of the r Y groups is different from hydrogen. Especially, 0 or 1 of the s Y groups is different from hydrogen. Especially, 0 or 1 of the t Y groups is different from hydrogen.

More preference is given to compounds of the formulae (I), (I.DP), (I.TRP), (I.TEP), (I), (I.DP), (I.TRP), (I.TEP), (I.DP-MAH-1), (I.DP-MAH-2), (I.DP-DAH-1), (I.DP-DAH-2), (I.DP-DAH-3), (I.DP-TRAH-1), (I.DP-TEAH-1), (I.TRP-MAH-1), (I.TRP-MAH-2), (I.TRP-MAH-3), (I.TRP-DAH-1), (I.TRP-DAH-2), (I.TRP-DAH-3), (I.TRP-TEAH-1), (I.TRP-TEAH-2), (I.TRP-TEAH-3), (I.TEP-MAH-1), (I.TEP-MAH-2), (I.TEP-DAH-1), (I.TEP-DAH-2), (I.TEP-DAH-3), (I.TEP-DAH-4), (I.DP-MA-1), (I.DP-MA-2), (I.DP-DA-1), (I.DP-DA-2), (I.DP-DA-3), (I.DP-TRA-1), (I.TRP-MA-1), (I.TRP-MA-2), (I.TRP-MA-3), (I.TRP-DA-1), (I.TRP-DA-2), (I.TRP-DA-3), (I.TRP-DA-4), (I.TRP-DA-5), (I.TRP.TRA-1), (I.TRP-TEA-1), (I.TRP-TEA-2), (I.TRP-TEA-3), (I.TEP-MA-1), (I.TEP-MA-2), (I.TEP-DA-1), (I.TEP-DA-2), (I.TEP-DA-3), (I.TEP-DA-4), in which each $(Y)_p$, $(Y)_q$, $(Y)_r$, if present, $(Y)_s$ and $(Y)_t$ are hydrogen.

Preference is also given to compounds of the formulae (I), (I.DP), (I.TRP), (I.TEP), (I.DP-MA-1), (I.DP-MA-2), (I.DP-DA-1), (I.DP-DA-2), (I.DP-DA-3), (I.DP-TRA-1), (I.DP-TEA-1), (I.TRP-MA-1), (I.TRP-MA-2), (I.TRP-MA-3), (I.TRP-DA-1), (I.TRP-DA-2), (I.TRP-DA-3), (I.TRP-DA-4), (I.TRP-DA-5), (I.TRP.TRA-1), (I.TRP-TEA-1), (I.TRP-TEA-2), (I.TRP-TEA-3), (I.TEP-MA-1), (I.TEP-MA-2), (I.TEP-DA-1), (I.TEP-DA-2), (I.TEP-DA-3), (I.TEP-DA-4) in which the group Ar, irrespectively of its occurrence, is selected from unsubstituted or substituted phenyl, unsubstituted or substituted naphthyl, unsubstituted or substituted phenanthryl, unsubstituted or substituted anthracenyl, unsubstituted or substituted fluorenyl, unsubstituted or substituted C-bound carbazolyl, unsubstituted or substituted dibenzofuranyl, unsubstituted or substituted dibenzothiophenyl, or 2 groups Ar together with the nitrogen atom to which they are attached form an unsubstituted or substituted N-bound carbazolyl.

More preferably, each Ar, irrespectively of its occurrence, is selected from
phenyl, biphenylyl, terphenylyl, quaterphenylyl, wherein phenyl, biphenylyl, terphenylyl and quaterphenylyl are unsubstituted or substituted by one or more substituents $R^{Ar1}$;
naphthyl, anthracenyl, phenanthryl, fluorenyl, spirofluorenyl, C-bound carbazolyl, dibenzofuranyl and dibenzothiophenyl, wherein naphthyl, phenanthryl, fluorenyl, spirofluorenyl, C-bound carbazolyl, dibenzofuranyl and dibenzothiophenyl are unsubstituted or substituted by one or more substituents $R^{Ar2}$; or
2 groups Ar together with the nitrogen atom to which they are attached may form an N-bound carbazolyl, which is unsubstituted or substituted by one or more substituents $R^{Ar3}$;
wherein
each $R^{Ar1}$ is independently selected from
$C_1$-$C_6$-alkyl, $C_1$-$C_6$-alkoxy, carbazol-9-yl, wherein carbazol-9-yl may be substituted by 1, 2, 3 or 4 substituents selected from $C_1$-$C_4$-alkyl, $C_1$-$C_4$-alkoxy and phenyl, wherein phenyl may be substituted by 1, 2, 3 or 4 different or identical substituents selected from $C_1$-$C_4$-alkyl and $C_1$-$C_4$-alkoxy, diphenylamino, $C_5$-$C_8$-cycloalkyl and naphthyl, wherein each of the cyclic rings in the three last-mentioned groups are unsubstituted or substituted by 1, 2, 3 or 4 different or identical substituents selected from $C_1$-$C_4$-alkyl, $C_1$-$C_4$-alkoxy and carbazol-9-yl, wherein carbazol-9-yl may be substituted by 1, 2, 3 or 4 different or identical substituents selected from C₁-C₄-alkyl, C₁-C₄-alkoxy and phenyl, wherein phenyl may be substituted by 1, 2, 3 or 4 different or identical substituents selected from C₁-C₄-alkyl and C₁-C₄-alkoxy, and two radicals $R^{Ar1}$ which are bound to adjacent carbon atoms together with the carbon atoms to which they are bound may form a saturated 5-membered heterocycle having 2 non-adjacent oxygen atoms as ring members which is unsubstituted or substituted by 1 or 2 radicals selected from C₁-C₄-alkyl;

each $R^{Ar2}$ is independently selected from

C₁-C₆-alkyl, C₁-C₆-alkoxy, carbazol-9-yl, wherein carbazol-9-yl may be substituted by 1, 2, 3 or 4 substituents selected from C₁-C₄-alkyl, C₁-C₄-alkoxy and phenyl, wherein phenyl may be substituted by 1, 2, 3 or 4 different or identical substituents selected from C₁-C₄-alkyl and C₁-C₄-alkoxy, diphenylamino, C₅-C₈-cycloalkyl and phenyl, wherein each of the cyclic rings in the three last-mentioned groups are unsubstituted or substituted by 1, 2, 3 or 4 different or identical substituents selected from C₁-C₄-alkyl, C₁-C₄-alkoxy and carbazol-9-yl, wherein carbazol-9-yl may be substituted by 1, 2, 3 or 4 different or identical substituents selected from C₁-C₄-alkyl, C₁-C₄-alkoxy and phenyl, wherein phenyl may be substituted by 1, 2, 3 or 4 different or identical substituents selected from C₁-C₄-alkyl and C₁-C₄-alkoxy, two radicals $R^{Ar2}$ which are bound to adjacent carbon atoms together with the carbon atoms to which they are bound may form a saturated 5-membered heterocycle having 2 non-adjacent oxygen atoms as ring members which is unsubstituted or substituted by 1 or 2 radicals selected from C₁-C₄-alkyl and, in addition, in the case of fluorenyl, two geminal radicals $R^{Ar2}$ may form an alkylene group (CH₂)ᵣ with r being 4, 5, 6 or 7, where 1 or 2 hydrogen atoms in this group may be replaced by a methyl group or a methoxy group; and each $R^{Ar3}$ is independently selected from C₁-C₆-alkyl, C₁-C₆-alkoxy, diphenylamino and phenyl, wherein each of the cyclic rings in the two last-mentioned groups are unsubstituted or substituted by 1, 2, 3 or 4 different or identical substituents selected from C₁-C₄-alkyl and C₁-C₄-alkoxy.

Particular examples of the group Ar include the following radicals of the formulae (AR-I) to (AR-XLV)

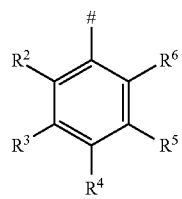
(AR-I)

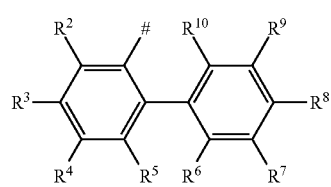
(AR-II)

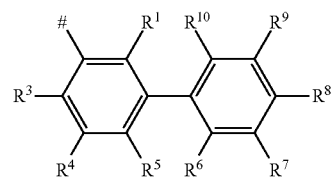
(AR-III)

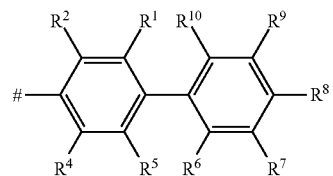
(AR-IV)

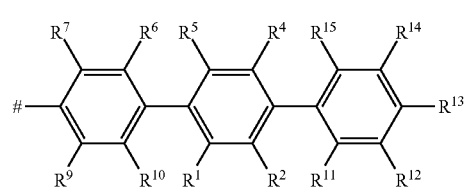
(AR-V)

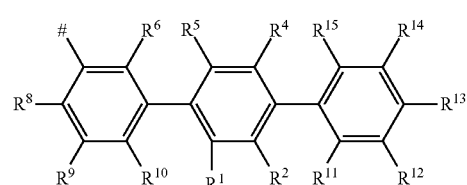
(AR-VI)

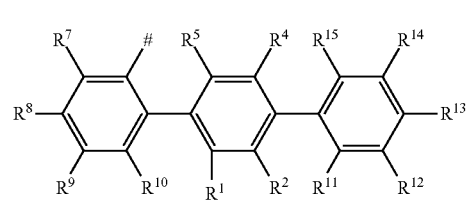
(AR-VII)

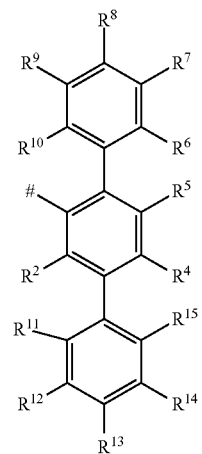
(AR-VIII)

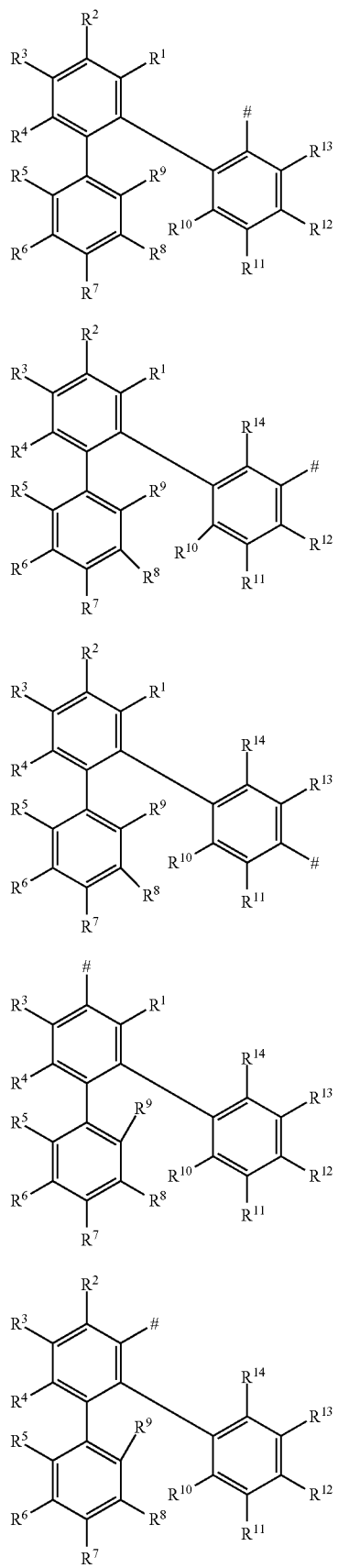
(AR-IX)
(AR-X)
(AR-XI)
(AR-XII)
(AR-XIII)
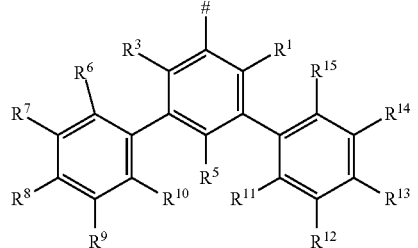
(AR-XIV)
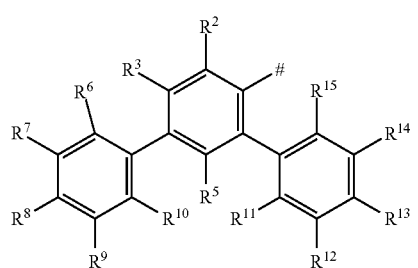
(AR-XV)
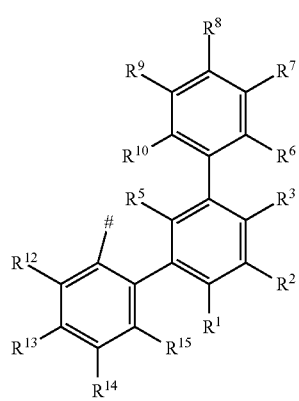
(XVI)
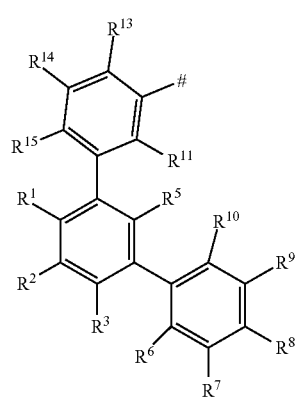
(AR-XVII)

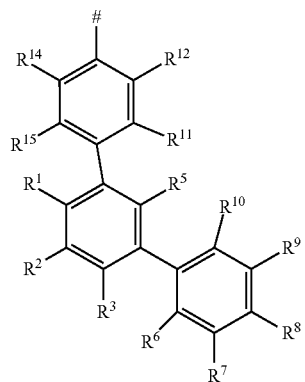
(AR-XVIII)
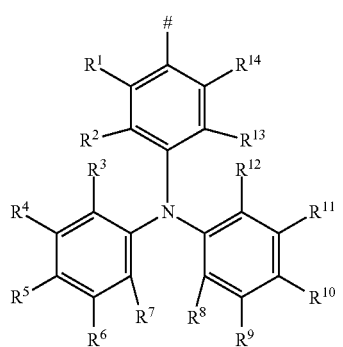
(AR-XIX)
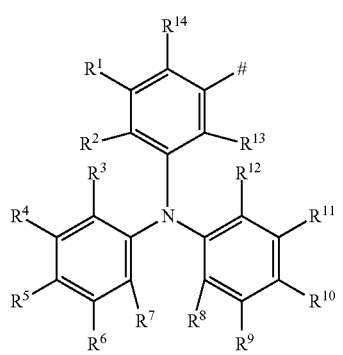
(AR-XX)
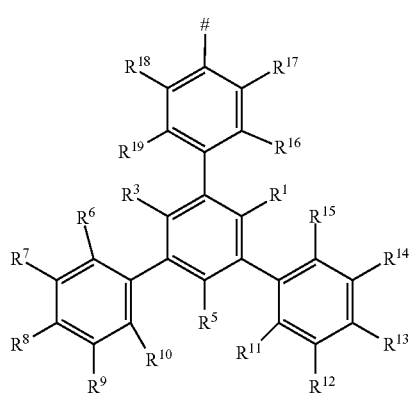
(AR-XXI)
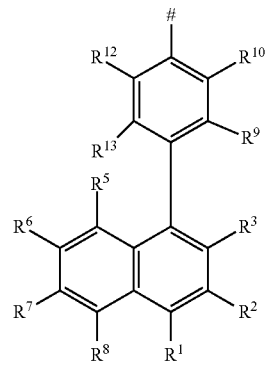
(AR-XXII)
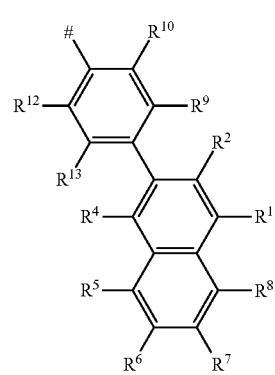
(AR-XXIII)
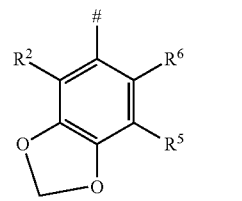
(AR-XXIV)
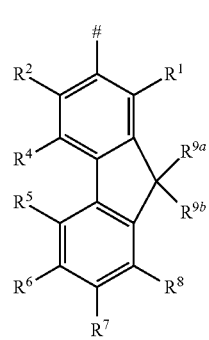
(AR-XXV)
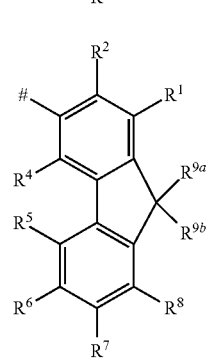
(AR-XXVI)

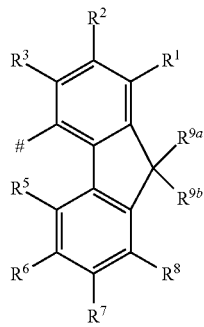
(AR-XXVII)
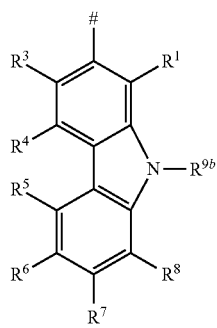
(AR-XXVIII)
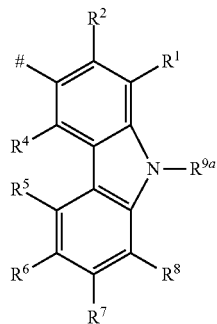
(AR-XXIX)
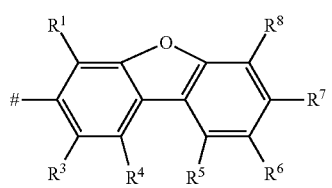
(AR-XXX)
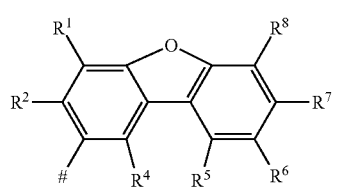
(AR-XXXI)
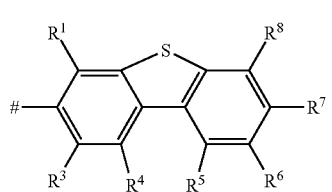
(AR-XXXII)
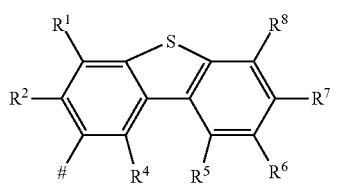
(AR-XXXIII)
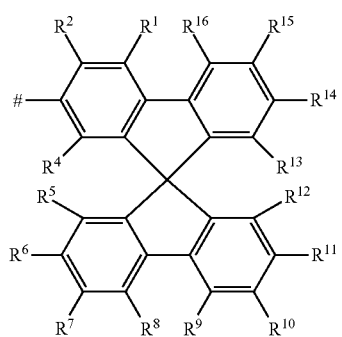
(AR-XXXIV)
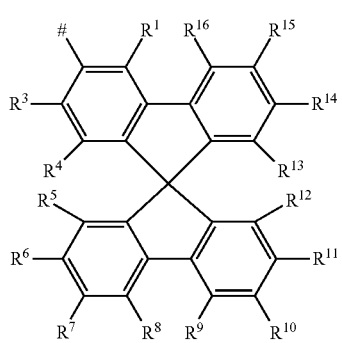
(AR-XXXV)
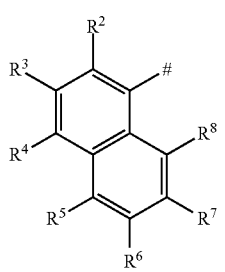
(AR-XXXVI)
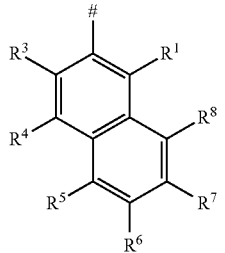
(AR-XXXVII)

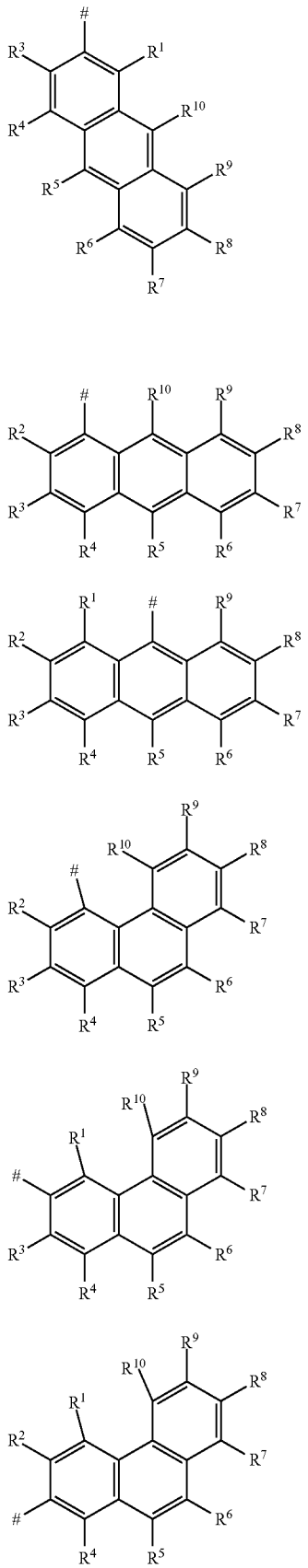

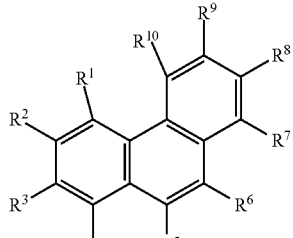

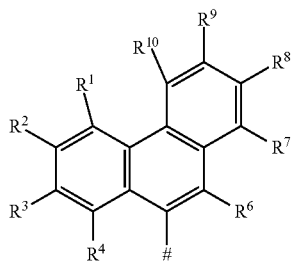

wherein
in each case denotes the bonding site to the nitrogen atom;

in formulae AR-I, AR-II, AR-III, AR-IV, AR-V, AR-VI, AR-VII, AR-VIII, AR-IX, AR-X, AR-XI, AR-XII, AR-XIII, AR-XIV, AR-XV, AR-XVI, AR-XVII, AR-XVIII, AR-XIX, AR-XX, AR-XXI, AR-XXII, AR-XXIII and Ar-XXIV:

$R^1, R^2, R^3, R^4, R^5, R^6, R^7, R^8, R^9, R^{10}, R^{11}, R^{12}, R^{13}, R^{14}, R^{15}, R^{16}, R^{17}, R^{18}$ and $R^{19}$, if present, independently of one another, are selected from hydrogen, straight-chain or branched $C_1$-$C_4$-alkyl, straight-chain or branched $C_1$-$C_4$-alkoxy and carbazol-9-yl, wherein carbazol-9-yl may be substituted by 1, 2, 3 or 4 different or identical substituents selected from $C_1$-$C_4$-alkyl, $C_1$-$C_4$-alkoxy, phenyl, tolyl, xylyl, mesityl and anisyl;

in formulae AR-XXV, AR-XXVI, AR-XXVII, AR-XXVIII, AR-XXIX, AR-XXX, AR-XXXI, AR-XXXII, AR-XXXIII, AR-XXXIV, AR-XXXV, AR-XXXVI, AR-XXXVII, AR-XXXVIII, AR-XXXIX, AR-XL, AR-XLI, AR-XLII, AR-XLIII, AR-XLIV and AR-XLV:

$R^1, R^2, R^3, R^4, R^5, R^6, R^7, R^8, R^9, R^{9a}, R^{9b}, R^{10}, R^{11}, R^{12}, R^{13}, R^{14}, R^{15}$ and $R^{16}$, if present, independently of one another, are selected from hydrogen, straight-chain or branched $C_1$-$C_4$-alkyl, straight-chain or branched $C_1$-$C_4$-alkoxy, carbazol-9-yl and phenyl, wherein carbazol-9-yl and phenyl are unsubstituted or substituted by 1, 2 or 3 different or identical substituents selected from $C_1$-$C_4$-alkyl, $C_1$-$C_4$-alkoxy, phenyl, tolyl, xylyl and mesityl and, in addition, $R^{9a}$ and $R^{9b}$ in formulae AR-XXV, AR-XXVI and AR-XXVII together may form an alkylene group $(CH_2)_r$ with r being 4, 5 or 6 where 1 or 2 hydrogen atoms in this group may be replaced by a methyl or methoxy group.

In formulae AR-I, AR-II, AR-III, AR-IV, AR-V, AR-VI, AR-VII, AR-VIII, AR-IX, AR-X, AR-XI, AR-XII, AR-XIII, AR-XIV, AR-XV, AR-XVI, AR-XVII, AR-XVIII, AR-XIX, AR-XX, AR-XXI, AR-XXII, AR-XXIII and Ar-XXIV, each radical $R^1, R^2, R^3, R^4, R^5, R^6, R^7, R^8, R^9, R^{10}, R^{11}, R^{12}, R^{13}, R^{14}, R^{15}, R^{16}, R^{17}, R^{18}$ and $R^{19}$, if present, is preferably selected from hydrogen, $C_1$-$C_2$-alkyl, $C_1$-$C_2$-alkoxy and carbazol-9-yl which may be substituted by 1 or 2 substituents selected from $C_1$-$C_2$-alkyl, $C_1$-$C_2$-alkoxy, phenyl, tolyl, xylyl, mesityl and anisyl. Especially, each radical $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$, if present, is selected from hydrogen, methyl, methoxy and carbazol-9-yl which is unsubstituted or substituted by 1 or 2 identical or different substituents selected from methyl, methoxy, phenyl, tolyl, xylyl, mesityl and anisyl.

In formulae AR-XXV, AR-XXVI, AR-XXVII, AR-XXVIII, AR-XXIX, AR-XXX, AR-XXXI, AR-XXXII, AR-XXXIII, AR-XXXIV, AR-XXXV, AR-XXXVI, AR-XXXVII, AR-XXXVIII, AR-XXXIX, AR-XL, AR-XLI, AR-XLII, AR-XLIII, AR-XLIV and Ar-XLV, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$, if present, is usually selected from hydrogen, $C_1$-$C_2$-alkyl, $C_1$-$C_2$-alkoxy and carbazol-9-yl which may be substituted by 1 or 2 substituents selected from $C_1$-$C_2$-alkyl, $C_1$-$C_2$-alkoxy, phenyl, tolyl, xylyl, mesityl and anisyl; $R^{9a}$ and $R^{9b}$, if present, are, independently of one another usually hydrogen, $C_1$-$C_2$-alkyl, phenyl or form together a group —$(CH_2)_4$— or —$(CH_2)_5$—. Especially, each radical $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$, if present, is selected from hydrogen, methyl, methoxy and carbazol-9-yl which may be substituted by 1 or 2 substituents selected from methyl, methoxy, phenyl, tolyl, xylyl, mesityl and anisyl. Especially, $R^{9a}$ and $R^{9b}$, if present, are independently of one another hydrogen, methyl, phenyl or form together a group —$(CH_2)_4$— or —$(CH_2)_5$—.

The groups Ar of the above-mentioned formulae (AR-I) to (AR-XLV) which are bonded to the nitrogen atom can be combined with one another as desired. The groups of the formulae (AR-I), (AR-II), (AR-III), (AR-IV), (AR-V), (AR-VI), (AR-VIII), (AR-IX), (AR-X), (AR-XIV), (Ar-XIX), (Ar-XX), (AR-XXIII), (AR-XXV), (Ar-XXVI), (AR-XXIX), (AR-XXX), (AR-XXXI), (AR-XXXII), (AR-XXXIII), (AR-XXXIV), (AR-XXXV), (AR-XXXVI) and (Ar-XXXVII) are particularly preferred here.

Particular examples of the group Ar include phenyl, 2-methylphenyl, 3-methylphenyl, 4-methylphenyl, 2,4-dimethylphenyl, 2,6-dimethylphenyl, 3,5-dimethylphenyl, 2,4,6-trimethylphenyl, 2-methoxyphenyl, 3-methoxyphenyl, 4-methoxyphenyl, 3,4-dimethoxyphenyl; 2-phenylphenyl, 3-phenylphenyl, 4-phenylphenyl, 4-(o-tolyl)phenyl, 4-(m-tolyl)phenyl, 4-(p-tolyl)phenyl, 4-(2,6-dimethylphenyl)phenyl, 1-methyl-4-phenyl-phenyl, 2-methyl-4-phenyl-phenyl, 3-methyl-4-phenyl-phenyl, 2,6-dimethyl-4-phenyl-phenyl, 3-methyl-4-(o-tolyl)phenyl, 3-methyl-4-(m-tolyl)phenyl, 3-methyl-4-(p-tolyl)phenyl, 3-methyl-4-(2,4,6-trimethylphenyl)phenyl, 3-methyl-4-(2,4-dimethylphenyl)phenyl, 3-methyl-4-(2,6-dimethylphenyl)phenyl, 4-(4-methoxyphenyl)phenyl, 4-methoxy-3-phenyl-phenyl, 3-methoxy-4-phenyl-phenyl, 2-methoxy-5-phenyl-phenyl, 2-methoxy-4,5-diphenyl-phenyl, 3,4-diphenylphenyl, 3,5-diphenylphenyl, 3-(4-phenylphenyl)phenyl, 4-(4-phenylphenyl)phenyl, 1,3-benzodioxol-5-yl, 3-(3,5-diphenylphenyl)phenyl, 4-diphenylaminophenyl, 1-naphthyl, 2-naphthyl, 1-phenanthryl, 2-phenanthryl, 3-phenanthryl, 4-phenanthryl, 9-phenanthryl, 9,9-dimethylfluoren-2-yl, 9-methyl-9-phenyl-fluoren-2-yl, 9,9-diphenylfluoren-2-yl, 9,9-dimethylfluoren-3-yl, 9-methyl-9-phenyl-fluoren-3-yl, 9,9-diphenylfluoren-3-yl, 9,9-dimethylfluoren-4-yl, 9-methyl-9-phenyl-fluoren-4-yl, 9,9-diphenylfluoren-4-yl, dibenzofuran-2-yl, dibenzofuran-3-yl, dibenzothiophen-2-yl, dibenzothiophen-3-yl, 9-methylcarbazol-2-yl, 9-phenylcarbazol-2-yl, 9-methylcarbazol-3-yl, 9-phenylcarbazol-3-yl, 4-(1-naphthyl)phenyl, 4-(2-naphthyl) phenyl, 4-(carbazol-9-yl)-phenyl, 4-(3,6-dimethoxycarbazol-9-yl) phenyl, 4-(3,6-dimethylcarbazol-9-yl)phenyl, 9,9'-spirobi (fluorene)-2-yl

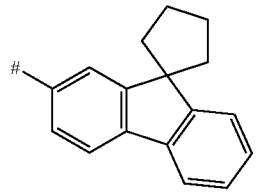

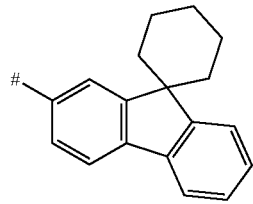

wherein # denotes the bonding site to the nitrogen atom.

Likewise preferably, 2 groups Ar together with the nitrogen atom to which they are attached form a N-bound carbazolyl, which is unsubstituted or substituted by one or more, e.g. one, two, three, four or more than four substituents $R^{Ar3}$, wherein $R^{Ar3}$ is as defined above. In particular, irrespectively of its occurrence, $R^{Ar3}$ is phenyl, 2-methylphenyl, 3-methylphenyl, 4-methylphenyl. Particular examples include carbazol-9-yl, 3-phenylcarbazol-9-yl, 3-(o-tolyl)carbazol-9-yl, 3-(m-tolyl)carbazol-9-yl, 3-(p-tolyl)carbazol-9-yl, 3-(o-anisyl)carbazol-9-yl, 3-(m-anisyl) carbazol-9-yl, 3-(p-anisyl)carbazol-9-yl, 3,6-diphenylcarbazol-9-yl, 3,6-bis(o-tolyl)carbazol-9-yl, 3,6-bis(m-tolyl) carbazoly-9-yl, 3,6-bis(p-tolyl)carbazol-9-yl, 3,6-bis(o-anisyl)carbazol-9-yl, 3,6-bis(m-anisyl)carbazoly-9-yl, 3,6-bis(p-anisyl)carbazol-9-yl, 3,6-dimethylcarbazol-9-yl and 3,6-dimethoxycarbazol-9-yl.

In particular, the group —$NAr_2$, irrespectively of its occurrence is selected from the formulae (A-1) to (A-97) listed in table A below.

TABLE A

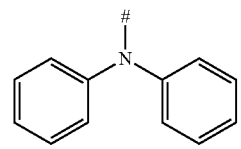

A-1

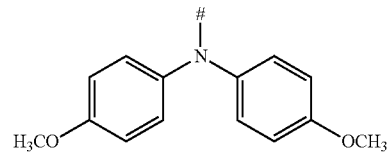

A-2

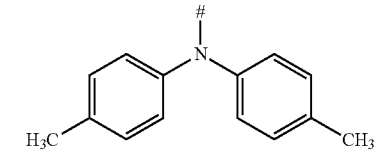

A-3

TABLE A-continued
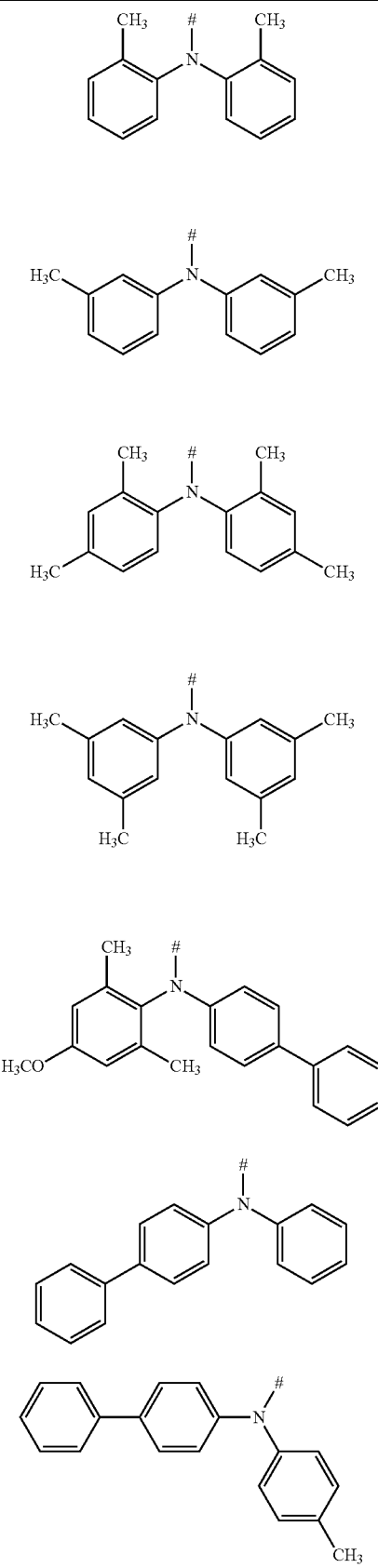
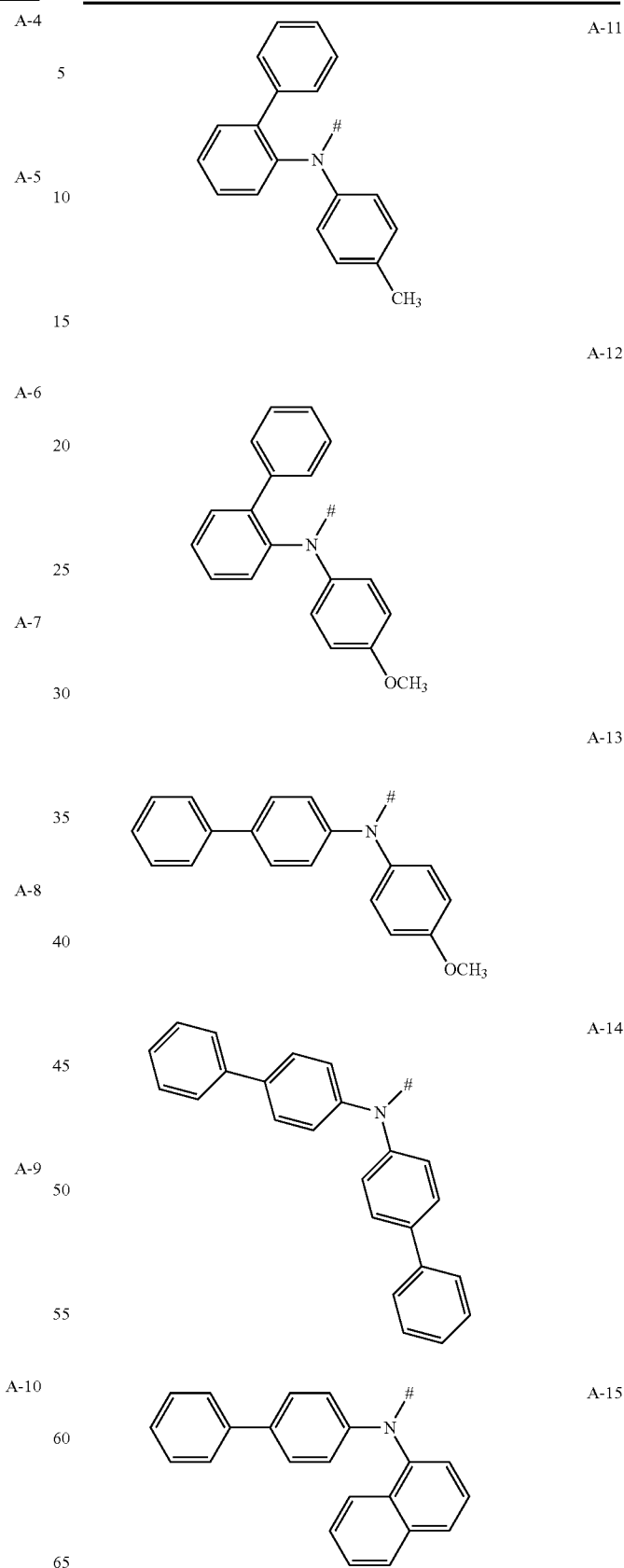

TABLE A-continued
A-16
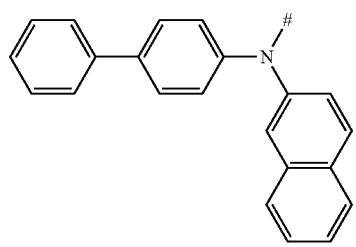
A-17
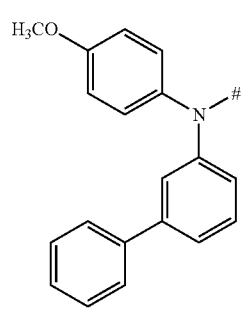
A-18
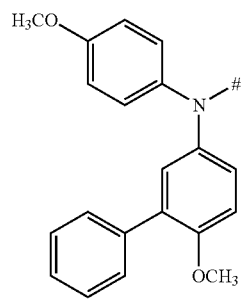
A-19
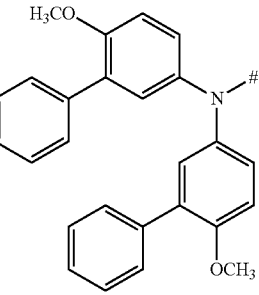
A-20
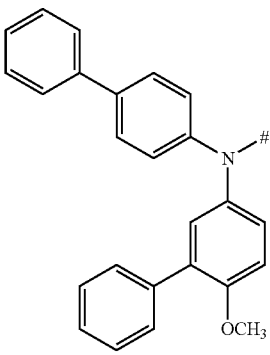
TABLE A-continued
A-21
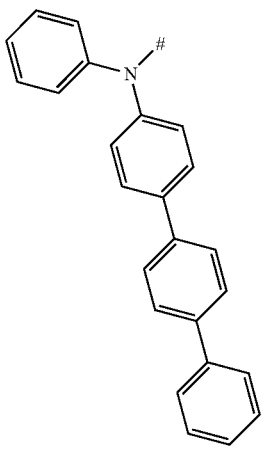
A-22
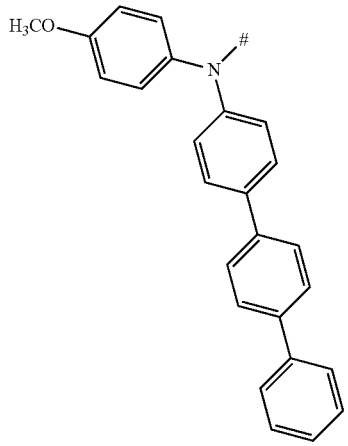
A-23
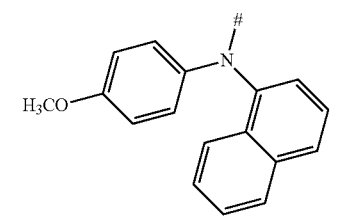
A-24
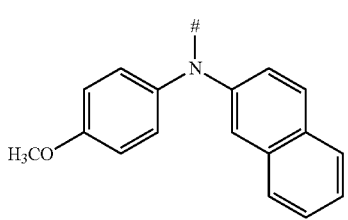
A-25
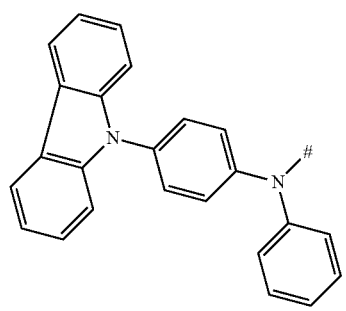

TABLE A-continued
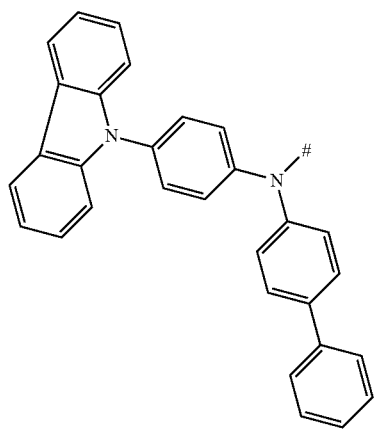
A-26
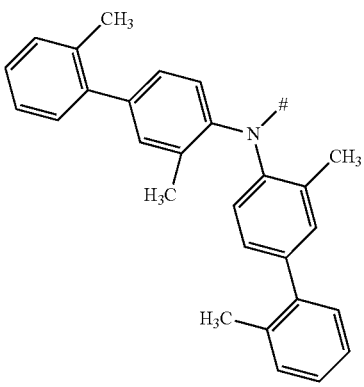
A-29
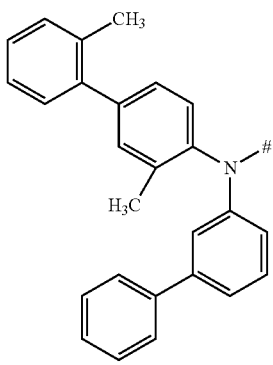
A-30
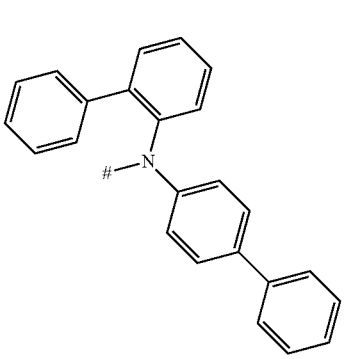
A-27
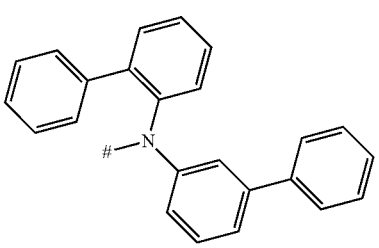
A-31
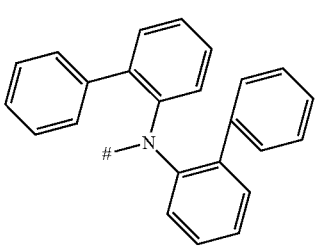
A-32
A-28
A-33

TABLE A-continued
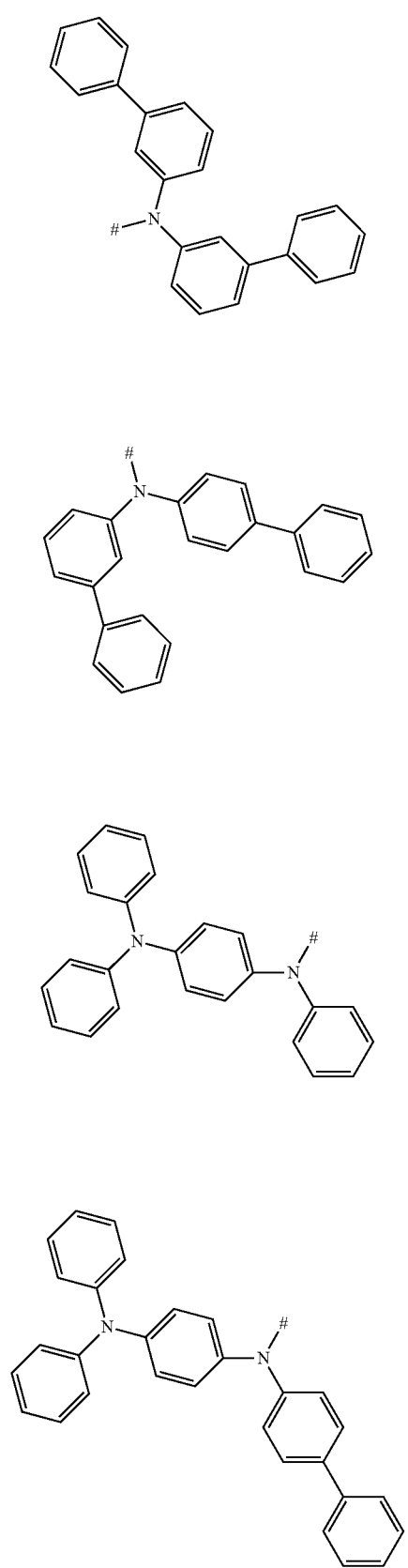
A-34
A-35
A-36
A-37
TABLE A-continued
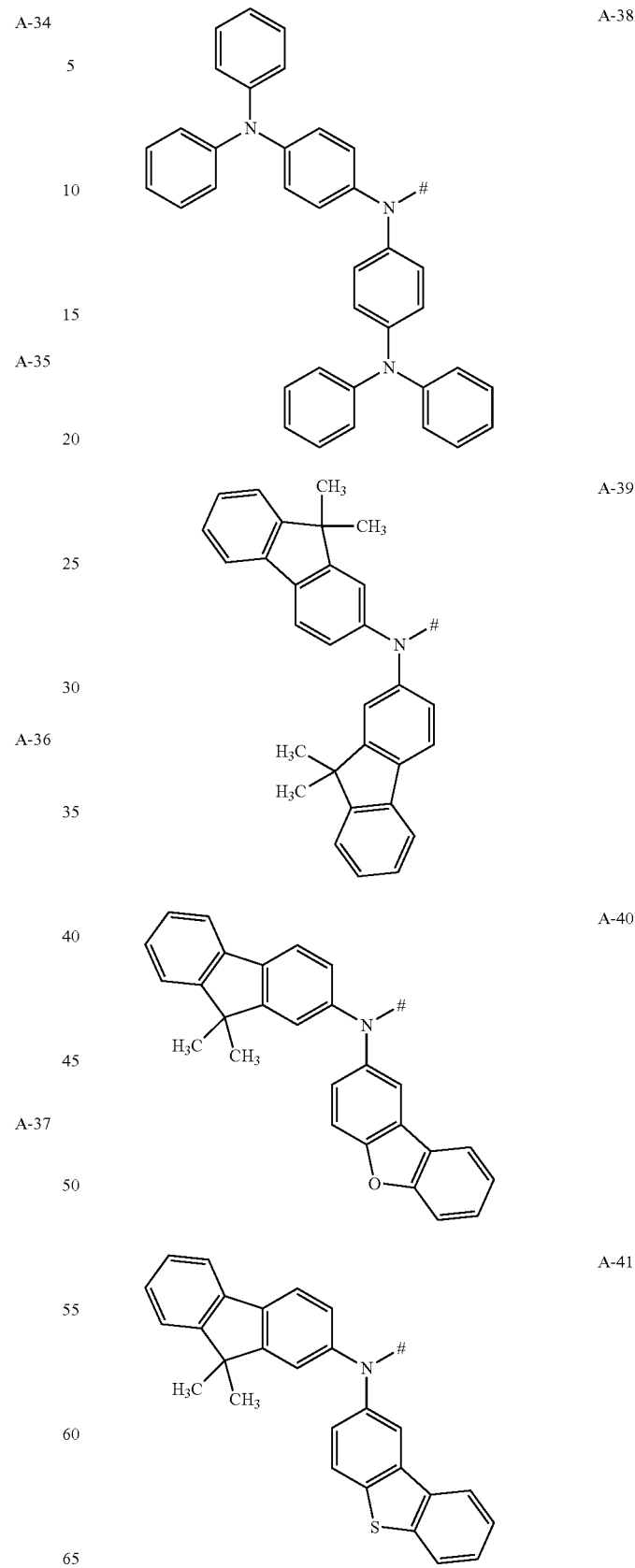
A-38
A-39
A-40
A-41

TABLE A-continued
A-42
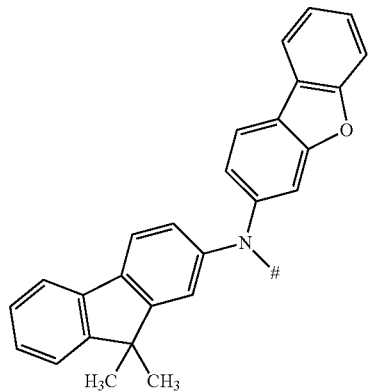
A-43
A-44
A-45
A-46
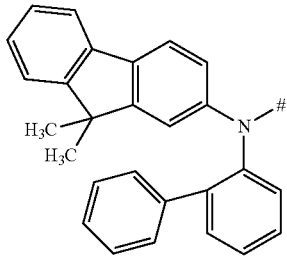
A-47
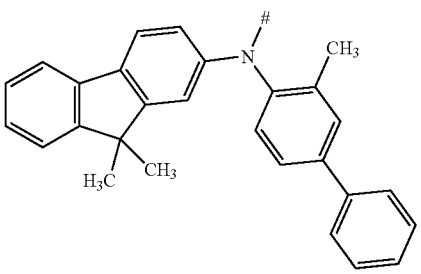
A-48
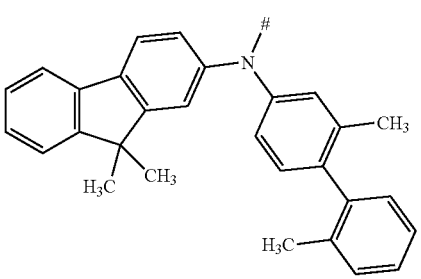
A-49
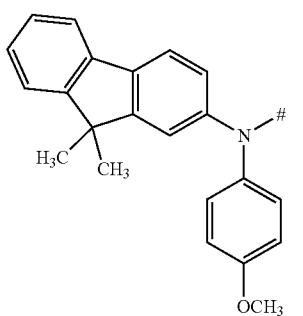
A-50
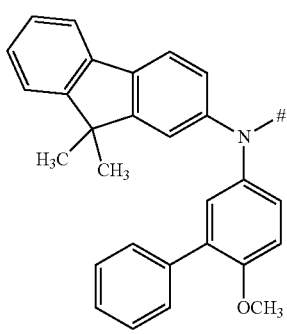

TABLE A-continued
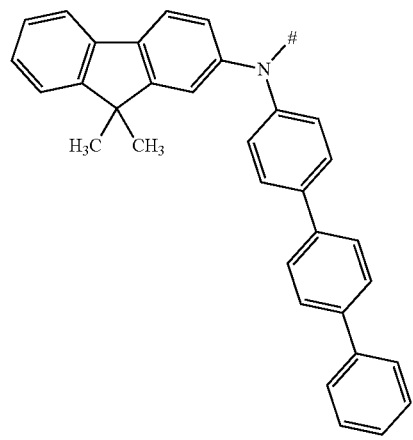
A-51
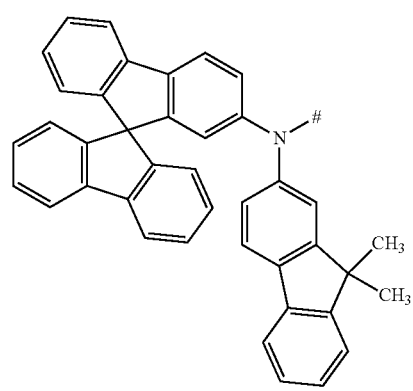
A-52
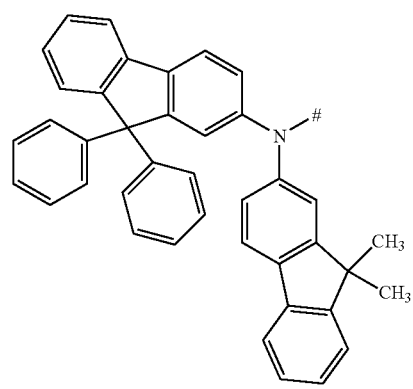
A-53
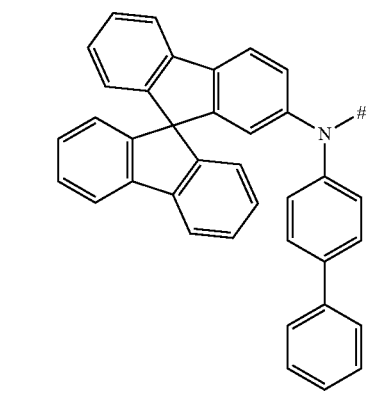
A-54
TABLE A-continued
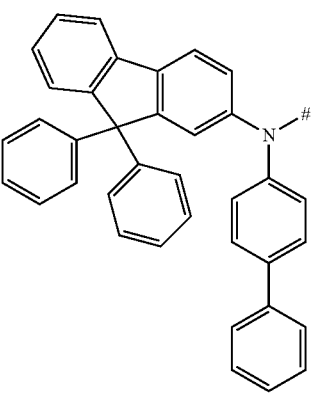
A-55
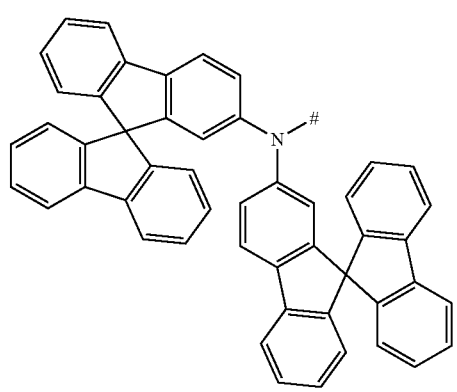
A-56
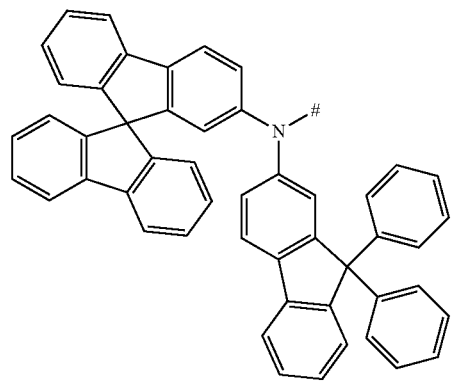
A-57
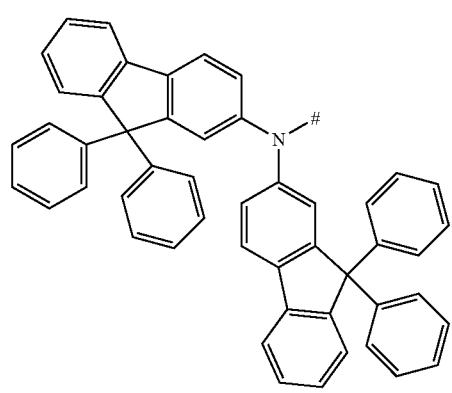
A-58

TABLE A-continued
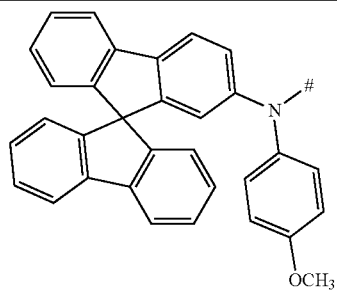
A-59
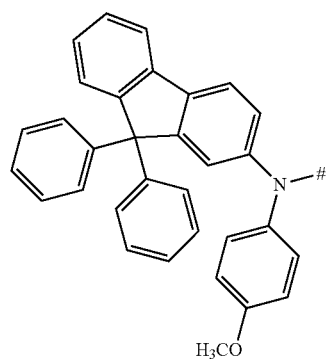
A-60
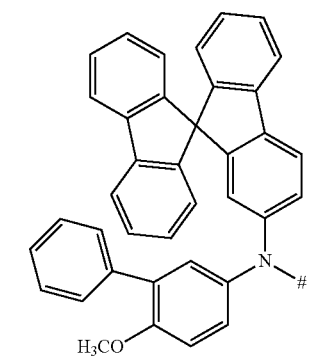
A-61
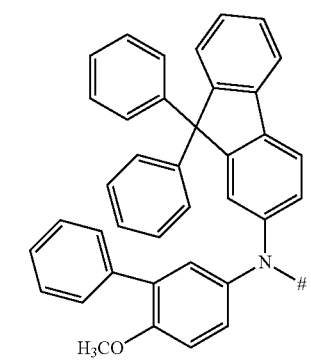
A-62
TABLE A-continued
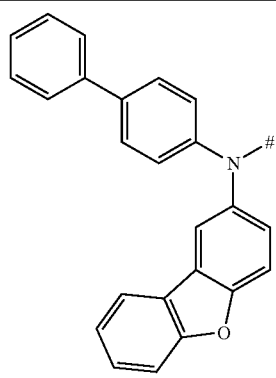
A-63
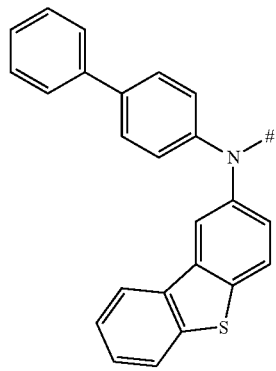
A-64
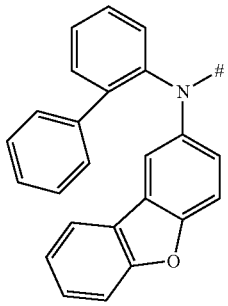
A-65
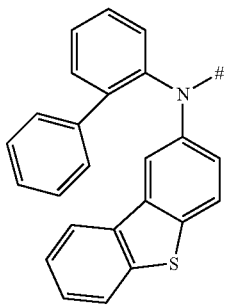
A-66

TABLE A-continued
A-67
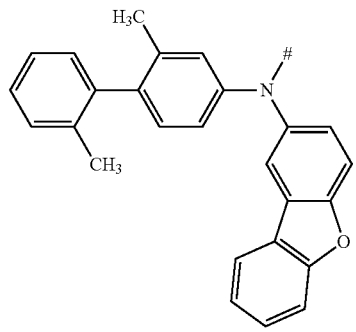
A-68
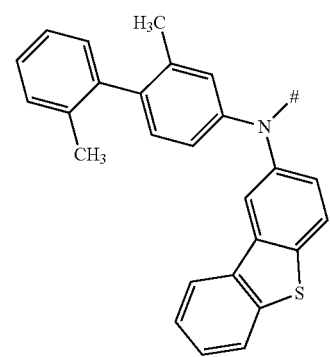
A-69
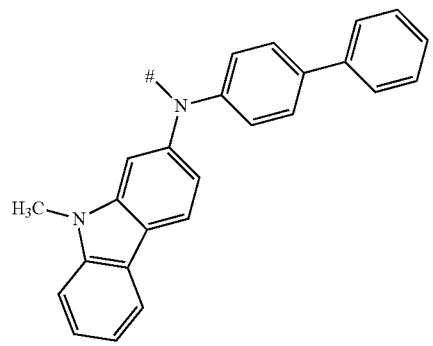
A-70
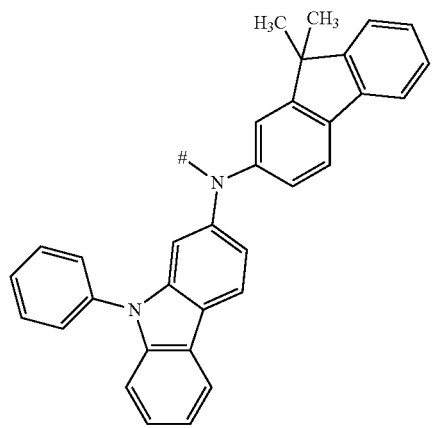
TABLE A-continued
A-71
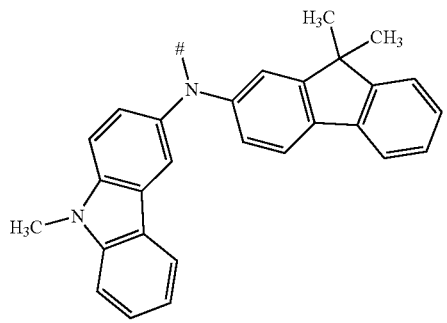
A-72
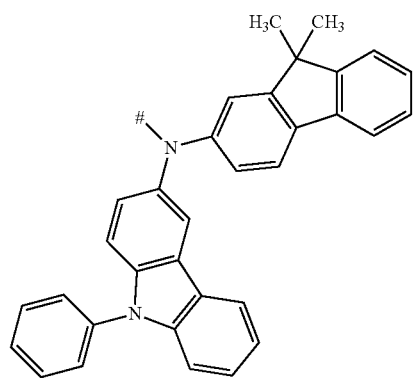
A-73
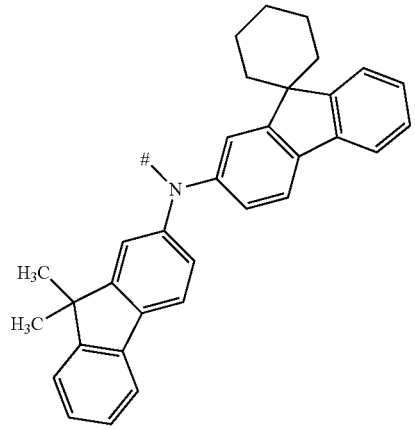
A-74
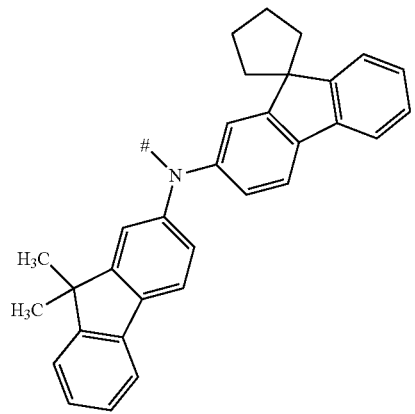

TABLE A-continued
A-75
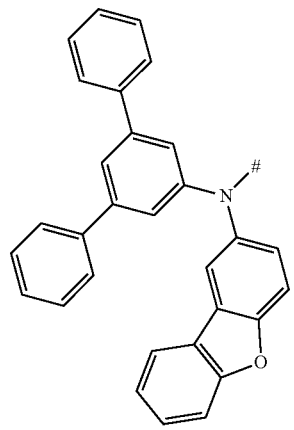
A-76
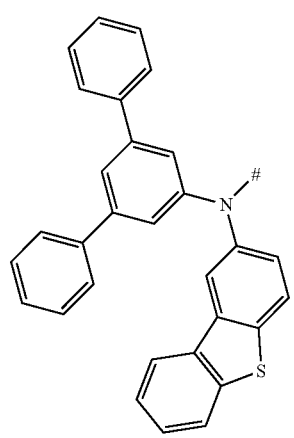
A-77
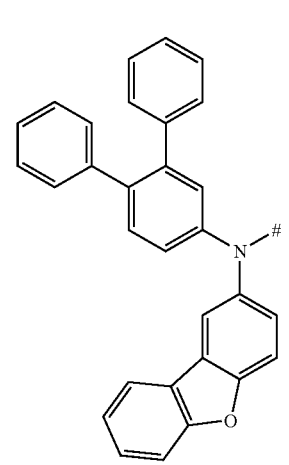
TABLE A-continued
A-78
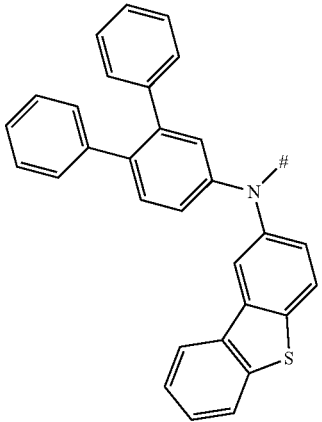
A-79
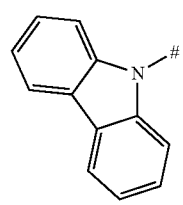
A-80
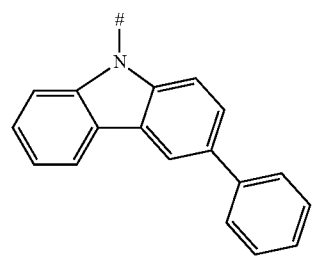
A-81
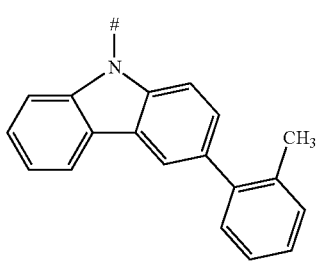
A-82
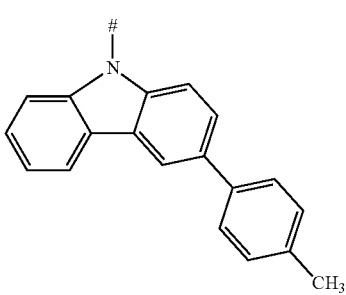

TABLE A-continued
A-83 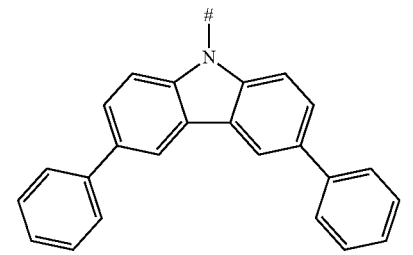
A-84 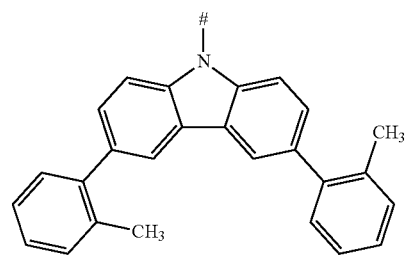
A-85 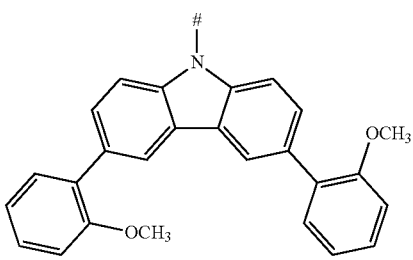
A-86 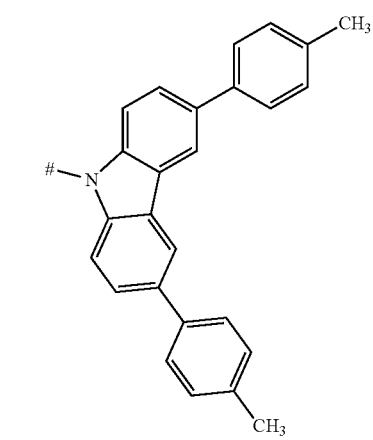
A-87 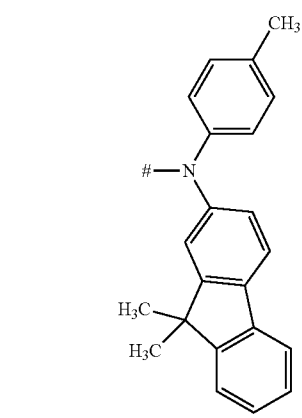
TABLE A-continued
A-88 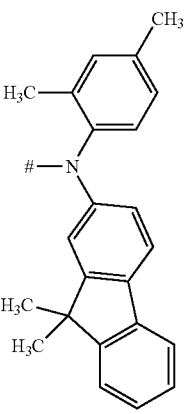
A-89 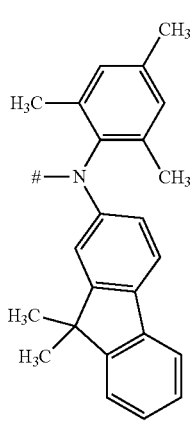
A-90 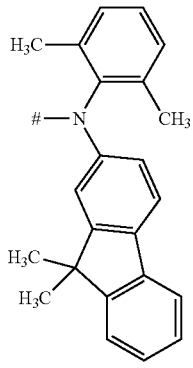
A-91 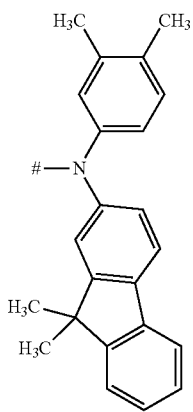

TABLE A-continued
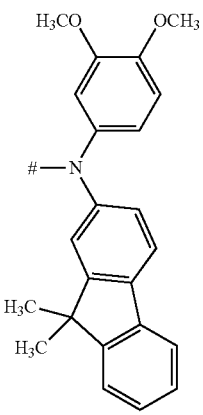
A-92
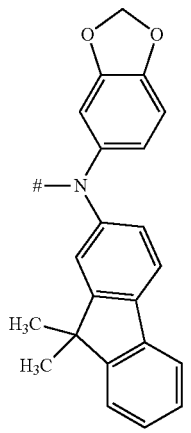
A-93
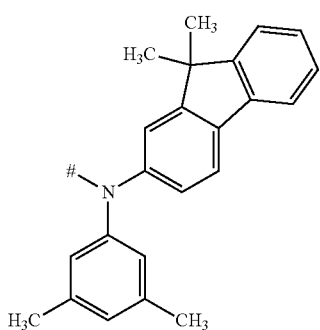
A-94
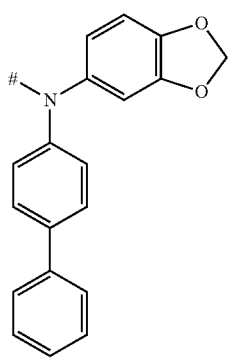
A-95
TABLE A-continued
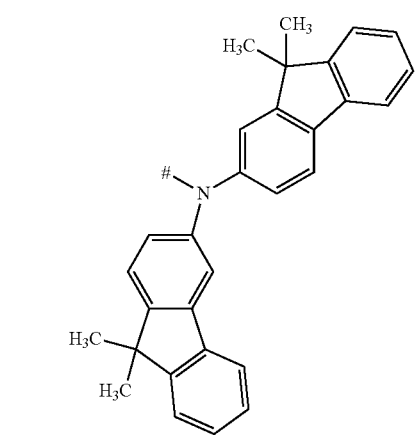
A-96
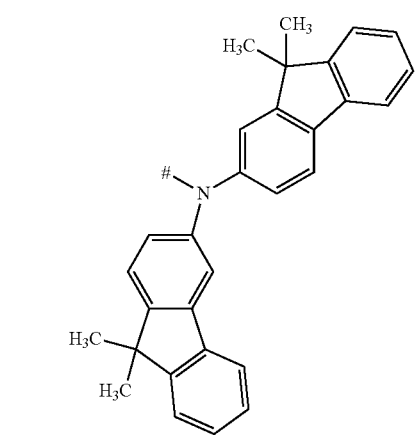
A-97
# denotes the bonding site to the remainder of the molecule.
Especially, the group —NAr$_2$, irrespectively of its occurrence, is selected from the groups of the formulae (1) to (51)
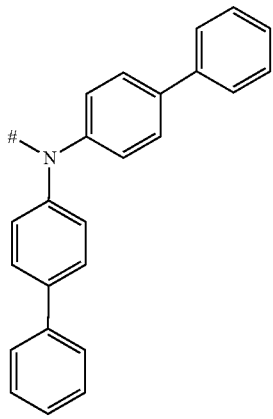
(1)
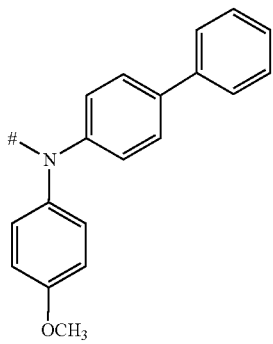
(2)

-continued
(3)
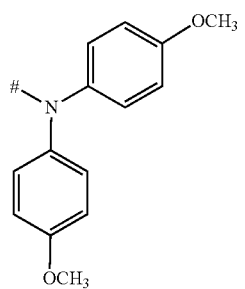
(4)
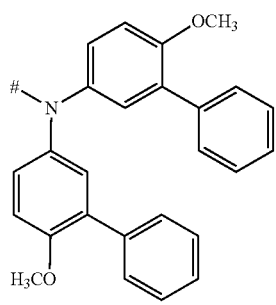
(5)
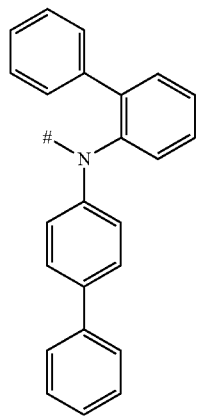
(6)
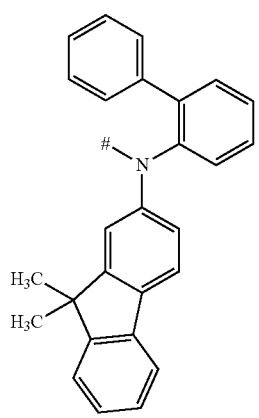
-continued
(7)
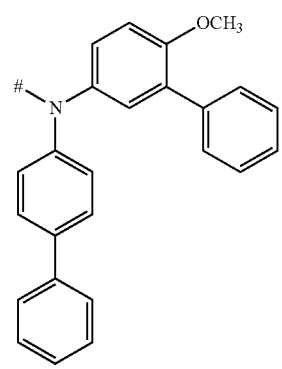
(8)
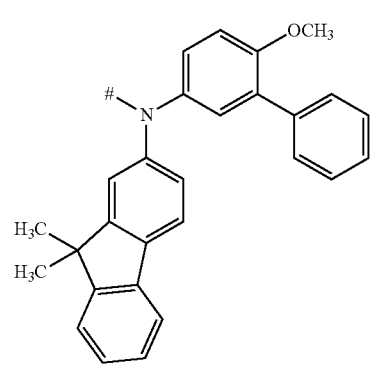
(9)
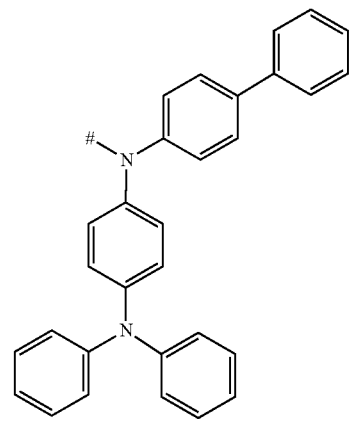
(10)
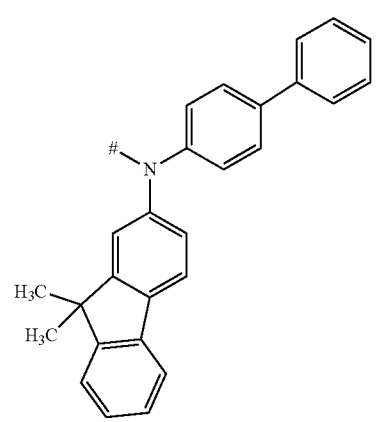

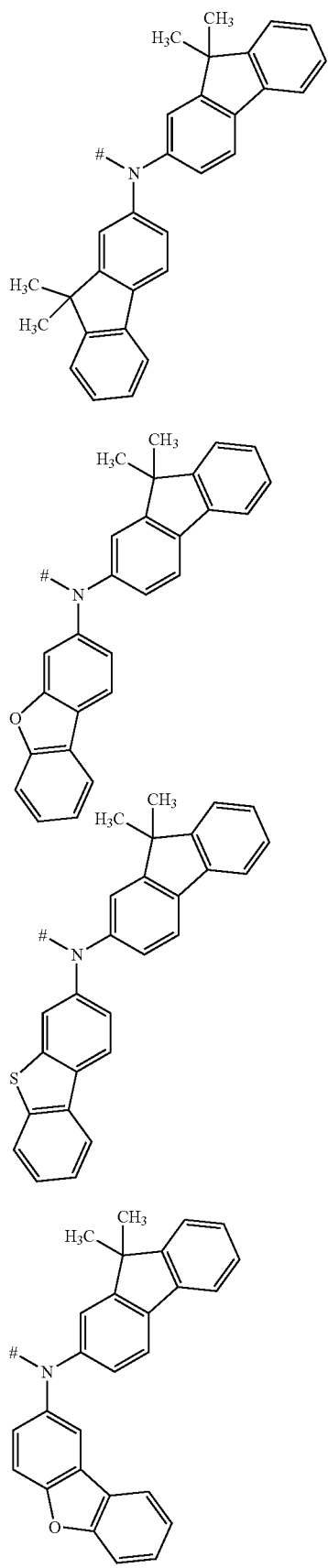
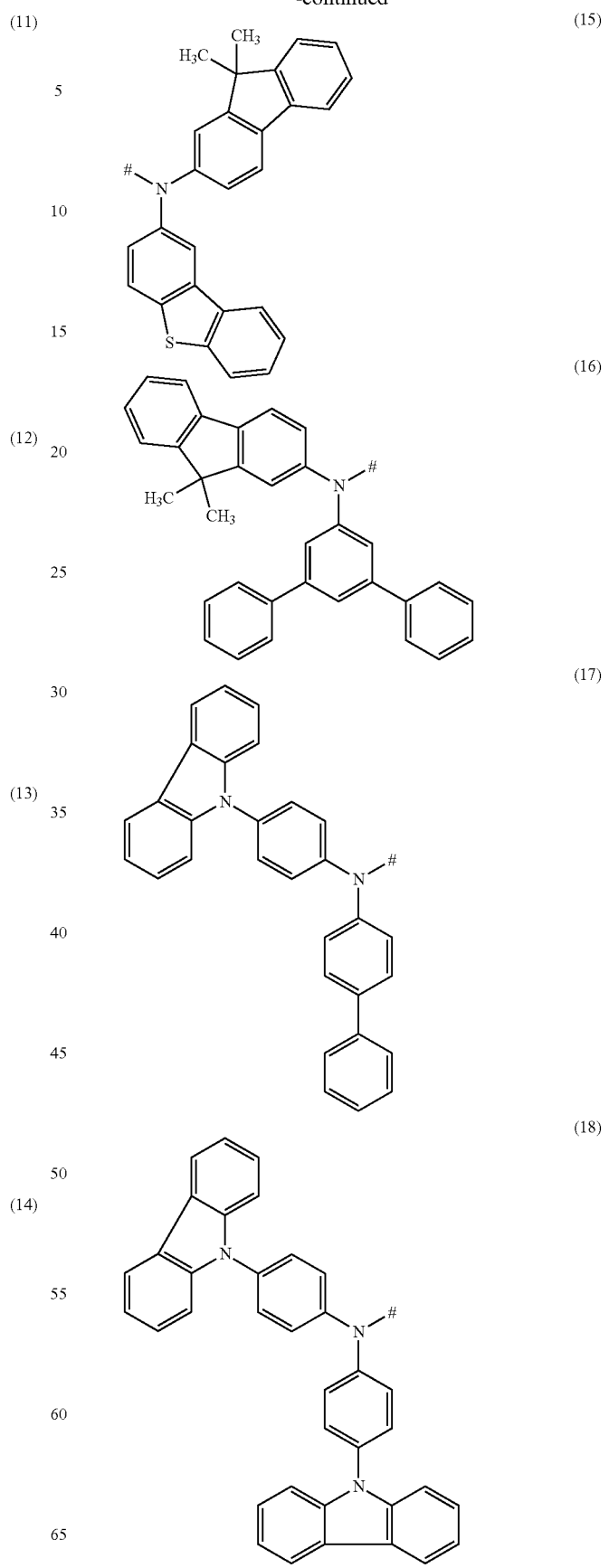

(19)
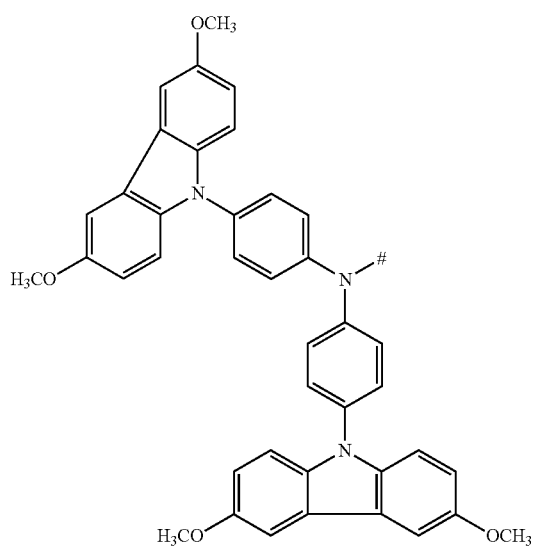
(20)
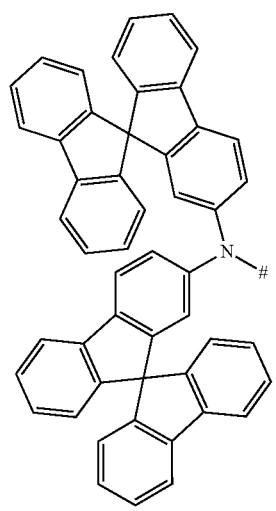
(21)
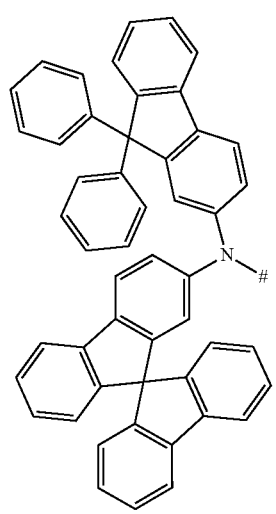
(22)
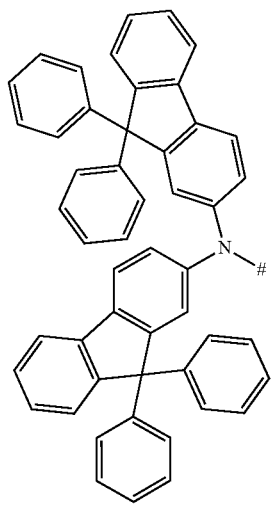
(23)
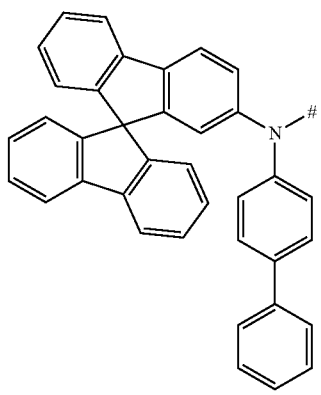
(24)
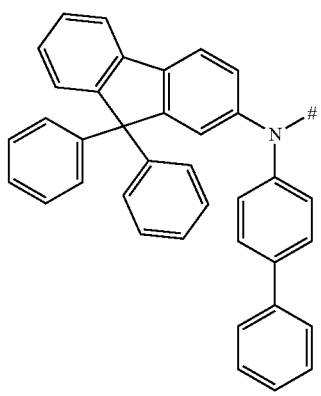

(25) 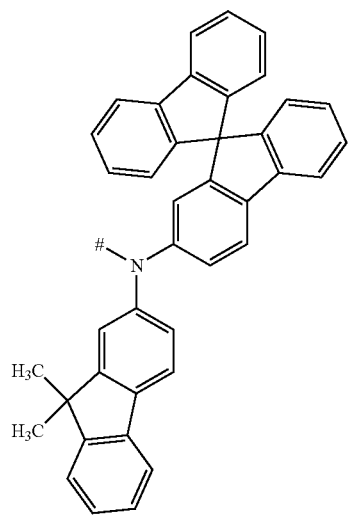
(26) 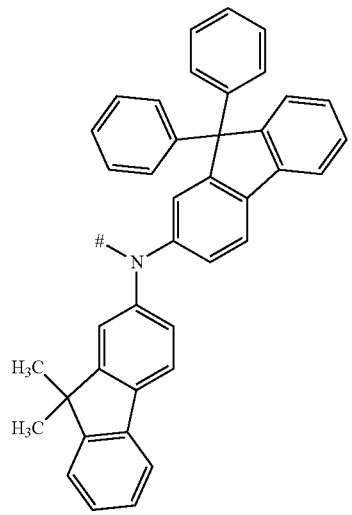
(27) 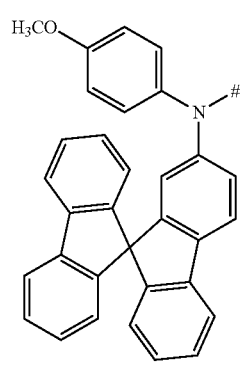
(28) 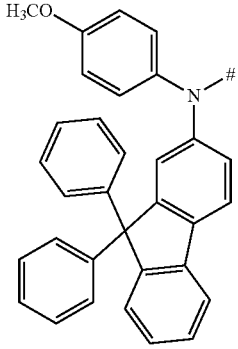
(29) 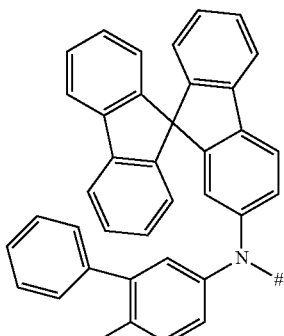
(30) 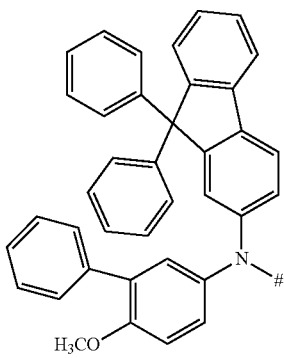
(31) 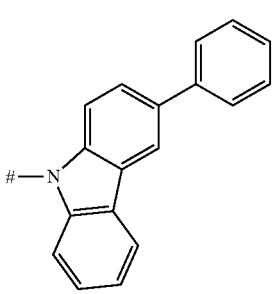
(32)

(33) 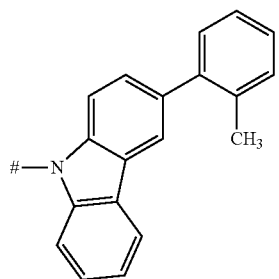
(34) 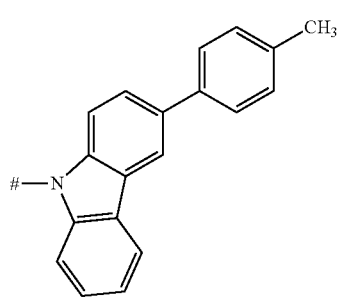
(35) 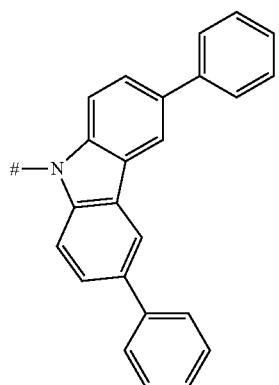
(36) 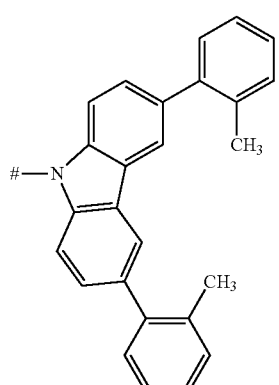
(37) 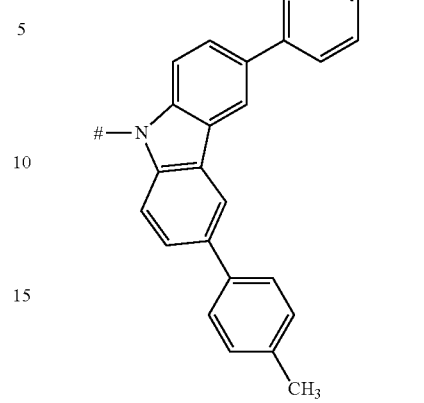
(38) 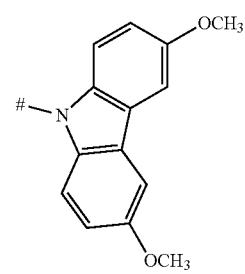
(39) 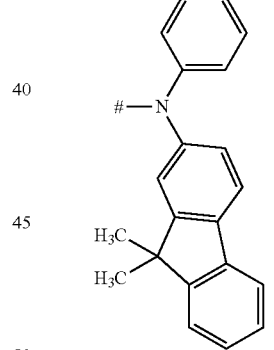
(40)

(41)
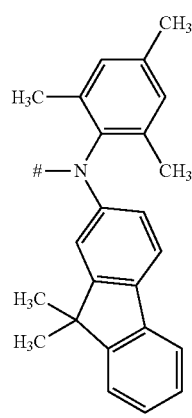
(42)
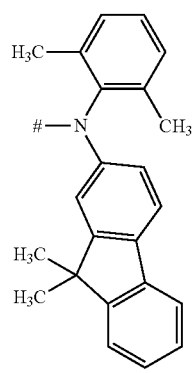
(43)
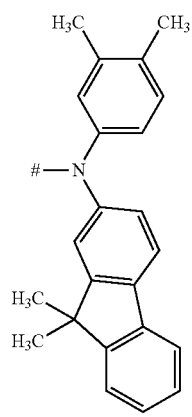
(44)
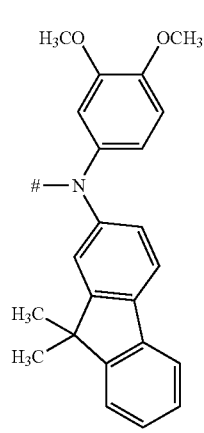
(45)
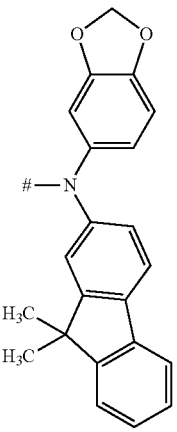
(46)
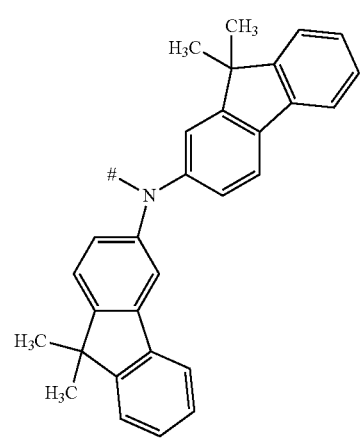
(47)
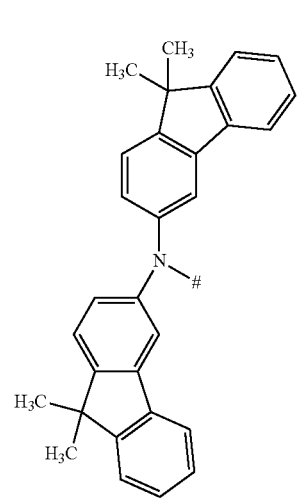

-continued

(48)
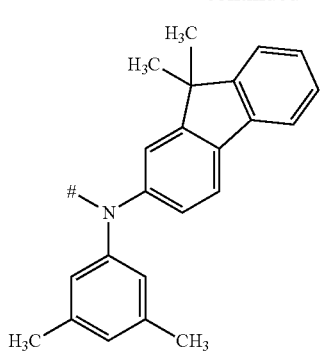

(49)
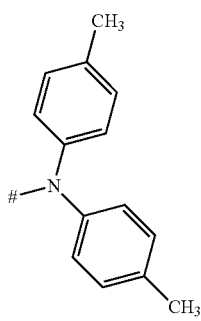

(50)
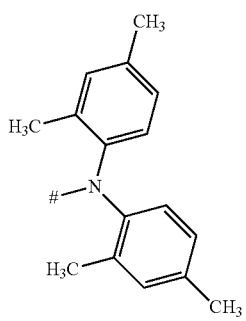

(51)
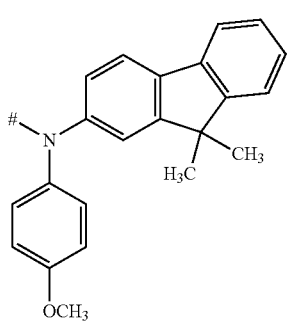

wherein
# denotes the bonding side to the remainder of the compound.

Preference is given to the compounds of formulae (I), (I.DP-MA-1), (I.DP-MA-2), (I.DP-DA-1), (I.DP-DA-2), (I.DP-DA-3), (I.DP-TRA-1), (I.DP-TEA-1), (I.TRP-MA-1), (I.TRP-MA-2), (I.TRP-MA-3), (I.TRP-DA-1), (I.TRP-DA-2), (I.TRP-DA-3), (I.TRP-DA-4), (I.TRP-DA-5), (I.TRP-TRA-1), (I.TRP-TEA-1), (I.TRP-TEA-2), (I.TRP-TEA-3), (I.TEP-MA-1), (I.TEP-MA-2), (I.TEP-DA-1), (I.TEP-DA-2), (I.TEP-DA-3), (I.TEP-DA-4), wherein all groups (NAr$_2$) have the same meaning and each of the two groups Ar bound to the same nitrogen atom have different meanings.

Likewise preference is given to the compounds of formulae (I), (I.DP-MA-1), (I.DP-MA-2), (I.DP-DA-1), (I.DP-DA-2), (I.DP-DA-3), (I.DP-TRA-1), (I.DP-TEA-1), (I.TRP-MA-1), (I.TRP-MA-2), (I.TRP-MA-3), (I.TRP-DA-1), (I.TRP-DA-2), (I.TRP-DA-3), (I.TRP-DA-4), (I.TRP-DA-5), (I.TRP.TRA-1) (I.TRP-TEA-1), (I.TRP-TEA-2), (I.TRP-TEA-3), (I.TEP-MA-1), (I.TEP-MA-2), (I.TEP-DA-1), (I.TEP-DA-2), (I.TEP-DA-3), (I.TEP-DA-4), wherein all groups Ar have the same meaning.

Examples of preferred compounds are the compounds of the formulae (I.DP-MA-1-1), (I.DP-MA-2-1), (I.DP-DA-1-1), (I.DP-DA-2-1), (I.DP-DA-3-1), (I.DP-TRA-1-1), (I.DP-TEA-1-1), (I.TRP-MA-1-1), (I.TRP-MA-2-1), (I.TRP-MA-3-1), (I.TRP-DA-1-1), (I.TRP-DA-2-1), (I.TRP-DA-3-1), (I.TRP-DA-4-1), (I.TRP-DA-5-1), (I.TRP.TRA-1-1) (I.TRP-TEA-1-1), (I.TRP-TEA-2-1), (I.TRP-TEA-3-1), (I.TEP-MA-1-1), (I.TEP-MA-2-1), (I.TEP-DA-1-1), (I.TEP-DA-2-1), (I.TEP-DA-3-1) and (I.TEP-DA-4-1), (I.DP-MA-1-1)
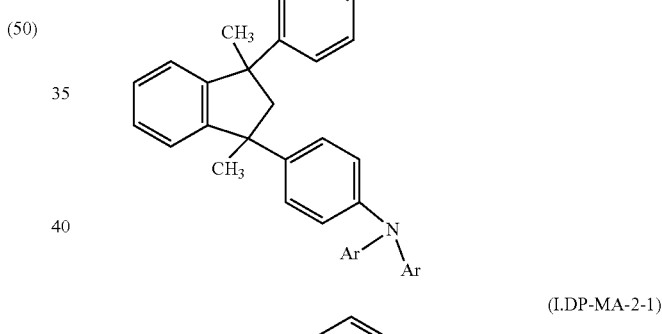

(I.DP-MA-2-1)
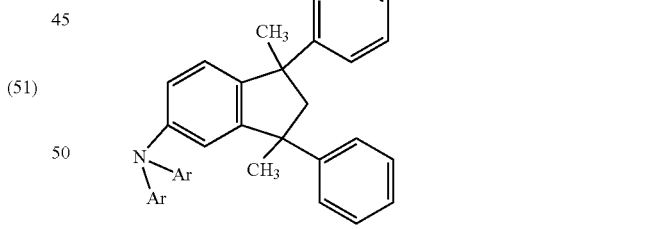

(I.TRP-MA-1-1)
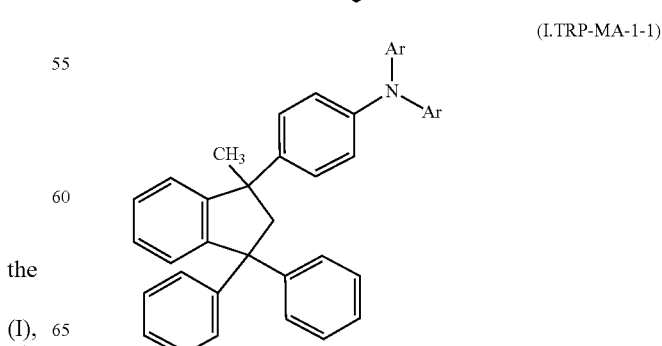

(I.TRP-MA-2-1)
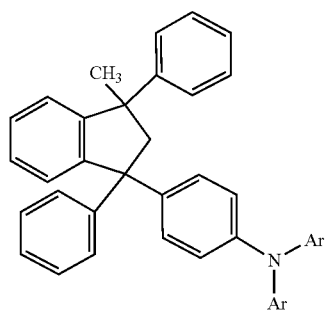
(I.TRP-MA-3-1)
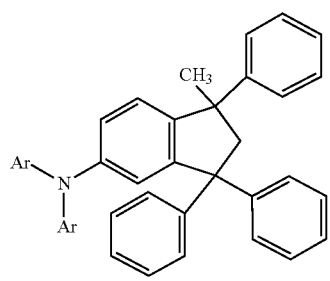
(I.TEP-MA-1-1)
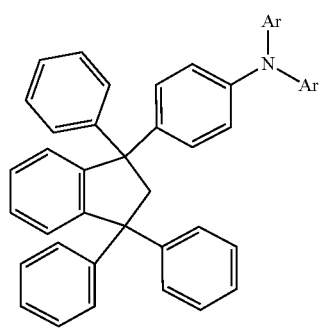
(I.TEP-MA-2-1)
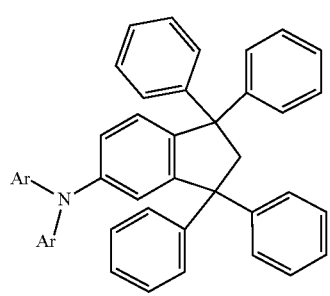
(I.DP-DA-1-1)
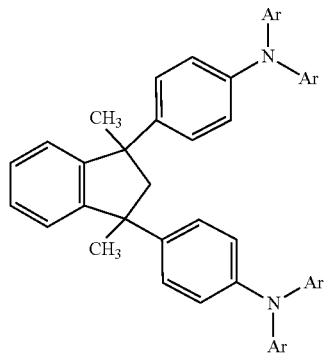
(I.DP-DA-2-1)
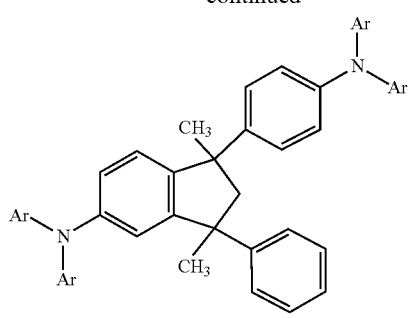
(I.DP-DA-3-1)
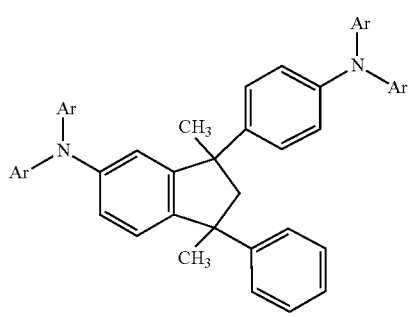
(I.TRP-DA-1-1)
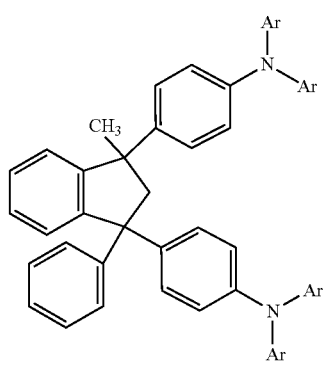
(I.TRP-DA-2-1)
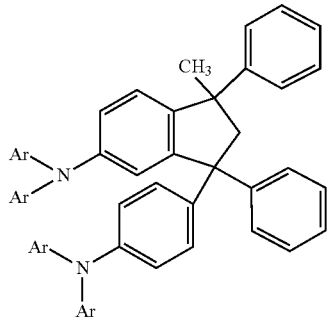

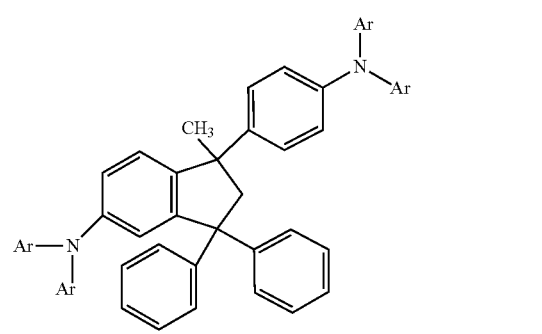
(I.TRP-DA-3-1)
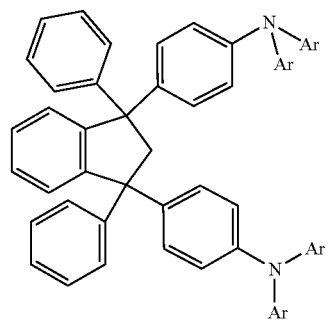
(I.TEP-DA-2-1)
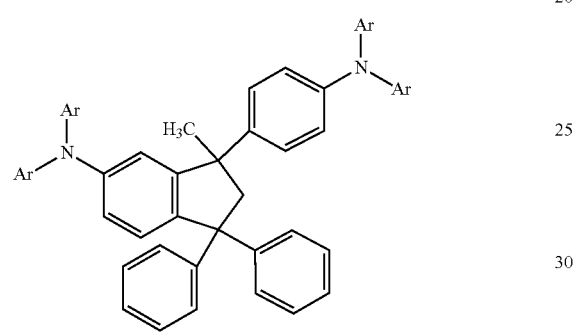
(I.TRP-DA-4-1)
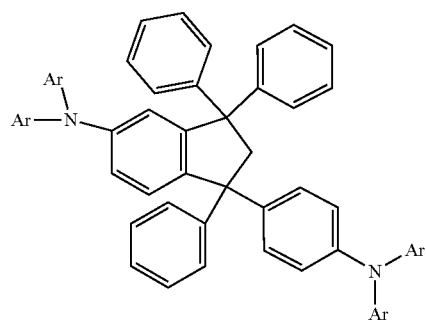
(I.TEP-DA-3-1)
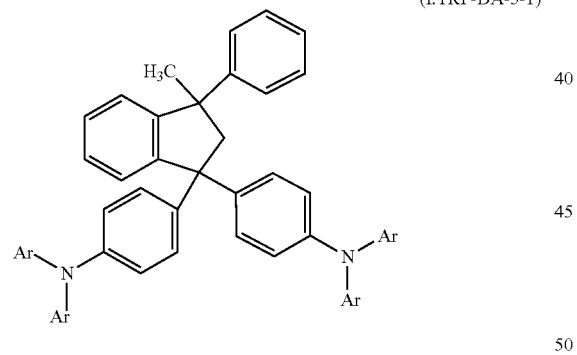
(I.TRP-DA-5-1)
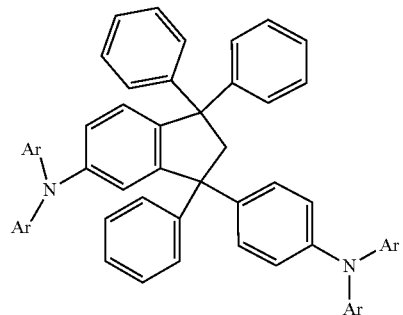
(I.TEP-DA-4-1)
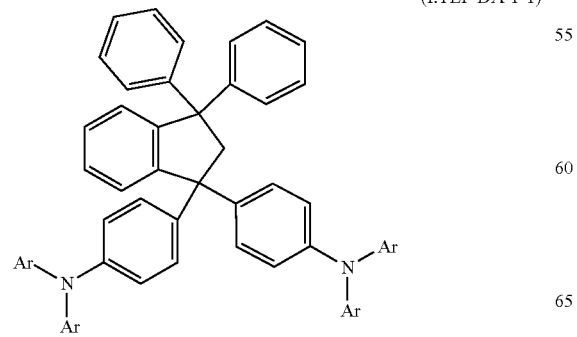
(I.TEP-DA-1-1)
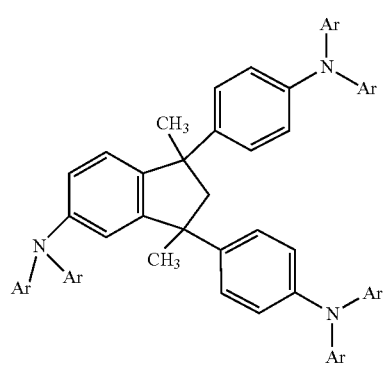
(I.DP-TRA-1-1)

(I.TRP-TRA-1-1)

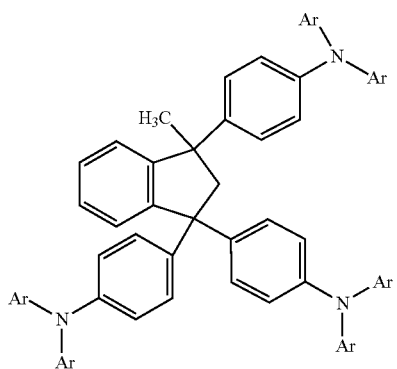

(I.DP-TEA-1-1)

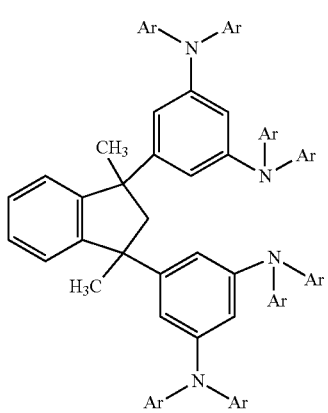

(I.TRP-TEA-1-1)

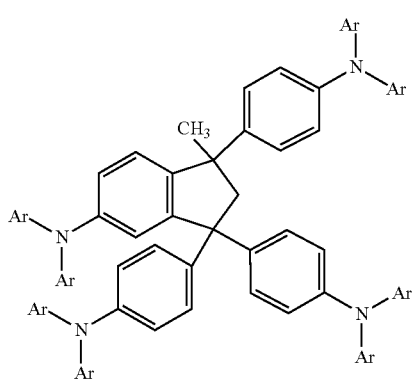

(I.TRP-TEA-2-1)

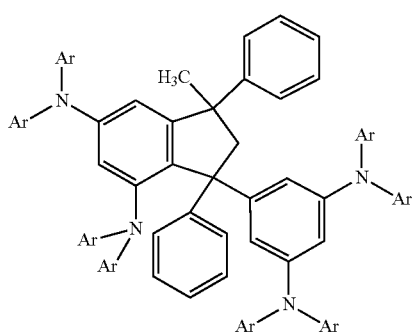

(I.TRP-TEA-3-1)

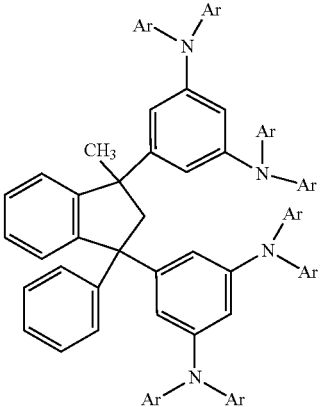

wherein each group (—NAr₂), irrespectively of its occurrence, is selected from the groups of the formulae (A-1) to (A-97) listed in Table A, especially from the groups of the formulae (1) to (51). Among these, more preference is given to the compounds of formulae (I.DP-MA-1-1); (I.TRP-MA-1-1); (I.TRP-MA-2-1); (I.DP-DA-1-1); (I.DP-DA-2-1); (I.DP-DA-3-1); (I.TRP-DA-1-1); (I.TRP-DA-3-1); (I.TRP-DA-4-1); (I.TRP-DA-5-1); I.TRP-TRA-1-1); (I.DP-TEA-1-1), (I.TRP-TEA-1-1) and (I.TRP-TA-3-1).

In a specific embodiment, the compounds of the formula (I) are selected from the compounds specified in the examples.

The compounds of the invention of the formula (I) and the starting materials used to prepare them can be prepared in analogy to known processes of organic chemistry as described in literature. The compounds of the formula (I) may be prepared by various routes.

The compounds of formula (I) can advantageously be prepared by the methods described below or and in the synthesis descriptions of the working examples, or by standard methods of organic chemistry. The substituents, variables and indices are as defined above for formula (I), if not otherwise specified.

The present invention provides processes for preparing compounds of formula (I) wherein X is —N—Ar₂ employing compounds of formula (I) wherein X is —NH₂. Depending on the substitution pattern, the compounds of the formula (I), wherein X is —NH₂ are in the following also referred to as compounds of formulae (V), (Va), (Vb), (Vc), (Vd), (Ve), (Vf), (Vg) and (Vh), respectively.

Compounds of the formula (I) can be obtained via the dityl (diphenylmethyl)/trityl (triphenylmethyl) route or via the dimerization route of an alpha olefin as described hereinbelow. Compounds of formula (I.DP) can also be obtained via the Grignard route as described hereinbelow.

Thus, a further aspect of the present invention relates to a process for the preparation of a compound of the formula (I), referred to as compound of the formula (I-MA-1)

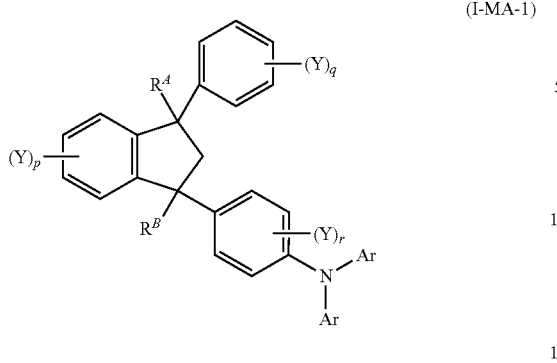

(I-MA-1)

wherein
each Ar is independently defined as above;
each Y is independently as defined above;
$R^A$ and $R^B$ are as defined above;
p is 4, wherein 0, 1, 2, 3 or 4 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
comprising the steps
a1) reacting an ethene compound of the formula (II) with a compound of the formula (III) or a salt thereof

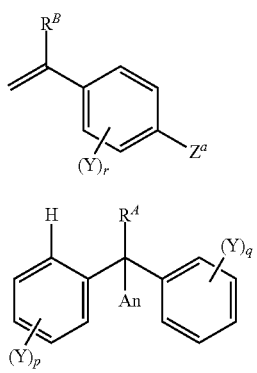

(II)

(III)

in which
An is Cl or Br; and
$Z^a$ is F, Cl, Br, I, $CH_3SO_3$, $CF_3SO_3$, $CH_3$-$C_6H_4$—$SO_3$, $C_6H_5$—$SO_3$, $c_2N$—$C_6H_4SO_3$, $CF_3(CF_2)_3SO_3$, $NHCOC(CH_3)_3$, $NHCOCH_3$, $NHSO_2C_6H_5$, $NHSO_2C_6H_4CH_3$ or $NO_2$;
to give a compound of the formula (IV)

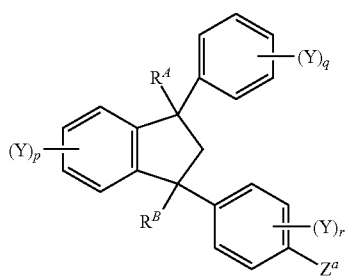

(IV)

b1) converting the compound of the formula (IV) from step a1) to an amine compound of the formula (V)

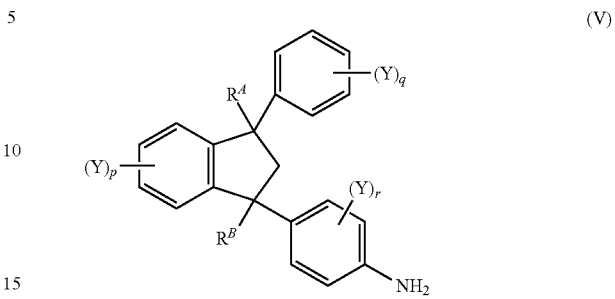

(V)

c1) subjecting the amine compound of the formula (V) to an arylation reaction with one aromatic compound of formula (VI)

Ar—$Z^b$ (VI)

wherein
$Z^b$ is selected from F, Cl, Br, I, $CH_3SO_3$, $CF_3SO_3$, $CH_3$—$O_6H_4$—$SO_3$, $C_6H_5$—$SO_3$, $O_2N$—$C_6H_4$—$SO_3$ or $CF_3(CF_2)_3SO_3$;
in the presence of a palladium complex catalyst and a base to give the compound of the formula (I-MA-1); or
d1) subjecting the compound of the formula (IV) from step a1) to an amination reaction with one aromatic amine of formula (VII)

$Ar_2NH$ (VII)

in the presence of a palladium complex catalyst and a base to give the compound of the formula (I-MA-1).

Step a1)

The compound of the formula (IV) can be obtained from the reaction of an alphaolefin compound of the formula (II) with a dityl or trityl compound of the formula (III) in the presence of a Lewis acid. Suitable Lewis acids include $BF_3*OEt_2$, $BCl_3$, $BBr_3$, $ZnCl_2$, $ZnBr_2$, $Zn(Otf)_2$, $MgCl_2$, $MgBr_2$, tin (IV) chloride, magnesium trifluorosulfonate, $FeCl_3$ and $AlCl_3$. Alternatively, the compound of the formula (IV) can be obtained from the reaction of the alpha-olefin compound of the formula (II) with a salt of the compound of formula (III). This salt can be obtained from the reaction of the compound of formula (III) with a Lewis acid, for example the Lewis acid as described above. The reaction can be performed in analogy to the procedure described in *Eur. J. Org. Chem.* 2002, 22, 3850-3854 and *J. Org. Chem.* 1983, 48, 1159-1165.

The starting material of formula (II) is either commercially available or can be prepared according to a standard procedure, for example by treating an appropriate ketone with an ylide generated from a phosphonium salt in the sense of a Wittig reaction, for example in analogy to the process described in *J. Org. Chem.*, 2015, 80, 11388. The starting material of the formula (III) is either commercially available or can be prepared according to a standard procedure, for example by treating an appropriate ketone with an appropriate phenyl or methyl magnesium chloride or bromide in the sense of a Grignard reaction, followed by the conversion of the alcohol into for example the chloride or bromide by standard procedure with for example thionyl chloride or bromide.

Step b1)

The compound of the formula (V) can be obtained from the reaction of the compound of formula (IV) with an alkali metal salt of a hexaalkyldisilazide of the formula M-N(Si (R')$_3$)$_2$, where M is an alkali metal and R' may be the same or a different C$_1$-C$_6$-alkyl, especially lithium bis(trimethylsilyl)amide in the presence of a palladium catalyst and subsequent hydrolysis.

An example for a suitable palladium catalyst is tris (dibenzylideneacetone)dipalladium(0) or palladium(II) chloride, optionally in the presence of a tri(substituted) phosphine, e.g. a triarylphosphine such as triphenylphosphine or tritolylphosphine, tri(cyclo)alkylphosphine such as tris-n-butylphosphine, tris(tert-butyl)phosphine, tris(cyclohexylphosphine), 2-(dicyclohexylphosphino)biphenyl or 1,1'-bis(diphenylphosphino)ferrocene. The reaction of compound (IV) with the alkalimetal hexaalkyldisilazide can be performed by analogy to a Buchwald-Hartig coupling. The alkalimetal hexaalkyldisilazide is commercially available or can be generated in-situ from the corresponding amine by a strong base such an alkalimetal alkoxide, e.g. potassium tert-butanolate, or an alkalimetal hydride such as lithium hydride, sodium hydride and the like. Removal of the trialkylsilyl group is simply achieved by aqueous work-up, preferably under acidic conditions, such as aqueous hydrochloric acid, sulfuric acid etc, or using fluoride sources such as HF, KF, ammonium fluoride or HF-pyridine.

Alternatively, the compound of the formula (IV) is subjected to a copper promoted amidation with an amide of the formula (VIII)

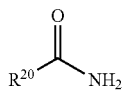

(VIII)

in which

R$^{20}$ is hydrogen, C$_1$-C$_{10}$-alkyl, C$_3$-C$_8$-cycloalkyl or CH$_2$-(C$_6$-C$_{10}$-aryl);

to give a amide of the formula (IX)

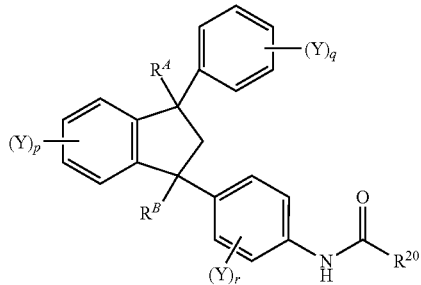

(IX)

and the amide of the formula (IX) is subjected to a hydrolysis to give the compound of formula (V).

In formula (VIII), R$^{20}$ is preferably linear C$_1$-C$_{10}$-alkyl or branched C$_3$-C$_{10}$-alkyl. In a preferred embodiment, the amide of formula (VIII) is pivalamide. The amination process can be carried out in the sense of a Goldberg type reaction using a copper catalyst, such as a copper(I) compound. Suitable copper(I) compounds are copper(I) oxide, copper(I) bromide or copper(I) iodide, in particular copper (I) iodide. The amount of copper(I) compound is typically in the range from 5 to 20 mol %, based on the amount of compound of formula (IV). The reaction usually is carried out in the presence of a ligand such as dimethylethylenediamine (dmeda) or 1,2-cyclohexanediamine. The ligand is typically present in the range from 0.01 to 300 mol %, based on the amount of the catalyst. In general, the reaction is carried out in an inert, aprotic solvent such as an ether, e.g. dimethoxyethane or dioxane or an amide, e.g. dimethylformamide or N-methylpyrrolidone, or an aromatic solvent, e.g. toluene. In general, the reaction is carried out in the presence of a base. Suitable bases are alkalimetal carbonates, in particular potassium carbonate, or alkalimetal phosphates such as potassium carbonate. Typically, the reaction is carried out under an inert atmosphere in the temperature range of 60-180° C. The amide (IX) can be hydrolyzed under basic or acidic conditions. Suitable basic conditions are for example a treatment of the amide (IX) with an alkalimetal hydroxide such as KOH or NaOH in an alcohol followed by addition of water. Suitable alcohols are for example C$_1$-C$_4$-alkanols such as n-butanol. Suitable acidic conditions are for example a treatment of the amide (IX) with an aqueous acid such as a mineral acid, e.g. sulfuric acid, hydrochloric acid, nitric acid or phosphoric acid, or with hydrobromic acid or hydroiodic acid.

Compounds of formula (IV) in which Z$^a$ is NO$_2$ can be reduced to compounds of formula (V) using for example hydrogen and palladium on carbon in the presence of glacial acetic acid.

Compounds of formula (IV) in which Z$^a$ is Cl or Br can be converted into compounds of formula (IV) in which Z$^a$ is a benzylamino group followed by benzyl cleavage using for example hydrogen and palladium on carbon in the presence of glacial acetic acid.

Compounds of formula (IV) in which Z$^a$ is NHCOC (CH$_3$)$_3$, NHCOCH$_3$, NHSO$_2$C$_6$H$_5$, NHSO$_2$C$_6$H$_4$CH$_3$ can be subjected to a hydrolysis to give the compound of formula (V).

Step c1)

Compounds of the formula (I-MA-1) can be obtained by an arylation reaction between the compound (V) and the compound of the formula (VI) in the presence of a palladium catalyst in terms of a Buchwald-Hartwig reaction. Suitable palladium catalyst or catalyst precursors are for example palladium(0) bis(dibenzylideneacetone) (Pd(dba)$_2$), tris-(dibenzylideneacetone)dipalladium(0) (Pd$_2$(dba)$_3$), [1,1-bis (diphenylphosphino)-ferrocene]dichloropalladium(II) (PdCl$_2$(dppf)), palladium chloride (PdCl$_2$), bis(acetonitrile) palladium chloride (Pd(ACN)$_2$Cl$_2$), [1,3-bis(2,6-diisopropylphenyl)imidazol-2-ylidene](3-chloropyridyl)palladium dichloride (PEPPSI-iPr), dichloro[1,3-bis(2,6-di-3-pentylphenyl)imidazol-2-ylidene](3-chloro-pyridyl)palladium (PEPPSI-iPent), or palladium acetate (Pd(OAc)$_2$). Preferably, the catalyst is palladium acetate, Pd(dba)$_2$ or Pd$_2$(dba)$_3$. The reaction is usually carried out in the presence of a ligand. The ligand is any molecule capable of coordinating to the palladium precursor and facilitating the Buchwald-Hartwig reaction, preferably an dialkylbiarylphosphines or tri-tert-butyl phosphine. Examples of dialkylbiarylphosphine ligands include 2-dicyclohexylphosphino-2'-(N,N-dimethylamino)biphenyl (DavePhos), 2-dicyclohexylphosphino-2',4',6'-triisopropylbiphenyl (Xphos), 2-dicyclohexylphosphino-2',6'-dimethoxybiphenyl (Sphos), 2-di-tert-butylphosphino-2',4',6'-triisopropylbiphenyl (tBuXPhos), (2-biphenyl)dicyclohexylphosphine, 2-(dicyclohexylphosphino)biphenyl (CyJohnPhos), (2-biphenyl)di-tert-butylphosphine (JohnPhos), 2-dicyclohexyl-phosphino-2',6'-diisopropoxybiphenyl (RuPhos), 2-di-tert-butylphosphino-2'-methylbiphenyl (tBuMePhos), 2-di-tertbutylphosphino-3,4,5,6-tetramethyl-2',4',6'-triisopropyl-1,1'-biphenyl 2-di-tert-butylphosphino-2'-methylbiphenyl (tBuMePhos), 2-di-tert-butylphosphino-3,4,5,6-tetramethyl-2',4',6'-triisopropyl-1,1'-biphenyl (Tetramethyl tBuXPhos), and 2-(dicyclohexylphosphino)3,6-dimethoxy-2',4',6'-triisopropyl-1,1-biphenyl (BrettPhos). The palladium catalyst and phosphine ligand are preferably used in a molar ratio in the range of from about 0.5 to about 5 moles of ligand per mole of palladium catalyst.

Usually, the reaction is performed in the presence of a base such as an alkali alkoxide, earth alkali alkoxide, alkali carbonate or earth alkali carbonate, alkali metal amide or trialkyl amine. Preferably, the base is sodium tert-butoxide, cesium carbonate, lithium bis(trimethylsilyl)amide, sodium bis(trimethylsilyl)amide, potassium bis(trimethylsilyl)amide, lithium diisopropylamide or lithium dicyclohexylamide. More preferably, the base is sodium tert-butoxide.

The reaction is generally carried out in a solvent. Suitable solvents are for example aliphatic hydrocarbons, such as pentane, hexane, cyclohexane and petroleum ether, aromatic hydrocarbons, such as toluene, o-, m- and p-xylene, ethers, such as diisopropyl ether, tert-butyl methyl ether, dioxane, anisole and tetrahydrofuran and dimethoxyethane, amide such as dimethylformamide or N-methylpyrrolidone. The reaction temperature generally ranges between 50° and 130° C. The reactions generally are run under an inert atmosphere (e.g. under dry nitrogen or argon).

Step d1)

In step d1), the compound of the formula (IV) from step a1) can be subjected to an amination reaction with one aromatic amine of formula (VII). Suitable reaction conditions are described above in step c1).

The intermediate compounds of formula (V) correspond to compounds of the formula (I), wherein X is NH$_2$. These compounds are novel and also subject of this invention as well as the process for preparing them.

A further aspect of the present invention relates to a process for the preparation of a compound of the formula (I), referred to as compound of the formula (I-MA-2)

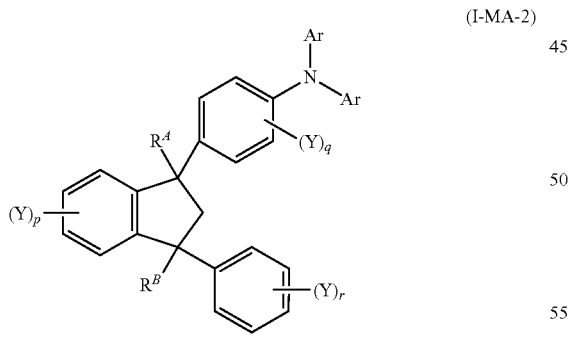

wherein
each Ar is independently defined as above;
each Y is independently as defined above;
R$^A$ and R$^B$ are as defined above;
p is 4, wherein 0, 1, 2, 3 or 4 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;

comprising the steps
a1a) reacting an ethene compound of the formula (IIa) with a compound of the formula (IIIa) or a salt thereof

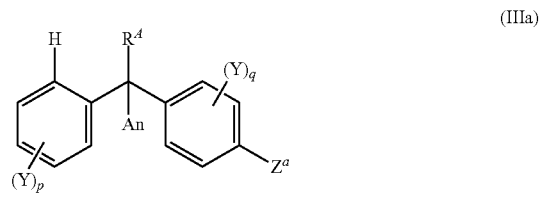

in which
An is Cl or Br; and
$Z^a$ is F, Cl, Br, I, CH$_3$SO$_3$, CF$_3$SO$_3$, CH$_3$-C$_6$H$_4$—SO$_3$, C$_6$H$_5$—SO$_3$, O$_2$N-C$_6$H$_4$SO$_3$, CF$_3$(CF$_2$)$_3$SO$_3$, NHCOC(CH$_3$)$_3$, NHCOCH$_3$, NHSO$_2$C$_6$H$_5$, NHSO$_2$C$_6$H$_4$CH$_3$ or NO$_2$;
to give a compound of the formula (IVa)

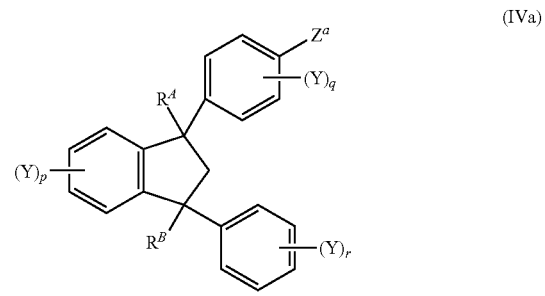

b1a) converting the compound of the formula (IVa) from step a1a) to an amine compound of the formula (Va)

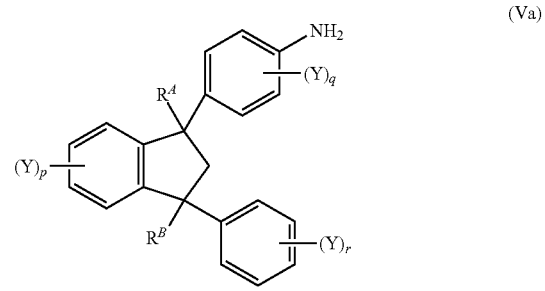

c1a) subjecting the amine compound of the formula (Va) to an arylation reaction with one aromatic compound of formula (VI)

Ar—Z$^b$ (VI)

wherein
$Z^b$ is selected from F, Cl, Br, I, CH$_3$SO$_3$, CF$_3$SO$_3$, CH$_3$—O$_6$H$_4$—SO$_3$, C$_6$H$_5$—SO$_3$, O$_2$N—C$_6$H$_4$—SO$_3$ or CF$_3$(CF$_2$)$_3$SO$_3$;

in the presence of a palladium complex catalyst and a base to give the compound of the formula (I-MA-2); or d1a) subjecting the compound of the formula (IVa) from step a1a) to an amination reaction with one aromatic amine of formula (VII)

Ar$_2$NH     (VII)

in the presence of a palladium complex catalyst and a base to give the compound of the formula (I-MA-2).

Step a1a) can be performed in analogy to step a1); step b1a) can be performed in analogy to step b1), step c1a) can be performed in analogy to step c1) and step d1a) can be performed in analogy to step d1).

The intermediate compounds of formula (Va) correspond to compounds of the formula (I), wherein X is NH$_2$ and R$^A$ and R$^B$ are as defined above. These compounds are novel and also subject of this invention as well as the process for preparing them.

The compounds of formula (IVa), wherein R$^A$=R$^B$=C$_1$-C$_6$-alkyl, especially methyl and Z$^a$=Cl or Br can also be prepared as shown below in Scheme A. Thus construction of the 1,3-diphenylindane core present in the compounds of formula (I.DP) can also be achieved, for example, by a copper(I)-catalyzed 1,4-addition of a phenyl Grignard reagent of formula (XI) to an enone compound of formula (X) using catalysts which comprise complexes of copper (I) compounds. The resulting ketone compound of formula (XII) is transformed into an alcohol of formula (XIII) using an alkyl Grignard reagent of the formula (XIV). Compound (XIII) is then treated with an acid such as trifluoroacetic acid to afford the compound of formula (IVa).

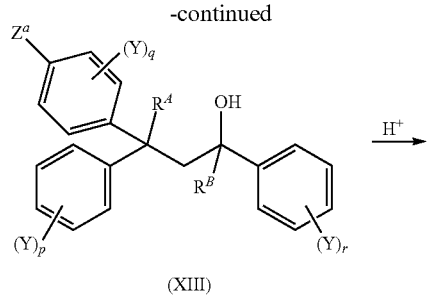

(XIII)

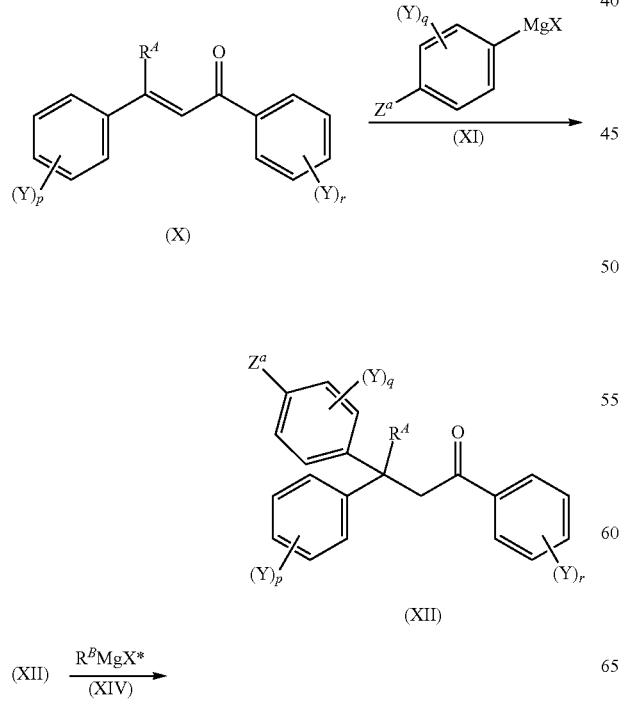

In Scheme A, (Y)$_p$, (Y)$_q$, and (Y)$_r$ are as defined above, R$^A$ is C$_1$-C$_6$-alkyl, especially methyl, R$^B$ is C$_1$-C$_6$-alkyl, especially methyl, X is Cl or Br, X* is Cl or Br, Z$^a$ is Cl or Br.

A further aspect of to present invention relates to a process for the preparation of a compound of the formula (I), referred to as compound of the formula (I-DA-1)

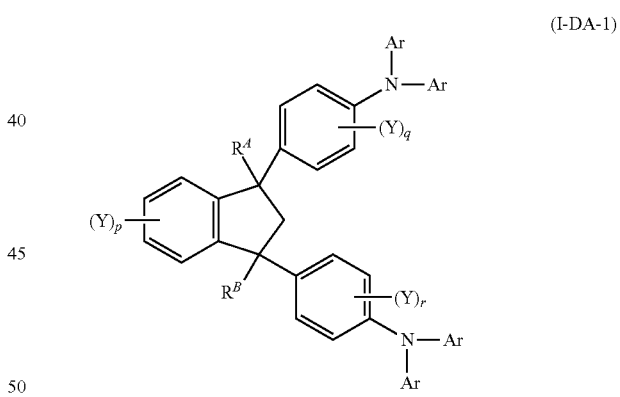

(I-DA-1)

wherein each Ar is independently defined as above;

each Y is independently as defined above;

R$^A$ and R$^B$ are as defined above;

p is 4, wherein 0, 1, 2, 3 or 4 of the p Y groups are different from hydrogen;

q is 4, wherein 0, 1, 2, 3 or 4 of the q Y groups are different from hydrogen;

r is 4, wherein 0, 1, 2, 3 or 4 of the r Y groups are different from hydrogen;

comprising the steps a2) reacting an ethene compound of the formula (II) with a compound of the formula (IIIb) or a salt thereof

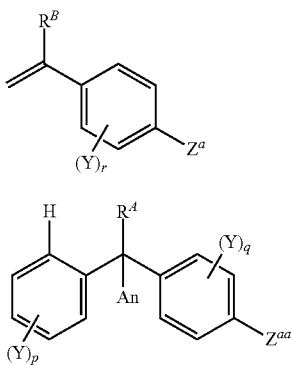

(II)

(IIIb)

in which
An is Cl or Br; and
$Z^a$ is F, Cl, Br, I, $CH_3SO_3$, $CF_3SO_3$, $CH_3$-$C_6H_4$—$SO_3$, $C_6H_5$—$SO_3$, $O_2N$-$C_6H_4SO_3$, $CF_3(CF_2)_3SO_3$, $NHCOC(CH_3)_3$, $NHCOCH_3$, $NHSO_2C_6H_5$, $NHSO_2C_6H_4CH_3$ or $NO_2$;
$Z^{aa}$ is F, Cl, Br, I, $CH_3SO_3$, $CF_3SO_3$, $CH_3$-$C_6H_4$—$SO_3$, $C_6H_5$—$SO_3$, $O_2N$-$C_6H_4SO_3$, $CF_3(CF_2)_3SO_3$, $NHCOC(CH_3)_3$, $NHCOCH_3$, $NHSO_2C_6H_5$, $NHSO_2C_6H_4CH_3$ or $NO_2$;
to give a compound of the formula (IVb)

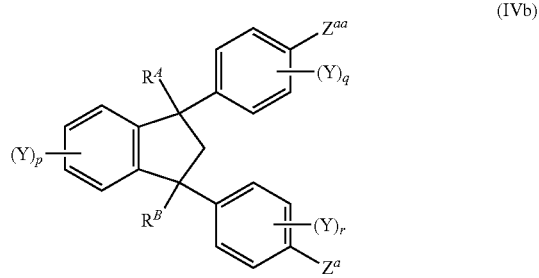

(IVb)

b2) converting the compound of the formula (IVb) from step a2) to a diamine compound of the formula (Vb)

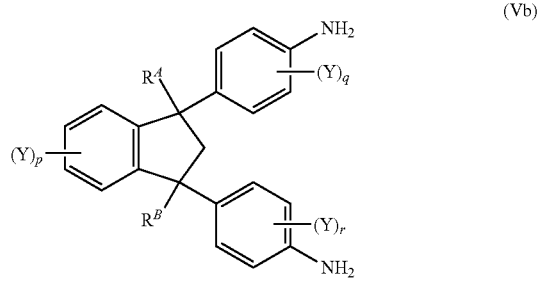

(Vb)

c2) subjecting the amine compound of the formula (Vb) to an arylation reaction with at least one aromatic compound of formula (VI)

Ar—$Z^b$ (VI)

wherein
$Z^b$ is selected from F, Cl, Br, I, $CH_3SO_3$, $CF_3SO_3$, $CH_3$—$O_6H_4$—$SO_3$, $O_6H_5$—$SO_3$, $O_2N$-$C_6H_4$—$SO_3$ or $CF_3(CF_2)_3SO_3$;

in the presence of a palladium complex catalyst and a base to give the compound of the formula (I-DA-1); or d2) subjecting the compound of the formula (IVb) from step a2) to an amination reaction with at least one aromatic amine of formula (VII)

$Ar_2NH$ (VII)

in the presence of a palladium complex catalyst and a base to give the compound of the formula (I-DA-1).

Step a2) can be performed in analogy to step a1). Step b2) can be performed in analogy to step b1). Step c2) can be performed in analogy to step c1), it being possible to use different aromatic compounds of the formula (VI). Step d2) can be performed in analogy to step di), it being possible to use different aromatic compounds of the formula (VI).

The intermediate compounds of formula (Vb) correspond to compounds of the formula (I), wherein X is $NH_2$ and $R^A$ and $R^B$ are as defined above. These compounds are novel and also subject of this invention as well as a process for preparing them.

The compounds of formula (IVb), wherein $R^A$=$R^B$=$C_1$-$C_6$-alkyl, especially methyl and $Z^a$ and $Z^{aa}$=Cl or Br can also be prepared as shown below in Scheme B. Thus construction of the 1,3-diphenylindane core present in the compounds of formula (I.DP) can also be achieved, for example, by a copper(I)-catalyzed 1,4-addition of a phenyl Grignard reagent of formula (XVI) to an enone compound of formula (XV) using catalysts which comprise complexes of copper (I) compounds. The resulting ketone compound of formula (XVII) is transformed into an alcohol of formula (XVIII) using an alkyl Grignard reagent of the formula (XIX). Compound (XVIII) is then treated with an acid such as trifluoroacetic acid to afford the compound of formula (IVb).

Scheme B

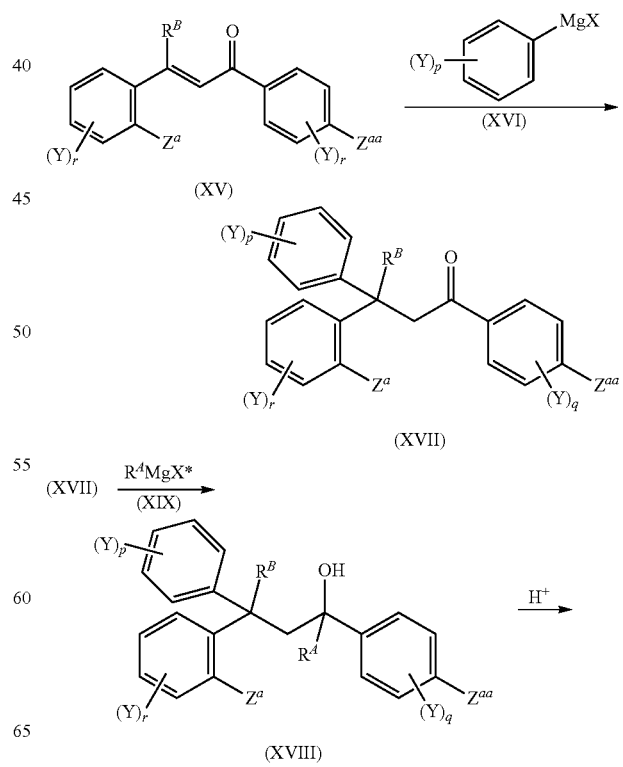

-continued

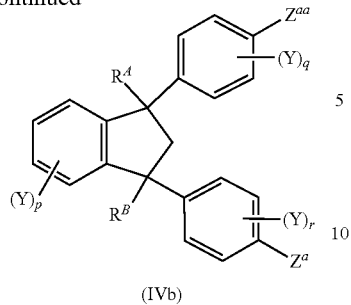

(IVb)

In Scheme B, $(Y)_p$, $(Y)_q$, and $(Y)_l$ are as defined above, $R^A$ is $C_1$-$C_6$-alkyl, especially methyl, $R^B$ is $C_1$-$C_6$-alkyl, especially methyl, X is Cl or Br, X* is Cl or Br, $Z^a$ is Cl or Br, $Z^{aa}$ is Cl or Br.

A further aspect of the present invention relates to a process for the preparation of a compound of the formula (I), referred to as compound of the formula (I-DA-2)

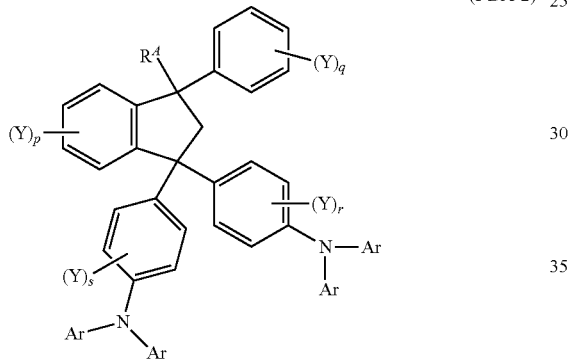

(I-DA-2)

wherein each Ar is independently defined as above;

each Y is independently as defined above;

$R^A$ is as defined above;

p is 4, wherein 0, 1, 2, 3 or 4 of the p Y groups are different from hydrogen;

q is 5, wherein 0, 1, 2, 3, 4 or 5 of the q Y groups are different from hydrogen;

r is 4, wherein 0, 1, 2, 3 or 4 of the r Y groups are different from hydrogen;

s is 4, wherein 0, 1, 2, 3 or 4 of the s Y groups are different from hydrogen;

comprising the steps e2) reacting an ethene compound of the formula (IIb) with a compound of the formula (III) or a salt thereof

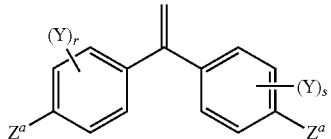

(IIb)

-continued

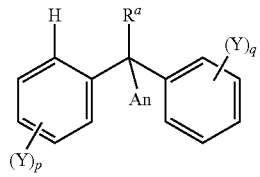

(III)

in which

An is Cl or Br; and each $Z^a$ is selected from F, Cl, Br, I, $CH_3SO_3$, $CF_3SO_3$, $CH_3$-$C_6H_4$—$SO_3$, $C_6H_5$—$SO_3$, $O_2N$-$C_6H_4SO_3$, $CF_3(CF_2)_3SO_3$, $NHCOC(CH_3)_3$, $NHCOCH_3$, $NHSO_2C_6H_5$, $NHSO_2C_6H_4CH_3$ or $NO_2$;

to give a compound of the formula (IVc)

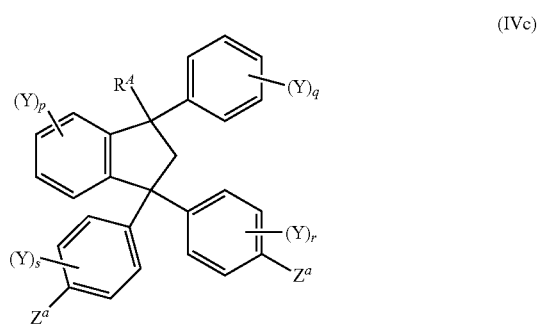

(IVc)

f2) converting the compound of the formula (IVc) from step e2) to a diamine compound of the formula (Vc)

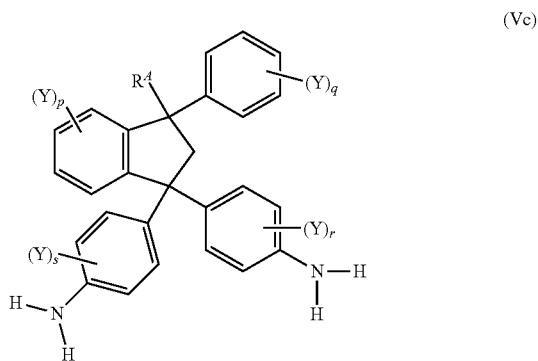

(Vc)

g2) subjecting the amine compound of the formula (Vc) to an arylation reaction with at least one aromatic compound of formula (VI)

Ar—$Z^b$ (VI)

wherein $Z^b$ is selected from F, Cl, Br, I, $CH_3SO_3$, $CF_3SO_3$, $CH_3$—$O_6H_4$—$SO_3$, $C_6H_5$—$SO_3$, $O_2N$-$C_6H_4$—$SO_3$ or $CF_3(CF_2)_3SO_3$;

in the presence of a palladium complex catalyst and a base to give the compound of the formula (I-DA-2); or h2) subjecting the compound of the formula (IVc) from step e2) to an amination reaction with at least one aromatic amine of formula (VII)

$Ar_2NH$ (VII)

in the presence of a palladium complex catalyst and a base to give the compound of the formula (I-DA-2).

Step e2) can be performed in analogy to step a1). Step f2) can be performed in analogy to step b1). Step g2) can be performed in analogy to step c1), it being possible to use different aromatic compounds of the formula (VI). Step h2) can be performed in analogy to step d1), it being possible to use different aromatic compounds of the formula (VI).

The intermediate compounds of formula (Vc) correspond to compounds of the formula (I), wherein X is $NH_2$, $R^A$ is as defined above and $R^B$ is a group (RB-I). These compounds are novel and also subject of this invention as well as a process for preparing them.

A further aspect of the present invention relates to a process for the preparation of a compound of the formula (I), referred to as compound of the formula (I.DP-TRA-1)

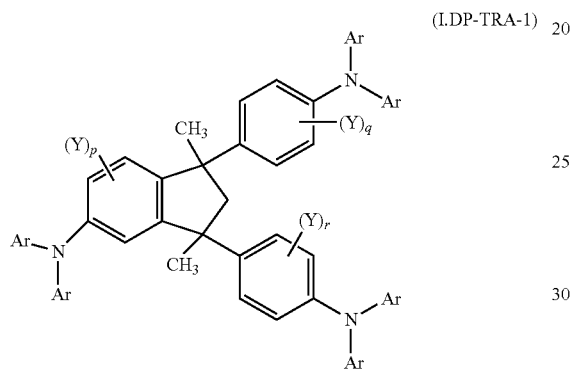

(I.DP-TRA-1)

wherein
each Ar is independently defined as above;
each Y is independently as defined above;
p is 3, wherein 0, 1, 2 or 3 of the p Y groups are different from hydrogen;
q is 4, wherein 0, 1, 2, 3 or 4 of the q Y groups are different from hydrogen; and
r is 4, wherein 0, 1, 2, 3 or 4 of the r Y groups are different from hydrogen;
comprising the steps
a3) reacting an ethene compound of the formula (IIc) with a compound of the formula (IIIc) or a salt thereof

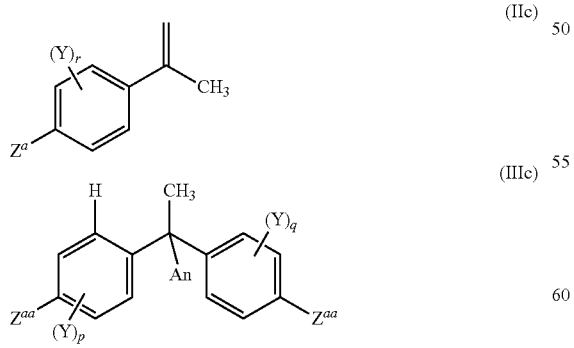

(IIc)

(IIIc)

in which
An is Cl or Br;
$Z^a$ is F, Cl, Br, I, $CH_3SO_3$, $CF_3SO_3$, $CH_3$-$C_6H_4$—$SO_3$, $C_6H_5$—$SO_3$, $O_2N$-$C_6H_4SO_3$, $CF_3(CF_2)_3SO_3$, $NHCOC(CH_3)_3$, $NHCOCH_3$, $NHSO_2C_6H_5$, $NHSO_2C_6H_4CH_3$ or $NO_2$; and
each $Z^{aa}$ is selected from F, Cl, Br, I, $CH_3SO_3$, $CF_3SO_3$, $CH_3$-$C_6H_4$—$SO_3$, $C_6H_5$—$SO_3$, $O_2N$-$C_6H_4SO_3$, $CF_3(CF_2)_3SO_3$, $NHCOC(CH_3)_3$, $NHCOCH_3$, $NHSO_2C_6H_5$, $NHSO_2C_6H_4CH_3$ or $NO_2$;
to give a compound of the formula (IVd)

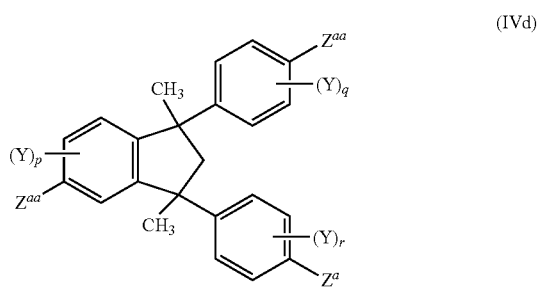

(IVd)

b3) converting the compound of the formula (IVd) from step a3) to a triamine compound of the formula (Vd)

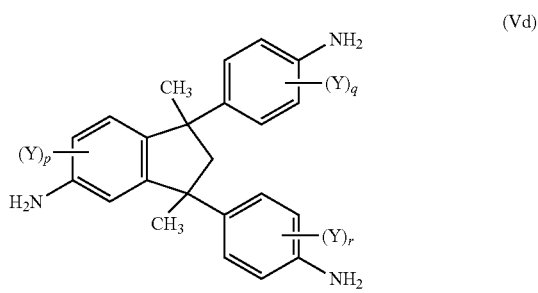

(Vd)

c3) subjecting the amine compound of the formula (Vd) to an arylation reaction with at least one aromatic compound of formula (VI)

Ar—$Z^b$ (VI)

wherein
$Z^b$ is selected from F, Cl, Br, I, $CH_3SO_3$, $CF_3SO_3$, $CH_3$—$O_6H_4$—$SO_3$, $C_6H_5$—$SO_3$, $O_2N$-$C_6H_4$—$SO_3$ or $CF_3(CF_2)_3SO_3$;
in the presence of a palladium complex catalyst and a base to give the compound of the formula (I.DP-TRA-1);
or
d3) subjecting the compound of the formula (IVd) from step a3) to an amination reaction with at least one aromatic amine of formula (VII)

$Ar_2NH$ (VII)

in the presence of a palladium complex catalyst and a base to give the compound of the formula (I.DP-TRA-1).

Step a3) can be performed in analogy to step a1). Step b3) can be performed in analogy to step b1). Step c3) can be performed in analogy to step c1), it being possible to use different aromatic compounds of the formula (VI). Step d3) can be performed in analogy to step d1), it being possible to use different aromatic compounds of the formula (VI).

The intermediate compounds of formula (Vd) correspond to compound of the formula (I), wherein X is $NH_2$, $R^A$ is methyl and $R^B$ is methyl. These compounds are novel and also subject of this invention as well as a process for preparing them.

A further aspect of the present invention is a process for the preparation of a compound of the formula (I), referred to as compounds of the formula (I.TRP-TEA-2)

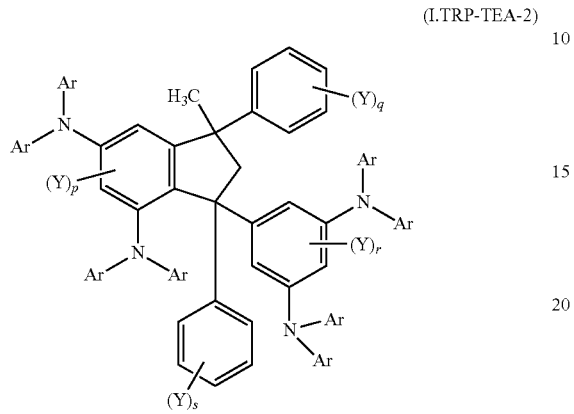

(I.TRP-TEA-2)

wherein
each Ar is independently defined as above;
each Y is independently as defined above;
p is 2, wherein 0, 1 or 2 of the p Y groups are different from hydrogen;
q is 5, wherein 0, 1, 2, 3, 4 or 5 of the q Y groups are different from hydrogen;
r is 3, wherein 0, 1, 2 or 3 of the r Y groups are different from hydrogen;
s is 5, wherein 0, 1, 2, 3, 4 or 5 of the s Y groups are different from hydrogen;
comprising the steps
a4) reacting an ethene compound of the formula (IId) with a compound of the formula (IIId) or a salt thereof

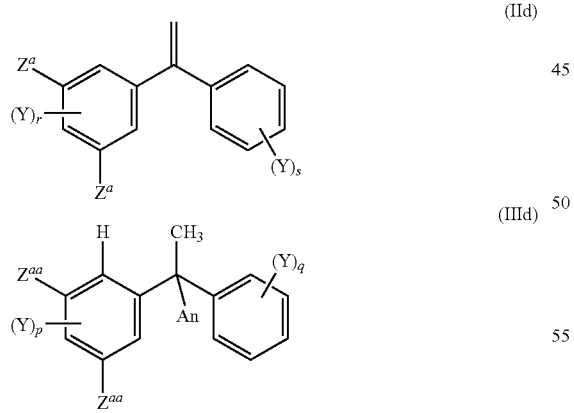

(IId)

(IIId)

in which
An is Cl or Br;
each $Z^a$ is selected from F, Cl, Br, I, $CH_3SO_3$, $CF_3SO_3$, $CH_3$-$C_6H_4$—$SO_3$, $C_6H_5$—$SO_3$, $O_2N$-$C_6H_4SO_3$, $CF_3(CF_2)_3SO_3$, $NHCOC(CH_3)_3$, $NHCOCH_3$, $NHSO_2C_6H_5$, $NHSO_2C_6H_4CH_3$ or $NO_2$; and
each $Z^{aa}$ is selected from F, Cl, Br, I, $CH_3SO_3$, $CF_3SO_3$, $CH_3$-$C_6H_4$—$SO_3$, $C_6H_5$—$SO_3$, $O_2N$-$C_6H_4SO_3$, $CF_3$ $(CF_2)_3SO_3$, $NHCOC(CH_3)_3$, $NHCOCH_3$, $NHSO_2C_6H_5$, $NHSO_2C_6H_4CH_3$ or $NO_2$;
to give a compound of the formula (IVe)

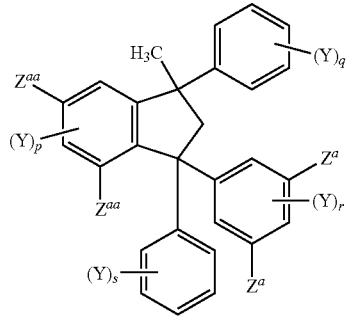

(IVe)

b4) converting the compound of the formula (IVe) from step a4) to a tetraamine compound of the formula (Ve)

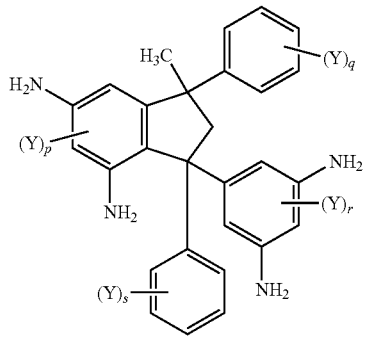

(Ve)

c4) subjecting the amine compound of the formula (Ve) to an arylation reaction with at least one aromatic compound of formula (VI)

Ar—$Z^b$ (VI)

wherein
$Z^b$ is selected from F, Cl, Br, I, $CH_3SO_3$, $CF_3SO_3$, $CH_3$—$C_6H_4$—$SO_3$, $C_6H_5$—$SO_3$, $O_2N$-$C_6H_4$—$SO_3$ or $CF_3(CF_2)_3SO_3$;
in the presence of a palladium complex catalyst and a base to give the compound of the formula (I.TRP-TEA-2);
or
d4) subjecting the compound of the formula (IVe) from step a4) to an amination reaction with at least one aromatic amine of formula (VII)

$Ar_2NH$ (VII)

in the presence of a palladium complex catalyst and a base to give the compound of the formula (I.TRP-TEA-2).

Step a4) can be performed in analogy to step a1). Step b4) can be performed in analogy to step b1). Step c4) can be performed in analogy to step c1), it being possible to use different aromatic compounds of the formula (VI). Step d4) can be performed in analogy to step di), it being possible to use different aromatic compounds of the formula (VI).

The intermediate compounds of formula (Ve) correspond to compounds of the formula (I), wherein X is $NH_2$, $R^A$ is methyl and $R^B$ is a group (RB-I). These compounds are novel and also subject of this invention as well as a process for preparing them.

A further aspect of the present invention relates to a process for the preparation of a compound of the formula (I.DP-TEA-1-1)

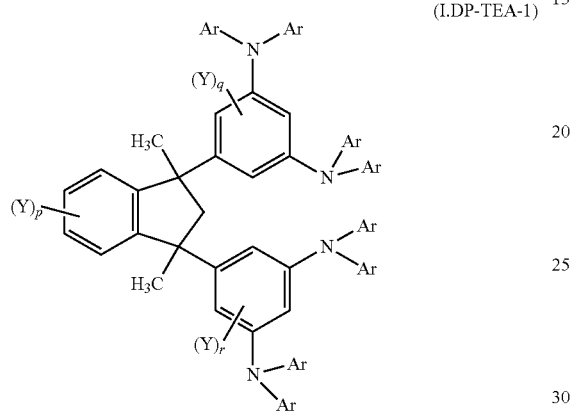

(I.DP-TEA-1)

wherein each Ar is independently defined as above;

each Y is independently as defined above;

p is 4, wherein 0, 1, 2, 3 or 4 of the p Y groups are different from hydrogen;

q is 3, wherein 0, 1, 2 or 3 of the q Y groups are different from hydrogen;

r is 3, wherein 0, 1, 2 or 3 of the r Y groups are different from hydrogen;

comprising the steps e4) reacting an ethene compound of the formula (IIe) with a compound of the formula (IIIf) or a salt thereof

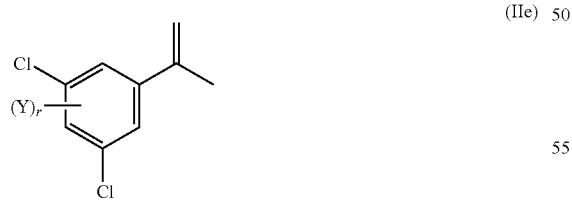

(IIe)

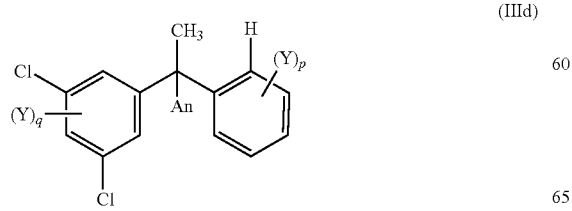

(IIId)

in which

An is Cl or Br;

to give a compound of the formula (IVf)

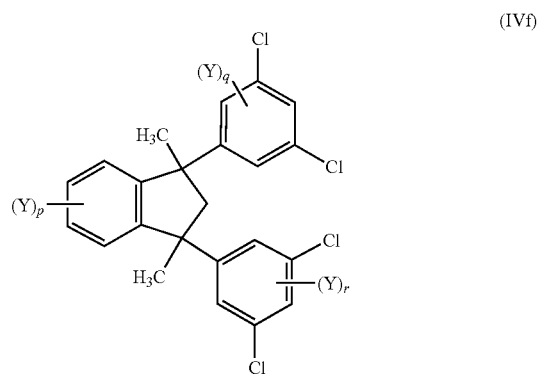

(IVf)

f4) converting the compound of the formula (IVf) from step e4) to a tetraamine compound of the formula (Vf)

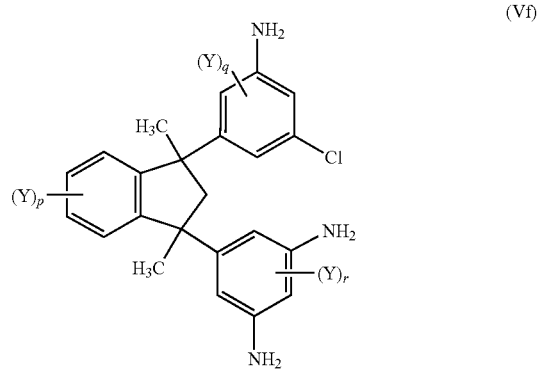

(Vf)

g4) subjecting the amine compound of the formula (Vf) to an arylation reaction with at least one aromatic compound of formula (VI)

Ar—$Z^b$ (VI)

wherein $Z^b$ is selected from F, Cl, Br, I, $CH_3SO_3$, $CF_3SO_3$, $CH_3$—$O_6H_4$—$SO_3$, $C_6H_5$—$SO_3$, $O_2N$-$C_6H_4$—$SO_3$ or $CF_3(CF_2)_3SO_3$;

in the presence of a palladium complex catalyst and a base to give the compound of the formula (I.DP-TEA-1);

or h4) subjecting the compound of the formula (IVf) from step e4) to an amination reaction with at least one aromatic amine of formula (VII)

$Ar_2NH$ (VII)

in the presence of a palladium complex catalyst and a base to give the compound of the formula (I.DP-TEA-1).

Step e4) can be performed in analogy to step a1). Step f4) can be performed in analogy to step b1). Step g4) can be performed in analogy to step c1), it being possible to use different aromatic compounds of the formula (VI). Step h4) can be performed in analogy to step d1), it being possible to use different aromatic compounds of the formula (VI).

The intermediate compounds of formula (Vf) correspond to a compound of the formula (I), wherein X is NH$_2$ and R$^A$=R$^B$=methyl. These compounds are novel and also subject of this invention as well as a process for preparing them.

A further aspect of the present invention relates to a process for the preparation of a compound of the formula (I), referred to as compound of the formula (I.TRP-DA-1)

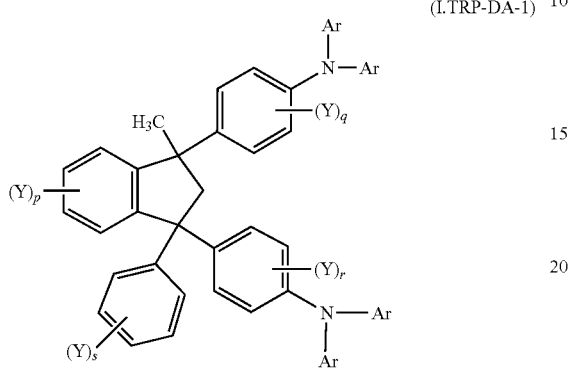

(I.TRP-DA-1)

wherein
each Ar is independently defined as above;
each Y is independently as defined above;
p is 4, wherein 0, 1, 2, 3 or 4 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
d-i) dimerization of a 1,1-diphenylethene compound of formula (IIf)

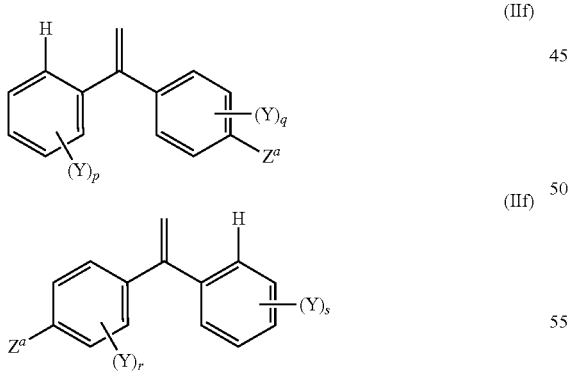

(IIf)

(IIf)

wherein
(Y)$_p$ has the same meaning as (Y)$_s$ and (Y)$_q$ has the same meaning as (Y)$_r$;
each Z$^a$ is independently selected from F, Cl, Br, I, CH$_3$SO$_3$, CF$_3$SO$_3$, CH$_3$-C$_6$H$_4$SO$_3$, C$_6$H$_5$SO$_3$, O$_2$NC$_6$H$_4$SO$_3$, CF$_3$(CF$_2$)$_3$SO$_3$, NHCOC(CH$_3$)$_3$, NHCOCH$_3$, NHSO$_2$C$_6$H$_5$, NHSO$_2$C$_6$H$_4$CH$_3$ or NO$_2$;

to yield a compound of formula (IVg)

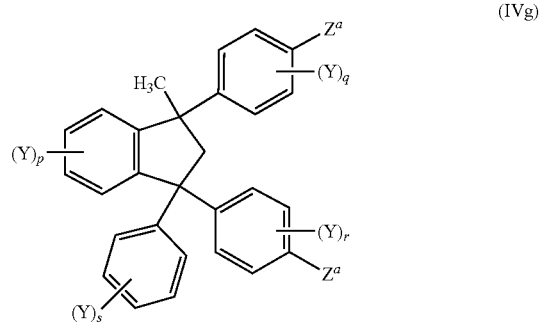

(IVg)

d-ii) subjecting the compound of the formula (IVg) from step d-i) to an amination to give a compound of the formula (Vg)

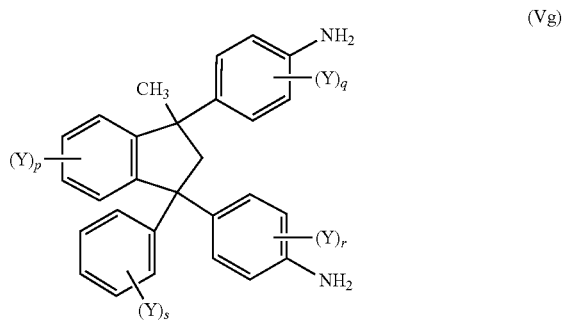

(Vg)

d-iii) subjecting the amine compound of the formula (Vg) to an arylation reaction with at least one aromatic compound of formula (VI)

Ar—Z$^b$ (VI)

wherein
Z$^b$ is selected from F, Cl, Br, I, CH$_3$SO$_3$, CF$_3$SO$_3$, CH$_3$—O$_6$H$_4$—SO$_3$, C$_6$H$_5$—SO$_3$, O$_2$N-C$_6$H$_4$—SO$_3$ or CF$_3$(CF$_2$)$_3$SO$_3$;
in the presence of a palladium complex catalyst and a base to give the compound of the formula (I.TRP-DA-1);

or
d-iv) subjecting the compound of the formula (IVg) from step d-i) to an amination reaction with at least one aromatic amine of formula (VII)

Ar$_2$NH (VII)

in the presence of a palladium complex catalyst and a base to give the compound of the formula (I.TRP-DA-1).

Step d-i)
The dimerization can be carried out in the presence of an acidic catalyst. Suitable catalysts are for example polyphosphoric acid, sulfuric acid, methanesulfuric acid, hydrochloric acid, trifluoracetic acid, p-toluenesulfonic acid, acidic ion exchangers and acidic montmorillonite-containing earths, preferably trifluoroacetic acid. The acid catalyst is generally used as solvent so that is present in large excess but the reaction can also be carried out in the presence of a solvent. Suitable solvents are for example nonpolar solvents, especially hydrocarbon solvents. The reaction is generally carried out at a temperature in the range of 40 to 120° C.

Step d-ii) can be performed in analogy to step b2); step d-iii) can be performed in analogy to step c2) and step d-iv) can be performed in analogy to step d2). The intermediate compounds of formula (Vg) correspond to a compound of the formula (I), wherein X is $NH_2$, $R^A$ is methyl and $R^B$ is a group (RB-I) These compounds are novel and also subject of this invention as well as a process for preparing them.

A further aspect of the present invention relates to a process for the preparation of a compound of the formula (I.TRP-TEA-1)

(I.TRP-TEA-1)

wherein
each Ar is independently defined as above;
each Y is independently as defined above;
p is 3, wherein 0, 1, 2 or 3 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
s is 4, wherein 0, 1, 2, 3 or 4 of the s Y groups are different from hydrogen;
d-v) dimerization of a 1,1-diphenylethene compound of formula (IIg)

(IIg)

(IIg)

wherein
$(Y)_p$ has the same meaning as $(Y)_s$ and $(Y)_q$ has the same meaning as $(Y)_r$
each $Z^a$ is independently selected from F, Cl, Br, I, $CH_3SO_3$, $CF_3SO_3$, $CH_3$-$C_6H_4SO_3$, $C_6H_5SO_3$, $O_2NC_6H_4SO_3$, $CF_3(CF_2)_3SO_3$, $NHCOC(CH_3)_3$, $NHCOCH_3$, $NHSO_2C_6H_5$, $NHSO_2C_6H_4CH_3$ or $NO_2$;
to yield a compound of formula (IVh)

(IVh)

d-vi) subjecting the compound of the formula (IVh) from step d-v) to an amination to give a compound of the formula (Vh)

(Vh)

d-vii) subjecting the amine compound of the formula (Vh) to an arylation reaction with at least one aromatic compound of formula (VI)

Ar—$Z^b$ (VI)

wherein
$Z^b$ is selected from F, Cl, Br, I, $CH_3SO_3$, $CF_3SO_3$, $CH_3$—$O_6H_4$—$SO_3$, $C_6H_5$—$SO_3$, $O_2N$-$C_6H_4$—$SO_3$ or $CF_3(CF_2)_3SO_3$;
in the presence of a palladium complex catalyst and a base to give the compound of the formula (I.TRP-TEA-1)
or
d-viii) subjecting the compound of the formula (IVh) from step d-v) to an amination reaction with at least one aromatic amine of formula (VII)

$Ar_2NH$ (VII)

in the presence of a palladium complex catalyst and a base to give the compound of the formula (I.TRP-TEA-1).

Step d-v) can be performed in analogy to step d-i); step d-vi) can be performed in analogy to step b2); step d-vii) can be performed in analogy to step c2) and step d-viii) can be performed in analogy to step d2). The intermediate compounds of formula (Vh) correspond to a compound of the formula (I), wherein X is NH$_2$, R$^A$ is methyl and R$^B$ is a group (RB-I). These compounds are novel and also subject of this invention as well as a process for preparing them.

A skilled person will appreciate that compounds of the formula (I.TRP-TEA-3) can be prepared in analogy to the method for preparing compounds of formula (I.TRP-TEA-1) but starting from an indane compound of formula (IVi) instead of an indane compound of formula (IVh)

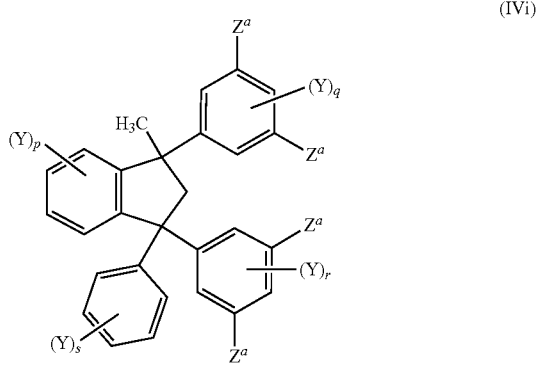

(IVi)

wherein
each Z$^a$ is independently selected from F, Cl, Br, I, CH$_3$SO$_3$, CF$_3$SO$_3$, CH$_3$—C$_6$H$_4$SO$_3$, C$_6$H$_5$SO$_3$, O$_2$NC$_6$H$_4$SO$_3$, CF$_3$(CF$_2$)$_3$SO$_3$, NHCOC(CH$_3$)$_3$, NHCOCH$_3$, NHSO$_2$C$_6$H$_5$, NHSO$_2$C$_6$H$_4$CH$_3$ or NO$_2$;
each Y is independently as defined above;
p is 4, wherein 0, 1, 2, 3 or 4 of the p Y groups are different from hydrogen;
q is 3, wherein 0, 1, 2 or 3 of the q Y groups are different from hydrogen;
r is 3, wherein 0, 1, 2 or 3 of the r Y groups are different from hydrogen;
s is 5, wherein 0, 1, 2, 3, 4 or 5 of the s Y groups are different from hydrogen.

Compounds of formula (IVi) can be prepared by a dimerization of a 1,1-diphenylethene compound of the formulae (IIh) and (IIh*).

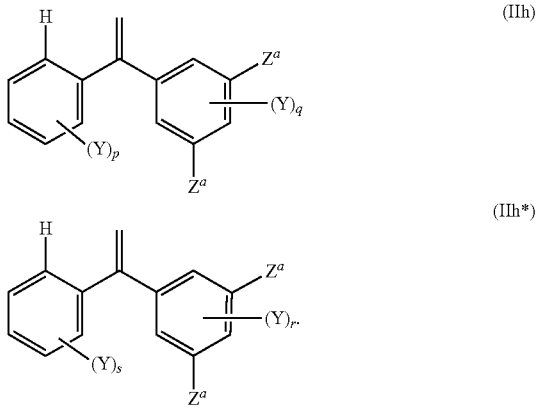

In the compounds of formulae (IIh) and (IIh*), the substituents Y, Z$^a$ and the indices p, q, r and s are defined as in compound of formula (Ivi). The dimerisation can be carried out as outlined in step d-v) above.

As a rule, the reactions generally are run under an inert atmosphere (e.g. under dry nitrogen or argon). As a rule, the compounds of formula (I) including their regioisomers and their precursors in the synthesis processes, can be prepared by the methods described above. If individual compounds can not be prepared via the above-described routes, they can be prepared by derivatization of other compounds (I) or the respective precursor or by customary modifications of the synthesis routes described.

The reaction mixtures are worked up in the customary manner, for example by mixing with water, separating the phases, and, if appropriate, purifying the crude products by chromatography, for example on alumina or on silica gel. If the end products are obtained as solids, they may be purified by recrystallization or sublimation.

The compounds according to the invention are in particular suitable for use in an electronic device. An electronic device here is taken to mean a device which comprises at least one layer which comprises at least one organic compound.

The present invention therefore furthermore relates to the use of the compounds of formulae (I), (I.DP), (I.TRP), (I.TEP), (I.DP-MA-1), (I.DP-MA-2), (I.DP-DA-1), (I.DP-DA-2), (I.DP-DA-3), (I.DP-TRA-1), (I.DP-TEA-1), (I.TRP-MA-1), (I.TRP-MA-2), (I.TRP-MA-3), (I.TRP-DA-1), (I.TRP-DA-2), (I.TRP-DA-3), (I.TRP-DA-4), (I.TRP-DA-5), (I.TRP.TRA-1), (I.TRP-TEA-1), (I.TRP-TEA-2), (I.TRP-TEA-3), (I.TEP-MA-1), (I.TEP-MA-2), (I.TEP-DA-1), (I.TEP-DA-2), (I.TEP-DA-3), (I.TEP-DA-4) or a mixture of at least two different compounds thereof
as a hole transport material (HTM) in organic electronics,
as an electron blocking material (EBM) in organic electronics,
as a semiconductor material in organic field-effect transistors (OFETs), in particular in thin-film transistors (TFTs),
in organic solar cells (OSCs), solid-state dye sensitized solar cells (DSSCs) or Perovskite solar cells, in particular as a hole transport material in organic solar cells,
as replacement of the liquid electrolyte in dye sensitized solar cells, as a hole transport material in Perovskite solar cells,
in organic light-emitting diodes (OLEDs), in particular for displays on electronic devices and lighting,
for electrophotography, in particular as photoconductive material in an organic photoconductor (OPC),
for organic optical detectors, organic photoreceptors, organic field-quench devices (O-FQDs), light-emitting electrochemical cells (LECs) and organic laser diodes.

The compounds according to the invention are especially suitable as a hole transport material (HTM) in organic electronics. HTMs are employed in a wide range of electronic devices and applications, such as in organic electroluminescent (EL) devices and in solar cells.

The compounds according to the invention may be employed as the sole HTM or in combination with at least one further HTM. Suitable further hole transport materials are well-known in the art. Preferred hole transport materials for combination are spiro-OMeTAD, 2,2',7,7'-tetrakis-(N,N'-di-4-methoxy-3,5-dimethylphenylamine)-9,9'-spirofluorene, tris(p-anisyl)amine, N,N,N',N'-tetrakis(4-methoxyphenyl)-1,1'-biphenyl-4,4'-diamine, 2,7-bis[N,N-bis(4-methoxy-phenyl)amino]-9,9-spirobifluorene, poly(3-hexylthiophene) (P3HT), poly(3,4-ethylenedioxythiophene)-poly(styrenesulfonate) (PEDOT:PSS), poly[bis(4-phenyl)(2,4,6-trimethylphenyl)amine] (PTAA), NiO and V$_2$O$_5$.

Furthermore, the compounds according to the invention used as HTMs may be combined with at least one further additive. Suitable additives are pyridine compounds such as tert-butylpyridine, imidazoles as disclosed in WO2013/026563, claims 1 to 15 and disclosed on pages 15 to 17 or polymer additives such as poly(4-vinylpyridine) or its copolymer with e.g. vinylstyrene or alkylmethacrylate. A preferred pyridine compound is tert-butylpyridine.

The compounds according to the invention used as the HTMs may be combined with lithium salts as described in Phys. Chem., Chem. Phys, 2013, 15, 1572-2579.

The usefulness of a pyridine compound is described in Sol. Energy Mater. & Solar Cells, 2007, 91, 424-426.

Furthermore, the compounds according to the invention used as HTMs may be combined with a p-dopant such as $N(C_6H_5Br)_3$, $SbCl_6$, $V_2O_5$, $MoO_3$, $WO_3$, $Re_2O_3$, $F_4$-TCNQ (tetrafluoro-tetracyanoquinodimethane), HAT-CN (1,4,5,8,9,11-hexaazatri-phenylene-hexacarbonitrile) F6-TCNNQ (1,3,4,5,7,8-hexafluorotetracyanonaphtho-quinodimethane, obtainable from Novaled), NDP-9 (a p-dopant obtainable from Novaled) or Co complex salts. Suitable dopants are described in Chem. Mater., 2013, 25, 2986-2990 or J. Am. Chem. Soc, 2011, 133, 18042. Also suitable [3]-radialenes as described in EP 2 180 029 A1 can be applied.

The invention furthermore relates to an electroluminescent arrangement comprising an upper electrode, a lower electrode, wherein at least one of said electrodes is transparent, an electroluminescent layer and optionally an auxiliary layer, wherein the electroluminescent arrangement comprises at least one compound of the formula (I). The preferences stated above likewise apply to the substrate. Especially, the at least one compound of the formula (I), (I.DP), (I.TRP), (I.TEP), (I.DP-MA-1), (I.DP-MA-2), (I.DP-DA-1), (I.DP-DA-2), (I.DP-DA-3), (I.DP-TRA-1), (I.DP-TEA-1), (I.TRP-MA-1), (I.TRP-MA-2), (I.TRP-MA-3), (I.TRP-DA-1), (I.TRP-DA-2), (I.TRP-DA-3), (I.TRP-DA-4), (I.TRP-DA-5), (I.TRP.TRA-1), (I.TRP-TEA-1), (I.TRP-TEA-2), (I.TRP-TEA-3), (I.TEP-MA-1), (I.TEP-MA-2), (I.TEP-DA-1), (I.TEP-DA-2), (I.TEP-DA-3), (I.TEP-DA-4), respectively, is employed in a hole-transporting layer or electron blocking layer.

The invention furthermore relates to an electroluminescent arrangement in form of an organic light-emitting diode (OLED). In an organic light emitting device, an electron blocking layer is disposed adjacent to an emissive layer. Blocking layers may be used to reduce the number of charge carriers (electrons or holes) and/or excitons that leave the emissive layer. An electron blocking layer may be disposed between emissive layer and an hole transport layer, to block electrons from leaving emissive layer in the direction of hole transport layer. Similarly, a hole blocking layer may be disposed between emissive layer and electron transport layer, to block holes from leaving emissive layer in the direction of electron transport layer.

The OLEDs can be employed for various applications, for example for monochromatic or polychromatic displays, for lighting applications or for medical and/or cosmetic applications, for example in phototherapy.

The organic electroluminescent device, particularly in form of an OLED, comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. Interlayers, which have, for example, an exciton-blocking function, may likewise be introduced between two emitting layers. However, it should be noted that each of these layers does not necessarily have to be present.

The organic electroluminescent device here may comprise one emitting layer or a plurality of emitting layers. If a plurality of emission layers is present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013). It is possible here for all emitting layers to be fluorescent or for all emitting layers to be phosphorescent or for one or more emitting layers to be fluorescent and one or more other layers to be phosphorescent.

The compound according to the invention in accordance with the embodiments indicated above can be employed here in different layers, depending on the precise structure. Preference is given to an organic electroluminescent device comprising a compound of the formula (I) or the preferred embodiments as hole-transport material in a hole-transport or hole-injection or electron-blocking layer or as matrix material for fluorescent or phosphorescent emitters, in particular for phosphorescent emitters. The preferred embodiments indicated above also apply to the use of the materials in organic electronic devices.

In a preferred embodiment of the invention, the compound of the formula (I) or the preferred embodiments is employed as hole-transport or hole-injection material in a hole-transport or hole-injection layer. The emitting layer here can be fluorescent or phosphorescent.

A hole-injection layer generally is a layer which facilitates electron injection from the anode to the organic layer. The hole-injection layer can be situated directly adjacent to the anode.

A hole-transport layer transports the holes from the anode to the emitting layer and is located between a hole-injection layer and an emitting layer.

To enhance the hole transport characteristics, doped hole transport layers can be employed. The architecture of actual OLEDs often improves quantum efficiency by using a graded heterojunction. In the graded heterojunction architecture, the composition of hole and electron-transport materials varies continuously within the emissive layer with a dopant emitter. The graded heterojunction architecture combines the benefits of both conventional architectures by improving charge injection while simultaneously balancing charge transport within the emissive region.

In still a further preferred embodiment of the invention, the compounds of the formula (I) or the preferred embodiments thereof are employed in an electron-blocking layer. An electron-blocking layer may be used to reduce the number of charge carriers (electrons) that leave the emissive layer. An electron-blocking layer usually is a layer which is directly adjacent to an emitting layer on the anode side. An electron blocking layer may be disposed between emissive layer and hole transport layer to block electrons from leaving the emissive layer in the direction of hole transport layer.

The compound of the formula (I) or the preferred embodiments thereof are particularly preferably employed in a hole-transport layer or electron blocking layer.

In a further preferred embodiment of the invention, the compound of the formula (I) or the preferred embodiments thereof are employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (I) or the preferred embodiments thereof are employed as matrix material for an emitting compound in an emitting layer, it is preferably employed in combination with one or more phosphorescent materials (triplet emitters). Phosphorescence in the sense of this invention is taken to mean the luminescence from an excited state having a spin multiplicity>1, in particular from an excited triplet state. For the purposes of this application, all luminescent complexes containing transition metals or lanthanoids, in particular all luminescent iridium, platinum and copper complexes, are to be regarded as phosphorescent compounds.

The mixture comprising the compound of the formula (I) or the preferred embodiments and the emitting compound comprises between 99.9 and 1% by weight, preferably between 99 and 10% by weight, particularly preferably between 97 and 60% by weight, in particular between 95 and 80% by weight, of the compound of the formula (I) or the preferred embodiments, based on the entire mixture comprising emitter and the compound of the formula (I). Correspondingly, the mixture comprises between 0.1 and 99% by weight, preferably between 1 and 90% by weight, particularly preferably between 3 and 40% by weight, in particular between 5 and 20% by weight, of the emitter, based on the entire mixture comprising emitter and the compound of the formula (I).

The present invention again furthermore relates to an organic field-effect transistor comprising a substrate having at least one gate structure, a source electrode and a drain electrode and at least one compound of the formula (I) above as a semiconductor material. The preferences stated above likewise apply to the organic field-effect transistor.

The present invention again furthermore relates to a substrate comprising a plurality of organic field-effect transistors, at least some of the field-effect transistors comprising at least one compound of the formula (I). The preferences stated above likewise apply to the substrate.

The invention furthermore relates to a semiconductor unit comprising at least one substrate as defined above.

Organic Solar Cells

A further object of the invention is the use of at least one compound of the general formula (I) as defined above in organic solar cells (OSCs). The compounds of the general formula (I) are used in particular as a hole transport material or electron blocking material in organic solar cells.

Organic solar cells generally have a layer structure and generally comprise at least the following layers: anode, photoactive layer and cathode. These layers are generally applied to a substrate suitable for this purpose. The structure of organic solar cells is described, for example, in US 2005/0098726 and US 2005/0224905.

The invention provides an organic solar cell which comprises a substrate with at least one cathode and at least one anode, and at least one compound of the general formula (I) as defined above as a material of at least one of the layers. The organic solar cell of the invention comprises at least one photoactive region. A photoactive region may comprise two layers, each of which has a homogeneous composition and forms a flat donor-acceptor heterojunction. A photoactive region may also comprise a mixed layer and form a donor-acceptor heterojunction in the form of a donor-acceptor bulk heterojunction.

Consequently, the invention also refers to an organic solar cell, comprising:
  a cathode,
  an anode,
  one or more photoactive regions comprising at least one donor material and at least one acceptor material in separate layers or in form of a bulk heterojunction layer,
  optionally at least one further layer selected from exciton blocking layers, electron conducting layers, hole transport layers,
wherein the organic solar cell comprises at least one compound of the formula (I) as defined above or of a composition comprising at least two different compounds of the general formula (I) as defined above.

In a first embodiment, the heterojunction can have a flat configuration (see: Two layer organic photovoltaic cell, C. W. Tang, Appl. Phys. Lett., 48 (2), 183-185 (1986) or N. Karl, A. Bauer, J. Holzäpfel, J. Marktanner, M. Möbus, F. Stölzle, Mol. Cryst. Liq. Cryst., 252, 243-258 (1994).

In a second embodiment, the heterojunction can be a bulk heterojunction, also referred to as an interpenetrating donor-acceptor network. Organic photovoltaic cells with a bulk heterojunction are described, for example, by C. J. Brabec, N. S. Sariciftci, J. C. Hummelen in Adv. Funct. Mater., 11 (1), 15 (2001) or by J. Xue, B. P. Rand, S. Uchida and S. R. Forrest in J. Appl. Phys. 98, 124903 (2005).

The compounds of the general formula (I) can be used in cells with MiM, pin, pn, Mip or Min structure (M=metal, p=p-doped organic or inorganic semiconductor, n=n-doped organic or inorganic semiconductor, i=intrinsically conductive system of organic layers; see, for example, J. Drechsel et al., Org. Electron., 5 (4), 175 (2004) or Maennig et al., Appl. Phys. A 79, 1-14 (2004)).

The compounds of the formula (I) can also be used in tandem cells. Tandem cells are described, for example, by P. Peumans, A. Yakimov, S. R. Forrest in J. Appl. Phys, 93 (7), 3693-3723 (2003). A tandem cell consists of two or more than two subcells. A single subcell, some of the subcells or all subcells may have photoactive donor-acceptor heterojunctions. Each donor-acceptor-heterojunction may be in the form of a flat heterojunction or in the form of a bulk heterojunction. The subcells which form the tandem cell may be connected in parallel or in series. There is preferably an additional recombination layer in each case between the individual subcells. The individual subcells have the same polarity, i.e. generally either only cells with normal structure or only cells with inverse structure are combined with one another.

Suitable substrates for organic solar cells are, for example, oxidic materials, polymers and combinations thereof. Preferred oxidic materials are selected from glass, ceramic, $SiO_2$, quartz, etc. Preferred polymers are selected from polyethylene terephthalates, polyolefins (such as polyethylene and polypropylene), polyesters, fluoropolymers, polyamides, polyurethanes, polyalkyl (meth)acrylates, polystyrenes, polyvinyl chlorides and mixtures and composites.

Suitable electrodes (cathode, anode) are in principle semiconductors, metal alloys, semiconductor alloys and combinations thereof. Preferred metals are those of groups 2, 8, 9, 10, 11 or 13 of the periodic table, e.g. Pt, Au, Ag, Cu, Al, In, Mg or Ca. Preferred semiconductors are, for example, doped Si, doped Ge, indium tin oxide (ITO), fluorinated tin oxide (FTO), gallium indium tin oxide (GITO), zinc indium tin oxide (ZITO), etc. Preferred metal alloys are for example alloys based on Pt, Au, Ag, Cu, etc.

The material used for the electrode facing the light (the anode in a normal structure, the cathode in an inverse structure) is preferably a material at least partly transparent to the incident light. This preferably includes electrodes which have glass and/or a transparent polymer as a carrier material. The electrical contact connection is generally effected by means of metal layers and/or transparent conductive oxides (TCOs). These preferably include ITO, doped ITO, FTO (fluorine doped tin oxide), AZO (aluminum doped tin oxide), ZnO, $TiO_2$, Ag, Au, Pt. In a specific embodiment, the material used for the electrode facing away from the light (the cathode in a normal structure, the anode in an inverse structure) is a material which at least partly reflects the incident light. This includes metal films, preferably of Ag, Au, Al, Ca, Mg, In, and mixtures thereof.

In a first embodiment, the organic solar cells according to the invention are present as an individual cell with flat heterojunction and normal structure. In a specific embodiment, the cell has the following structure:
    an at least partly transparent conductive layer (top electrode, anode)
    a hole-conducting layer (hole transport layer, HTL)
    a layer which comprises a donor material
    a layer which comprises an acceptor material
    an exciton-blocking and/or electron-conducting layer
    a second conductive layer (back electrode, cathode)

In a second embodiment, the organic solar cells according to the invention are present as an individual cell with a flat heterojunction and inverse structure. In a specific embodiment, the cell has the following structure:
    an at least partly transparent conductive layer (cathode)
    an exciton-blocking and/or electron-conducting layer
    a layer which comprises an acceptor material
    a layer which comprises a donor material
    a hole-conducting layer (hole transport layer, HTL)
    a second conductive layer (back electrode, anode)

In a third embodiment, the organic solar cells according to the invention are present as an individual cell with normal structure and have a bulk heterojunction. In a specific embodiment, the cell has the following structure:
    an at least partly transparent conductive layer (anode)
    a hole-conducting layer (hole transport layer, HTL)
    a mixed layer which comprises a donor material and an acceptor material, which form a donor-acceptor heterojunction in the form of a bulk heterojunction
    an electron-conducting layer
    an exciton-blocking and/or electron-conducting layer
    a second conductive layer (back electrode, cathode)

In a fourth embodiment, the organic solar cells according are present as an individual cell with inverse structure and have a bulk heterojunction.

Examples of different kinds of donor-acceptor heterojunctions are a donor-acceptor double layer with a flat heterojunction, or the heterojunction is configured as a hybrid planar-mixed heterojunction or gradient bulk heterojunction or annealed bulk heterojunction. The production of a hybrid planar-mixed heterojunction is described in Adv. Mater. 17, 66-70 (2005). In this structure, mixed heterojunction layers which were formed by simultaneous evaporation of acceptor and donor material are present between homogeneous donor and acceptor material. In a further specific embodiment, the donor-acceptor-heterojunction is in the form of a gradient bulk heterojunction. In the mixed layers composed of donor and acceptor materials, the donor-acceptor ratio changes gradually. In a further specific embodiment, the donor-acceptor-heterojunction is configured as an annealed bulk heterojunction; see, for example, Nature 425, 158-162, 2003. The process for producing such a solar cell comprises an annealing step before or after the metal deposition. As a result of the annealing, donor and acceptor materials can separate, which leads to more extended percolation paths.

Solid-State Dye Sensitized Solar Cells (DSSCs) and Perovskite Solar Cells.

A further object of the invention is the use of at least one compound of the general formula (I), (I.DP), (I.TRP), (I.TEP), (I.DP-MA-1), (I.DP-MA-2), (I.DP-DA-1), (I.DP-DA-2), (I.DP-DA-3), (I.DP-TRA-1), (I.DP-TEA-1), (I.TRP-MA-1), (I.TRP-MA-2), (I.TRP-MA-3), (I.TRP-DA-1), (I.TRP-DA-2), (I.TRP-DA-3), (I.TRP-DA-4), (I.TRP-DA-5), (I.TRP.TRA-1), (I.TRP-TEA-1), (I.TRP-TEA-2), (I.TRP-TEA-3), (I.TEP-MA-1), (I.TEP-MA-2), (I.TEP-DA-1), (I.TEP-DA-2), (I.TEP-DA-3), (I.TEP-DA-4) as defined above in solid-state dye sensitized solar cells (DSSCs) or Perovskite solar cells. These compounds are used in particular as replacement of the liquid electrolyte in dye sensitized solar cells and as a hole transport material in Perovskite solar cells.

The compounds of the invention, i.e. at least one compound of formula (I), (I.DP), (I.TRP), (I.TEP), (I.DP-MA-1), (I.DP-MA-2), (I.DP-DA-1), (I.DP-DA-2), (I.DP-DA-3), (I.DP-TRA-1), (I.DP-TEA-1), (I.TRP-MA-1), (I.TRP-MA-2), (I.TRP-MA-3), (I.TRP-DA-1), (I.TRP-DA-2), (I.TRP-DA-3), (I.TRP-DA-4), (I.TRP-DA-5), (I.TRP.TRA-1), (I.TRP-TEA-1), (I.TRP-TEA-2), (I.TRP-TEA-3), (I.TEP-MA-1), (I.TEP-MA-2), (I.TEP-DA-1), (I.TEP-DA-2), (I.TEP-DA-3), (I.TEP-DA-4), respectively can be used advantageously as HTMs in perovskite solar cells. They can also be used to replace the liquid electrolyte of conventional DSSCs to provide solid-state DSSC devices.

The compounds of the invention are then preferably employed in a photosensitized nanoparticle layer comprising a sensitizing dye or a perovskite and at least one compound of the general formula (I) according to the invention.

In a first embodiment, the compounds of the invention are employed in a DSSC. The construction of a DSSC is generally based on a transparent substrate, which is coated with a transparent conductive layer, the working electrode. An n-conductive metal oxide is generally applied to this electrode or in the vicinity thereof, for example a nanoporous $TiO_2$ layer of approximately 2 to 20 μm thickness. On the surface thereof, in turn, a monolayer of a light-sensitive dye is typically adsorbed, which can be converted to an excited state by light absorption. This layer which carries the light-sensitive dye is generally referred to as the light absorbing layer of the DSSC. The counter electrode may optionally have a catalytic layer of a metal, for example platinum, with a thickness of a few μm.

Suitable are in principle all sensitizing dyes, as long as the LUMO energy state is marginally above the conduction bandedge of the photoelectrode to be sensitized. Examples of dyes are disclosed in Nanoenergy, de Souza, Flavio Leandro, Leite, Edson Roberto (Eds.), Springer, ISBN 978-3-642-31736-1, pages 58 to 74 or black dyes as described in U.S. Pat. No. 8,383,553. Preferred dyes are described in WO 2015049031 A1 which is incorporated herein by reference.

In a second embodiment, the compounds of the invention are employed in a Perovskite solar cell. Suitable Perovskites for Perovskite solar cells (PSCs) are known in the art. In principle, the perovskite material comprised in the devices according to the invention may be part of the charge transport layer but may also be part of another layer or scaffold within the device.

Suitable perovskite materials may comprise two halides corresponding to formula $Xa_{p-x}Xb(x)$, wherein Xa and Xb are each independently selected from Cl, Br, or I, and x is greater than 0 and less than 3. Suitable pervoskite materials are also disclosed in WO 2013/171517, claims 52 to 71 and claims 72 to 79, which is entirely incorporated herein by reference. Suitable pervoskite materials are $CsSnI_3$, $CH_3NH_3PbI_2Cl$, $CH_3NH_3PbI_3$, $CH_3NH_3Pb(I_{1-x}Br_x)_3$, $CH_3NH_3SnI_2Cl$, $CH_3NH_3SnI_3$ or $CH_3NH_3Sn(I_{1-x}Br_x)_3$, with $0<x<1$.

Preferred perovskite materials are disclosed in WO 2013/171517 on page 18, lines 5 to 17. As described, the perovskite is usually selected from $CH_3NH_3PbBrI_2$, $CH_3NH_3PbBrCl_2$, $CH_3NH_3PbIBr_2$, $CH_3NH_3PbICl_2$, $CH_3NH_3SnF_2Br$, $CH_3NH_3SnF_2I$ and $(H_2N=CH-NH_2)PbI_{3z}Br_{3(1-z)}$, wherein z is greater than 0 and less than 1.

The charge transport layer according to the invention as described before or the device according to the invention as described before or below may furthermore comprise an insulator such as alumina as described in Michael M. Lee et al, Science, 338, 643, 2012.

The charge transport layer according to the invention or the device according to the invention as described before or below may furthermore comprise semiconductor oxide nanoparticles. The charge transport layer according to the invention or the device according to the invention preferably comprises semiconductor oxide nanoparticles.

According to a preferred embodiment of the invention, the semiconductor is based on material selected from the group of Si, $TiO_2$, $SnO_2$, $Fe_2O_3$, $WO_3$, ZnO, $Nb_2O_5$, CdS, ZnS, PbS, $Bi_2S_3$, CdSe, GaP, InP, GaAs, CdTe, $CuInS_2$, and/or $CuInSe_2$.

Preferably, the charge transport layer according to the invention as described before is present on a glass support or plastic or metal foil, optionally together with a dense layer of $TiO_2$. Preferably, the support is conductive.

The present invention furthermore relates to a electronic device or optoelectronic device comprising a charge transport layer as described or preferably described before. Preferably, the invention relates furthermore to a solid-state dye-sensitized solar cell comprising a charge transport layer as described or preferably described before. Suitable device structures according to the invention comprising further a mixed halide perovskite are described in WO 2013/171517, claims 52 to 71 and claims 72 to 79, which is entirely incorporated herein by reference.

Suitable device structures according to the invention comprising further a dielectric scaffold together with perovskite material are described in WO 2013/171518, claims 1 to 90 or WO 2013/171520, claims 1 to 94 which are entirely incorporated herein by reference.

Suitable device structures according to the invention comprising further a semiconductor and a perovskite material are described in WO 2014/020499, claims 1 and 3 to 14, which is entirely incorporated herein by reference The surface-increasing scaffold structure described therein comprises nanoparticles which are applied and/or fixed on a support layer, e.g. porous $TiO_2$.

Suitable device structures according to the invention comprising a planar heterojunction are described in WO 2014/045021, claims 1 to 39, which is entirely incorporated herein by reference. Such a device is characterized in having a thin film of a light-absorbing or light-emitting perovskite disposed between n-type (electron conducting) and p-type (hole-conducting) layers. Preferably, the thin film is a compact thin film. Additionally, the invention relates to a method of preparing an electrochemical device and/or optoelectronic device as described or preferably described before, the method comprising the steps of:

providing a first and a second electrode;

providing a charge transport layer according to the invention as described before. There are no restrictions per se with respect to the choice of the first and second electrode. The substrate may be rigid or flexible.

Abbreviations which have been used in the examples that follow are: a/a for area percentage; Al for aluminium; BPhen for 4,7-diphenyl-1,10-phenanthroline, can be purchased from Luminescence Technology Corp., Taiwan; C60 for fullerene, can be purchased from CreaPhys GmbH Dresden, Germany; EBL for electron blocking layer, EIL for electron injection layer; EML for emission layer; ETL for electron transport layer; F6TCNNQ for 2,2'-(perfluoronaphthalene-2,6-diylidene)dimalononitrile, can be purchased from Novaled AG, Germany; GC for gas chromatography; HAT-CN or $HAT(CN)_6$ for 1,4,5,8,9,11-hexaazatriphenylene-hexanitrile, can be purchased from Jilin OLED Material Tech Co., LTD, China; HBL for hole blocking layer; HIL for hole injection layer; HPLC for high-performance liquid chromatography; HTL for hole transport layer; iPrOH for isopropanol; $Ir(MDQ)_2(acac)$ for bis(2-methyldibenzo[f,h]quinoxaline)(acetylacetonate)iridium(III), can be purchased from Luminescence Technology Corp., Taiwan; ITO for indium tin oxide; LiQ for 8-hydroxyquinolatolithium, can be purchased from Nichem Fine Technology Co. Ltd, Taiwan; NDP-9, NHT-18, Novaled n-dopant, can be purchased from Novaled AG, Germany; NPB for N,N'-bis(naphthalen-1-yl)-N,N'-bis(phenyl)benzidine, can be purchased from Sensient, Germany; OMe for methoxy; $Pd(dba)_2$ for palladium(0) bis(dibenzylideneacetone); $Pd_2(dba)_3$ for tris(dibenzylideneacetone)dipalladium(0); RuPhos for 2-dicyclohexylphosphino-2',6'-diisopropoxybiphenyl; SPhos for 2-dicyclohexyl-phosphino-2',6'-dimethoxybiphenyl; TDSF for 1,3,5-triazine,2,4-diphenyl-6-(9,9'-spiro-b/[9H-fluoren]-2-yl; $T_g$ for glass temperature; THF for tetrahydrofuran; v/v for volume/volume; ZnPc for zinc phthalocyanine, can be purchased from CreaPhys GmbH Dresden, Germany.

Further definitions: Room temperature means a temperature range of from ca. 20 to 25° C. Over night means a time period in the range of from 14 to 20 h.

PREPARATION EXAMPLES

I. Preparation of Intermediates

The starting materials used in the examples were either commercially available or could be synthesized following routine laboratory practice as outlined below.

a) (1-phenylvinyl)benzene Compounds a1) 1-bromo-4-(1-phenylvinyl)benzene

To 388 g (1.15 mol) of phenyllmagnesium chloride (3 M in THF) was added a solution of 250 g (0.96 mol) of 4'-bromoacetophenone in 500 mL of THF. After 1 h, the reaction mixture was poured onto aqueous hydrochloric acid. The phases were separated and the organic phase was washed with aqueous $NaHCO_3$ solution, saturated aqueous NaCl solution and dried with $Na_2SO_4$. After evaporated to dryness, the residue was dissolved in toluene and 3.30 g (0.02 mol) of p-toluenesulfonic acid was added. The reaction mixture was refluxed, and the forming water azeotropically removed by a Dean-Stark trap. After the water removal was completed, the solvent was evaporated and the crude product was crystallized from ethanol to obtain the title compound as a yellow solid (230 g, 93%; purity (GC): 98.6%).

a2) 1-chloro-4-(1-phenylvinyl)benzene

To 93.2 g (277 mmol) of phenylmagnesium chloride (3 M in THF) was added a solution of 50 g (231 mmol) 4'-chloroacetophenone in 100 mL of THF. After 1 h, the reaction mixture was poured onto aqueous hydrochloric acid. The phases were separated and the organic phase was washed with aqueous $NaHCO_3$ solution and saturated aqueous NaCl solution, dried with $Na_2SO_4$ and evaporated to dryness. The residue was dissolved in toluene and 0.79 g (4.6 mmol) of p-toluenesulfonic acid was added. The reaction mixture was refluxed, and the forming water was azeotropically removed by a Dean-Stark trap. After the water removal was completed, the solvent was evaporated and the crude product was crystallized from ethanol to obtain the title compound as a yellow solid (30.3 g, 61%; purity (GC): 97.7%).

a3) 1-nitro-4-(1-phenylvinyl)benzene

A solution of 44.0 g (123 mmol) methyltriphenylphosphonium bromide in 200 mL of THF was cooled to 0° C. before 2.58 g (97 mmol) sodium hydride were added and the mixture stirred for 0.5 h. Then, 20.0 g (88.0 mmol) of 4'-nitrobenzophenone were added and the reaction mixture was stirred at room temperature for 2 h. 500 mL of water were added. The phases were separated and the organic phase was then washed with aqueous NaOH solution, three times with water and saturated aqueous NaCl solution. The organic phase was dried with $Na_2SO_4$ and evaporated to dryness. After column chromatography (ethyl acetate/n-heptane) the title compound was obtained as a yellow oil (13.61 g, 69%; purity (HPLC at 210 nm): 98.2%).

a4) 4,4'-(ethene-1,1-diyl)bis(bromobenzene)

A suspension of 157 g (0.46 mol) bis(4-bromophenyl)methanone in a mixture of 500 mL of THF and toluene was added to 184 mL (0.55 mol) of methylmagnesium chloride (3 M in THF). The reaction mixture was stirred overnight and then poured onto aqueous hydrochloric acid. The phases were separated and the organic phase was washed with aqueous $NaHCO_3$ solution and saturated aqueous NaCl solution, dried with $MgSO_4$ and evaporated to dryness. The residue was dissolved in toluene and 0.79 g (4.6 mmol) of p-toluenesulfonic acid was added. The reaction mixture was refluxed under simultaneous water separation by distillation. After the water removal was complete, the solvent was evaporated and the crude product crystallized from ethanol to obtain the title compound as yellow needles (113 g, 73%; purity (GC): 99.8%).

a5) 4,4'-(ethene-1,1-diyl)bis(chlorobenzene)

In 150 mL of THF were dissolved 30 g (0.12 mol) of bis(4-chlorophenyl)methanone and 64 g (0.18 mol) of methyltriphenylphosphonium bromide. The solution was cooled to −20° C. and 26 g (0.27 mol) of sodium tert-butanolate was added. The mixture was stirred for 1 h and a mixture of 500 mL of acetone and tert-butyl methyl ether was added. After filtration, the solvent was removed and the residue was purified by column chromatography (hexane/$CH_2Cl_2$) to give 15.5 g (52%; purity (GC): 99.1%) of the title compound.

b) (prop-1-en-2-yl)benzene Compounds b1) 1-bromo-4-(prop-1-en-2-yl)benzene

The title compound was prepared in analogy to the process described in literature: *J. Org. Chem.*, 2015, 80, 11388 c) 1-methyl-1,3,3-triphenylindane Compounds c1) 1,3-bis(4-bromophenyl)-1-methyl-3-phenyl-2,3-dihydro-1H-indene (mixture of diastereomers)

In 300 mL of 1,2-dichloroethane was dissolved 50.0 g (0.10 mol) of 1-bromo-4-(1-phenylvinyl)benzene from a1), and 46.4 g (0.48 mol) of methanesulfonic acid was added. The reaction mixture was stirred at 80° C. over night. After cooling to room temperature the solvent was evaporated and the mixture was quenched with tert-butyl methyl ether and aqueous $NaHCO_3$ solution. The phases were separated and the organic phase was washed for three times with water and and saturated aqueous NaCl solution, dried with $Na_2SO_4$ and evaporated to dryness to obtain the title compound as a light brown solid (50.0 g, quantitative; purity (HPLC): 98.8%). HPLC analysis at 220 nm indicated a purity of 95% and a ratio of the diastereomers of approximately 1:1.

1:1 Mixture of diastereomers: $^{13}C$ NMR (101 MHz, $CDCl_3$): δ 149.79 (10, q), 149.71 (10, q), 148.47 (10, q), 148.45 (10, q), 148.10 (20, q), 147.72 (10, q), 147.60 (10, q), 146.27 (10, q), 146.15 (10, q), 131.15 (20, p), 131.02 (20, p), 130.94 (20, p), 130.78 (20, p), 130.62 (20, p), 130.53 (20, p), 128.77 (20, p), 128.75 (20, p), 128.64 (20, p), 128.58 (20, p), 128.23 (20, p), 127.90 (40, p), 127.33 (20, p), 127.31 (20, p), 126.40 (10, p), 126.10 (10, p), 125.05 (10, p), 125.03 (10, p), 120.24 (10, q), 120.01 (10, q), 119.74 (10, q), 119.65 (10, q), 61.12 (20, s), 60.61 (20, q), 50.95 (20, q), 29.07 (10, t), 28.98 (10, t).

c2) 1,3-bis(4-chlorophenyl)-1-methyl-3-phenyl-2,3-dihydro-1H-indene

Under an inert atmosphere, 50.0 g (0.12 mol) of 1-chloro-4-(1-phenylvinyl)benzene from a2) was dissolved in 300 mL of 1,2-dichloroethane, 56.0 g (0.58 mol) of methanesulfonic acid was added and the reaction mixture was stirred at 80° C. over night. After cooling to room temperature the solvent was evaporated and the mixture was quenched with tert-butyl methyl ether and 5% aqueous $NaHCO_3$ solution. The phases were separated and the organic phase was washed for three times with water and saturated aqueous NaCl solution, dried with $Na_2SO_4$ and evaporated to dryness to obtain the title compound as a light brown solid (52.0 g, quantitative; purity (GC): 97.6%; purity (HPLC at 220 nm): 93.8%. The ratio of the diastereomers was about 1:1.

1:1 Mixture of diastereomers: $^{13}C$ NMR (101 MHz, $CDCl_3$): δ 149.86 (10, q), 149.78 (10, q), 148.56 (10, q), 148.54 (10, q), 147.85 (10, q), 147.58 (20, q), 147.06 (10, q), 146.36 (10, q), 145.60 (10, q), 132.04 (10, q), 131.80 (10, q), 131.59 (10, q), 131.47 (10, q), 130.21 (20, p), 130.13 (20, p), 128.64 (20, p), 128.59 (20, p), 128.36 (20, p), 128.33 (20, p), 128.21 (20, p), 128.18 (20, p), 128.03 (20, p), 127.96 (20, p), 127.87 (40, p), 127.80 (20, p), 127.32 (20, p), 127.30 (20, p), 126.37 (10, p), 126.08 (10, p), 125.05 (10, p), 125.03 (10, p), 61.20 (20, s), 60.53 (10, q), 50.88 (10, q), 29.13 (10, t), 29.08 (10, t).

c3) 1-methyl-1,3-bis(4-nitrophenyl)-3-phenyl-2,3-dihydro-1H-indene

Under an inert atmosphere, 5.0 g (11 mmol) of 1-nitro-4-(1-phenylvinyl)benzene from a3) was dissolved in 30 mL of 1,2-dichloroethane, 7.21 g (75 mmol) of methanesulfonic acid was added and the reaction mixture was stirred at 80° C. for 2 days. After cooling to 0° C., n-heptane was added and the formed suspension was filtered. The solid was washed with n-heptane and water and dried to obtain the title compound as a white solid (3.06 g, 64%; purity (HPLC at 220 nm): 99.8%; ratio of the diastereomers 1:50).

Major isomer: $^{13}$C NMR (75 MHz, CDCl$_3$): δ 155.83, 155.78, 148.35, 147.94, 146.34, 145.81, 143.88, 129.54, 128.50, 128.40, 128.05, 127.96, 127.63, 127.29, 126.63, 125.16, 123.24, 122.96, 60.95, 60.47, 51.50, 29.50.

c4) 5-bromo-1,3,3-tris(4-bromophenyl)-1-methyl-2,3-dihydro-1H-indene 30.0 g (888 mmol) of 4,4'-(ethene-1,1-diyl)bis(bromobenzene) from a4) was suspended in 240 mL of methanesulfonic acid and heated to 120° C. over night under argon. After cooling to room temperature, the mixture was poured onto water, extracted with CH$_2$Cl$_2$ and the organic phase was dried over MgSO$_4$. The compound was purified by column chromatography (heptane/5% CH$_2$Cl$_2$) to give the title compound as a white solid (11.3 g, 38%; purity (HPLC at 220 nm): 98.0%).

$^{13}$C NMR (101 MHz, CDCl$_3$): δ 150.21 (q), 148.72 (q), 147.10 (q), 146.12 (q), 144.61 (q), 131.47 (p), 131.40 (p), 131.15 (p), 131.0 (p)9, 130.28 (p), 130.22 (p), 129.97 (p), 128.51 (p), 126.80 (p), 121.36 (q), 120.79 (q), 120.55 (q), 120.03 (q), 60.97 (s), 60.18 (q), 50.63 (q), 28.90 (t).

c5) 5-chloro-1,3,3-tris(4-chlorophenyl)-1-methyl-2,3-dihydro-1H-indene

Route a):
30 g (0.12 mol) of 4,4'-(ethene-1,1-diyl)bis(chlorobenzene) from a5) was suspended in 120 mL of methanesulfonic acid and heated to 120° C. over night. After cooling to room temperature, the mixture was poured on water, extracted with CH$_2$Cl$_2$ and the organic phase was dried over MgSO$_4$. The compound was purified by column chromatography (heptane/CH$_2$Cl$_2$) to give the title compound as a white solid (15.6 g, 52%; purity (GC): 99.9%).

Route b):
A suspension of 100 g (0.40 mol, 1.0 eq.) of 4,4'-(ethene-1,1-diyl)bis(chlorobenzene) from a5) and 97 g (1.0 mol, 2.5 eq.) of methanesulfonic acid in 600 mL of 1,2-dichloroethane was heated to 100° C. for 16 h under an argon atmosphere. Reaction control (HPLC at 220 nm) indicated complete conversion and the formation of 82.5% of the title product. The mixture was concentrated and then quenched with an aqueous sodium bicarbonate solution. Water (1.2 L) was added, and then the mixture was extracted with tert-butyl methyl ether.

The organic layer was washed with water and saturated brine, followed by drying over anhydrous Na$_2$SO$_4$. After removal of the organic solvent, 105 g of the crude title product was obtained. This was dissolved in refluxing heptane, to which slowly isopropanol was added. The solution was cooled and a few seed crystals were added at a temperature of 50 to 55° C. On cooling to room temperature, a precipitate was formed which was dried at 60° C./5 mbar to give the title compound (54 g; 54%) as a solid in a purity of 98.6% (HPLC at 220 nm).

$^{13}$C NMR (101 MHz, CDCl$_3$): δ 150.01 (q), 148.24 (q), 146.68 (q), 145.72 (q), 144.16 (q), 133.29 (q), 132.56 (q), 132.32 (q), 131.87 (q), 129.89 (p), 129.84 (p), 128.49 (p), 128.47 (p), 128.15 (p), 128.10 (p), 128.08 (p), 127.03 (p), 126.37 (p), 61.14 (s), 60.01 (q), 50.49 (q), 29.04 (t).

c6) 1-(4-bromophenyl)-1-methyl-3,3-diphenyl-2,3-dihydro-1H-indene 17.1 g (86.7 mmol) of 1-bromo-4-(prop-1-en-2-yl)benzene from b1), 23.7 g (85.0 mmol) of trityl chloride and 11.8 g (85.0 mmol) of K$_2$CO$_3$ were suspended in 340 mL of CH$_2$Cl$_2$ followed by addition of 85 mL (85 mmol) of boron trichloride solution (1.0 M in CH$_2$Cl$_2$). The mixture was heated to reflux over night. After cooling, the mixture was poured onto a mixture of aqueous NaOH solution and methyltetrahydrofuran. The phases were separated and the aqueous phase was extracted two times with CH$_2$Cl$_2$. The combined organic phases were washed with saturated aqueous NaCl solution, dried with MgSO$_4$ and evaporated to dryness. After purification by column chromatography (heptane/CH$_2$Cl$_2$) the crude product was crystallized from heptane. The title compound was obtained as white crystals (22.1 g, 59%; purity (GC): 100%).

$^{13}$C NMR (101 MHz, CDCl$_3$): δ 149.83 (q), 148.97 (q), 148.38 (q), 148.31 (q), 146.95 (q), 130.86 (p), 128.78 (p), 128.76 (p), 128.68 (p), 128.03 (p), 127.72 (p), 127.63 (p), 127.49 (p), 127.10 (p), 126.12 (p), 125.83 (p), 124.88 (p), 119.51 (q), 61.19 (s), 60.92 (q), 50.92 (q), 28.90 (t).

c7) 1-(4-bromophenyl)-3-methyl-1,3-diphenyl-2,3-dihydro-1H-indene

To 104 g (307 mmol, 1.00 eq.) of (4-bromophenyl)diphenylmethanol dissolved in 600 mL of chlorobenzene were added 38.2 g (323 mmol, 1.05 eq.) of alpha methyl-styrene, followed by 11.6 g (77 mmol, 0.25 eq.) of triflic acid. The red mixture was heated to 110° C. external temperature for 12 h. After cooling, the triflic acid was neutralized by adding potassium carbonate. The reaction mixture was then reduced to ca. half of its volume on a rotavapor.

The residue was filtered over silica gel. The solvent was evaporated and the residue was purified by fractional recrystallization from either heptane or binary and ternary mixtures of heptane with toluene and iso-propanol. Diastereomerically enriched fractions were obtained by fractional recrystallizations. A total yield of 77.7 g (58%) of colorless solids was obtained.

Diastereomer 1: $^{13}$C NMR (75 MHz, CD$_2$Cl$_2$) δ 150.84 (q), 149.51 (q), 148.88 (q), 148.58 (q), 147.13 (q), 131.14 (p), 131.03 (p), 129.10 (p) (p), 128.61 (p), 128.40 (p), 128.18 (p), 127.65 (p), 127.52 (p), 127.36 (p), 126.73 (p), 126.12 (p), 125.74 (p), 120.09 (q), 61.43 (s), 61.08 (q), 51.68 (q), 29.57 (t).

Diastereomer 2: $^{13}$C NMR (75 MHz, CD$_2$Cl$_2$) δ 151.04 (q), 149.68 (q), 148.84 (q), 148.55 (q), 147.47 (q), 131.51 (p), 131.18 (p), 129.10 (p), 128.39 (p), 128.24 (p), 128.21 (p), 127.67 (p), 127.52 (p), 127.39 (p), 126.41 (p), 126.15 (p), 125.72 (p), 120.46 (q), 61.60 (s), 61.15 (q), 51.72 (q), 29.51 (t).

c8) 1,1-bis(4-chlorophenyl)-3-methyl-3-phenyl-2,3-dihydro-1H-indene

In 1.2 L of chlorobenzene was dissolved 449 g (1.36 mol, 1.0 eq.) of bis(4-chlorophenyl) phenylmethanol. At 20° C. internal temperature, 30.2 mL (34.1 mmol, 0.25 eq.) of trifluoromethanesulfonic acid was added though a dropping funnel, which was then rinsed with 100 mL of chlorobenzene.

A slightly exothermic reaction was observed, resulting in a red-brown solution. Then, alpha-methylstyrene (161 g, 1.36 mol, 1.0 eq.) was added through a dropping funnel. The dropping funnel was rinsed with another 400 mL of chlorobenzene. The reaction mixture was heated to an internal temperature of 110° C. After 6.5 h at 110° C., an azeotropic distillation was started at a pressure of 500-600 mbar. 200 mL of a water/chlorobenzene azeotrope was collected.

This was followed by the slow addition of 16 g (0.13 mol, 0.1 eq.) of alpha-methylstyrene. After 1 h, the reaction was cooled to room temperature and stirred over night. It was then quenched by the addition of a solution of 48 g of sodium bicarbonate in 500 mL of water. At 40° C., the dark brown organic layer was separated. To this was added 250 mL of water, and then subjected to azeotropic distillation at an internal temperature of 70-85° C. and a pressure of 500-600 mbar. This resulted in a residual volume of ca. 700 mL, whilst a total volume of 2 L was distilled off from the reaction mixture.

The product was crystallized by the addition of 1.5 L of iso-propanol to the residue. The reaction flask was rinsed with 250 mL of iso-propanol, with witch the filter cake was washed. The reaction flask was further washed with 500 mL with a 35:65 v/v mixture of iso-propanol and n-heptane. The wet product was re-suspended twice in 250 mL 35:65 v/v iso-propanol/heptane and finally dried at 40° C./5 mbar to give 295.1 g of an off-white product. An additional crop of product was obtained by concentrating the combined mother- and washing liquors to 150 mL, followed by crystallization and washing the second crop twice with 35:65 v/v iso-propanol/n-heptane, to give another 19.6 g of product after drying. Total yield 53.7% with a GC purity of 97%.

$^{13}$C NMR (75 MHz, CD$_2$Cl$_2$): δ 150.59 (q), 149.11 (q), 148.39 (q), 147.27 (q), 145.74 (q), 132.32 (q), 131.93 (q), 130.47 (p, two signals overlapping), 128.47 (p), 128.25 (p), 128.19 (p), 128.00 (p), 127.50 (p), 127.32 (p), 127.16 (p), 126.00 (p), 125.65 (p), 61.32 (s), 60.44 (q), 51.51 (q), 29.46 (t).

c9) Mixture of 3,3-bis(4-chlorophenyl)-1-methyl-5-nitro-1-(4-nitrophenyl)-2,3-dihydro-1H-indene and 1,1-bis(4-chlorophenyl)-3-methyl-5-nitro-3-(4-nitrophenyl)-2,3-dihydro-1H-indene 85.9 g (0.20 mol, 1.0 eq.) of 1,1-bis(4-chlorophenyl)-3-methyl-3-phenyl-2,3-dihydro-1H-indene from c8) were dissolved under an inert atmosphere in a mixture of 300 mL of chloroform and 100 mL of glacial acetic acid. To this were added 50 mL (0.53 mol, 2.6 eq.) of acetic anhydride. The solution was stirred, until a homogenous solution was obtained and then cooled to 0° C. A mixture of 17 mL (0.40 mol, 2 eq.) of fuming nitric acid and 14 mL (0.26 mol, 1.3 eq.) of sulfuric acid (96%) was added slowly within 90 minutes, whilst an internal temperature between −5 and +5° C. was maintained. Stirring at 0° C. was continued for another 15 minutes, then the reaction mixture was allowed to warm to ambient temperature within 30 minutes, and then quenched by the addition of 100 mL of water.

Analysis of the organic layer by HPLC at 220 nm indicated the formation of 75% of the title products, along with 11% of a major mononitrated impurity.

The organic layer was washed twice with 20% aqueous sodium hydroxide and then dried over anhydrous Na$_2$SO$_4$. Removal of the solvent gave the crude product as a sticky foam. The foam was dissolved at 60° C. in 100 mL of ethyl acetate, which resulted in the spontaneous crystallization of one isomer. Recrystallization from 200 mL ethyl acetate gave a solid, which was filtered off, washed for three times with ethyl acetate to give 24.7 g of a material, which contained 92% of 3,3-bis(4-chlorophenyl)-1-methyl-5-nitro-1-(4-nitrophenyl)-2,3-dihydro-1H-indene.

Evaporation of the mother liquor and dissolving the residue in 50 mL of toluene at 60° C. gave a solution, from which on cooling to room temperature a white solid spontaneously crystallized. This was filtered off, and washed twice. Another recrystallization of this material from 50 mL of toluene gave a solid, which was washed twice with toluene to give after drying 16.1 g of the regioisomer 1,1-bis(4-chlorophenyl)-3-methyl-5-nitro-3-(4-nitrophenyl)-2,3-dihydro-1H-indene in a purity of 96%).

The mother liquors of the above two final recrystallizations were combined and evaporated to dryness. Crystallization of the residue from a mixture of 60 mL of heptane and 30 mL of iso-propanol (60° C. to 20° C.) gave a solid, which was filtered off and washed twice with 10 mL of iso-propanol to give another 6.1 g of 1,1-bis(4-chlorophenyl)-3-methyl-5-nitro-3-(4-nitrophenyl)-2,3-dihydro-1H-indene in 87% purity.

From the mother liquor finally a mixture (20.7 g) containing 25% of 3,3-bis(4-chlorophenyl)-1-methyl-5-nitro-1-(4-nitrophenyl)-2,3-dihydro-1H-indene and 68% of the regioisomer 1,1-bis(4-chlorophenyl)-3-methyl-5-nitro-3-(4-nitrophenyl)-2,3-dihydro-1H-indene was obtained.

Total yield: 67.6 g, 65%. The purity of all samples was determined by HPLC with detection at 220 nm.

3,3-bis(4-chlorophenyl)-1-methyl-5-nitro-1-(4-nitrophenyl)-2,3-dihydro-1H-indene: $^{13}$C NMR (75 MHz, CD$_2$Cl$_2$) δ 156.21 (q), 154.95 (q), 150.75 (q), 148.78 (q), 146.67 (q), 145.20 (q), 143.22 (q), 133.36 (q), 133.13 (q), 130.48 (p), 130.45 (p), 130.37 (p), 130.34 (p), 129.09 (p), 129.04 (p), 128.67 (p), 128.65 (p), 128.62 (p), 128.11 (p), 126.66 (p), 124.37 (p), 123.71 (p), 122.79 (p), 60.86 (s), 60.26 (q), 52.05 (q), 29.26 (t).

1,1-bis(4-chlorophenyl)-3-methyl-5-nitro-3-(4-nitrophenyl)-2,3-dihydro-1H-indene: $^{13}$C NMR (75 MHz, CD$_2$Cl$_2$) δ 155.97 (q), 154.98 (q), 150.94 (q), 149.02 (q), 146.69 (q), 145.23 (q), 143.09 (q), 133.35 (q), 133.15 (q), 130.50 (p), 130.39 (p), 129.06 (p), 128.68 (p), 128.64 (p), 128.12 (p), 123.90 (p), 123.74 (p), 121.10 (p), 60.87 (s), 60.53 (q), 51.91 (q), 29.51 (t).

c10) 1-(4-bromophenyl)-3,3-bis(4-chlorophenyl)-1-methyl-2,3-dihydro-1H-indene To a mixture of bis(4-chlorophenyl)phenylmethanol (15.1 g, 45.9 mmol, 1.0 eq.) and 1-bromo-4-(prop-1-en-2-yl)benzene (9.40 g, 45.9 mmol, 1.0 eq.) in chlorobenzene (200 mL) was added 1.1 g of (7.34 mmol, 0.16 eq.) of trifluoromethanesulfonic acid. A deep red reaction mixture was obtained, which was heated to 110° C. After 14 h of heating, the reaction was complete as monitored by GC. The mixture was cooled to ambient temperature, and filtered over a silica plug. The filtrate was evaporated, and the remaining crude title compound was crystallized from a mixture (5:12, v/v) of iso-propanol and heptane. The precipitate was filtered off, washed twice with a mixture of iso-propanol and heptane (1:2, v/v), and dried to give 18.93 g (81%) of the white, crystalline title compound with a purity of 98% (GC).

$^{13}$C NMR (75 MHz, CD$_2$Cl$_2$): δ 149.90 (q), 148.43 (q), 148.24 (q), 146.95 (q), 145.31 (q), 132.40 (q), 132.14 (q), 131.17 (p), 130.45 (p), 130.42 (p), 129.12 (p), 128.50 (p), 128.34 (p), 128.09 (p), 127.73 (p), 127.40 (p), 125.49 (p), 119.82 (q), 61.10 (s), 60.38 (q), 51.21 (q), 29.30 (t).

c11) 1,3-bis(3,5-dibromophenyl)-1-methyl-3-phenyl-indane 1,3-dibromo-5-(1-phenylvinyl)benzene (11.2 g, 33.1 mmol) was dissolved in a mixture of 100 mL of chlorobenzene and 100 mL of trifluoroacetic acid. The reaction was held at reflux temperature for 7 days, then cooled to room temperature and poured into 200 mL of water. The organic layer was separated and washed with 20% aqueous sodium hydroxide solution. The organic layer was separated, dried over anhydrous Na$_2$SO$_4$ and filtered. The solvent from the filtrate was removed and the crude title compound was obtained as amber oil, which was purified by column chromatography (silica gel, heptane). A white crystalline solid (3.15 g, 28%) was finally obtained by crystallization from acetone.

$^{13}$C NMR (101 MHz, CDCl$_3$) δ 152.29 (q), 152.18 (q), 148.12 (q), 147.79 (q), 143.85 (q), 132.05 (p), 131.23 (p), 130.54 (p), 128.83 (p), 128.52 (p), 128.34 (p), 127.93 (p), 127.89 (p), 127.17 (p), 126.64 (p), 125.03 (p), 122.80 (q), 122.36 (q), 60.43 (q), 60.20 (s), 50.99 (q), 29.40 (t).

d) 2,4,4-triphenylpentan-2-ol Compounds d1) 4-(4-chlorophenyl)-2,4-diphenylpentan-2-ol d1.1) 3-(4-chlorophenyl)-1,3-diphenylbutan-1-one Dypnone ((E)-1,3-diphenylbut-2-en-1-one), 99.0 g (0.445 mol)) was dissolved in 150 mL of anhydrous THF under an inert atmosphere. Then 1.83 g (8.91 mmol, 2 mol-%) of copper(I) bromide dimethyl sulfide complex was added. The mixture was cooled to −10° C. and 530 mL (1.2 eq.) of 4-chlorophenylmagnesium bromide (1 M in THF) was slowly added such that the internal temperature was maintained between −20 and 0° C. After complete addition, the reaction mixture was stirred for an additional 10 minutes at 0° C. The reaction mixture was then quenched by pouring it into a mixture of 600 g of ice and 200 mL of aqueous HCl (32% by weight). The organic layer was separated, and washed with a 1:1:1 (volumes) mixture of aqueous HCl (32% by weight), saturated brine and water. The organic layer was separated, stirred with 10 g of NaHCO$_3$, dried over anhydrous Na$_2$SO$_4$ and filtered over silica gel. The solvent was removed. The crude title compound was then purified by bulb-to-bulb distillation (185 to 190° C.; 0.001 mbar) to afford a yellow oil (74.8 g; yield: 50%; purity: 87% (GC)).

d1.2) 4-(4-chlorophenyl)-2,4-diphenylpentan-2-ol

In a flask equipped with a reflux condenser was placed under an inert atmosphere 150 mL (0.45 mol, 2 eq.) of methylmagnesium chloride solution (3 M in THF). To this was added a solution of 74 g (0.22 mol, 1 eq.) of 3-(4-chlorophenyl)-1,3-diphenylbutan-1-one in 100 mL of toluene such that a gentle reflux was maintained.

The reaction mixture was then cooled to room temperature, and then poured onto a mixture of 400 g of ice and 100 mL of aqueous HCl (32% by weight). The organic layer was separated and washed with a mixture of saturated brine, aqueous HCl (32% by weight) and water, followed by washing with 20% aqueous NaOH solution. The organic layer was dried over anhydrous Na$_2$SO$_4$, filtered and concentrated to yield the title compound (74 g; yield: 95%) as yellow oil. The product was obtained as a 1:1 mixture of diasteromers as indicated by $^1$H-NMR.

d2) 2,4-bis(4-chlorophenyl)-4-phenylpentan-2-ol d2.1) 1,3-bis(4-chlorophenyl)-3-phenylbutan-1-one Under an inert atmosphere 130 g (0.446 mol) of 4,4'-dichlorodypnone ((E)-1,3-bis(4-chlorophenyl)but-2-en-1-one) was dissolved in 150 mL of anhydrous THF. Then 1.84 g (8.91 mmol, 2 mol-%) of copper(I) bromide dimethyl sulfide complex was added. The mixture was cooled to −10° C., and 600 mL (1.3 eq.) of phenylmagnesium bromide (1 M in THF) was added slowly such that the internal temperature was maintained between −20 and −10° C. After complete addition, the reaction mixture was allowed to reach room temperature within 30 minutes.

The reaction mixture was then quenched by pouring it into a mixture of 600 g of ice and 200 mL of aqueous HCl (32% by weight). The reaction flask was rinsed with approximately 10% aqueous HCl and toluene. The organic layer was washed with a 1:1:1 (by volume) mixture of aqueous HCl (32% by weight), saturated brine and water. The organic layer was neutralized by stirring it with 10 g of NaHCO$_3$. It was then dried over anhydrous Na$_2$SO$_4$ and filtered over silica gel. The filtrate was concentrated to yield the crude product as a honey-like oil. Upon addition of heptane, the title product spontaneously crystallized. The title product was filtered off, washed twice with heptane and dried to yield 145 g (88%) of a beige solid (100% purity by GC).

d2.2) 2,4-bis(4-chlorophenyl)-4-phenylpentan-2-ol

In a flask equipped with a reflux condenser was placed under an inert atmosphere 250 mL (0.75 mol, 3 M in THF, 1.9 eq.) of methylmagnesium chloride. To this was added a solution of 143 g (0.39 mol, 1 eq.) of 2,4-bis(4-chlorophenyl)-4-phenylpentan-2-ol in 250 mL of toluene such that a gentle reflux was maintained.

After cooling to ambient temperature, the reaction mixture was poured into a mixture of 400 g of ice and 100 mL of aqueous HCl (32% by weight). The organic layer was separated, washed with a mixture of saturated brine, aqueous HCl (32% by weight) and water, followed by a washing with 20% aqueous NaOH. The organic phase was dried over anhydrous Na$_2$SO$_4$. Removal of the solvent gave the title compound (150 g "quant.") as a yellow oil which was used in the next step without further purification. The title compound was obtained as a 1:1 mixture of diastereomers as indicated by $^1$H-NMR.

e) 1,3-dimethyl-1,3-diphenylindane Compounds e1) 1-(4-chlorophenyl)-1,3-dimethyl-3-phenyl-2,3-dihydro-1H-indene A solution of 54 g (0.15 mol) of 4-(4-chlorophenyl)-2,4-diphenylpentan-2-ol from d1) in 110 mL of chlorobenzene was slowly added to 100 mL of refluxing trifluoroacetic acid over a period of six hours. The obtained reaction mixture was then poured into water and then toluene was added. The organic layer was washed with 20% aqueous NaOH, dried over anhydrous $Na_2SO_4$ and filtered over silica gel. The filtrate was concentrated to give the crude title product, which was purified by column chromatography (silica gel, heptane) in order to remove the main side-products. From the combined product fractions, removal of the solvent gave a highly viscous oil. This was distilled twice (160-180° C., $10^{-3}$ mbar) to yield 14.6 g (29%) of the title product as a highly viscous, glass-like oil. Based on $^1$H-NMR spectroscopy, the title product was a 2.1:1 mixture of the cis- and trans-isomers.

Cis-isomer: $^{13}$C NMR (101 MHz, $CDCl_3$): δ 149.94 (q), 149.52 (q), 149.09 (q), 147.93 (q), 131.09 (q), 128.12 (p), 127.83 (p), 127.75 (p), 127.41 (p), 127.35 (p), 126.58 (p), 125.51 (p), 125.30 (p), 124.99 (p), 60.91 (s), 51.10 (q), 50.71 (q), 30.76 (t), 30.69 (t).

Trans-isomer: $^{13}$C NMR (101 MHz, $CDCl_3$): δ 150.32 (q), 150.18 (q), 149.72 (q), 149.16 (q), 131.54 (q), 128.31 (p), 128.19 (p), 128.16 (p), 127.39 (p), 127.32 (p), 126.78 (p), 125.82 (p), 125.22 (p), 124.93 (p), 62.25 (s), 51.34 (q), 50.99 (q), 29.58 (t), 29.43 (t).

e2) 1,3-bis(4-chlorophenyl)-1,3-dimethyl-2,3-dihydro-1H-indene

A solution of 150 g of 2,4-bis(4-chlorophenyl)-4-phenylpentan-2-ol from d.2) in 100 mL of chlorobenzene was slowly added to a refluxing mixture of 150 mL of trifluoroacetic acid and 600 mL of chlorobenzene, over a period of six hours. The obtained red solution was then kept at reflux for 16 hours. After cooling to room temperature, the mixture was quenched by the addition of water. The organic phase was separated, washed with a 1:1 mixture of saturated brine and of water, followed by 20% aqueous sodium hydroxide solution.

Then, the organic layer was separated, dried over anhydrous $Na_2SO_4$ and filtered over a pad of silica gel. Removal of the solvent gave the crude product (150 g) as a highly viscous oil. This oil was then purified by distillation (twice) at $10^{-3}$ mbar to give the main fraction (70.2 g) as a highly viscous oil; boiling point 185° C. at $10^{-3}$ mbar. The less pure fractions of the second distillation run were combined (ca. 30 g) and purified by column chromatography (silica gel/heptane). After discarding the initial fractions containing a side product, 5 column fractions of 2 L each were collected, where the initial fractions were rich in the trans-isomer and the later fractions rich in the cis-isomer. The fractions were concentrated to ca. 20 mL. Slow evaporation of the solvent gave seed crystals, which were triturated with 20 mL of isopropanol and filtered off, yielding 1.55 g of the cis-isomer.

Also, a fraction enriched in the trans-isomer (cis/trans=27:69%), weighing 6.54 g was obtained.

Dissolving of the distilled product in 260 mL of isopropanol at 70° C. and seeding at 40° C. with the seed crystals obtained above gave 18.52 g of the pure cis-isomer after crystallization for one hour at room temperature.

The mother liquor was concentrated to 150 mL and 15 mL of n-heptane were added. Seed crystals were added again to the obtained solution, and stirring at room temperature for 16 hours gave 24.67 g of product with a cis/trans ratio of 63:37%.

The combined mother liquors gave another 36.46 g of product as a colorless oil with a cis/trans-ratio of 68:20%. Total yield: 87.74 g, 61%.

Cis-isomer: $^{13}$C NMR (101 MHz, CDCl3): δ 149.39 (q), 147.70 (q), 131.31 (q), 128.05 (p), 127.88 (q), 127.59 (p), 125.13 (p), 60.79 (s), 50.72 (q), 30.69 (t).

e3) 5-bromo-1,3-bis(4-chlorophenyl)-1,3-dimethyl-2,3-dihydro-1H-indene, cis-isomer To 3.36 g (9.1 mmol, 1.0 eq) of 1,3-bis(4-chlorophenyl)-1,3-dimethyl-2,3-dihydro-1H-indene (cis isomer from e2)) and 1.80 g (10 mmol, 1.1 eq) of N-bromosuccinimide. were added 7 mL of dichloromethane followed by 7 mL of trifluoroacetic acid. The resulting solution was stirred until all solids were dissolved. This was followed by the slow addition of 1 mL of 98% sulfuric acid. An exothermic reaction was observed. Stirring was continued at room temperature for another 30 minutes, then the reaction was quenched by the addition of water.

The organic phase was separated, washed with saturated $NaHCO_3$ solution, followed by 40% sodium bisulfite solution in order to remove traces of bromine. The organic phase was separated, dried over anhydrous $Na_2SO_4$ and filtered. The solvent was removed. The obtained yellow oil was crystallized from heptane. The solid was filtered off and washed with heptane. After drying, 3.15 g (77%) of a yellowish solid was obtained with a GC purity of 95%.

$^{13}$C NMR (101 MHz, $CDCl_3$) δ 151.90 (q), 148.46 (q), 147.06 (q), 146.87 (q), 131.61 (q), 131.55 (q), 130.79 (p), 128.24 (p), 128.04 (p), 128.00 (p), 127.89 (p), 127.87 (p), 126.76 (p), 121.41 (q), 60.83 (s), 50.78 (q), 50.48 (q), 30.53 (p), 30.48 (p).

II. Preparation of Compounds of Formula (I)

Unless stated otherwise, the compounds according to the present invention were prepared according to the general procedure A depicted below.

General Procedure A for Buchwald-Hartwig Aminations:

Under an inert atmosphere, the aryl halide, the mono- or di-arylamine and sodium tert-butanolate were suspended in toluene (ca. 15 mL/mmol aryl halide). To the obtained suspension was added the catalyst $Pd_2(dba)_3$ or $Pd(OAc)_2$ and the appropriate ligand (RuPhos or SPhos) under an inert atmosphere. The reaction mixture was heated at reflux for 16 hours.

Workup A:

After cooling, aqueous ammonium chloride solution (ca. 20%, 10 ml/mmol product) was added to the reaction mixture. The resulting emulsion was filtered through a filter layer made up of Celite, which has been slurried up in ethyl acetate. Later, the Celite pad was washed with ethyl acetate (ca. 15 mL/mmol). From the filtrate, after separation of the layers, the organic layer was washed subsequently with water (10 mL/mmol), saturated sodium chloride solution (10 mL/mmol), and then dried with anhydrous sodium sulfate. Filtration and removal of the solvent from the filtrate gave the crude product which was purified further as described for the corresponding examples.

Workup B:

After cooling, aqueous ascorbic acid solution (5%, ca.ca. 10 ml/mmol) was added to the reaction mixture. The resulting emulsion was filtered through a Celite pad which has been made up as described in Workup A, and subsequently washed with ethyl acetate (ca. 15 mL/mmol). From the filtrate, the organic layer was washed subsequently with water (10 mL/mmol), saturated sodium chloride solution (10 mL/mmol), and then dried with anhydrous sodium sulfate.

Filtration and removal of the solvent from the filtrate gave the crude product which was purified further as described for the corresponding examples.

Workup C:

After cooling, silica gel (ca. 2 g/mmol) was added to the reaction mixture. The suspension was stirred, until it appears to be homogenous. It was then filtered over a pad of silica gel which was then washed with about the same volume of toluene as the volume of the column. After removal of the solvent from the combined filtrates, the product was purified further as described for the corresponding examples.

Example 1

4,4'-(1-methyl-3-phenyl-2,3-dihydro-1H-indene-1,3-diyl)dianiline

Route a)

1.1 N,N-((1-methyl-3-phenyl-2,3-dihydro-1H-indene-1,3-diyl)bis(4,1-phenylene))bis(2,2-dimethylpropanamide)

20.0 g (0.04 mol) of 1,3-bis(4-bromophenyl)-1-methyl-3-phenyl-2,3-dihydro-1H indene from c1), 9.76 g (0.10 mol) of pivalamide, 13.3 g (0.10 mol) of potassium carbonate, 1.10 g (0.06 mol) of copper(I) iodide and 1.02 g (0.01 mol) of 1,2-dimethylethylenediamine were dissolved in 80 mL of 1,4-dioxane under argon. The reaction mixture was refluxed over night. After cooling, aqueous $NH_3$ solution was added followed by the addition of tert-butyl methyl ether and water.

The organic layer was separated and the aqueous layer extracted with t-butyl methyl ether. The combined organic layers were washed with a 1:4 (v/v) mixture of 25% aqueous ammonia solution and water, followed by two washings with water and saturated brine. After drying over $Na_2SO_4$, filtration and removal of the solvent from the filtrate, the title compound was obtained as a beige solid (115%; purity (GC): 92.0%; ratio of diastereomers: 1.4:1).

1.2 4,4'-(1-methyl-3-phenyl-2,3-dihydro-1H-indene-1,3-diyl)dianiline

Under an argon blanket, a mixture of 10.6 g (0.16 mol) of potassium hydroxide and 40 mL of n-butanol was heated to 85° C. Then, 20.0 g (0.04 mol) of N,N-((1-methyl-3-phenyl-2,3-dihydro-1H-indene-1,3-diyl)bis(4,1-phenylene))bis(2,2-dimethylpropanamide) from 1.1 was added in one portion and the reaction mixture was stirred at 135° C. for 3 h before it was cooled to 0° C. The formed suspension was filtered and washed with water. The mother liquor was evaporated and the residue was crystallized from ethyl acetate/n-heptane. Both solids were combined to obtain the title compound as a beige solid (13.6 g, 98%; purity 93.7 (GC)).

Route b)

1.3 4,4'-(1-methyl-3-phenyl-2,3-dihydro-1H-indene-1,3-diyl)bis(N-benzylaniline) 10.0 g (23 mmol) of 1,3-bis(4-chlorophenyl)-1-methyl-3-phenyl-2,3-dihydro-1H-indene from c2), 0.43 g (0.47 mmol) of $Pd_2(dba)_3$, 0.87 g (1.86 mmol) RuPhos, 6.71 g (70 mmol) of sodium tert-butoxide and 7.47 g (70 mmol) benzylamine were suspended in 100 mL of toluene (100 mL) and heated to 100° C. over night under inert atmosphere. The mixture was filtered through celite and the filtrate was evaporated. The residue was extracted with tert-butyl methyl ether and water. The organic phase was washed three times with water and saturated aqueous NaCl solution, dried with $Na_2SO_4$ and evaporated to dryness. After column chromatography (ethyl acetate/n-heptane, gradient 1.9 to 1.2)) the title compound was obtained as a white powder (4.69 g, 35%; purity (HPLC at 220 nm, 1.1 ratio of diastereomers): 96.0%) and a second fraction weighting 3.93 g (28%, HPLC: 93%, 1.37:1 ratio of diasteromers.

1.4 4,4'-(1-methyl-3-phenyl-2,3-dihydro-1H-indene-1,3-diyl)dianiline 1.0 g (1.75 mmol) of 4,4'-(1-methyl-3-phenyl-2,3-dihydro-1H-indene-1,3-diyl)bis(N-benzylaniline) from 1.3 and 0.25 g of 5% Pd/C (10%-w/w) were suspended in 50 mL of glacial acetic acid and a hydrogen balloon was applied. The reaction mixture was stirred at room temperature under hydrogen atmosphere for 16 hours. The reaction mixture was filtered over celite and the filtrate was concentrated.

The crude title compound was dissolved in t-butyl methyl ether and neutralized with 5% aqueous $NaHCO_3$ solution. The organic layer was washed with water and saturated brine; and then dried over $Na_2SO_4$. After filtration and evaporation of the solvent, 0.89 g of a beige solid was obtained. This consisted of 70.1% (HPLC at 220 nm) of the desired title compound along with 21.7% of a mono-acetyl species.

The crude product was dissolved in n-butanol and treated with 0.25 g of 85% potassium hydroxide at reflux temperature for 2.5 h. It was then cooled to 70° C. and water was added. After 10 minutes, the layers had separated. This process was repeated and then the organic layer was partitioned between 30 mL of t-butyl methyl ether and 5 mL of water. The organic layer was washed with water and saturated brine, dried over sodium sulfate and evaporated to dryness. The title product was obtained as brown foam, which solidified after cooling to room temperature. Purity 48.1% (HPLC at 220 nm).

Route c)

1.5 4,4'-(1-methyl-3-phenyl-2,3-dihydro-1H-indene-1,3-diyl)dianiline 0.10 g (0.22 mmol) of 1-methyl-1,3-bis(4-nitrophenyl)-3-phenyl-2,3-dihydro-1H-indene from c3) and 0.02 g of 5% Pd/C (10%-w/w) were suspended in 4 mL of glacial acetic acid and a hydrogen balloon was applied. The reaction mixture was stirred at room temperature under hydrogen atmosphere for 1 h before it was filtered through celite. The filtrate was extracted with tert-butyl methyl ether and aqueous $NaHCO_3$ solution. The organic phase was washed three times with water and saturated aqueous NaCl solution, dried with $Na_2SO_4$ and evaporated to dryness to obtain the title compound as a white solid (0.08 g, 93%; purity (HPLC at 220 nm): 93.4%).

Example 2

4,4',4''-(6-amino-3-methyl-2,3-dihydro-1H-indene-1,1,3-triyl)trianiline

To 13.5 g (27.1 mmol) of 5-chloro-1,3,3-tris(4-chlorophenyl)-1-methyl-2,3-dihydro-1H-indene from c5), 1.24 g (1.35 mmol) of $Pd_2(dba)_3$ and 947 mg (2.70 mmol) of 2-(dicyclohexylphosphino)biphenyl was added 163 mL of lithium bis(trimethylsilyl)amide in THF (1 M solution, 0.16 mol). The mixture was heated to 75° C. over night. After cooling to room temperature the mixture was acidified with aqueous hydrochloric acid solution, extracted twice with toluene and the organic phase was discarded. KOH was added until a basic pH was reached. The precipitate was filtered off, washed with water and purified by column chromatography ($CH_2Cl_2$/MeOH) to give 5.1 g (45%; purity (HPLC at 329 nm): 75.0%) of the title compound as an ochre solid.

$^1$H NMR (300 MHz, $CDCl_3$): δ 7.01 (d, J=8.6 Hz, 2H), 6.97 (d, J=8.6 Hz, 2H), 6.84 (d, J=8.6 Hz, 2H), 6.80 (d, J=0.5 Hz, 1H), 6.59 (d, J=8.6 Hz, 2H, overlapping with a doublet, 1H), 6.54 (d, J=8.6 Hz, 2H), 6.46 (d, J=8.6 Hz, 2H), 6.29 (dd, J=2.3, 0.5 Hz, 1H), 3.44 (s, 8H), 3.16 (d, J=13.3 Hz, 1H), 2.89 (d, J=13.3 Hz, 1H), 1.40 (s, 3H).

Example 3

N,N-((1-methyl-3-phenyl-2,3-dihydro-1H-indene-1,3-diyl)bis(4,1-phenylene))bis(N-(9,9-dimethyl-9H-fluoren-2-yl)-9,9-dimethyl-9H-fluoren-2-amine)

2.00 g (5.12 mmol) of 4,4'-(1-methyl-3-phenyl-2,3-dihydro-1H-indene-1,3-diyl)dianiline from example 1, 6.99 g (25.6 mmol) of 2-bromo-9,9-dimethyl-9H-fluorene, 2.46 g (25.6 mmol) of sodium tert-butanolate, 94 mg (0.10 mmol) of $Pd_2(dba)_3$ and 191 mg (0.41 mmol) of RuPhos were suspended in 60 mL of toluene. The mixture was heated at 115° C. over night. After cooling, half saturated aqueous $NH_4Cl$ solution was added. The mixture was filtered through celite. The phases were separated and the organic phase was washed with saturated aqueous NaCl solution, dried with $Na_2SO_4$ and evaporated to dryness. Purification by column chromatography (heptane/$CH_2Cl_2$) provided the title compound as an off white solid (5.0 g, 84%; purity (HPLC at 340 nm): 95.5%).

1.42 g of the title compound were further purified by vacuum zone sublimation ($10^{-6}$-$10^{-7}$ mbar, 180-370° C.) to give the title compound as a yellowish solid (1.38 g, purity (HPLC at 340 nm): 99.5%). $T_g$: 177.1° C.

Example 4

N,N-((1-methyl-3-phenyl-2,3-dihydro-1H-indene-1,3-diyl)bis(4,1-phenylene))bis(9,9-dimethyl-N-(p-tolyl)-9H-fluoren-2-amine)

6.00 g (11.6 mmol) of 1,3-bis(4-bromophenyl)-1-methyl-3-phenyl-2,3-dihydro-1H-indene from c1), 8.32 g (27.8 mmol) of 9,9-dimethyl-N-(p-tolyl)-9H-fluoren-2-amine, 2.73 g (28.4 mmol) of sodium tert-butanolate, 212 mg (0.23 mmol) of $Pd_2(dba)_3$ and 432 mg (0.93 mmol) of RuPhos were suspended in 150 mL of toluene. The mixture was heated at 115° C. over night. After cooling, half saturated aqueous $NH_4C_1$ solution was added. The mixture was filtered through celite. The phases were separated and the organic phase was washed with saturated aqueous NaCl solution, dried with $Na_2SO_4$ and evaporated to dryness. Purification by column chromatography (heptane/$CH_2Cl_2$) for three times provided the title compound as an off white solid (3.19 g, 29%; purity (HPLC at 340 nm): 97.8%).

0.45 g of the title compound were further purified by vacuum zone sublimation ($10^{-6}$-$10^{-7}$ mbar, 180-360° C.) to give the title compound as a yellowish solid (0.35 g, purity (HPLC at 340 nm): 99.7%). $T_g$: 141.6° C.

Example 5

4,4',4''-(6-(bis(4-methoxyphenyl)amino)-3-methyl-2,3-dihydro-1H-indene-1,1,3-triyl)tris(N,N-bis(4-methoxyphenyl)aniline)

3.00 g (4.44 mmol) of 5-bromo-1,3,3-tris(4-bromophenyl)-1-methyl-2,3-dihydro-1H-indene from c4), 6.10 g (26.6 mmol) of bis(4-methoxyphenyl)amine, 2.56 g (26.6 mmol) of sodium tert-butanolate, 201 mg (0.22 mmol) of $Pd_2(dba)_3$ and 205 mg (0.44 mmol) of RuPhos were suspended in 60 mL of toluene. The mixture was heated at 100° C. over night. After cooling, half saturated aqueous $NH_4Cl$ solution was added. The mixture was filtered through celite, phases were separated and the aqueous phase was extracted with toluene. The combined organic phases were dried with $MgSO_4$ and evaporated to dryness. Purification by column chromatography (heptane/$CH_2Cl_2$) provided the title compound as an off white solid (2.5 g, 44%; purity according to HPLC (at 340 nm): 95.0%).

Example 6

4,4',4''-(6-(di-p-tolylamino)-3-methyl-2,3-dihydro-1H-indene-1,1,3-triyl)tris(N,N-p-tolylaniline)

3.00 g (4.44 mmol) of 5-bromo-1,3,3-tris(4-bromophenyl)-1-methyl-2,3-dihydro-1H-indene from c4), 5.25 g (26.6 mmol) of di-p-tolylamine, 2.56 g (26.6 mmol) of sodium tert-butanolate, 201 mg (0.22 mmol) of $Pd_2(dba)_3$ and 205 mg (0.44 mmol) of RuPhos were suspended in 50 mL toluene. The mixture was heated at 100° C. over 2 days. After cooling, saturated aqueous $NH_4Cl$ solution was added. The phases were separated and the aqueous phase was extracted with toluene. The combined organic phases were dried with $MgSO_4$ and evaporated to dryness. Purification by column chromatography (heptane/$CH_2Cl_2$) provided the title compound as an off white solid (3.3 g, 65%; purity (HPLC at 340 nm): 98.1%).

1.22 g of the title compound were further purified by vacuum zone sublimation ($10^{-6}$-$10^{-7}$ mbar, 210-360° C.) to give the title compound as a yellowish solid (1.10 g, purity (HPLC at 340 nm): 99.5%). $T_g$: 137.7° C.

Example 7

N-([1,1'-biphenyl]-4-yl)-9,9-dimethyl-N-(4-(1-methyl-3,3-diphenyl-2,3-dihydro-1H-inden-1-yl)phenyl)-9H-fluoren-2-amine 1.54 g (3.5 mmol) of 1-(4-bromophenyl)-1-methyl-3,3-diphenyl-2,3-dihydro-1H-indene from c6), 1.52 g (4.2 mmol) of N-([1,1'-biphenyl]-4-yl)-9,9-dimethyl-9H-fluoren-2-amine and 0.4 g (4.2 mmol) of sodium tert-butanolate, 64 mg (0.07 mmol) of $Pd_2(dba)_3$ and 131 mg (0.28 mmol) of RuPhos were suspended in 50 mL of toluene. The mixture was heated at 115° C. over night. After cooling, half saturated aqueous $NH_4Cl$ solution was added. The mixture was filtered through celite. The phases were separated and the organic phase was washed with saturated aqueous NaCl solution, dried with $Na_2SO_4$ and evaporated to dryness. Purification by column chromatography (heptane/$CH_2Cl_2$) provided the title compound as a white solid (2.19 g, 87%; purity (HPLC at 340 nm): 98.2%).

0.82 g of the title compound were further purified by vacuum zone sublimation ($10^{-6}$-$10^{-7}$ mbar, 180-300° C.) to give the title compound as a yellowish solid (0.72 g, purity (HPLC at 340 nm): 99.2%). $T_g$: 120.1° C.

Example 8

N-([1,1'-biphenyl]-2-yl)-9,9-dimethyl-N-(4-(1-methyl-3,3-diphenyl-2,3-dihydro-1H-inden-1-yl)phenyl)-9H-fluoren-2-amine 4.39 g (10.0 mmol) of 1-(4-bromophenyl)-1-methyl-3,3-diphenyl-2,3-dihydro-1H-indene from c6), 4.34 g (12.0 mmol) of N-([1,1'-biphenyl]-2-yl)-9,9-dimethyl-9H-fluoren-2-amine and 1.15 g (12.0 mmol) of sodium tert-butanolate, 183 mg (0.2 mmol) of Pd$_2$(dba)$_3$ and 373 mg (0.8 mmol) of RuPhos were suspended in 120 mL toluene. The mixture was heated at 115° C. over night. After cooling, half saturated aqueous NH$_4$C$_1$ solution was added. The mixture was filtered through celite. The phases were separated and the organic phase was washed with water and saturated aqueous NaCl solution, dried with Na$_2$SO$_4$ and evaporated to dryness. The crude title compound was crystallized from acetone/isopropanol to provide the title compound as a yellowish solid (5.2 g, 72%; purity (HPLC at 340 nm): 90.5%).

3.5 g of the title compound were further purified by vacuum zone sublimation ($10^{-6}$-$10^{-7}$ mbar, 180-280° C.) to give the title compound as a yellowish solid (2.85 g, purity (HPLC at 340 nm): 99.5%). T$_g$: 112.2° C.

Example 9

N-(9,9-dimethyl-9H-fluoren-2-yl)-9,9-dimethyl-N-(4-(1-methyl-3,3-diphenyl-2,3-dihydro-1H-inden-1-yl)phenyl)-9H-fluoren-2-amine 4.39 g (10.0 mmol) of 1-(4-bromophenyl)-1-methyl-3,3-diphenyl-2,3-dihydro-1H-indene from c6), 4.82 g (12.0 mmol) of bis(9,9-dimethyl-9H-fluoren-2-yl)amine and 1.15 g (12.0 mmol) of sodium tert-butanolate, 183 mg (0.2 mmol) of Pd$_2$(dba)$_3$ and 373 mg (0.8 mmol) of RuPhos were suspended in 120 mL of toluene. The mixture was heated at 115° C. over night. After cooling, half saturated aqueous NH$_4$Cl solution was added. The mixture was filtered through celite. The phases were separated and the organic phase was washed with water and saturated aqueous NaCl solution, dried with Na$_2$SO$_4$ and evaporated to dryness. Purification by column chromatography (heptane/CH$_2$Cl$_2$) provided the title compound as an off white solid (6.5 g, 85%; purity (HPLC at 340 nm): 97.6%).

3.06 g of the title compound were further purified by vacuum zone sublimation ($10^{-6}$-$10^{-7}$ mbar, 180-300° C.) to give the title compound as a yellowish solid (2.32 g, purity (HPLC at 340 nm): 99.5%). T$_g$: 133.1° C.

Example 10

N-(4-(1,3-dimethyl-3-phenyl-2,3-dihydro-1H-inden-1-yl)phenyl)-N-(9,9-dimethyl-9H-fluoren-3-yl)-9,9-dimethyl-9H-fluoren-2-amine Prepared according to the general procedure A from 1-(4-chlorophenyl)-1,3-dimethyl-3-phenyl-2,3-dihydro-1H-indene from e1) (3.35 g, 10.0 mmol, 1.0 eq; 2.1:1 cis/trans ratio) and bis(9,9-dimethyl-9H-fluoren-2-yl)amine (4.22 g, 10.5 mmol, 1.05 eq.) in 120 mL of toluene, using sodium tert-butanolate (1.04 g, 10.8 mmol, 1.08 eq.), 0.185 g (0.40 mmol, 4 mol-%) of RuPhos, and 0.09 g (0.10 mmol, 1 mol-%) of Pd$_2$(dba)$_3$.

Workup was done according to procedure C. The crude title compound was crystallized by fractional precipitation (30 mL ethyl acetate and stepwise addition of a total of 3 volume equivalents of iso-propanol). A total of 6 fractions was obtained with the main fraction weighing 2.55 g (36%) of the desired title compound; purity 90.4% (65:25% cis/trans ratio; HPLC at 340 nm).

Example 11

N-(2,4-dimethylphenyl)-9,9-dimethyl-N-(4-(1-methyl-3,3-diphenyl-2,3-dihydro-1H-inden-1-yl)phenyl)-9H-fluoren-2-amine Prepared according to the general procedure A from 1-(4-bromophenyl)-1-methyl-3,3-diphenyl-2,3-dihydro-1H-indene from c6) (4.39 g, 10.0 mmol, 1.0 eq.) and N-(2,4-dimethylphenyl)-9,9-dimethyl-9H-fluoren-2-amine (3.29 g, 10.5 mmol, 1.05 eq.) in toluene (120 mL), using 1.03 g of sodium tert-butanolate (10.7 mmol, 1.07 eq.), 183 mg of Pd$_2$(dba)$_3$ (0.20 mmol, 2.0 mol-%), and 373 mg of RuPhos (0.80 mmol, 8.0 mol-%). Workup was done according to procedure A.

Purification of the crude product by crystallization from acetone provided the crude compound as an off white solid (6.0 g, 89%); purity 99.6% (HPLC at 340 nm).

This material (4.02 g) was further purified by vacuum zone sublimation ($10^{-6}$-$10^{-7}$ mbar, 160-230° C.) to give the title compound as a yellowish solid. The fraction with the highest purity was 3.76 g of the title product in 99.9% purity (HPLC at 340 nm). T$_g$: 107.9° C.

Example 12

N-(4-methoxyphenyl)-9,9-dimethyl-N-(4-(1-methyl-3,3-diphenyl-2,3-dihydro-1H-inden-1-yl)phenyl)-9H-fluoren-2-amine Prepared according to the general procedure A from 1-(4-bromophenyl)-1-methyl-3,3-diphenyl-2,3-dihydro-1H-indene from c6) (5.27 g, 12.0 mmol, 1.0 eq.) and N-(4-methoxyphenyl)-9,9-dimethyl-9H-fluoren-2-amine (3.97 g, 12.6 mmol, 1.05 eq.) in toluene (120 mL), using 1.23 g of sodium tert-butanolate (12.8 mmol, 1.07 eq.), 220 mg of Pd$_2$(dba)$_3$ (0.24 mmol, 2.0 mol-%), and 448 mg of RuPhos (0.96 mmol, 8.0 mol-%). Workup was done according to procedure A.

Purification of the crude product by crystallization from acetone/iso-propanol provided title product as an off white solid (5.8 g, 72%) purity 99.0% (according to HPLCat 340 nm). This material (3.41 g) was further purified by vacuum zone sublimation ($10^{-6}$-$10^{-7}$ mbar, 160-230° C.) to give the title compound as a yellowish solid. The fraction with the highest purity was 3.15 g with a purity of to 99.8% (HPLC at 340 nm).

Example 13

9,9-dimethyl-N-(4-(1-methyl-3,3-diphenyl-2,3-dihydro-1H-inden-1-yl)phenyl)-N-(p-tolyl)-9H-fluoren-2-amine Prepared according to the general procedure A from 1-(4-bromophenyl)-1-methyl-3,3-diphenyl-2,3-dihydro-1H-indene from c6) (5.83 g, 13.3 mmol, 1.0 eq.) and 9,9-dimethyl-N-(p-tolyl)-9H-fluoren-2-amine (4.14 g, 13.9 mmol, 1.04 eq.) in toluene (120 mL), using 1.20 g of sodium tert-butanolate (14.2 mmol, 0.94 eq.), 243 mg of Pd$_2$(dba)$_3$ (0.27 mmol, 2.0 mol-%), and 495 mg of RuPhos (1.06 mmol, 8.0 mol-%). Workup was done according to procedure A.

Purification of the crude product by crystallization from acetone/iso-propanol provided the title compound as an off white solid (7.8 g, 90%); purity 99.7% (HPLC at 340 nm). This material (4.61 g) was further purified by vacuum zone sublimation ($10^{-6}$-$10^{-7}$ mbar, 150-240° C.) to give the title compound as a yellowish solid. The fraction with the highest purity was 4.44 g with a purity of 99.9% (HPLC at 340 nm).

Example 14

N-(9,9-dimethyl-9H-fluoren-2-yl)-9,9-dimethyl-N-(4-(3-methyl-1,3-diphenyl-2,3-dihydro-1H-inden-1-yl)phenyl)-9H-fluoren-2-amine Prepared according to the general procedure A from 1-(4-bromophenyl)-3-methyl-1,3-diphenyl-2,3-dihydro-1H-indene from c7) (5.71 g, 13.0 mmol, 1.0 eq.) and bis(9,9-dimethyl-9H-fluoren-2-yl)amine (5.48 g, 13.65 mmol, 1.05 eq.) in toluene (120 mL), using sodium tert-butanolate (1.37 g, 14.3 mmol, 1.1 eq.), 0.24 g (0.52 mmol, 4 mol-%) RuPhos, and 0.13 g (0.13 mmol, 1 mol-%) of $Pd_2(dba)_3$. Workup according to procedure B.

The crude compound was recrystallized from a 1:6 (v/v) mixture of acetone/iso-propanol to give 6.55 g of the title compound; purity 99.0% (HPLC at 340 nm). Upon reduction of the mother liquor to ca. one third of its volume, an additional crop of the title product was obtained. (2.45 g, purity 96.7% (HPLC at 340 nm). Total yield: 91%.

Example 15

N,N'-((1,3-dimethyl-2,3-dihydro-1H-indene-1,3-diyl)bis(4,1-phenylene))bis(N-(9,9-dimethyl-9H-fluoren-2-yl)-9,9-dimethyl-9H-fluoren-2-amine)

Prepared according to the general procedure A from 1,3-bis(4-chlorophenyl)-1,3-dimethyl-2,3-dihydro-1H-indene from e2), (3.67 g, 10.0 mmol, 1.0 eq; 3.7:1 cis/trans ratio) and bis(9,9-dimethyl-9H-fluoren-2-yl)amine (8.30 g, 20.7 mmol, 2.07 eq.) in toluene (120 mL), using sodium tert-butanolate (2.00 g, 20.3 mmol, 2.08 eq.), 0.185 g (0.40 mmol, 4 mol-%) RuPhos, and 0.09 g (0.10 mmol, 1 mol-%) of $Pd_2(dba)_3$. Workup was done according to procedure C.

The crude compound was crystallized from a 1:1 (v/v) mixture of ethyl acetate and iso-propanol. It was filtered off and washed with a 3:2 (v/v) mixture of ethyl acetate and iso-propanol and then with isopropanol to give 6.07 g (55%) of the title compound; purity 96.5% (93:4% cis/trans ratio; HPLC at 340 nm).

$^{13}$C NMR (101 MHz, $CD_2Cl_2$): δ 154.94 (q), 153.52 (q), 149.78 (q), 147.58 (q), 145.16 (q), 143.72 (q), 139.03 (q), 133.65 (q), 127.67 (p), 127.07 (p), 126.94 (p), 126.33 (p), 125.09 (p), 123.44 (p), 122.85 (p), 122.47 (p), 120.58 (p), 119.29 (p), 118.08 (p), 60.30 (q), 50.52 (q), 46.74 (s), 30.67 (t), 26.90 (t).

Example 16

N,N-((1-methyl-3-phenyl-2,3-dihydro-1H-indene-1,3-diyl)bis(4,1-phenylene))bis(N-(2,4-dimethylphenyl)-9,9-dimethyl-9H-fluoren-2-amine)

Prepared according to the general procedure A from 1,3-bis(4-bromophenyl)-1-methyl-3-phenyl-2,3-dihydro-1H-indene from c1) (6.32 g, 12.2 mmol, 1.0 eq.) and N-(2,4-dimethylphenyl)-9,9-dimethyl-9H-fluoren-2-amine (7.86 g, 25.1 mmol, 2.06 eq.) in toluene (120 mL), using sodium tert-butanolate (2.47 g, 25.7 mmol, 2.11 eq.), 113 mg (0.12 mmol, 1.0 mol-%) of $Pd_2(dba)_3$ and 230 mg (0.49 mmol, 4.0 mol-%) of RuPhos. Workup was done according to procedure B.

Purification by crystallization from acetone/iso-propanol provides the title compound as an off white solid (6.3 g, 52%; purity 92.8% (HPLC at 340 nm), ratio of isomers: 1:1.3). 3.72 g of the title compound was further purified by vacuum zone sublimation ($10^{-6}$-$10^{-7}$ mbar, 200-320° C.) to give the title compound as a yellowish solid. The fraction with the highest purity was 3.13 g in a purity of 97.3% (HPLC at 340 nm); ratio of isomers: 1.7:1.

Example 17

N,N-((1-methyl-3-phenyl-2,3-dihydro-1H-indene-1,3-diyl)bis(4,1-phenylene))bis(N-([1,1'-biphenyl]-2-yl)-9,9-dimethyl-9H-fluoren-2-amine)

Prepared according to the general procedure A from 1,3-bis(4-bromophenyl)-1-methyl-3-phenyl-2,3-dihydro-1H-indene from c1) (5.68 g, 11.0 mmol) and N-([1,1'-biphenyl]-2-yl)-9,9-dimethyl-9H-fluoren-2-amine (8.12 g, 22.5 mmol, 2.05 eq.) in 120 mL toluene, using sodium tert-butanolate (2.19 g, 22.7 mmol, 2.08 eq.), 100 mg (0.11 mmol, 1.0 mol-%) of $Pd_2(dba)_3$ and 207 mg (0.44 mmol, 4.0 mol-%) of RuPhos. Workup was done according to procedure B.

Purification by crystallization from acetone/iso-propanol gave the title compound as an off white solid (10.3 g, 88%; purity 92% (HPLC at 340 nm), ratio of isomers: 1:1.3). 4.52 g of the title compound was further purified by vacuum zone sublimation ($10^{-6}$-$10^{-7}$ mbar, 220-330° C.) to give the title compound as a yellowish solid. The fraction with the highest purity was 3.84 g with a purity of 97.8% (HPLC at 340 nm), ratio of isomers: 1:1.

Example 18

1-(4-aminophenyl)-1-methyl-3,3-diphenyl-2,3-dihydro-1H-inden-5-amine 15.0 g (28.9 mmol, 1.00 eq.) of 3,3-bis(4-chlorophenyl)-1-methyl-5-nitro-1-(4-nitrophenyl)-2,3-dihydro-1H-indene from c9), 1.0 g (1.7 mol-%) of 5% Pd/C, 6.60 g (2.30 mmol) of potassium acetate and 75 mL of iso-propanol were placed in an autoclave. The autoclave was pressurized for three times with 5 bar of nitrogen, followed by pressurizing it twice with 20 bar of hydrogen. Then the autoclave was heated to 80° C. for 16 hours while stirring. After cooling to room temperature, the reaction mixture was neutralized by the addition of anhydrous sodium carbonate. Then, the suspension was filtered over a layered pad consisting of silica gel/Celite. The filtrate was evaporated to dryness and re-dissolved in dichloromethane. Insoluble material was removed by filtration over a short plug of Celite. After removal of the solvent, the crude title product was recrystallized from toluene. The crystallization was brought to completion by dropwise addition of heptane. Finally, after cooling in an ice bath, the title product was filtered off and washed with a 1:1 (v/v) mixture of toluene and heptane, followed by heptane. The product was dried to give 9.86 g (87%) of a white solid in a purity of 92% (HPLC at 220 nm).

$^{13}$C NMR (75 MHz, $CD_2Cl_2$): δ 150.07 (q), 149.30 (q), 148.59 (q), 146.01 (q), 144.53 (q), 141.59 (q), 140.36 (q), 129.16 (p), 129.08 (p), 128.22 (p), 128.01 (p), 127.89 (p), 126.20 (p), 125.86 (p), 115.24 (p), 114.73 (p), 113.49 (p), 62.12 (s), 61.18 (q), 50.07 (q), 29.46 (t). Two signals of the CH-carbon atoms are overlapping.

Example 19

N-(4-(5-(bis(9,9-dimethyl-9H-fluoren-2-yl)amino)-1-methyl-3,3-diphenyl-2,3-dihydro-1H-inden-1-yl)phenyl)-N-(9,9-dimethyl-9H-fluoren-2-yl)-9,9-dimethyl-9H-fluoren-2-amine Prepared according to the general procedure A from 1-(4-aminophenyl)-1-methyl-3,3-diphenyl-2,3-dihydro-1H-inden-5-amine from example 18 (2.50 g, 6.40 mmol, 1.0 eq.) and 2-bromo-9,9-dimethyl-9H-fluorene (7.30 g 27.0 mmol, 4.2 eq.) in toluene (80 mL), using sodium tert-butanolate (2.70 g, 28.0 mmol, 4.4 eq.), 0.12 g (0.26 mmol, 4 mol-%) of RuPhos and 0.060 g (0.064 mmol, 1 mol-%) of $Pd_2(dba)_3$.

Workup was done according to procedure C. The crude compound was crystallized by dissolving it in ethyl acetate at room temperature followed by dropwise addition of iso-propanol. After stirring for 16 hours, the solid was filtered off, washed with a 2:3-mixture of ethyl acetate and iso-propanol and dried at 60° C./5 mbar to give 4.64 g of the title compound, purity according to HPLC at 340 nm: 95.0%.

A second crop of product was obtained by addition of iso-propanol to the combined filtrate/mother liquor to give further 0.80 g of the title compound, purity according to HPLC at 340 nm: 97.6%; total yield: 73%.

Example 20

N,N,N'-((6-(bis(2,4-dimethylphenyl)amino)-3-methyl-2,3-dihydro-1H-indene-1,1,3-triyl)tris(benzene-4,1-diyl))tris(2,4-dimethylphenyl)-2,4-dimethylaniline)

Prepared in analogy by a slightly modified general procedure A by suspending 5-chloro-1,3,3-tris(4-chlorophenyl)-1-methyl-2,3-dihydro-1H-indene from c5) (4.70 g, 9.4 mmol, 1.0 eq.), $PdOAc_2$ (174 mg, 0.77 mmol, 2.0 mol-%) and SPhos (657 mg, 1.54 mmol, 4.0 mol-%) in 80 mL of toluene under an argon atmosphere. In another flask, lithium bis(2,4-dimethylphenyl)amide was generated from a cooled (0° C.) solution of 8.70 g (38.6 mmol, 4.1 eq.) of bis(2,4-dimethylphenyl)amine in 50 mL THF by deprotonation with n-BuLi (2.5 M, 50.2 mmol, 5.3 eq.). The amide solution was added slowly into the suspension obtained above and the mixture was heated at 95° C. for 16 hours. Workup was done according to procedure B.

The residue was crystallized from acetone/iso-propanol to give the crude title compound (8.1 g, 69% yield based on the starting aryl-tetrachloride from c5); purity 84.9% (HPLC at 340 nm). A small amount of the crude title compound (2.1 g) was purified by column chromatography (heptane/methylene chloride) and gave the title compound as an off white solid (1.7 g; purity according to HPLC at 340 nm: 82.5%).

Example 21

3-(4-aminophenyl)-3-methyl-1,1-diphenyl-2,3-dihydro-1H-inden-5-amine 15.0 g (28.9 mmol, 1.00 eq.) of 1,1-bis(4-chlorophenyl)-3-methyl-5-nitro-3-(4-nitrophenyl)-2,3-dihydro-1H-indene from c9), 1.0 g (1.7 mol-%) of 5% Pd/C, 6.60 g (2.30 mmol) of potassium acetate were suspended in 75 mL of iso-propanol in an autoclave. The autoclave was pressurized for three times with 5 bar of nitrogen, followed by pressurizing it twice with 20 bar of hydrogen. The autoclave was heated to 80° C. for 16 hours under mechanical stirring. After cooling to room temperature the reaction mixture was neutralized by the addition of anhydrous $Na_2CO_3$.

The resulting suspension was filtered over a layered pad consisting of silica gel/Celite, which was subsequently washed twice with iso-propanol. The filtrate was evaporated to dryness and the crude product re-dissolved in dichloromethane. Residual insoluble matter was removed by filtration over a short plug of Celite.

After evaporation of the solvent, the crude product was recrystallized from a 1:2 (v/v) mixture of toluene/cyclohexane (70° C. to room temperature). Acetone was added dropwise to re-dissolve a sticky, gum-like by-product, which otherwise inhibits crystallization. The mixture was cooled in an ice bath, until the crystallization process was complete, then the solid was filtered off, washed twice with a 1:1 mixture (v/v) of toluene and heptane, and dried to give 6.41 g (57%) of an off-white solid in a purity of 85% (HPLC at 220 nm).

$^{13}C$ NMR (75 MHz, $CD_2Cl_2$) δ 153.07 (q), 149.60 (q), 149.38 (q), 146.72 (q), 144.70 (q), 139.86 (q), 138.91 (q), 129.0 (p), 128.89 (p), 128.18 (p), 128.16 (p), 128.08 (p), 127.88 (p), 126.10 (p), 125.76 (p), 114.76 (p), 114.39 (p), 111.02 (p), 62.07 (s), 60.52 (q), 50.68 (q), 28.70 (t).

Example 22

N-(4-(6-(bis(9,9-dimethyl-9H-fluoren-2-yl)amino)-1-methyl-3,3-diphenyl-2,3-dihydro-1H-inden-1-yl)phenyl)-N-(9,9-dimethyl-9H-fluoren-2-yl)-9,9-dimethyl-9H-fluoren-2-amine Prepared according to the general procedure A from 3-(4-aminophenyl)-3-methyl-1,1-diphenyl-2,3-dihydro-1H-inden-5-amine from example 21 (2.50 g, 6.40 mmol, 1.0 eq.) and 2-bromo-9,9-dimethyl-9H-fluorene (7.30 g, 27.0 mmol, 4.2 eq.) in toluene (80 mL) using sodium tert-butanolate (2.70 g, 28.0 mmol, 4.4 eq.), 0.12 g (0.26 mmol, 4 mol-%) of RuPhos, and 0.060 g (0.064 mmol, 1 mol-%) of $Pd_2(dba)_3$.

Workup according to procedure C. The crude compound was recrystallized by dissolving it in ethyl acetate at room temperature and dropwise addition of iso-propanol. This solution was stirred for 4 h, and then the resulting crystals were filtered off, washed with a 1:1 mixture of ethyl acetate/iso-propanol (v/v), and dried. A first crop of the product 4.58 g (61.7%) was obtained; purity 95.9% (HPLC at 340 nm).

Example 23

N-[4-[1-[4-[bis(9,9-dimethylfluoren-2-yl)amino]phenyl]-3-methyl-3-phenyl-2,3-dihydro-1H-inden-1-yl]phenyl]-N-(9,9-dimethylfluoren-2-yl)-9,9-dimethyl-fluoren-2-amine Prepared according to the general procedure A from 1,1-bis(4-chlorophenyl)-3-methyl-3-phenyl-2,3-dihydro-1H-indene from c8) (3.00 g, 6.99 mmol, 1.0 eq) and bis(9,9-dimethyl-9H-fluoren-2-yl)amine (5.75 g, 14.3 g, 2.05 eq.) in toluene (80 mL), using sodium tert-butanolate (1.50 g, 15.4 mmol, 2.2 eq.), 0.13 g (0.28 mmol, 4 mol-%) of RuPhos and 0.064 g (0.070 mmol, 1 mol-%) of $Pd_2(dba)_3$. Workup was done according to procedure C.

The crude title compound was crystallized from acetone. After filtration, washing with aceton and drying 7.50 g (92.5%) of the title product were obtained, purity 94.1% (HPLC at 340 nm).

Example 24

N,N',N''-((3-methyl-2,3-dihydro-1H-indene-1,1,3-triyl)tris(benzene-4,1-diyl))tris(9,9-dimethyl-N-(p-tolyl)-9H-fluoren-2-amine Prepared according to the general procedure A from 1-(4-bromophenyl)-3,3-bis(4-chlorophenyl)-1-methyl-2,3-dihydro-1H-indene from c10) (3.00 g, 5.90 mmol, 1.0 eq) and 9,9-dimethyl-N-(p-tolyl)-9H-fluoren-2-amine (5.39 g, 18.0 mmol, 3.05 eq.) in toluene (80 mL), using sodium tert-butanolate (1.87 g 19.5 mmol, 3.3 eq.), 0.12 g (0.24 mmol, 4 mol-%) of RuPhos, and 0.056 g (0.059 mmol, 1 mol-%) of $Pd_2(dba)_3$. Workup was done according to procedure C.

The crude title compound was crystallized by dissolving it at room temperature in ethyl acetate followed by the slow addition of iso-propanol. After stirring for 2 hours, the product was filtered off, washed twice with a 1:1 mixture (v/v) of iso-propanol and ethyl acetate, and dried to give 5.89 g (79.7% yield) in 89.3% purity (HPLC at 340 nm).

Example 25

N,N'-((5-(bis(9,9-dimethyl-9H-fluoren-2-yl)amino)-1,3-dimethyl-2,3-dihydro-1H-indene-1,3-diyl)bis(4,1-phenylene))bis(N-(9,9-dimethyl-9H-fluoren-2-yl)-9,9-dimethyl-9H-fluoren-2-amine)

Prepared according to the general procedure A from 5-bromo-1,3-bis(4-chlorophenyl)-1,3-dimethyl-2,3-dihydro-1H-indene from e3) (2.23 g, 5.0 mmol, 1.0 eq; cis isomer) and bis(9,9-dimethyl-9H-fluoren-2-yl)amine (6.60 g, 16.5 mmol, 3.3 eq.) in toluene (120 mL), using sodium tert-butanolate (1.55 g, 3.23 mmol, 3.23 eq.), 0.185 g (0.40 mmol, 8 mol-%) RuPhos, and 0.09 g (0.10 mmol, 2 mol-%) of $Pd_2(dba)_3$. Workup was done according to procedure C.

The crude title compound was crystallized from a 1:2 (v/v) mixture of acetone and iso-propanol to give 3.88 g of the desired compound. By a stepwise removal of solvent from the mother liquor two additional crops of product were obtained (1.66 and 0.87 g), total yield 6.41 g (86%).

Example 26

N-(9,9-dimethyl-9H-fluoren-2-yl)-N-(4-(1-methyl-3,3-diphenyl-2,3-dihydro-1H-inden-1-yl)phenyl)-9,9'-spirobi[fluoren]-2-amine Prepared according to the general procedure A from 1-(4-bromophenyl)-1-methyl-3,3-diphenyl-2,3-dihydro-1H-indene from c6) (4.39 g, 10.0 mmol, 1.0 eq) and N-(9,9-dimethyl-9H-fluoren-2-yl)-9,9'-spirobi[fluoren]-2-amine (5.50 g, 10.5 mmol, 1.05 eq.) in toluene (120 mL), using 1.03 g of sodium tert-butanolate (10.7 mmol, 1.07 eq.), 183 mg of $Pd_2(dba)_3$ (0.20 mmol, 2.0 mol-%), and 373 mg of RuPhos (0.80 mmol, 8.0 mol-%). Workup was done according to procedure A.

Purification by crystallization from acetone/iso-propanol provided the title compound as an off white solid (7.6 g, 86%; purity 97.8% (HPLC at 340 nm). 3.33 g of the title compound was further purified by vacuum zone sublimation ($10^{-6}$-$10^{-7}$ mbar, 200-290° C.) to give the title compound as a yellowish solid (3.11 g, purity up to 99.8% according to HPLC at 340 nm). $T_g$: 158.2° C.

Example 27

5,5'-(1-methyl-3-phenyl-2,3-dihydro-1H-indene-1,3-diyl)bis($N^1,N^1,N^3,N^3$-tetra-p-tolylbenzene-1,3-diamine)

Prepared according to the general procedure A from 1,3-bis(3,5-dibromophenyl)-1-methyl-3-phenyl-indane from c11) (0.67 g, 1.0 mmol, 1.0 eq) and 4-methyl-N-(p-tolyl)aniline (0.81 g, 4.1 mmol, 4.1 eq.) in toluene (12 mL) at 95° C., using 0.42 g of sodium tert-butanolate (4.4 mmol, 4.4 eq.), 8 mg of $Pd_2(dba)_3$ (0.01 mmol, 1.0 mol-%), and 19 mg of RuPhos (0.04 mmol, 4.0 mol-%). Workup was done according to procedure C.

Purification by crystallization from acetone/iso-propanol and recrystallization from acetone provided the title compound as a white solid (0.65 g, 57%; purity 82.7% (HPLC at 340 nm).

Use Example 1

Conductivity Measurement Using NDP-9 as p-Dopant Material

Glass substrates (35 mm×50 mm) were thoroughly cleaned and then coated with a 155-nm-thick layer of indium tin oxide (ITO) having trenches with a width of 20 μm, i.e. a trench separated two ITO sections. The trench was filled with the compound of formula (I) and NDP-9 as p-dopant material by co-evaporation of the compound of formula (I) and the p-dopant material. Each doped layer had a thickness of 50 nm. After applying a voltage from 10 V between two ITO stripes, the conductivity was determined.

For each doping ratio (1%, 3%, 5% and 10% by volume), conductivity was determined for two different sample geometries (sample geometry A having a length of trench of 188 mm; sample geometry B having a length of trench of 146 mm), whereby the sample to be tested contained both geometries.

TABLE I

| Sample Geometry | compound | 1% Doping sigma [S/cm] | 3% Doping sigma [S/cm] | 5% Doping sigma [S/cm] | 10% Doping sigma [S/cm] |
|---|---|---|---|---|---|
| A | example 3 | 8.7E−06 | 4.0E−05 | 8.5E−05 | — |
|   | example 4 | 1.2E−05 | 2.4E−05 | 3.3E−05 | — |
|   | example 6 | 4.2E−06 | 7.8E−06 | 9.4E−06 | — |
|   | example 7 | 9.6E−07 | — | 8.2E−06 | — |
|   | example 8 | 3.6E−07 | 1.6E−06 | 2.0E−06 | — |
|   | example 9 | 4.5E−06 | 1.5E−05 | 2.6E−05 | — |
|   | example 11 | 1.6E−07 | 1.6E−06 | 5.7E−06 | 6.0E−06 |
| B | example 3 | 8.7E−06 | 4.3E−05 | 8.9E−05 |   |
|   | example 4 | 1.2E−05 | 2.3E−05 | 3.3E−05 |   |
|   | example 6 | 4.2E−06 | 7.5E−06 | 9.4E−06 |   |

TABLE I-continued

| Sample Geometry | compound | 1% Doping sigma [S/cm] | 3% Doping sigma [S/cm] | 5% Doping sigma [S/cm] | 10% Doping sigma [S/cm] |
|---|---|---|---|---|---|
| | example 7 | 7.4E−07 | — | 8.1E−06 | |
| | example 8 | 4.3E−07 | 1.7E−06 | 2.0E−06 | — |
| | example 9 | 5.0E−06 | 1.5E−05 | 2.6E−05 | — |

The invention claimed is:

1. A compound of the general formula (I)

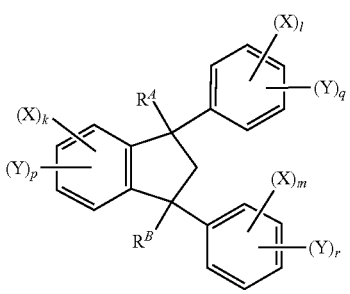

and mixtures thereof,
wherein
$R^A$ is $C_1$-$C_6$-alkyl;
$R^B$ is $C_1$-$C_6$-alkyl, $C_3$-$C_8$-cycloalkyl or a group of the formula (RB-I)

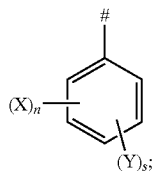

# denotes the bonding site to the remainder of the molecule;
X is -A-($NAr_2$), wherein
  A is independently on each occurrence a chemical bond or phenylene which is unsubstituted or substituted by 1, 2, 3 or 4 substituents independently selected from the group consisting of $C_1$-$C_6$ alkyl and $C_1$-$C_6$-alkoxy;
  Ar is independently on each occurrence selected from in each case unsubstituted or substituted aryl, wherein two groups Ar bound to the same nitrogen atom may together with the nitrogen atom also form a fused ring system having 3 or more than 3 unsubstituted or substituted rings;
Y is independently on each occurrence selected from hydrogen, $C_1$-$C_6$-alkyl, $C_1$-$C_6$-alkoxy, $C_3$-$C_8$-cycloalkyl, $C_3$-$C_8$-cycloalkoxy, phenyl and phenoxy, wherein each of the cyclic rings in the four last-mentioned groups are unsubstituted or substituted by 1, 2 or 3 $C_1$-$C_6$-alkyl groups;
k is 0, 1 or 2; l is 0, 1 or 2; m is 0, 1 or 2; n is 0, 1 or 2; with the proviso that the sum of k, l, m, and n is 1, 2, 3 or 4;
p is 2, 3 or 4, wherein 0, 1, 2, 3 or 4 of the p Y groups are different from hydrogen;
q is 3, 4 or 5, wherein 0, 1, 2, 3, 4 or 5 of the q Y groups are different from hydrogen;
r is 3, 4 or 5, wherein 0, 1, 2, 3, 4 or 5 of the r Y groups are different from hydrogen;
s is 3, 4 or 5, wherein 0, 1, 2, 3, 4 or 5 of the s Y groups are different from hydrogen;
the sum of k and p is 4; and the sum of q and l is 5, the sum of m and r is 5, and the sum of s and n is 5.

2. A compound of the formula (I) according to claim 1, which is selected from compounds (I.DP), or (I.TRP),

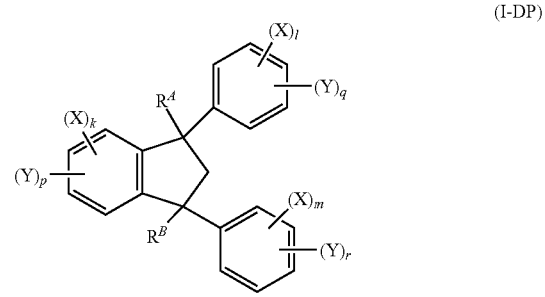

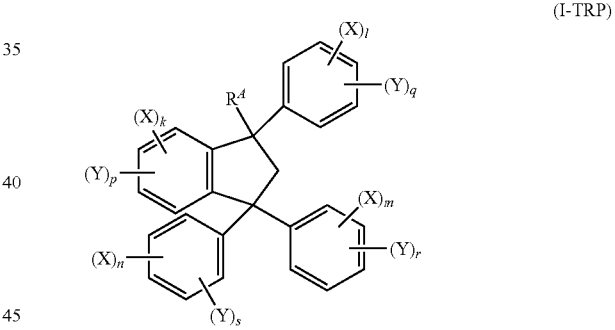

wherein X, Y, k, l, m, n, p, q, r, and s are defined as in claim 1.

3. A compound of the formula (I) according to claim 1, which is selected from compounds

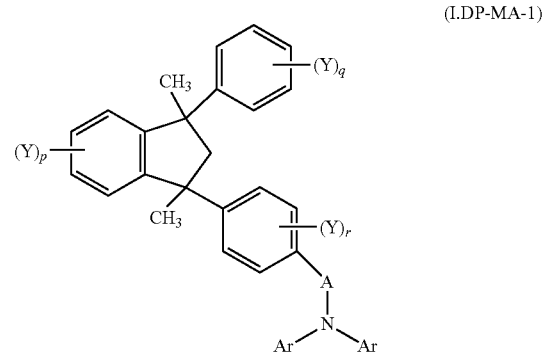

(I.DP-MA-2)
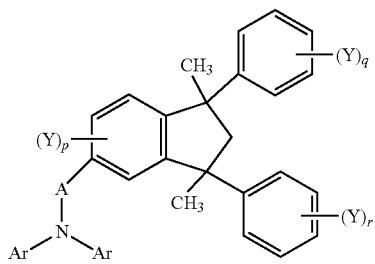
(I.DP-DA-1)
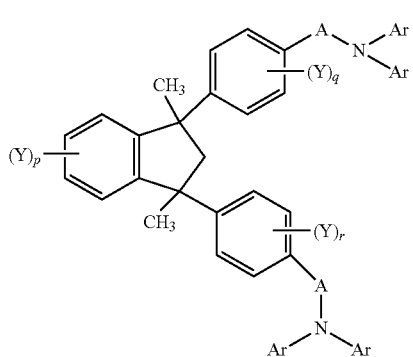
(I.DP-DA-2)
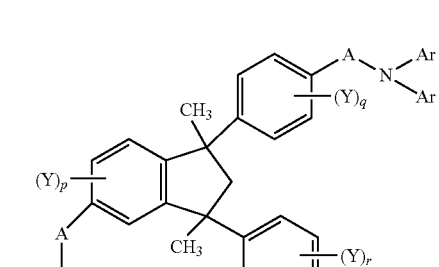
(I.DP-DA-3)
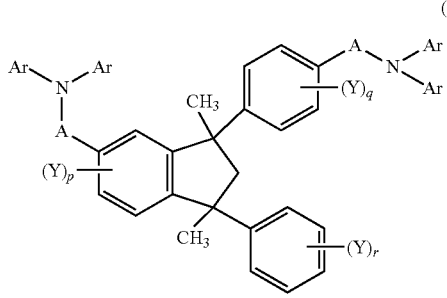
(I.DP-TRA-1)
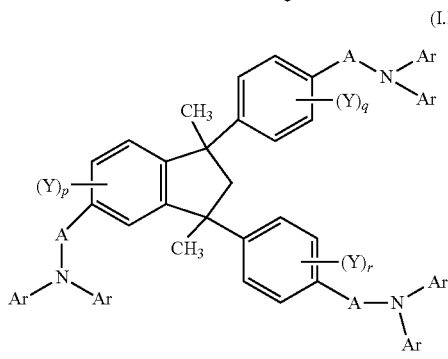
(I.DP-TEA-1)
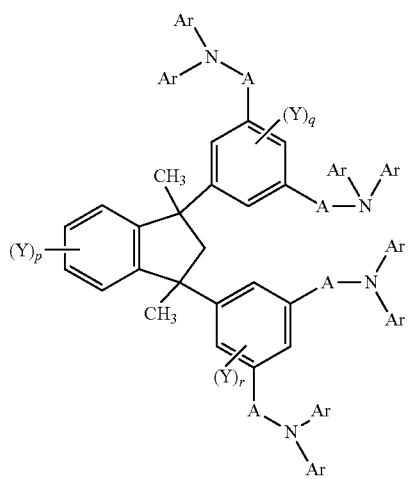
(I.TRP-MA-1)
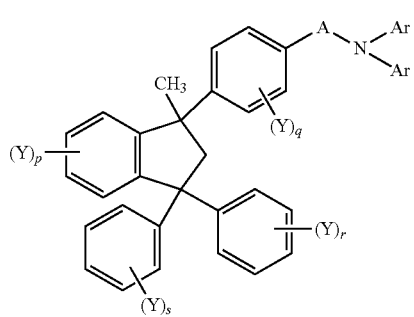
(I.TRP-MA-2)
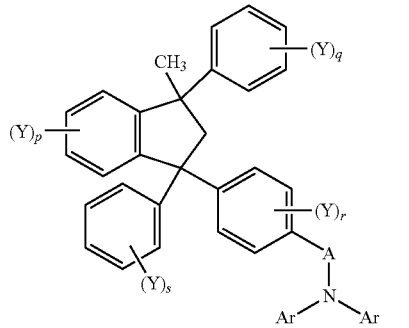
(I.TRP-MA-3)

-continued
(I.TRP-DA-1)
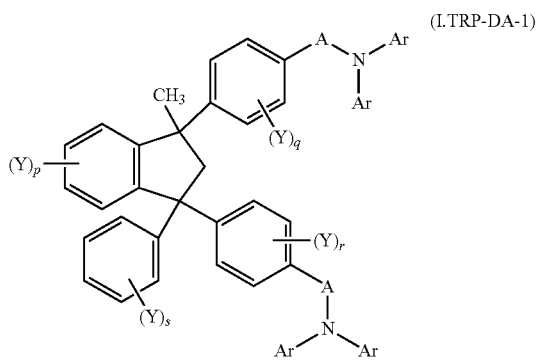
(I.TRP-DA-2)
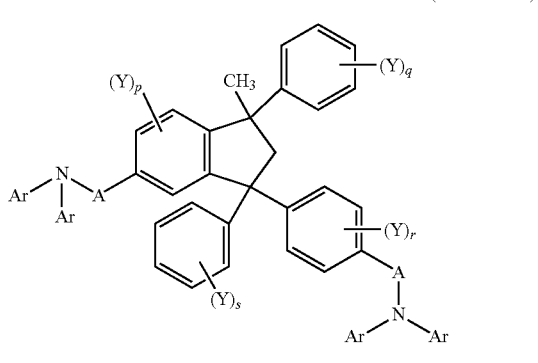
(I.TRP-DA-3)
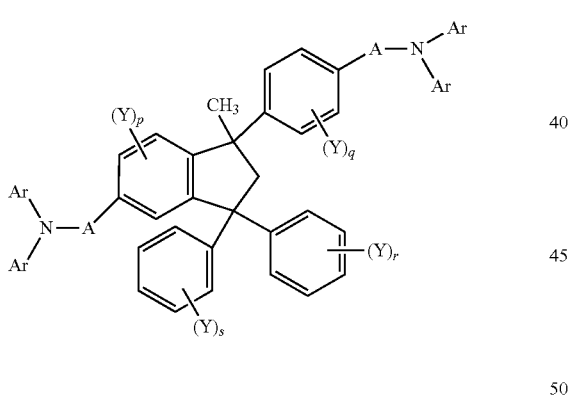
(I.TRP-DA-4)
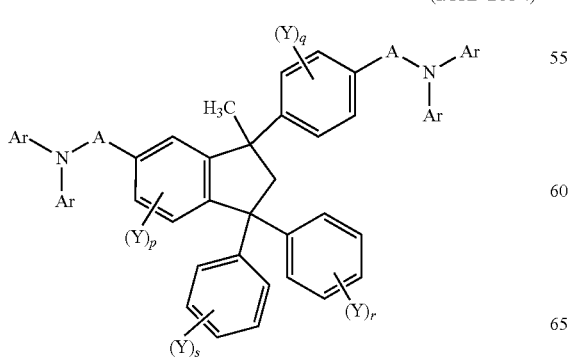
-continued
(I.TRP-DA-5)
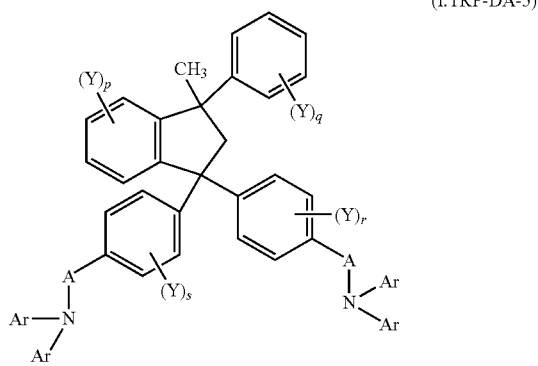
(I.TRP-TRA-1)
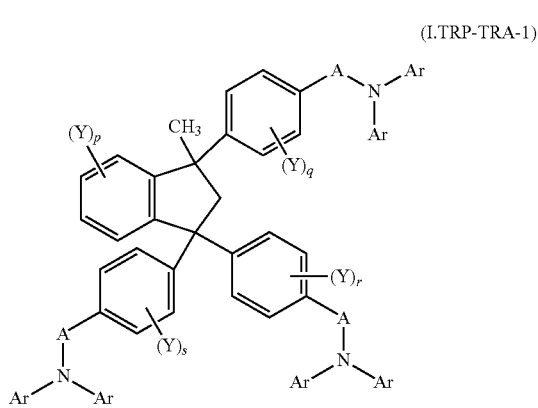
(I.TRP-TEA-1)
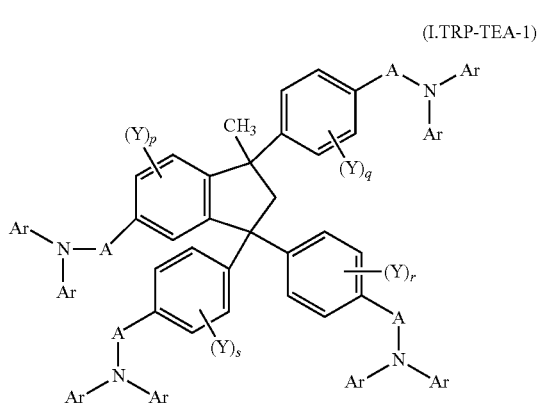
(I.TRP-TEA-2)
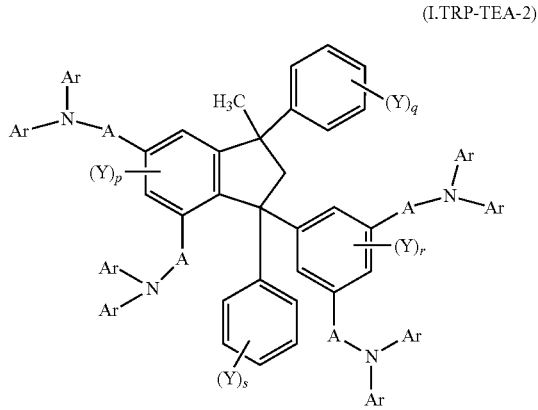

-continued (I.TRP-TEA-3)

wherein Y, A and Ar are defined as in claim 1;
where in formula (I.DP-MA-1):
p is 4, wherein 0, 1, 2, 3 or 4 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
where in formula (I.DP-MA-2):
p is 3, wherein 0, 1, 2 or 3 of the p Y groups are different from hydrogen;
q is 5, wherein 0, 1, 2, 3, 4 or 5 of the q Y groups are different from hydrogen;
r is 5, wherein 0, 1, 2, 3, 4 or 5 of the r Y groups are different from hydrogen;
where in formula (I.DP-DA-1):
p is 4, wherein 0, 1, 2, 3 or 4 of the p Y groups are different from hydrogen;
q is 4, wherein 0, 1, 2, 3, or 4 of the q Y groups are different from hydrogen;
r is 4, wherein 0, 1, 2, 3 or 4 of the r Y groups are different from hydrogen;
where in formula (I.DP-DA-2):
p is 3, wherein 0, 1, 2 or 3 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
where in formula (I.DP-DA-3):
p is 3, wherein 0, 1, 2 or 3 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
where in formula (I.DP-TRA-1):
p is 3, wherein 0, 1, 2 or 3 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
where in formula (I.DP-TEA-1):
p is 4, wherein 0, 1, 2, 3 or 4 of the p Y groups are different from hydrogen;
q is 3, wherein 0, 1, 2 or 3 of the q Y groups are different from hydrogen;
r is 3, wherein 0, 1, 2 or 3 of the r Y groups are different from hydrogen;
where in formula (I.TRP-MA-1):
p is 4, wherein 0, 1, 2, 3 or 4 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
where in formula (I.TRP-MA-2):
p is 4, wherein 0, 1, 2, 3 or 4 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
where in formula (I.TRP-MA-3):
p is 3, wherein 0, 1, 2 or 3 of the p Y groups are different from hydrogen;
q is 5, wherein 0, 1, 2, 3, 4 or 5 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
where in formula (I.TRP-DA-1):
p is 4, wherein 0, 1, 2, 3 or 4 of the p Y groups are different from hydrogen;
q is 4, wherein 0, 1, 2, 3 or 4 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
where in formula (I.TRP-DA-2):
p is 3, wherein 0, 1, 2 or 3 of the p Y groups are different from hydrogen;
q is 5, wherein 0, 1, 2, 3, 4 or 5 of the q Y groups are different from hydrogen;
r is 4, wherein 0, 1, 2, 3 or 4 of the r Y groups are different from hydrogen;
s is 5, wherein 0, 1, 2, 3, 4 or 5 of the s Y groups are different from hydrogen;
where in formula (I.TRP-DA-3):
p is 3, wherein 0, 1, 2 or 3 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;
where in formula (I.TRP-DA-4):
p is 3, wherein 0, 1, 2 or 3 of the p Y groups are different from hydrogen;
q is 4, wherein 0, 1, 2, 3 or 4 of the q Y groups are different from hydrogen;
r is 5, wherein 0, 1, 2, 3, 4 or 5 of the r Y groups are different from hydrogen;
s is 5, wherein 0, 1, 2, 3, 4 or 5 of the s Y groups are different from hydrogen;

where in formula (I.TRP-DA-5):
p is 4 wherein 0, 1, 2, 3 or 4 of the p Y groups are different from hydrogen;
q is 5, wherein 0, 1, 2, 3, 4 or 5 of the r Y groups are different from hydrogen;
r is 4, wherein 0, 1, 2, 3 or 4 of the q Y groups are different from hydrogen;
s is 4, wherein 0, 1, 2, 3 or 4 of the q Y groups are different from hydrogen;
where in formula (I.TRP-TRA-1):
p is 4 wherein 0, 1, 2, 3 or 4 of the p Y groups are different from hydrogen;
q is 4, wherein 0, 1, 2, 3 or 4 of the r Y groups are different from hydrogen;
r is 4, wherein 0, 1, 2, 3 or 4 of the q Y groups are different from hydrogen;
s is 4, wherein 0, 1, 2, 3 or 4 of the q Y groups are different from hydrogen;
where in formula (I.TRP-TEA-1):
p is 3, wherein 0, 1, 2 or 3 of the p Y groups are different from hydrogen,
q is 4, wherein 0, 1, 2, 3 or 4 of the q Y groups are different from hydrogen,
r is 4, wherein 0, 1, 2, 3 or 4 of the r Y groups are different from hydrogen,
s is 4, wherein 0, 1, 2, 3 or 4 of the s Y groups are different from hydrogen,
where in formula (I.TRP-TEA-2):
p is 2, wherein 0, 1 or 2 of the p Y groups are different from hydrogen;
q is 5, wherein 0, 1, 2, 3, 4 or 5 of the q Y groups are different from hydrogen;
r is 3, wherein 0, 1, 2 or 3 of the r Y groups are different from hydrogen;
s is 5, wherein 0, 1, 2, 3, 4 or 5 of the s Y groups are different from hydrogen;
where in formula (I.TRP-TEA-3):
p is 4, wherein 0, 1, 2, 3 or 4 of the p Y groups are different from hydrogen;
q is 3, wherein 0, 1, 2 or 3 of the q Y groups are different from hydrogen;
r is 3, wherein 0, 1, 2 or 3 of the r Y groups are different from hydrogen;
s is 5, wherein 0, 1, 2, 3, 4 or 5 of the s Y groups are different from hydrogen.

4. A compound of the formula (I) according to claim 1, wherein each of the groups A is a chemical bond.

5. A compound according to claim 1, wherein the groups Ar are independently on each occurrence selected from:
phenyl, biphenylyl, terphenylyl, quaterphenylyl, wherein phenyl, biphenylyl, terphenylyl and quaterphenylyl are unsubstituted or substituted by one or more substituents $R^{Ar1}$;
naphthyl, anthracenyl, phenanthryl, fluorenyl, spirofluorenyl, C-bound carbazolyl, dibenzofuranyl and dibenzothiophenyl, wherein naphthyl, phenanthryl, fluorenyl, spirofluorenyl, C-bound carbazolyl, dibenzofuranyl and dibenzothiophenyl are unsubstituted or substituted by one or more substituents $R^{Ar2}$; or
2 groups Ar together with the nitrogen atom to which they are attached may form an N-bound carbazolyl, which is unsubstituted or substituted by one or more substituents $R^{Ar3}$;

wherein
each $R^{Ar1}$ is independently selected from
$C_1$-$C_6$-alkyl, $C_1$-$C_6$-alkoxy, carbazol-9-yl, wherein carbazol-9-yl may be substituted by 1, 2, 3 or 4 substituents selected from $C_1$-$C_4$-alkyl, $C_1$-$C_4$-alkoxy and phenyl,
wherein phenyl may be substituted by 1, 2, 3 or 4 different or identical substituents selected from $C_1$-$C_4$-alkyl and $C_1$-$C_4$-alkoxy,
diphenylamino, $C_5$-$C_8$-cycloalkyl and naphthyl, wherein each of the cyclic rings in the three last-mentioned groups are unsubstituted or substituted by 1, 2, 3 or 4 different or identical substituents selected from $C_1$-$C_4$-alkyl, $C_1$-$C_4$-alkoxy and carbazol-9-yl, wherein carbazol-9-yl may be substituted by 1, 2, 3 or 4 different or identical substituents selected from $C_1$-$C_4$-alkyl, $C_1$-$C_4$-alkoxy and phenyl, wherein phenyl may be substituted by 1, 2, 3 or 4 different or identical substituents selected from $C_1$-$C_4$-alkyl and $C_1$-$C_4$-alkoxy,
and two radicals $R^{Ar1}$ which are bound to adjacent carbon atoms together with the carbon atoms to which they are bound may form a saturated 5-membered heterocycle having 2 non-adjacent oxygen atoms as ring members which is unsubstituted or substituted by 1 or 2 radicals selected from $C_1$-$C_4$-alkyl;
each $R^{Ar2}$ is independently selected from
$C_1$-$C_6$-alkyl, $C_1$-$C_6$-alkoxy, carbazol-9-yl, wherein carbazol-9-yl may be substituted by 1, 2, 3 or 4 substituents selected from $C_1$-$C_4$-alkyl, $C_1$-$C_4$-alkoxy and phenyl,
wherein phenyl may be substituted by 1, 2, 3 or 4 different or identical substituents selected from $C_1$-$C_4$-alkyl and $C_1$-$C_4$-alkoxy,
diphenylamino, $C_5$-$C_8$-cycloalkyl and phenyl, wherein each of the cyclic rings in the three last-mentioned groups are unsubstituted or substituted by 1, 2, 3 or 4 different or identical substituents selected from $C_1$-$C_4$-alkyl, $C_1$-$C_4$-alkoxy and carbazol-9-yl, wherein carbazol-9-yl may be substituted by 1, 2, 3 or 4 different or identical substituents selected from $C_1$-$C_4$-alkyl, $C_1$-$C_4$-alkoxy and phenyl, wherein phenyl may be substituted by 1, 2, 3 or 4 different or identical substituents selected from $C_1$-$C_4$-alkyl and $C_1$-$C_4$-alkoxy,
two radicals $R^{Ar2}$ which are bound to adjacent carbon atoms together with the carbon atoms to which they are bound may form a saturated 5-membered heterocycle having 2 non-adjacent oxygen atoms as ring members which is unsubstituted or substituted by 1 or 2 radicals selected from $C_1$-$C_4$-alkyl and,
in addition, in the case of fluorenyl, two geminal radicals $R^{Ar2}$ may form an alkylene group (CH2), with r being 4, 5, 6 or 7, where 1 or 2 hydrogen atoms in this group may be replaced by a methyl group or a methoxy group; and
each $R^{Ar3}$ is independently selected from $C_1$-$C_6$-alkyl, $C_1$-$C_6$-alkoxy, diphenylamino and phenyl, wherein each of the cyclic rings in the two last-mentioned groups are unsubstituted or substituted by 1, 2, 3 or 4 different or identical substituents selected from $C_1$-$C_4$-alkyl and $C_1$-$C_4$-alkoxy.

6. A compound according to claim 1, wherein the groups Ar are independently on each occurrence selected from groups of the formulae (AR-I) to (AR-XLV)

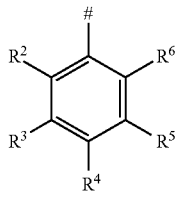
(AR-I)
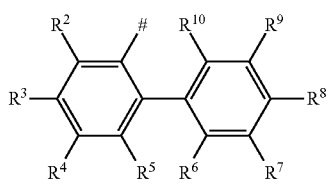
(AR-II)
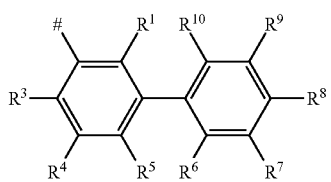
(AR-III)
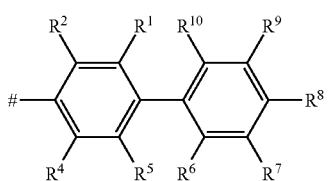
(AR-IV)
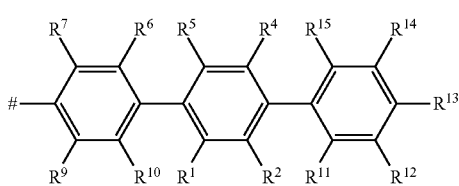
(AR-V)
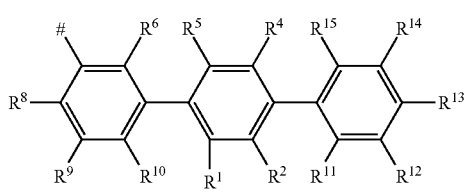
(AR-VI)
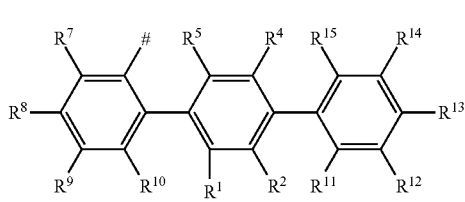
(AR-VII)
-continued
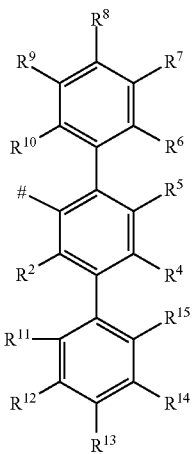
(AR-VIII)
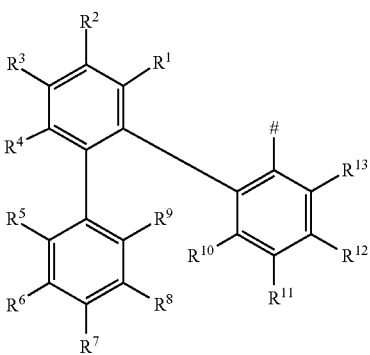
(AR-IX)
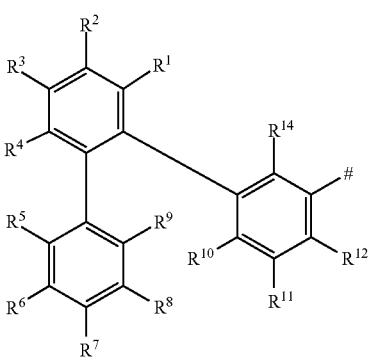
(AR-X)
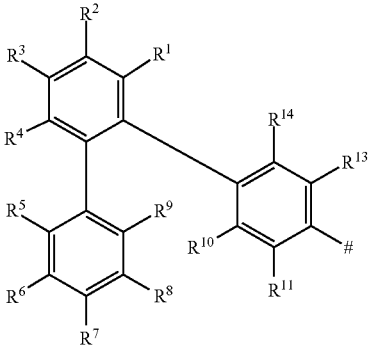
(AR-XI)

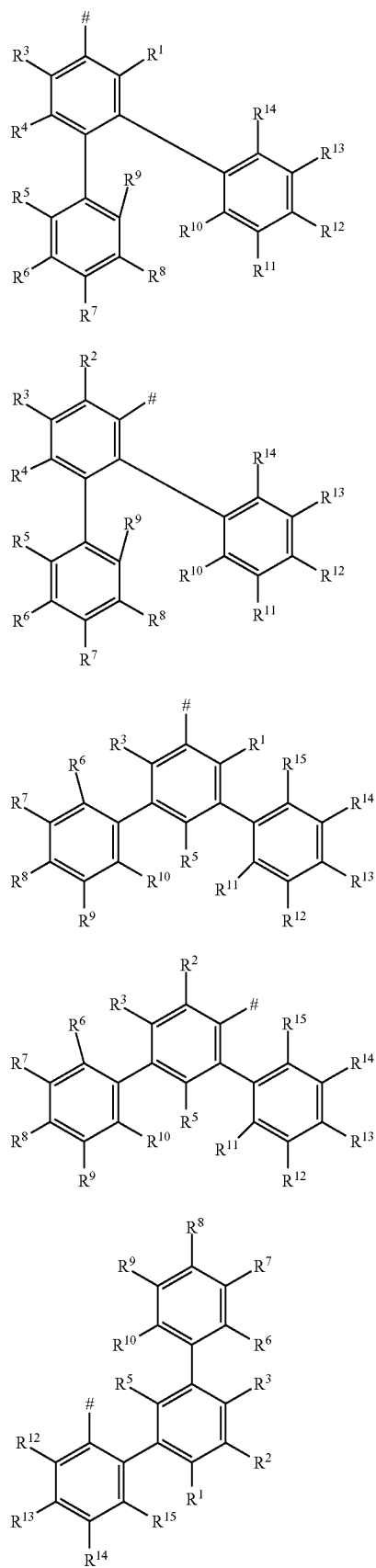
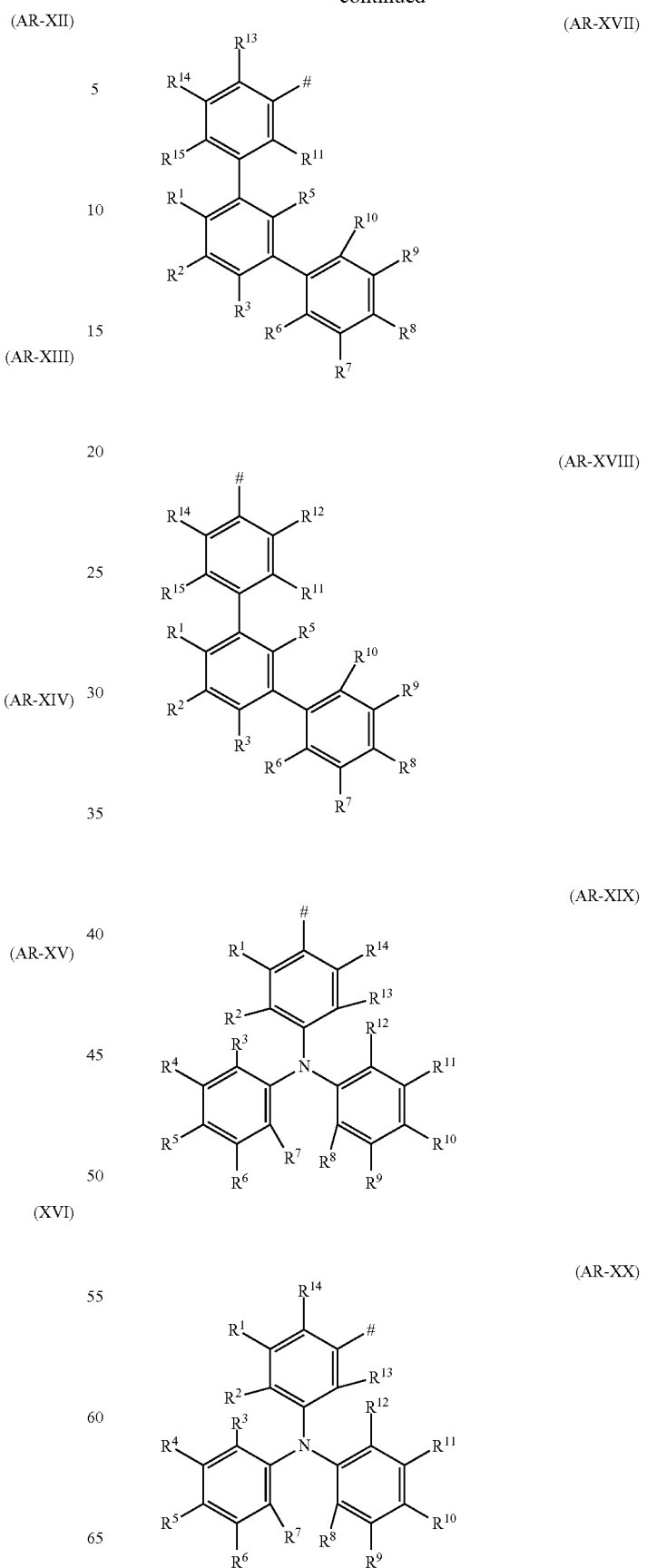

(AR-XXI)
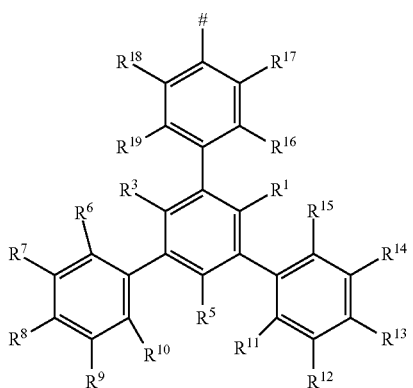
(AR-XXII)
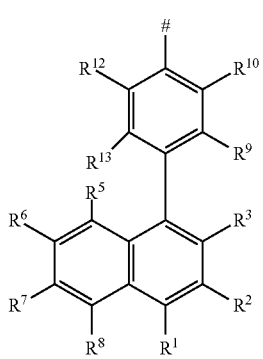
(AR-XXIII)
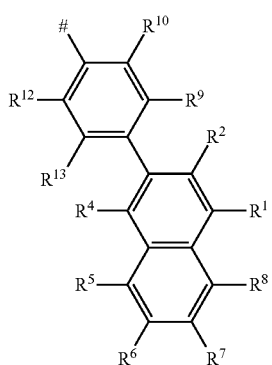
(AR-XXIV)
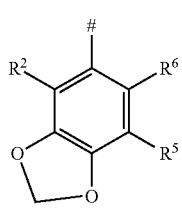
(AR-XXV)
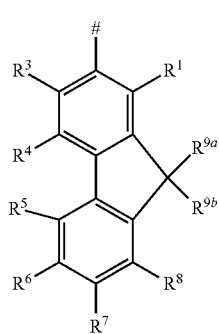
(AR-XXVI)
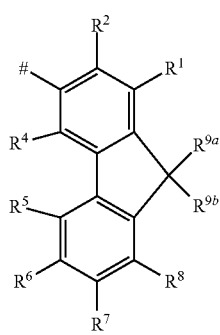
(AR-XXVII)
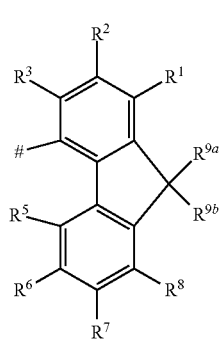
(AR-XXVIII)
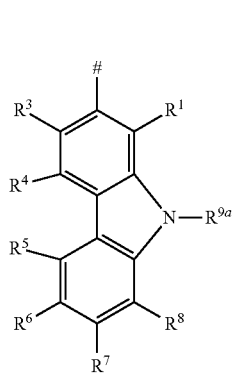
(AR-XXIX)
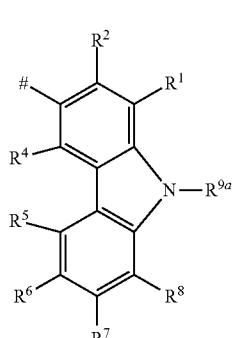
(AR-XXX)
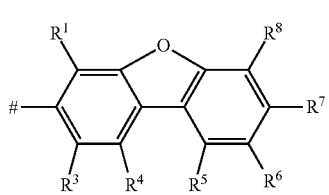

-continued
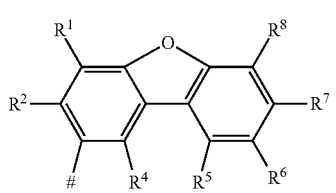
(AR-XXXI)
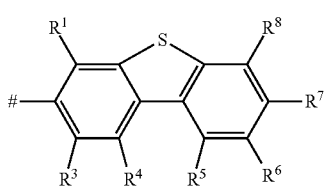
(AR-XXXII)
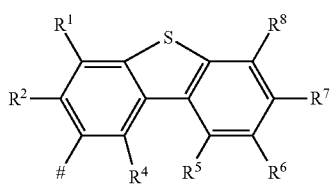
(AR-XXXIII)
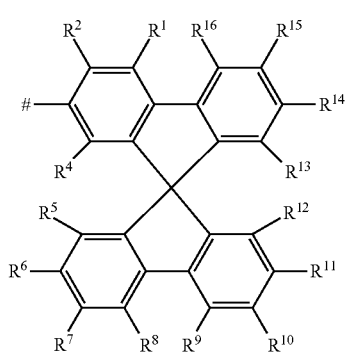
(AR-XXXIV)
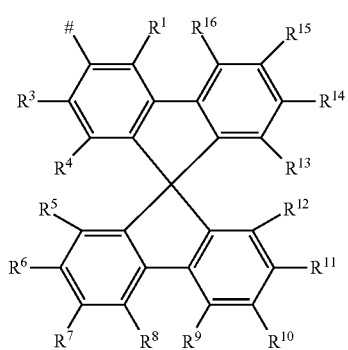
(AR-XXXV)
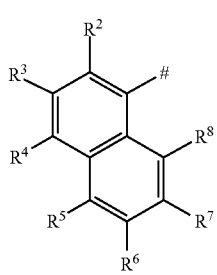
(AR-XXXVI)
-continued
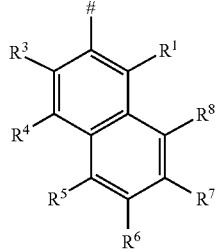
(AR-XXXVII)
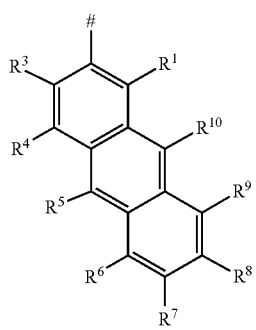
(AR-XXXVIII)
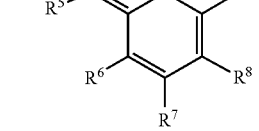
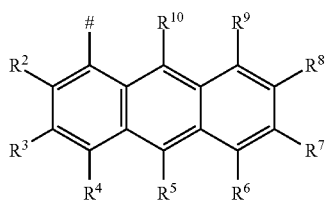
(AR-XXXIX)
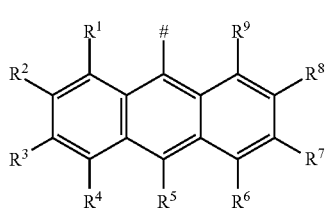
(AR-XL)
(AR-XLI)
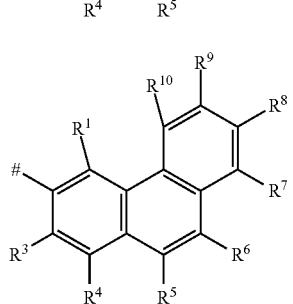
(AR-XLII)

-continued (AR-XLIII)
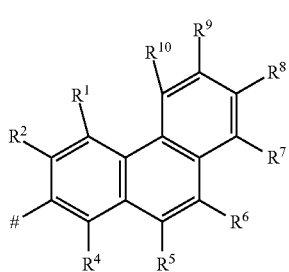

(AR-XLIV)
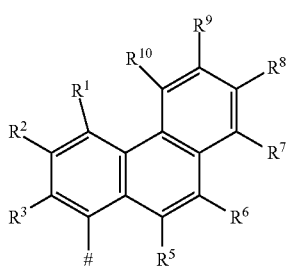

(AR-XLV)
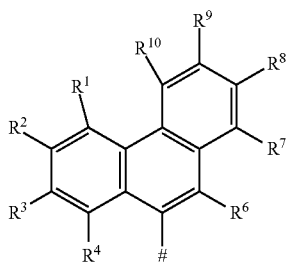

wherein
in each case denotes the bonding site to the nitrogen atom;
in formulae AR-I, AR-II, AR-III, AR-IV, AR-V, AR-VI, AR-VII, AR-VIII, AR-IX, AR-X, AR-XI, AR-XII, AR-XIII, AR-XIV, AR-XV, AR-XVI, AR-XVII, AR-XVIII, AR-XIX, AR-XX, AR-XXI, AR-XXII, AR-XXIII and Ar-XXIV:
$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$ and $R^{19}$, if present, independently of one another, are selected from hydrogen, straight-chain or branched $C_1$-$C_4$-alkyl, straight-chain or branched $C_1$-$C_4$-alkoxy and carbazol-9-yl, wherein carbazol-9-yl may be substituted by 1, 2, 3 or 4 different or identical substituents selected from $C_1$-$C_4$-alkyl, $C_1$-$C_4$-alkoxy, phenyl, tolyl, xylyl, mesityl and anisyl;
in formulae AR-XXV, AR-XXVI, AR-XXVII, AR-XXVIII, AR-XXIX, AR-XXX, AR-XXXI, AR-XXXII, AR-XXXIII, AR-XXXIV, AR-XXXV, AR-XXXVI, AR-XXXVII, AR-XXXVIII, AR-XXXIX, AR-XL, AR-XLI, AR-XLII, AR-XLIII, AR-XLIV and AR-XLV:
$R^1$, $R^2$, $R^3$, $R^4$, $R^5$, $R^6$, $R^7$, $R^8$, $R^9$, $R^{9a}$, $R^{9b}$, $R^{10}$, $R^{11}$, $R^{12}$, $R^{13}$, $R^{14}$, $R^{15}$ and $R^{16}$, if present, independently of one another, are selected from hydrogen, straight-chain or branched $C_1$-$C_4$-alkyl, straight-chain or branched $C_1$-$C_4$-alkoxy, carbazol-9-yl and phenyl, wherein carbazol-9-yl and phenyl are unsubstituted or substituted by 1, 2 or 3 different or identical substituents selected from $C_1$-$C_4$-alkyl, $C_1$-$C_4$-alkoxy, phenyl, tolyl, xylyl and mesityl and, in addition, $R^{9a}$ and $R^{9b}$ in formulae AR-XXV, AR-XXVI and AR-XXVII together may form an alkylene group $(CH_2)_r$ with r being 4, 5 or 6 where 1 or 2 hydrogen atoms in this group may be replaced by a methyl or methoxy group.

7. A compound according to claim 1, wherein the groups (NAr$_2$) are independently on each occurrence selected from groups of the formulae (1)-(51)

(1)
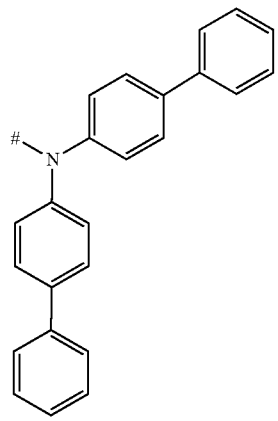

(2)
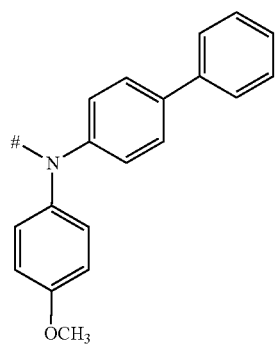

(3)
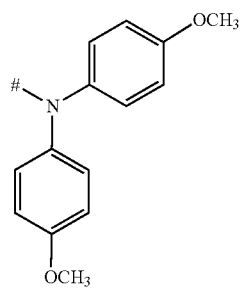

(4)
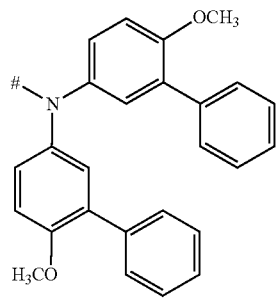

(5)
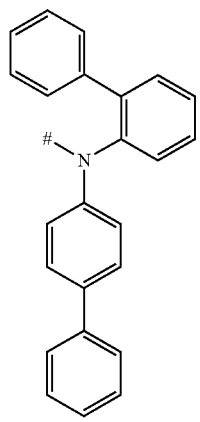
(6)
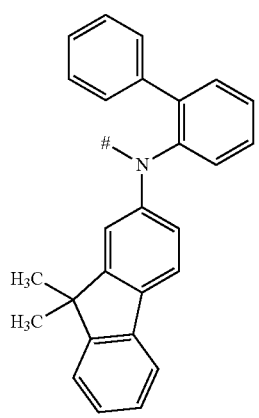
(7)
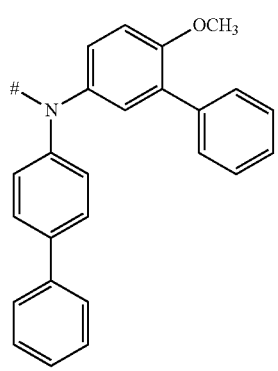
(8)
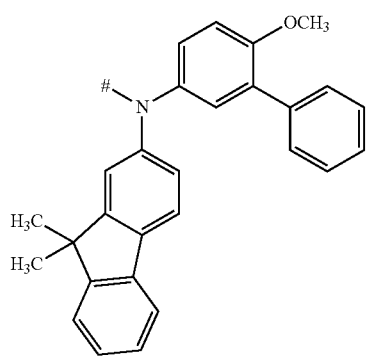
(9)
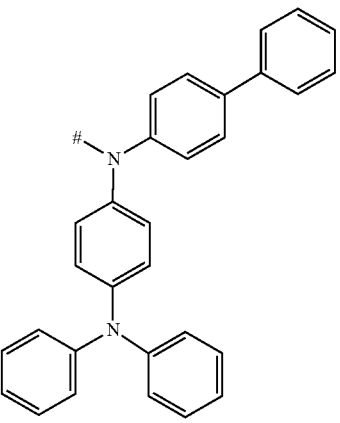
(10)
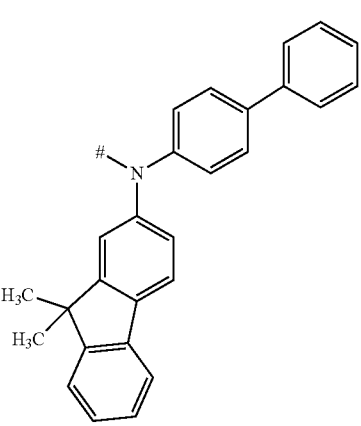
(11)
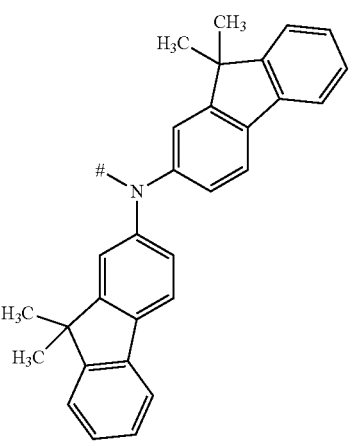

(12)
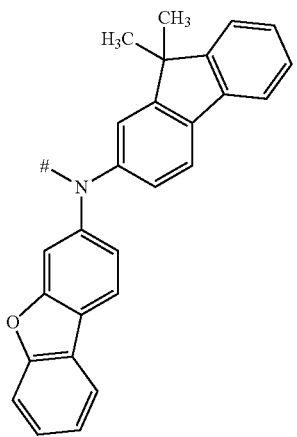
(13)
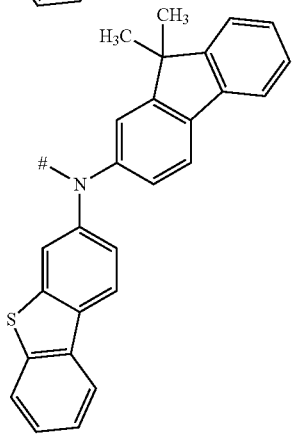
(14)
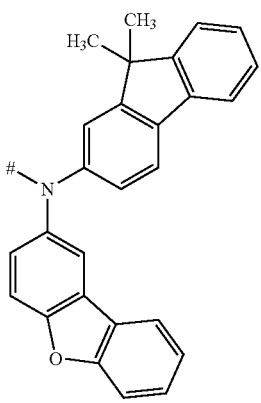
(15)
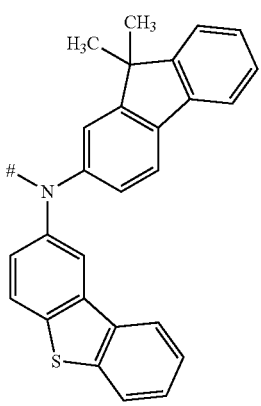
(16)
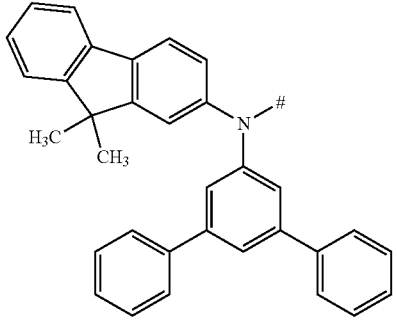
(17)
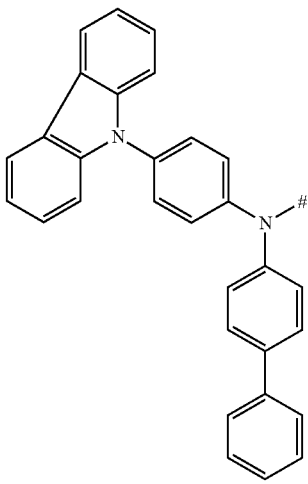
(18)
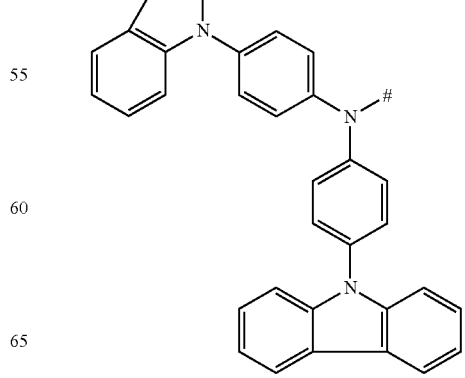

(19)
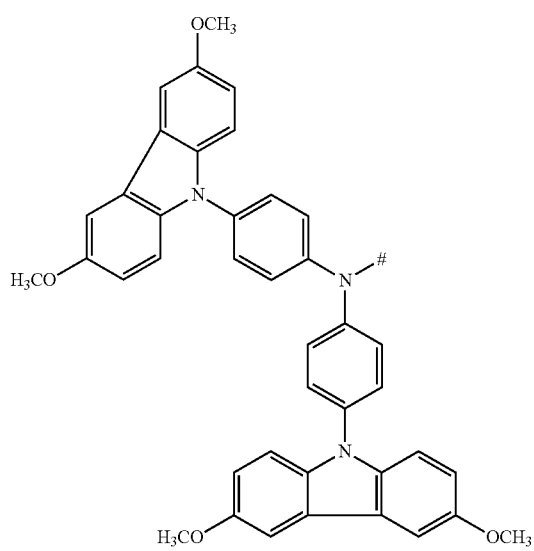
(22)
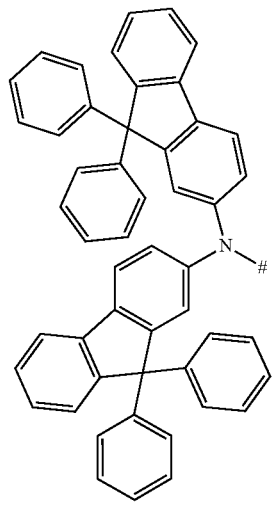
(20)
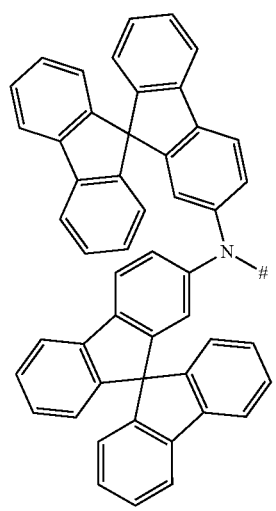
(23)
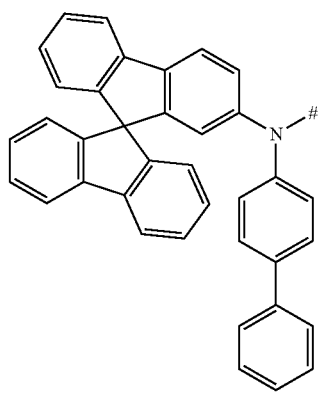
(21)
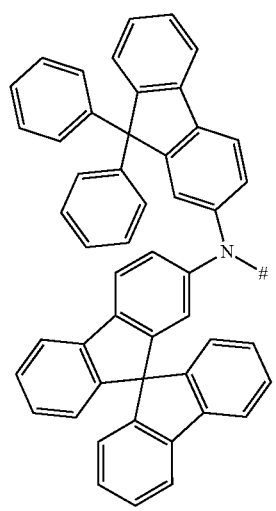
(24)

(25)
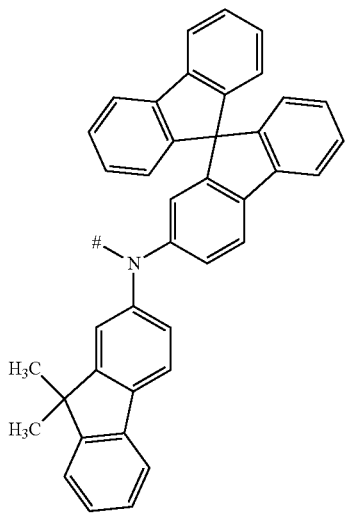
(26)
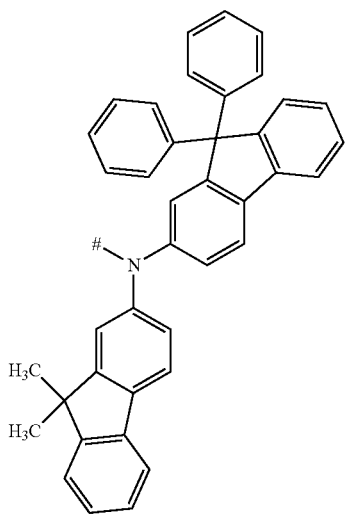
(27)
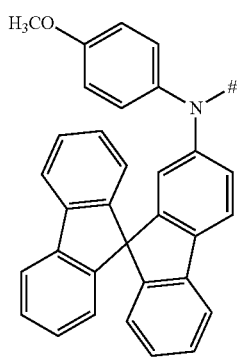
(28)
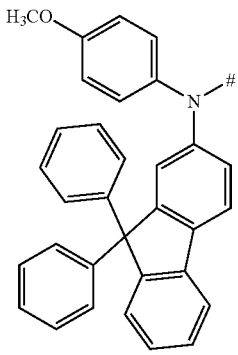
(29)
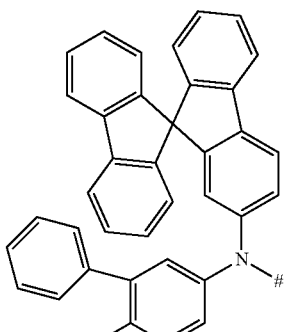
(30)
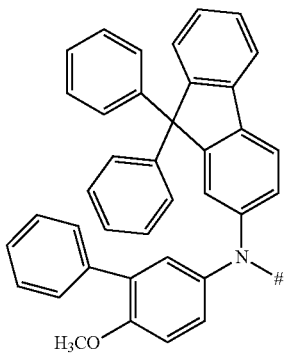
(31)
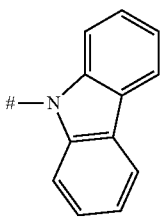
(32)
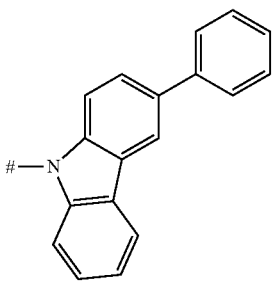

(33) 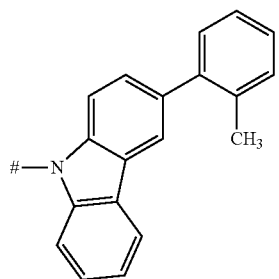
(34) 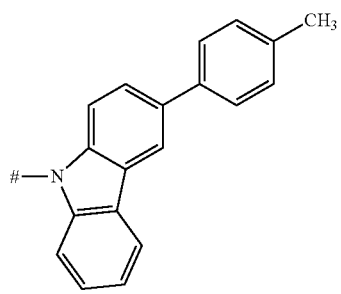
(35) 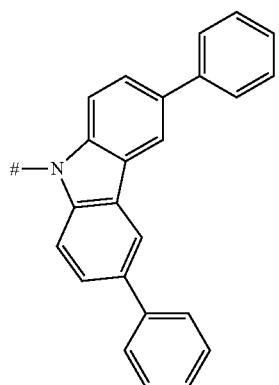
(36) 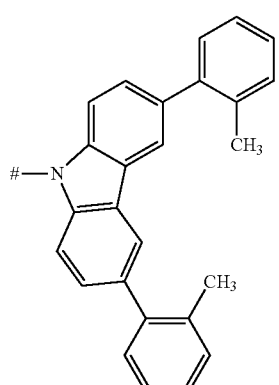
(37) 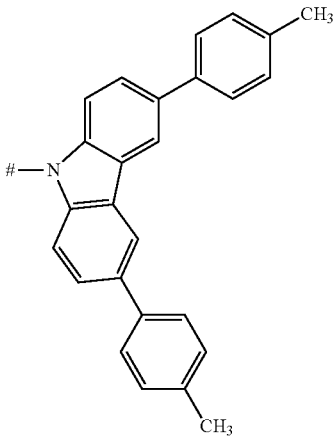
(38) 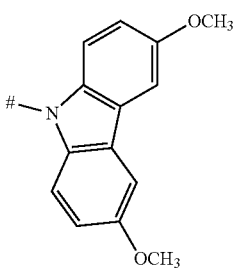
(39) 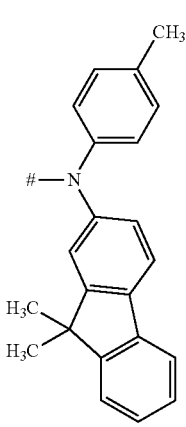
(40) 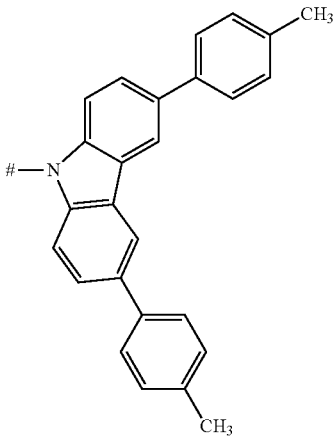

-continued
(41) 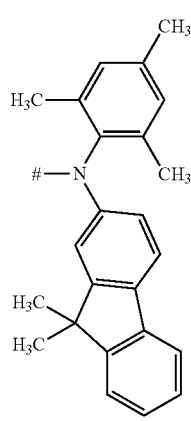
(42) 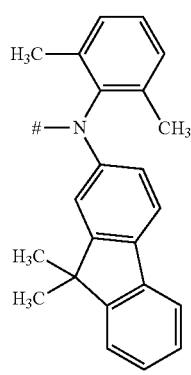
(43) 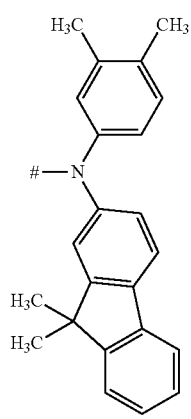
(44) 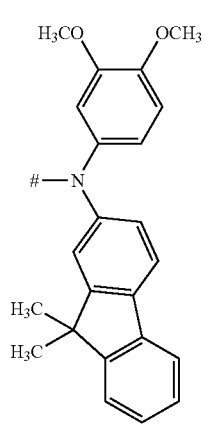
(45) 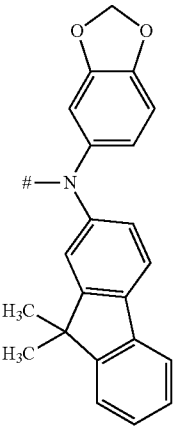
(46) 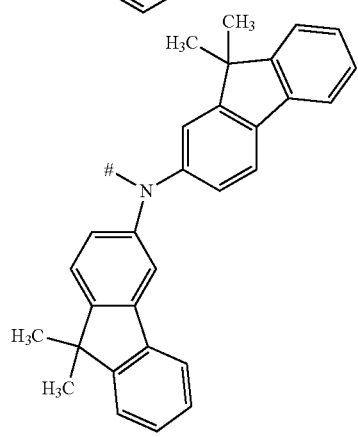
(47) 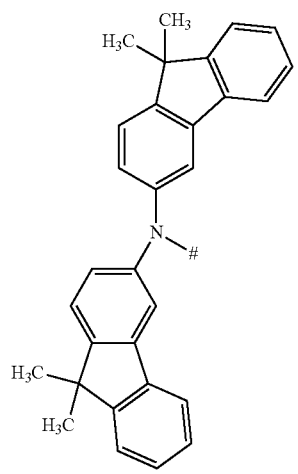
(48) 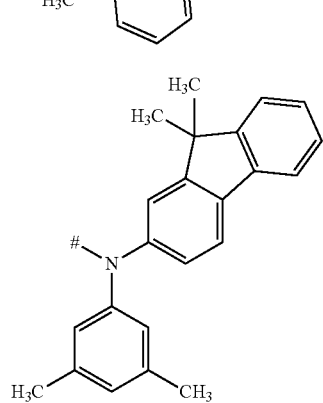

-continued

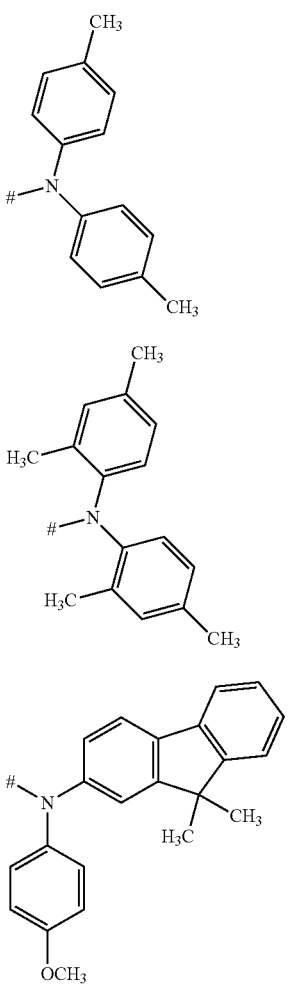

wherein

\# denotes the bonding side to the remainder of the compound.

8. A compound of the formula (I) according to claim 1, wherein all groups Ar have the same meaning.

9. An organic field-effect transistor comprising a substrate having at least one gate structure, a source electrode and a drain electrode and at least one compound of the formula (I) as defined in claim 1 or of a composition comprising at least two different compounds of the general formula (I) as defined in claim 1 as a semiconductor material.

10. An electroluminescent arrangement comprising an upper electrode, a lower electrode, wherein at least one of said electrodes is transparent, an electroluminescent layer and optionally an auxiliary layer, wherein the electroluminescent arrangement comprises at least one compound of the formula (I) as defined in claim 1 or of a composition comprising at least two different compounds of the general formula (I) as defined in claim 1, preferably in a hole-transporting layer or electron blocking layer.

11. The electroluminescent arrangement as claimed in claim 10 in form of an organic light-emitting diode (OLED).

12. An organic solar cell, comprising:
   a cathode,
   an anode,
   one or more photoactive regions comprising at least one donor material and at least one acceptor material in separate layers or in form of a bulk heterojunction layer,
   optionally at least one further layer selected from exciton blocking layers, electron conducting layers, hole transport layers,
   wherein the organic solar cell comprises at least one compound of the formula (I) as defined in claim 1 or of a composition comprising at least two different compounds of the general formula I as defined in claim 1.

\* \* \* \* \*